(12) United States Patent
Miick et al.

(10) Patent No.: US 11,447,835 B2
(45) Date of Patent: Sep. 20, 2022

(54) COMPOSITIONS AND METHODS FOR DETECTING OR QUANTIFYING HEPATITIS C VIRUS

(71) Applicant: GEN-PROBE INCORPORATED, San Diego, CA (US)

(72) Inventors: Siobhan Miick, San Diego, CA (US); Paul M. Darby, San Diego, CA (US); Jo Ann Jackson, Lakeside, CA (US); Sheila M. J. Aubin, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 287 days.

(21) Appl. No.: 15/787,344

(22) Filed: Oct. 18, 2017

(65) Prior Publication Data
US 2018/0291474 A1    Oct. 11, 2018

Related U.S. Application Data

(60) Provisional application No. 62/410,188, filed on Oct. 19, 2016.

(51) Int. Cl.
*C12Q 1/70*     (2006.01)
*C12Q 1/6876*   (2018.01)
*C12Q 1/6806*   (2018.01)
*C12Q 1/686*    (2018.01)

(52) U.S. Cl.
CPC ........... *C12Q 1/706* (2013.01); *C12Q 1/6806* (2013.01); *C12Q 1/6876* (2013.01); *C12Q 1/686* (2013.01); *C12Q 2600/16* (2013.01)

(58) Field of Classification Search
CPC .... C12Q 1/706; C12Q 1/6806; C12Q 1/6876; C12Q 2600/16; C12Q 1/686
See application file for complete search history.

(56) References Cited

U.S. PATENT DOCUMENTS

| | | |
|---|---|---|
| 4,581,333 A | 4/1986 | Kourilsky et al. |
| 4,683,195 A | 7/1987 | Mullis et al. |
| 4,683,202 A | 7/1987 | Mullis |
| 4,786,600 A | 11/1988 | Kramer et al. |
| 4,800,159 A | 1/1989 | Mullis et al. |
| 4,868,105 A | 9/1989 | Urdea et al. |
| 5,118,801 A | 6/1992 | Lizard et al. |
| 5,124,246 A | 6/1992 | Urdea et al. |
| 5,130,238 A | 7/1992 | Malek et al. |
| 5,185,439 A | 2/1993 | Arnold, Jr. et al. |
| 5,283,174 A | 2/1994 | Arnold, Jr. et al. |
| 5,312,728 A | 5/1994 | Lizard et al. |
| 5,378,825 A | 1/1995 | Cook et al. |
| 5,399,491 A | 3/1995 | Kacian et al. |
| 5,422,252 A | 6/1995 | Walker et al. |
| 5,424,413 A | 6/1995 | Hogan et al. |
| 5,427,930 A | 6/1995 | Birkenmeyer et al. |
| 5,437,990 A | 8/1995 | Burg et al. |
| 5,451,503 A | 9/1995 | Hogan et al. |
| 5,516,663 A | 5/1996 | Backman et al. |
| 5,547,861 A | 8/1996 | Nadeau et al. |
| 5,554,516 A | 9/1996 | Kacian et al. |
| 5,585,481 A | 12/1996 | Arnold et al. |
| 5,639,604 A | 6/1997 | Arnold, Jr. et al. |
| 5,648,211 A | 7/1997 | Fraiser et al. |
| 5,656,207 A | 8/1997 | Woodhead et al. |
| 5,656,744 A | 8/1997 | Arnold, Jr. et al. |
| 5,658,737 A | 8/1997 | Nelson et al. |
| 5,846,704 A * | 12/1998 | Maertens ............ C12Q 1/6834 435/5 |
| 5,849,481 A | 12/1998 | Urdea et al. |
| 5,925,517 A | 7/1999 | Tyagi et al. |
| 6,110,678 A | 8/2000 | Weisburg et al. |
| 6,150,097 A | 11/2000 | Tyagi et al. |
| 6,180,340 B1 | 1/2001 | Nelson |
| 6,350,579 B1 | 2/2002 | Nelson |
| 6,361,945 B1 | 3/2002 | Becker et al. |
| 6,534,274 B2 | 3/2003 | Becker et al. |
| 6,835,542 B2 | 12/2004 | Becker et al. |
| 6,849,412 B2 | 2/2005 | Becker et al. |
| 6,949,367 B1 | 9/2005 | Dempcy et al. |
| 7,374,885 B2 | 5/2008 | Becker et al. |
| 7,785,844 B2 | 8/2010 | Linnen et al. |
| 8,034,554 B2 | 10/2011 | Becker et al. |
| 9,139,870 B2 | 9/2015 | Nelson et al. |
| 2003/0003463 A1* | 1/2003 | Rothberg ............ C12Q 1/6809 435/6.16 |
| 2003/0044780 A1* | 3/2003 | Lapidus ............... C12Q 1/6818 435/6.12 |
| 2006/0068417 A1 | 3/2006 | Becker et al. |
| 2006/0068433 A1* | 3/2006 | Godfrey ............... C12Q 1/6851 435/6.18 |
| 2006/0194240 A1 | 8/2006 | Arnold, Jr. et al. |
| 2006/0276972 A1 | 12/2006 | Light, II et al. |
| 2008/0081328 A1* | 4/2008 | Linnen .................. C12Q 1/703 435/5 |
| 2011/0236983 A1* | 9/2011 | Beechem ........... G01N 21/6428 436/94 |
| 2012/0252007 A1 | 10/2012 | Rabbani et al. |

FOREIGN PATENT DOCUMENTS

| | | |
|---|---|---|
| FR | 2884522 A1 | 10/2006 |
| WO | 88/10315 A1 | 12/1988 |

(Continued)

OTHER PUBLICATIONS

Lindenbach et al. Nature 2005; 436: 933-938 (Year: 2005).*

(Continued)

*Primary Examiner* — Angela M. Bertagna
(74) *Attorney, Agent, or Firm* — Michael J. Gilly; Adam M. Breier

(57) ABSTRACT

This disclosure provides oligomers, compositions, and kits for detecting and quantifying Hepatitis C virus (HCV), including different genotypes and variants thereof, and related methods and uses. In some embodiments, oligomers target the 5' untranslated region of HCV and are configured to provide substantially equivalent quantification of different genotypes and variants of HCV.

21 Claims, 43 Drawing Sheets

Specification includes a Sequence Listing.

(56) References Cited

FOREIGN PATENT DOCUMENTS

| WO | 89/002476 A1 | 3/1989 |
| WO | 93/13121 A1 | 7/1993 |
| WO | 95/32305 A1 | 11/1995 |
| WO | 88/01302 A1 | 2/1998 |
| WO | 2003/106714 A1 | 12/2003 |
| WO | 2014/136124 A1 | 9/2014 |

OTHER PUBLICATIONS

Gen Bank Accession No. AY163829 for Hepatitis C virus isolate N26 5' untranslated region, partial sequence, Aug. 25, 2006 [online], [retrieved on Jan. 15, 2020], retrieved from the Internet: <URL: www.ncbi.nlm.nih.gov/nuccore/AY163829> (Year: 2006).*

Gen Bank Accession No. AF165050 for Hepatitis C virus subtype 1b strain MD3-2, complete genome, Sep. 5, 2007 [online], [retrieved on Jan. 15, 2020], retrieved from the Internet: <URL: www.ncbi.nlm.nih.gov/nuccore/AF165050> (Year: 2007).*

Gen Bank Accession No. KP666629 for Hepatitis C virus clone 110069_5R_c6 polyprotein gene, partial cds, Mar. 11, 2015 [online], [retrieved on Jan. 15, 2020], retrieved from the Internet: <URL: www.ncbi.nlm.nih.gov/nuccore/KP666629> (Year: 2015).*

Weiner, M.P. & Slatko, B.E. BioTechniques 2008; 44: 701-704 (Year: 2008).*

GenBank Accession No. M62321 for Hepatitis C virus subtype 1a, complete genome, Sep. 5, 2007 [online], [retrieved on Jan. 15, 2020], retrieved from the Internet: <URL: www.ncbi.nlm.nih.gov/nuccore/M62321> (Year: 2007).*

Smith et al. Hepatology 2014; 59: 318-327 (Year: 2014).*

Li et al. A new class of homogeneous nucleic acid probes based on specific displacement hybridization. Nucleic Acids Research 2002; 30: e5 (Year: 2002).*

International Search Report for PCT/US2017/057178, dated Apr. 13, 2020, 13 pages.

PCT Written Opinion, International Application No. PCT/US2017/057178, dated Apr. 13, 2018.

Abraham et al., "Nucleobase analogs for degenerate hybridization devised through conformational pairing analysis," *BioTechniques* 2007, 43(5):617-24.

Chevaliez et al. "525 Hepatitis virus C RNA quantification by automated cobas ampliprep-cobas taqman 48 (CAP-CTM) real-time PCR assay. An evaluation of performance," *Journal of Hepatology*, 2006, vol. 44, Supplement 2, pp. S195-S196.

Cook et al. "Multiplex real-time reverse transcription-PCR assay for determination of hepatitis C virus genotypes," *Journal of Clinical Microbiology*, American Society for Microbiology, US, 2006, 44(11):4149-4156.

Irshad et al. "Novel single-step multiplex real-time polymerase chain reaction assay for simultaneous quantification of hepatitis virus A, B, C, and E in serum" *Journal of Gastroenterology and Hepatology*, 2013, 28(12):1869-1876.

Lee et al. "Detection of hepatitis C virus subtypes 6a, 6n, 6w and mixed infections using a modified chain reaction protocol," *Journal of the Formosan Medical Association, Excerpta Medica Asia*, Hong Kong, 2010, 110(12):762-767.

Liu et al., "Development and validation of a T& based linear amplification for genomic DNA," *BMC Genomics*, 2003, 4(19):1-11.

Majessi et al., "Advantages of 2'-O-methyl oligoribonucleotide probes for detecting RNA targets," *Nucleic Acids Res.*, 1988, 26(9):2224-2229.

Ohno et al. (New Hepatitis C Virus (HCV) Genotyping System That Allows of Identification of HCV Genotypes 1a, 1b, 2a, 2b, 3a, 3b, 4, 5a, and 6a *Journal of Clinical Microbiology*, 1997, 35(1):201-207.

Yang et al. "A reliable multiplex genotyping assay for HCV using a suspension bead array" *Microbial Biotechnology*, 2014, 8(1):1751-7915.

* cited by examiner

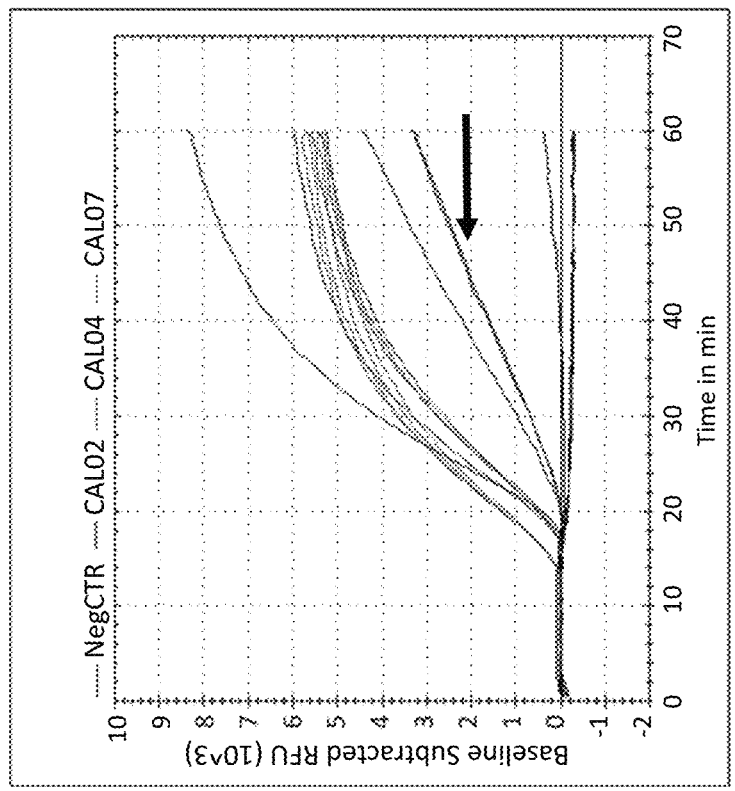
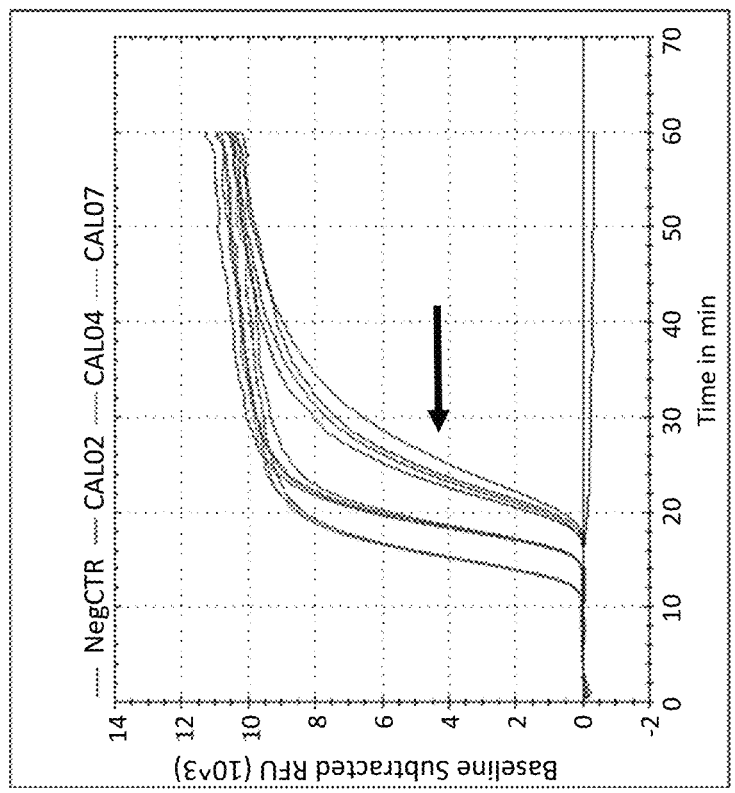
*Fig. 7A*
*Fig. 7B*

| subtype | mutate in what location(s) | frequency | # of mutations | IVT name | Accession ref | HCV ave log diff c/ml |
|---|---|---|---|---|---|---|
| 1b | NT7 | 1 | 5 | HCV-1a NT7 T-T-A | AF165050 | -1.84 |
| 5 | NT7 | 1 | 3 | HCV-5a NT7 T | AM502711 | -0.49 |
| 3a | NT7 | 2 | 4 | HCV-3a NT TTCA AJ621233 | AJ621233 | -0.44 |
| 7a | NT7 | 1 | 4 | HCV-5a NT7 C-C | EF108306 | -0.43 |
| 1 | T7/torch | 1 | 4 | HCV-1a T7 CTTC FJ696503 | FJ696503 | -2.06 |
| 3 | T7 | 1 | 3 | HCV-1a T7 CCT FJ696420 | FJ696420 | -1.62 |
| 6q | T7 | 1 | 4 | HCV-1A T7 C-T-A-A | EF424625 | -1.18 |
| 1 | T7/torch | 1 | 4 | HCV-1a T7 CTTG FJ696476 | FJ696476 | -0.60 |
| 2a | T7 | 1 | 3 | HCV-1a T7 T-C | D31604 | -0.55 |
| 3a | torch | 1 | 2 | HCV-1a tch CC AJ621232 | AJ621232 | -0.43 |
| 3 | Torch | 1 | 1 | HCV-1a Tch C | AJ621232 | -0.42 |
| 1b | torch | 1 | 3 | HCV-1a tch TGC GU451220 | GU451220 | 1.45 |
| 4a | T7/NT7/TCO | 1 | 9 | T7nT7TCO DQ295833 | DQ295833 | -0.51 |

Note: IVT mutants were tested at 1e4 c/ml.

Fig. 23

```
                              SEQUENCE LISTING

<160> NUMBER OF SEQ ID NOS: 275

<210> SEQ ID NO 1
<211> LENGTH: 9538
<212> TYPE: DNA
<213> ORGANISM: Hepatitis C virus 1b
<300> PUBLICATION INFORMATION:
<308> DATABASE ACCESSION NUMBER: AB016785
<309> DATABASE ENTRY DATE: 1999-09-28
<313> RELEVANT RESIDUES IN SEQ ID NO: (1)..(9538)

<400> SEQUENCE: 1
gccagccccc tgatgggggc gacactccac catagatcac tccctgtga ggaactactg      60 tcttcacgca gaaagcgtct agccatggcg ttagtatgag tgtcgtgcag cctccaggcc    120
cccccctccc gggagagcca tagtggtctg cggaaccggt gagtacaccg gaattgccag    180
gacgaccggg tcctttcttg gatcaatccc gctcaatgcc tggagatttg ggcgtgcccc    240
cgcgagactg ctagccgagt agtgttgggt cgcgaaaggc cttgtggtac tgcctgatag    300
ggtgcttgcg agtgccccgg gaggtctcgt agaccgtgca ccatgagcac aaatcctaaa    360
cctcaaagaa aaaccaaacg taacaccaac cgccgcccac aggacgtcaa gttcccgggc    420
ggtggtcaga tcgttggtgg agtttacctg ttgccgcgca ggggcccag gttgggtgtg    480 cgcgcgacta ggaagacttc cgagcggtca caacctcgtg gaaggcgaca acctatcccc    540
aaggctcgcc ggcccgaggg caggacctgg gctcagcccg ggtacccttg gcccctctac    600
ggcaatgagg gcctggggtg ggcagaatgg ctcctgtcac cccgtggctc tcggcccagt    660
tggggcccca cggaccccg gcgtaggtcg cgtaatttgg gtaaggtcat cgatacctc     720 acatgcggct tcgccgacct catggggtac attccgctcg tcggcgcccc cctgggggc     780 gctgccaggg ccctggcgca tggcgtccgg gttctggagg acggcgtgaa ctacgcaaca    840
gggaatctcc ccggttgctc tttctctatc ttcctcctgg ctttgctgtc ctgtttgacc    900
atcccagctt ccgcttatga agtgcgcaac gtgtccgggg tgtaccatgt cacgaacgac    960
tgctccaact caagtattgt gtatgggcg gcggacatga tcatgcacac cccgggtgc    1020 gtgccctgcg tccgggagaa caattcctct cgttgctggg tagcgcttac ccccacgctc    1080
gcggccagga acaggagcat ccccactacg acaatacgac gccatgtcga tttgctcgtt    1140
ggggcggctg ctttctgctc cgccatgtac gtgggggatc tctgcggatc tgtcttcctc    1200
gtctcccagc tgttcacttt ctcacctcgc cggtatgaga cagtacaaga ctgcaattgc    1260
tcgctctatc ccggccacgt atcaggtcat cgcatggctt gggatatgat gatgaactgg    1320
tcacctacag cagccttggt ggtatcgcag ctactccgga tcccacaagc cgtcgtggac    1380
atggtgacgg gggcccactg gggagtcctg gcgggccttg cctactattc catggtgggg    1440
aactgggcta aggtcttgat tgtgatgcta ctctttgccg gcgttgacgg gagaaccacc    1500
catgtaacgg gggcaaac aggccggacc accctgggca ttacgccat gtttgcgttt    1560 ggcccgcatc aaaagctcca actcattaac accaatgca gctggcacat caacaggacc    1620
gccctgaact gcaatgactc tctcaacact gggttcctag ctgcgctgtt ttacgcacgc    1680
aagttcaact cgtctggatg cccagagcgc atggccagct gccgccccat tgacaagttt    1740
gttcagggat ggggtcccat cactcatgct gtgcctgaca acttggacca gaggccttac    1800
```

```
tgctggcact acgcgcccca accgtgcggt atcatacccg cgtcacaggt gtgtggtcca   1860
gtgtattgtt tcacccccaag ccccgttgtg gtggggacga ccgaccgttt cggcgcccct   1920
acttacacct gggggggagaa tgagacggac gtgctgctcc ttaacaacac gcggccgccg   1980
caaggcaact ggttcggctg tacatggatg aatggcaccg ggttcgccaa gacgtgcgga   2040
ggcccccat gtaacatcgg gggggtcggc aacaacacct tgacctgccc tacggattgc    2100
ttccgcaagc accccgaggc cacttacacc aaatgcggct cggggccctg gttgacgcct   2160
aggtgcatgg ttgactaccc atacagactt tggcactacc cctgcactgt caacttcacc   2220
atctttaaag ttaggatgta tgtgggggt gtggagcaca ggctcaccgc cgcgtgcaat   2280
tggactcgag gagagcgttg tgacttggag gacagggaca gatcagaact tagcccgctg   2340
ctactgtcca cgacagagtg gcaggtgctg ccctgctcct tcaccaccct accggctttg   2400
tccaccggtc tgatccacct ccatcagaac atcgtggacg tgcaatacct gtatggcgtg   2460
gggtcagcgc tcgtctccat tgtcatcaag tgggagtata tcctgctgct cttccttctc   2520
ctcgcggacg cacgcgtctg cgcctgctta tggatgatgc tgctgatagc ccaggctgag   2580
gccgctttgg aaaacctggt ggtcctcaat gcggcgtccg tggccggagc gcatggcact   2640
ctctccttcc ttgtgttctt ctgtgctgcc tggtacatca agggtaggct ggtccctggg   2700
gcggcatatg cttttacgg cgtatgcccg ctgctcctgc tcctgctggc gttaccacca   2760
cgagcatacg ccatggaccg ggagatggct gcatcgtgcg ggggcgcggt tttcataggt   2820
ctagtactct tgaccttgtc gccacactac aaaccatttc tcgccaggct catatggtgg   2880
ttacaatact ttatcaccag ggccgaggcg ctagtacagg tgtggatccc cccctcaac    2940
gttcgggggg gccgcgatgc catcatcctc ctcacgtgcg cggtccatcc ggggctgatt   3000
tttgaagtca ccaaaatctt gctcgccata cttggtccgc tcacgatact ccaggctggc   3060
ctaaccagag tgccgtactt cgtgcgcgct caagggctca ttcgtgcgtg catgttggtg   3120
cggaaagtcg ctgggggcca ctatgttcaa atggctttca tgaagctggc cgcactgacg   3180
ggcacgtacg tttacaacca tcttactccg ctgcaggact gggcccacgc gggcctacga   3240
gaccttgcgg tggcagttga gcccgtcgtc ttctctgaca tggagaccaa gatcatcacc   3300
tgggggggcag acaccgcggc gtgtggggac atcatctcag gtctacccgt ctccgcccga   3360
agggggaggg agatacttct gggaccggcc gacagtttg aggggcgggg gtggcgactc   3420
cttgcccta tcacggccta ctcccaacag acgcggggcc ttcttggcag tatcatcacc   3480
agcctcacag gtcgggataa gaaccgggtc gaggggagg ttcaagtggt ctccaccgca   3540
acgcaatctt tcctggcgac ctgtatcaac ggcgtgtgct ggactgtcta ccatggtgcc   3600
ggctcaaaga ccctagccgg gccaaagggt ccaattaccc aaatgtacac caatgtagac   3660
caggacctcg tcggctggcc ggcgccctcc ggggcgcgtt ccctgacatc atgcacctgc   3720
ggcagttcgg acctttactt ggtcacgaga catgctgacg tcattccggt gcgccggcgg   3780
ggcgacagca gggggagcct actttccccc aggcctgtct cctacttgaa gggctcctcg   3840
ggtggtccgc tgctctgccc ctcagggcat actgtgggca tcttccgggc tgctgtgtgc   3900
acccggggg ttgcgaaggc ggtggacttt ataccggtag agtctatgga aaccactatg   3960
cggtctccgg tcttcacgga caactcatct ccccggccg taccgcagac attccaagtg   4020
gcccatctac acgcccccac cggcagcggt aagagcacta agtgccggc tgcatatgca   4080
gcccaagggt ataaggtact cgtcctgaac ccgtccgttg ccgccaccct aggttttggg   4140
```

```
gcgtatatgt ctaaggcaca tggtattgac cctaacatta gaactggggt aaggaccatc    4200
accacgggcg cccccatcac gtattccacc tatggcaagt tccttgccga cggtggttgt    4260
tctgggggcg cctatgacat cataatatgt gatgagtgcc actcaactga ctcgacttcc    4320
atcttgggca ttggcacagt cctggaccaa gcggagacgg ctggagcgcg gctcgtcgtg    4380
ctcgccaccg ctacgcctcc gggatcggtc accgtgccac accccaacat cgaggaggtg    4440
gccttgtcca atactggaga gatccccttc tatggcaaag ccatccccat cgagaccatc    4500 aagggggaa ggcatctcat cttctgtcac tccaagaaga aatgtgatga gctcgccgca    4560
aagctgtcgg cccttggaat caatgctgta gcgtactacc ggggcctgga tgtgtccgtc    4620
ataccgacaa gcggagacgc cgttgtcgtg gcaacagacg ctctcatgac gggctatacc    4680
ggcgactttg actcggtgac cgactgcaac acgtgtgtca cccagacagt cgacttcagc    4740
ttggacccta ccttcaccat cgaaacgaca accgtgcctc aagactcggt gtcgcgctcg    4800
cagcggcgag gcaggactgg tagggggcaga ggggggcatat acaggtttgt gattccaggg    4860
gagcggccct caggcatgtt cgattcttcg gtcctgtgtg agtgttatga cgcgggctgc    4920
gcttggtatg agctcacgcc cgccgagacc acggtcaggt tgcgggctta cctgaataca    4980
ccagggttgc ccgtctgcca ggaccacctg gagttctggg agggcgtctt cacaggcctc    5040
acccacatag atgcccactt cttgtcccag actaaacagg caggagacaa cttcccctac    5100
ctggtagcat accaggctac agtgtgcgcc agggcccagg ctccacctcc atcgtgggat    5160
caaatgtgga gtgtctcat acggctaaag ccgacgctac acgggccaac acccctgttg    5220
tataggctag gggccgttca aaacgaggtc accctcacac accccataac caaatacatc    5280
atgacatgca tgtcggctga cctagaggtc gtcactagca cttgggtgct ggtgggcggg    5340
gtcctcgcag ccctggccgc gtactgccta acaacgggca gcgtggtcat tgtgggcagg    5400
atcattttgt ctgggaggcc ggctatcatc cccgacaggg aagttctcta ccgggagttc    5460
gatgaaatgt aagagtgcgc ctcacacctc ccttacatcg aacagggaat acagctcgcc    5520
gagcaattca gcagaaggc gctcgggttg ctgcaaacgg ccaccaagca gcggaggct    5580 gccgcccccg tggtggagtc caagtggcgt accctagagg ccttctgggc gaagcacatg    5640
tggaatttca tcagcgggat acagtaccta gcaggcttgt ccactctgcc tgggaatccc    5700
gcgatagcat cattgatggc attcacagcc tctatcacca gcccgctcac catccaacat    5760
accctcctgt ttaacatctt ggggggggtgg gtggccgccc aacccgcccc cccagcgct    5820 gcttcagctt tcgtaggcgc tggcattgcc ggcgcggctg ttggtagcat aggtgttggg    5880
aaggtgcttg tggacgtttt ggcgggttat ggagcagggg tggcaggcgc tctcgtggcc    5940
tttaaggtca tgagcggtga agtgcctcc actgaggacc tggtcaactt actccttgcc    6000
atcctctctc ctggtgccct ggtcgtcgga gttgtgtgcg cggcaatact gcgtcggcat    6060
gtgggcccag gggaggggc tgtgcagtgg gtgaaccggt tgatagcgtt cgcttcgcgg    6120
ggtaaccatg tttcccccac gcactatgtg cccgagagcc acgctgcagc gcgtgtcacc    6180
cagattctct ccagccttac catcactcag ctgttgaaga ggctccacca gtggattaat    6240
gaggactgct ccacaccatg ctccggctcg gtgctcaggg atgtttggga ctggatatgc    6300
acggtgttga ccgacttcaa gacctggctc cagtccaagc tcctgccgcg gttgccagga    6360
gttcctttcc tttcatgcca acgtgggtac aggggagtct ggcgagggga tggcatcatg    6420
cacaccacct gcccatgtgg agcacaaatc actggacatg tcaagaacgg ctccatgagg    6480
attgttgggc caaaaacctg tagcaacacg tggcatggaa cattccccat caacacatac    6540
```

```
accacgggcc cctgcacacc ctccccagcg ccaaactatt ccaaggcgtt gtggcgggtg   6600
gctgctgagg agtacgtgga ggtcacgcgg gtggggatt tccattacgt gacgggcatg   6660
accactgaca acgtaaaatg cccatgccag gttccggccc ccgaattctt tacagaactg   6720
gacggggtgc ggctacacag gtacgctccg gcgtgcaaac ctctcctacg ggatgaggtc   6780
acactccagg tcgggctcaa ccaatacccg gtcgggtcac agctcccatg tgagcccgaa   6840
ccggatgtaa cagtgctcac ctccatgctc accgaccct cccacatcac agcagagacg   6900
gctaagcgta ggctggctag ggggtctggg gtctccctt ccttggccag ctcttcggct   6960
agccagttgt ctgcgccttc cttgaaggcg acatgcacta cccatcatga ctccccagat   7020
gctgacctca ttgaggccaa cctcctgtgg cggcaggaga tgggcgggaa catcacccgc   7080
gtggagtcag agaatagggt agtaattcta gactcttttg acccgcttcg agcggaagag   7140
gatgagaggg aaatatccgt tgcggcggat atcttgcgga aaaccaagaa atttccctca   7200
gcgatgccca tatgggcacg cccggactac aacccaccac tgctggagtc ttggaagaac   7260
ccggactacg tccctccggt ggtacacggg tgcccattgt cacctaccag ggcccctcca   7320
ataccgcctc cacggaggaa gaggacagtt gtcttgacag aatccgccgt gtcttctgcc   7380
ttggcggagc ttgctacaaa gaccttcggc agctccgaat cgtcggccgt cgacagcggc   7440
acagcgaccg ccccccccgg ccagtcctct gatgacggtg gtacgggatc cgacgttgag   7500
tcgtactcct ccatgccccc ccttgagggg gagccggggg accccgatct cagcgacggg   7560
tcttggtcta ctgtaagcga ggaggctagc gaggacgtcg tctgctgctc aatgtcctac   7620
acgtggacgg gtgccctgat cacgccatgc gccgcggagg agagcaagct gcccatcaat   7680
gcgctgagca actcttttgct gcgtcaccac aacatggtct atgccacaac atcccgcagc   7740
gcaagccagc ggcagaagaa ggtcacctt gacagactgc aagtcctgga cgaccactac   7800
cgggacgtgc tcaaggagat gaaggcgaag gcgtccacag ttaaggctaa gcttctatcc   7860
gtagaagaag cctgcaagct gacgccccca cattcggcca gatccaagtt tggctatggg   7920
gcaaaggacg tccggaacct gtccagcaag gccgttaacc acatccactc cgtgtggaag   7980
gacttgctgg aagacgatga acaccaatc aataccacca tcatggcaaa aaatgaggtc   8040
ttctgtgttc aaccagaaaa aggaggccgc aagccagctc gccttatcgt attcccagat   8100
ttaggggtcc gcgtgtgcga gaaaatggcc ctctacgacg tggtctccac tcttcctcag   8160
gccgtgatgg gctcctcata cgggtttcag tactctcctg gacagcgggt cgagttcttg   8220
gtgaatgcct ggaaatcaaa gaagaacccc atgggcttcg catatgacgc ccgctgtttt   8280
gactcaacgg tcaccgagaa tgatatccgt gttgaggagt caatttacca atgttgtgac   8340
ttagcccccg aggccagaca ggccataagg tcgctcacag agcggctta catcggggc   8400 cccctgacta actcaaaagg gcagaactgc ggttatcgcc ggtgccgcgc cagcggcgtg   8460
ctgacgacca ggtgcggtaa taccttaca tgtcacttga aggcctctgc agcctgtcga   8520
gctgcaaagc tccaggattg cacgatgctc gtgtgcggag atgaccttgt cgttatctgt   8580
gaaagcgcgg gaacccagga ggatgcggcg agcctacgag tcttcacgga ggctatgact   8640
aggtattccg cccccccgg ggacccgccc caaccggagt acgacttgga gctaataaca   8700
tcatgctcct ccaacgtgtc ggtcgcgcac gatgcatctg gcaaacgggt atactacctc   8760 accgcgacc ccaccacccc ccttgcgcgg gctgcgtggg agacagctag gcacactcca   8820
gtcaactcct ggctaggcaa cattatcatg tatgcgccca cccttatgggc aagaatgatt   8880
```

```
ctgatgactc acttcttctc catccttcta gctcaggagc aacttgaaaa agccctagat    8940
tgtcagatct acggggccac ttactccatt gaaccacttg acctacctca gatcattcag    9000
cgactccatg gtcttagcgc attttcactc catagttact ctccaggtga gatcaatagg    9060
gtggcttcat gcctcaggaa acttgggta ccgcccttgc gagtctggag acatcgggcc     9120
agaagtgtcc gcgctaagct actgtcccaa ggggggaggg ccgccacttg tgcaaatac     9180 ctcttcaatt gggcagtaag gaccaagctc aaactcactc caattccggc tgcgtcccag    9240
ttggacttgt ccggctggtt cgttgctggt tacagcgggg gagacatata tcacagcctg    9300
tctcgtgccc gacccgctg gttcatgtgg tgcctactcc tactctctgt aggggtaggc     9360
atctacttgc tccccaaccg gtgaacgggg agctaaacac tccaggccaa taggccgtcc    9420
tgtttttttt ttttttttt ggtggctcca tcttagccct agtcacggct agctgtgaaa     9480
ggtccgtgag ccgcatgact gcagagagtg ctgatactgg cctctctgca gatcatgt     9538
```

```
<210> SEQ ID NO 2
<211> LENGTH: 27
<212> TYPE: DNA
<213> ORGANISM: Hepatitis C virus
<220> FEATURE:
<221> NAME/KEY: misc_feature
<222> LOCATION: (1)..(27)
<223> OTHER INFORMATION: Amplification oligomer 52-78-1

<400> SEQUENCE: 2
ggaacttctg tcttcacgcg gaaagcg                                        27

<210> SEQ ID NO 3
<211> LENGTH: 27
<212> TYPE: DNA
<213> ORGANISM: Hepatitis C virus
<220> FEATURE:
<221> NAME/KEY: misc_feature
<222> LOCATION: (1)..(27)
<223> OTHER INFORMATION: Amplification oligomer 52-78-2

<400> SEQUENCE: 3
ggaattactg ttttaacgca gaaagcg                                        27

<210> SEQ ID NO 4
<211> LENGTH: 67
<212> TYPE: DNA
<213> ORGANISM: Hepatitis C virus
<220> FEATURE:
<221> NAME/KEY: misc_feature
<222> LOCATION: (1)..(67)
<223> OTHER INFORMATION: T7 amplification oligomer 80-119

<400> SEQUENCE: 4
aatttaatac gactcactat agggagacct ggaggctgca cgacactcat actaacgcca    60
tggctag                                                              67

<210> SEQ ID NO 5
<211> LENGTH: 54
<212> TYPE: DNA
<213> ORGANISM: Hepatitis C virus
<220> FEATURE:
<221> NAME/KEY: misc_feature
<222> LOCATION: (1)..(54)
<223> OTHER INFORMATION: T7 amplification oligomer 93-119

<400> SEQUENCE: 5
aatttaatac gactcactat agggagacct ggaggctgca cgacactcat acta          54
```

```
<210> SEQ ID NO 6
<211> LENGTH: 40
<212> TYPE: DNA
<213> ORGANISM: Hepatitis C virus
<220> FEATURE:
<221> NAME/KEY: misc_feature
<222> LOCATION: (1)..(40)
<223> OTHER INFORMATION: Amplification oligomer 80-119

<400> SEQUENCE: 6
cctggaggct gcacgacact catactaacg ccatggctag                              40

<210> SEQ ID NO 7
<211> LENGTH: 27
<212> TYPE: DNA
<213> ORGANISM: Hepatitis C virus
<220> FEATURE:
<221> NAME/KEY: misc_feature
<222> LOCATION: (1)..(27)
<223> OTHER INFORMATION: Amplification oligomer 93-119

<400> SEQUENCE: 7
cctggaggct gcacgacact catacta                                            27

<210> SEQ ID NO 8
<211> LENGTH: 18
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(18)
<223> OTHER INFORMATION: Exemplary T7 promoter

<400> SEQUENCE: 8
taatacgact cactatag                                                      18

<210> SEQ ID NO 9
<211> LENGTH: 23
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(23)
<223> OTHER INFORMATION: Sequence comprising T7 promoter

<400> SEQUENCE: 9
taatacgact cactataggg aga                                                23

<210> SEQ ID NO 10
<211> LENGTH: 22
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(22)
<223> OTHER INFORMATION: Sequence comprising T7 promoter

<400> SEQUENCE: 10
aatttaatac gactcactat ag                                                 22

<210> SEQ ID NO 11
```

```
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: Sequence comprising T7 promoter

<400> SEQUENCE: 11
aatttaatac gactcactat agggaga                                              27

<210> SEQ ID NO 12
<211> LENGTH: 21
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(21)
<223> OTHER INFORMATION: Molecular torch hybridization probe
<220> FEATURE:
<221> NAME/KEY: misc_feature
<222> LOCATION: (16)..(17)
<223> OTHER INFORMATION: Non-nucleotide C9 linker located between base
      positions 16-17

<400> SEQUENCE: 12
uagccauggc guuaguggcu a                                                    21

<210> SEQ ID NO 13
<211> LENGTH: 16
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(16)
<223> OTHER INFORMATION: Probe oligomer 81-96 target-hybridizing
      sequence

<400> SEQUENCE: 13
uagccauggc guuagu                                                          16

<210> SEQ ID NO 14
<211> LENGTH: 10
<212> TYPE: DNA
<213> ORGANISM: Hepatitis C virus
<220> FEATURE:
<221> NAME/KEY: misc_feature
<222> LOCATION: (1)..(10)
<223> OTHER INFORMATION: HCV 1b subsequence, posiitons 86-95

<400> SEQUENCE: 14
uggcguuagu                                                                 10

<210> SEQ ID NO 15
<211> LENGTH: 57
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(57)
<223> OTHER INFORMATION: Control capture oligomer
<220> FEATURE:
<221> NAME/KEY: misc_feature
```

```
<222> LOCATION: (25)..(57)
<223> OTHER INFORMATION: Immobilized probe-binding region: Tail

<400> SEQUENCE: 15
cguucacuau uggucucugc auucutttaaa aaaaaaaaaa aaaaaaaaaa aaaaaaa        57

<210> SEQ ID NO 16
<211> LENGTH: 52
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(52)
<223> OTHER INFORMATION: Capture oligomer 0297
<220> FEATURE:
<221> NAME/KEY: misc_feature
<222> LOCATION: (20)..(52)
<223> OTHER INFORMATION: Immobilized probe-binding region: Tail

<400> SEQUENCE: 16
gggcacucgc aagcacccut ttaaaaaaaa aaaaaaaaaa aaaaaaaaaa aa        52

<210> SEQ ID NO 17
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(51)
<223> OTHER INFORMATION: Capture oligomer 0327b
<220> FEATURE:
<221> NAME/KEY: misc_feature
<222> LOCATION: (19)..(51)
<223> OTHER INFORMATION: Immobilized probe-binding region: Tail

<400> SEQUENCE: 17
cauggugcac ggucuacgtt taaaaaaaaa aaaaaaaaa aaaaaaaaaa a        51

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(19)
<223> OTHER INFORMATION: Control non-T7 amplification oligomer

<400> SEQUENCE: 18
gattatatag gacgacaag        19

<210> SEQ ID NO 19
<211> LENGTH: 49
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(49)
<223> OTHER INFORMATION: Control T7 amplification oligomer

<400> SEQUENCE: 19
aatttaatac gactcactat agggagagat gattgacttg tgattccgc        49
```

<210> SEQ ID NO 20
<211> LENGTH: 23
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(23)
<223> OTHER INFORMATION: Molecular torch hybridization probe
<220> FEATURE:
<221> NAME/KEY: misc_feature
<222> LOCATION: (5)..(6)
<223> OTHER INFORMATION: Non-nucleotide C9 linker located between base
      positions 5-6

<400> SEQUENCE: 20
gcauggugcg aauugggaca ugc                                        23

<210> SEQ ID NO 21
<211> LENGTH: 33
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(33)
<223> OTHER INFORMATION: T3A30 segment of capture oligomer

<400> SEQUENCE: 21
tttaaaaaaa aaaaaaaaaa aaaaaaaaaa aaa                             33

<210> SEQ ID NO 22
<211> LENGTH: 30
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(30)
<223> OTHER INFORMATION: A30 segment of capture oligomer

<400> SEQUENCE: 22
aaaaaaaaaa aaaaaaaaaa aaaaaaaaaa                                 30

<210> SEQ ID NO 23
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 52-78-1 subsequence

<400> SEQUENCE: 23
gcggaaagcg                                                       10

<210> SEQ ID NO 24
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)

```
<223> OTHER INFORMATION: Amplification oligomer 52-78-1 subsequence

<400> SEQUENCE: 24
ttcacgcgga                                                                10

<210> SEQ ID NO 25
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 52-78-1 subsequence

<400> SEQUENCE: 25
ctgtcttcac                                                                10

<210> SEQ ID NO 26
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 52-78-1 subsequence

<400> SEQUENCE: 26
aacttctgtc                                                                10

<210> SEQ ID NO 27
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 52-78-1 subsequence

<400> SEQUENCE: 27
ggaacttctg                                                                10

<210> SEQ ID NO 28
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 52-78-2 subsequence

<400> SEQUENCE: 28
gcagaaagcg                                                                10

<210> SEQ ID NO 29
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
```

```
<222> LOCATION: (1)..(10)
<223> OTHER INFORMATION: Amplification oligomer 52-78-2 subsequence

<400> SEQUENCE: 29
ttaacgcaga                                                           10

<210> SEQ ID NO 30
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 52-78-2 subsequence

<400> SEQUENCE: 30
ctgttttaac                                                           10

<210> SEQ ID NO 31
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 52-78-2 subsequence

<400> SEQUENCE: 31
aattactgtt                                                           10

<210> SEQ ID NO 32
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 52-78-2 subsequence

<400> SEQUENCE: 32
ggaattactg                                                           10

<210> SEQ ID NO 33
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 93-119 subsequence

<400> SEQUENCE: 33
actcatacta                                                           10

<210> SEQ ID NO 34
<211> LENGTH: 10
<212> TYPE: DNA
<213> ORGANISM: Artificial Sequence
<220> FEATURE:
<223> OTHER INFORMATION: Synthetic Oligomer
<220> FEATURE:
```

```
<221> NAME/KEY: misc_feature
<222> LOCATION: (1)..(10)
<223> OTHER INFORMATION: Amplification oligomer 93-119 subsequence

<400> SEQUENCE: 34
acgacactca                                                                  10

<210> SEQ ID NO 35
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 93-119 subsequence

<400> SEQUENCE: 35
gctgcacgac                                                                  10

<210> SEQ ID NO 36
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 93-119 subsequence

<400> SEQUENCE: 36
tggaggctgc                                                                  10

<210> SEQ ID NO 37
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 93-119 subsequence

<400> SEQUENCE: 37
cctggaggct                                                                  10

<210> SEQ ID NO 38
<211> LENGTH: 13
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(13)
<223> OTHER INFORMATION: Amplification oligomer 80-119 subsequence

<400> SEQUENCE: 38
acgccatggc tag                                                              13

<210> SEQ ID NO 39
<211> LENGTH: 10
<212> TYPE: DNA
<213> ORGANISM: Artificial Sequence
<220> FEATURE:
<223> OTHER INFORMATION: Synthetic Oligomer
```

```
<220> FEATURE:
<221> NAME/KEY: misc_feature
<222> LOCATION: (1)..(10)
<223> OTHER INFORMATION: Amplification oligomer 80-119 subsequence

<400> SEQUENCE: 39
ccatggctag                                                          10

<210> SEQ ID NO 40
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 80-119 subsequence

<400> SEQUENCE: 40
taacgccatg                                                          10

<210> SEQ ID NO 41
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Amplification oligomer 80-119 subsequence

<400> SEQUENCE: 41
tactaacgcc                                                          10

<210> SEQ ID NO 42
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: T7 amplification oligomer 93-119 subsequence

<400> SEQUENCE: 42
ggagacctgg                                                          10

<210> SEQ ID NO 43
<211> LENGTH: 13
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(13)
<223> OTHER INFORMATION: T7 amplification oligomer 93-119 subsequence

<400> SEQUENCE: 43
tagggagacc tgg                                                      13

<210> SEQ ID NO 44
<211> LENGTH: 28
<212> TYPE: DNA
<213> ORGANISM: Artificial Sequence
<220> FEATURE:
```

```
<223> OTHER INFORMATION: Synthetic Oligomer
<220> FEATURE:
<221> NAME/KEY: misc_feature
<222> LOCATION: (1)..(28)
<223> OTHER INFORMATION: T7 amplification oligomer 93-119 subsequence

<400> SEQUENCE: 44
taatacgact cactataggg agacctgg                                              28

<210> SEQ ID NO 45
<211> LENGTH: 15
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(15)
<223> OTHER INFORMATION: T7 amplification oligomer 93-119 subsequence

<400> SEQUENCE: 45
ggagacctgg aggct                                                           15

<210> SEQ ID NO 46
<211> LENGTH: 18
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(18)
<223> OTHER INFORMATION: T7 amplification oligomer 93-119 subsequence

<400> SEQUENCE: 46
tagggagacc tggaggct                                                        18

<210> SEQ ID NO 47
<211> LENGTH: 33
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(33)
<223> OTHER INFORMATION: T7 amplification oligomer 93-119 subsequence

<400> SEQUENCE: 47
taatacgact cactataggg agacctggag gct                                       33

<210> SEQ ID NO 48
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Probe oligomer 81-96 subsequence

<400> SEQUENCE: 48
uuaguggcua                                                                 10

<210> SEQ ID NO 49
<211> LENGTH: 10
<212> TYPE: DNA
<213> ORGANISM: Artificial Sequence
```

```
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Probe oligomer 81-96 subsequence
<220> FEATURE:
<221> NAME/KEY: misc_feature
<222> LOCATION: (5)..(6)
<223> OTHER INFORMATION: Non-nucleotide C9 linker located between base
      positions 5-6

<400> SEQUENCE: 49
uuaguggcua                                                                10

<210> SEQ ID NO 50
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Probe oligomer 81-96 subsequence

<400> SEQUENCE: 50
uggcguuagu                                                                10

<210> SEQ ID NO 51
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Probe oligomer 81-96 subsequence

<400> SEQUENCE: 51
agccauggcg                                                                10

<210> SEQ ID NO 52
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Probe oligomer 81-96 subsequence

<400> SEQUENCE: 52
uagccauggc                                                                10

<210> SEQ ID NO 53
<211> LENGTH: 24
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(24)
<223> OTHER INFORMATION: Control capture oligomer target-hybridizing
      sequence

<400> SEQUENCE: 53
```

```
cguucacuau uggucucugc auuc                                            24

<210> SEQ ID NO 54
<211> LENGTH: 19
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(19)
<223> OTHER INFORMATION: Capture oligomer 0297 target-hybridizing
      sequence

<400> SEQUENCE: 54
gggcacucgc aagcacccu                                                  19

<210> SEQ ID NO 55
<211> LENGTH: 18
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(18)
<223> OTHER INFORMATION: Capture oligomer 0327b target-hybridizing
      sequence

<400> SEQUENCE: 55
cauggugcac ggucuacg                                                   18

<210> SEQ ID NO 56
<211> LENGTH: 22
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(22)
<223> OTHER INFORMATION: Control amplification oligomer target-
      hybridizing sequence

<400> SEQUENCE: 56
gatgattgac ttgtgattcc gc                                              22

<210> SEQ ID NO 57
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Capture oligomer 0297 subsequence

<400> SEQUENCE: 57
caagcacccu                                                            10

<210> SEQ ID NO 58
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
```

```
<223> OTHER INFORMATION: Capture oligomer 0297 subsequence

<400> SEQUENCE: 58
acucgcaagc                                                            10

<210> SEQ ID NO 59
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Capture oligomer 0297 subsequence

<400> SEQUENCE: 59
gggcacucgc                                                            10

<210> SEQ ID NO 60
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Capture oligomer 0327b subsequence

<400> SEQUENCE: 60
acggucuacg                                                            10

<210> SEQ ID NO 61
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Capture oligomer 0327b subsequence

<400> SEQUENCE: 61
uggugcacgg                                                            10

<210> SEQ ID NO 62
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(10)
<223> OTHER INFORMATION: Capture oligomer 0327b subsequence

<400> SEQUENCE: 62
cauggugcac                                                            10

<210> SEQ ID NO 63
<211> LENGTH: 926
<212> TYPE: DNA
<213> ORGANISM: Hepatitis C virus
<220> FEATURE:
<221> NAME/KEY: misc_feature
<222> LOCATION: (1)..(926)
<223> OTHER INFORMATION: HCV 1a transcript 926b
```

<400> SEQUENCE: 63

```
gggcgaauug gagcuccacc gcggugggcgg ccgcucuaga acuaguggau cccccgggcu    60
gcaggaauuc gcccuuucac uccccuguga ggaacuacug ucuucacgca gaaagcgucu   120
agccauggcg uuaguaugag ugucgugcag ccuccaggac cccccucccc gggagagcca   180
uaguggucug cggaaccggu gaguacaccg gaauugccag gacgaccggg uccuuucuug   240
gaucaacccg cucaaugccu ggagauuugg gcgugccccc gcaagacugc uagccgagua   300
uguugggguc gcgaaaggcc uugugguacu gccugauagg gugcuugcga gugccccggg   360
aggcucgua daccgugcac caugagcacg aauccuaaac cucaaaaaaa aaacaaacgu    420
aacaccaacc gucgcccaca ggacgucaag uucccgggug gcggucagau cguuggugga   480
guuuacuugu gccgcgcag gggcccuaga uuggguuguc gcgcgacgag aaagacuucc    540
gagcggucgc aaccucgagg uagacgucag ccuauccccca ggcucgucg gcccgagggc   600
aggaccuggg cucagcccgg guacccuugg ccccucuaug gcaaugaggg cugcggguggg   660
gcgggauggc uccugucucc cguggcucu cggccuagcu ggggcccac agaccccgg      720
cguaggucgc gcaauuuggg uaaggucauc gauacccuua cgucggcuu cgccgaccuc    780
augggguaca uaccgcucgu cggcgccccu cuuggaggcg cugccagggc ccuggcgcau    840
ggcguccggg uucuggaaga cggcgugaac uaugcaacag gaaccuucc ugguugcucu    900
uucucuaucu uccgaauucg auauca                                         926
```

```
<210> SEQ ID NO 64
<211> LENGTH: 998
<212> TYPE: DNA
<213> ORGANISM: Hepatitis C virus
<220> FEATURE:
<221> NAME/KEY: misc_feature
<222> LOCATION: (1)..(998)
<223> OTHER INFORMATION: HCV2b transcript 998b
```

<400> SEQUENCE: 64

```
gggcgaauug gguaccgggc ccccccucga ggucgacggu aucgauaagc uugauaucga    60
auuccugcag cccggggggau ccacuaguaa cggccgccag ugugcuggaa uucgcccuuu   120
cacuccccug ugaggaacua cugucuucac gcagaaagcg cuagccaug gcguuaguau    180
gagugucgua cagccuccag gccccccccu cccgggagag ccauaguggu cugcggaacc   240
ggugaguaca ccggaauugc ggaaagacu gggguccuuuc uuggauaaac ccacucuaug   300
uccggucauu ugggcgugcc cccgcaagac ugcuagccua guagcguugg guugcgaacg   360
gccuuguggu acugccugau agggugcuug cgagugcccc gggaggucuc guagaccgug   420
caucaugagc acaaauucua aaccucaaag aaaaaccaaa agaaacacaa accgccgccc   480
acaggacguc aaguucccgg guggcggcca gaucguuggc ggaguuuacu gcugccgcg   540
cagggggcccc agguugggug ugcgcgcgac aaggaagacu ucugagcgau cccagccgcg   600
ugggagacgc cagcccauc cgaaagaucg gcgcuccacc ggcaaguccu ggggaaagcc   660
aggauauccu uggccucugu augggaaacga gggcuguggc ugggcagguu ggcuccuguc   720
cccccgcggg ucucguccua cuuggggccc cacugacccc cggcauagau cacgcaaaucu   780
ggcagagguc aucgauacca uuacguguggg uuuugccgac cucaugggggu acauccccugu   840
cguuggcgcc ccagcggag gcgucgccag agcuugggca cacgguguua ggguccugga   900
agacgggaua aauuaugcaa cagggaaccu accugguugc ucuuuuucua ucuuuuugcu    960
```
ugcuaagggc gaauucugca gauauccauc acacuggc                                998

<210> SEQ ID NO 65
<211> LENGTH: 861
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(861)
<223> OTHER INFORMATION: pBluescript II SK (+) HCV 3a V1 861b

<400> SEQUENCE: 65
gggcgaauug gguaccgggc cccccucga ggucgacggu aucgauaagc uugugaggaa        60
cuucugucuu cacgcggaaa gcgccuagcc auggcguuag uacgaguguc gugcagccuc      120
caggcccccc ccucccggga gagccauagu ggucugcgga accggugagu acaccggaau      180
cgcuggggug accggguccu uucuuggagc aacccgcuca auacccagaa auuugggcgu      240
gcccccgcga gaucacuagc cgaguagugc ugucgcgca aggccuugu gguacugccu        300 gauagggugc uugcgagugc cccgggaggu cucguagacc augcaacaug agcacacuuc      360
cuaaaccuca agaaaaacc aaagaaaca ccauccgucg cccacaggac guuaaguucc        420
cgggcggcgg acagaucguu gguggaguau acguuugcc gcgcagggc ccacgauugg        480 augugcgcgc gacgcguaaa acuucugaac ggucgcagcc ucgcggacga cgacagccua      540 ucccaaggc acgucggagu gaaggccggu ccugggcuca gcccgggu ac ccuuggcccc     600 ucuauggu aa cgagggcugc ggguggggag gauggcuccu guccacgu ggcuccguc       660 caucuugggg cccaaaacgac cccggcgac ggucccacaa cuuggguaaa gucaucgaua      720
cccuuacgua cggauucgcc gaccucaugg gguacauccc gcucguggc gcucccguag      780 gaggcgucgc aagagcccuc gcacauggcg ugagggcccu ugaggacggg auaaauuucg      840
caacagggaa cuugcggaau u                                              861

<210> SEQ ID NO 66
<211> LENGTH: 345
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(345)
<223> OTHER INFORMATION: pBluescript II SK (+) HCV 3a V2 351b

<400> SEQUENCE: 66 auugggua cc gggcccccc c ucgaggucga cgguaucgau aagcuuguga ggaacuucug      60
ucuucacgcg gaaagcgccu agccauggcg uuaguacgag ugucgugcag ccuccaggcc      120 cccccucc c gggagagcca uaguggucug cggaaccggu gaguacaccg gaaucgcugg      180
ggugaccggg uccuuucuug gagcaacccg cucaauaccc agaaauuugg gcgugccccc      240
gcgagaucac uagccgagua gugcugucgu cgcgaaaggcc uuggguacu gccugauagg      300 gugcuugcga gucccccggg aggucucgua gaccaugcag gaauu                    345

<210> SEQ ID NO 67
<211> LENGTH: 325
<212> TYPE: DNA
<213> ORGANISM: Artificial Sequence
<220> FEATURE:
<223> OTHER INFORMATION: Synthetic Oligomer

```
<220> FEATURE:
<221> NAME/KEY: misc_feature
<222> LOCATION: (1)..(325)
<223> OTHER INFORMATION: pBluescript II SK (+) HCV 3a V3 325b

<400> SEQUENCE: 67
gggcgaauug guaccucac uccccuguga ggaacuucug ucuucacgcg gaaagcgccu    60
agccauggcg uuaguacgag ugucgugcag ccuccaggcc cccccuccc gggagagcca   120 uaguggucug cggaaccggu gaguacaccg gaaucgcugg ggugaccggg uccuuucuug  180
gagcaacccg cucaauaccc agaaauuugg gcgugccccc gcgagaucac uagccgagua  240
gugcugaguc gcgaaaggcc uuguggaucu gccugauagg gugcuugcga gugcccggg   300 aggucucgua gaccgugcag gaauu                                       325

<210> SEQ ID NO 68
<211> LENGTH: 422
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(422)
<223> OTHER INFORMATION: TOPO HCV 3b 422b

<400> SEQUENCE: 68
gaauacucaa gcuaugcauc aagcuuggua ccgagcucgg auccacuagu aacggccgcc    60
agugugcugg aauucgcccu uucacucccc ugugaggaac uacugucuuc acgcggaaag   120
cgucuagcca uggcguuagu acgagugucg ugcagccucc aggcccccccc cucccgggag   180 agccauagug gucugcggaa ccggugagua caccggaauc gccggaugac cgggucccuu    240
ucuuggaaca acccgcucaa ugccuggaaa uuugggcgug ccccgcgag aucacuagcc    300 gaguagguu gggucgcgaa aggccuugug uacugccug auaggugcu ugcgagugcc    360 ccgggagguc ucguagaccg ugcaaagggc gaauucugca gauauccauc acacuggcgg   420
cc                                                                 422

<210> SEQ ID NO 69
<211> LENGTH: 325
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(325)
<223> OTHER INFORMATION: pBluescript II SK (+) HCV 3b 325b

<400> SEQUENCE: 69
gggcgaauug guaccucac uccccuguga ggaacuucug ucuucacgcg gaaagcgucu    60
agccauggcg uuaguacgag ugucgugcag ccuccaggcc cccccuccc gggagagcca   120 uaguggucug cggaaccggu gaguacaccg gaaucgccgg gaugaccggg uccuuucuug  180
gaacaacccg cucaaugccu ggaaauuugg gcgugccccc gcgagaucac uagccgagua  240 guguggguc gcgaaaggcc uugugguacu gccugauagg gugcuugcga gugcccggg   300 aggucucgua gaccgugcag gaauu                                       325

<210> SEQ ID NO 70
<211> LENGTH: 422
<212> TYPE: DNA
```

```
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(422)
<223> OTHER INFORMATION: TOPO HCV 4h 422b

<400> SEQUENCE: 70
gaauacucaa gcuaugcauc aagcuuggua ccgagcucgg auccacuagu aacggccgcc      60
agugugcugg aauucgcccu uucacucccc ugugaggaac uacugucuuc acgcagaaag     120
cgucuagcca uggcguuagu augagucuug ugcagccucc aggauccccc ucccgggag      180 agccauagug gucugcggaa ccggugagua caccggaauc gccgggauga ccgguccuu      240 ucuuggauua acccgcucaa ugcccggaaa uuugggcgug ccccccgcgag acugcuagcc    300 gaguaguguu gggucgcgaa aggccuugug guacugccug auagggugcu ugcgagugcc    360 ccggggagguc ucguagaccg ugcaaagggc gaauucugca gauauccauc acacuggcgg    420
cc                                                                    422

<210> SEQ ID NO 71
<211> LENGTH: 325
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(325)
<223> OTHER INFORMATION: pBluescript II SK (+) HCV 4h 325b

<400> SEQUENCE: 71
gggcgaauug gguaccucac ucccuguga ggaacuacug ucuucacgca gaaagcgucu      60
agccauggcg uuaguaugag uguugugcag ccuccaggau ccccccuccc gggagagcca    120
uaguggucug cggaaccggu gaguacaccg gaaucgccgg gaugaccggg uccuuucuug    180
gauuaacccg cucaaugccc ggaaauuugg gcgugccccc gcgagacugc uagccgagua    240
guguuggguc gcgaaaggcc uugugguacu gccugauagg gugcuugcga gugccccggg    300
aggucucgua gaccgugcag gaauu                                           325

<210> SEQ ID NO 72
<211> LENGTH: 435
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(435)
<223> OTHER INFORMATION: TOPO HCV 5a 435b

<400> SEQUENCE: 72
gggcgaauug ggcccucuag augcaugcuc gagcggccgc cagugugaug gauaucugca     60
gaauucgccc uuucacuccc cugugaggaa cuacugucuu cacgcagaaa gcgucuagcc    120
auggcguuag uaugaguguc gaacagccuc caggaccccc cucccggga gagccauagu    180 ggucugcgga accggugagu acaccggaau ugccgggacg accggguccu uucuuggaua    240
aacccgcuca ugcccggag auuugggcgu gccccgcga gacugcuagc cgaguagugu    300
ugggucgcga aggccuugu ggacugccu gaugggugc uugcgagugc ccggggagg      360 cucguagacc gugcaaaggg cgaauuccag cacacuggcg gccguuacua guggauccga    420
```
gcucgguacc aagcu                                                          435

<210> SEQ ID NO 73
<211> LENGTH: 328
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(328)
<223> OTHER INFORMATION: pBluescript II SK (+) HCV 6a 328b

<400> SEQUENCE: 73
gggcgaauug gguaccucac uccccuguga ggaacuacug ucuucacgca gaaagcgucu       60
agccauggcg uuaguaugag ugucguacag ccuccaggcc ccccccuccc gggagagcca      120
uaguggucug cggaaccggu gaguacaccg gaauugccag gaugaccggg uccuuuccau      180
uggaucaaac ccgcucaaug ccuggagauu ugggcgugcc cccgcaagac ugcuagccga      240
guagcguugg guugcgaaag gccuuguggu acugccugau agggugcuug cgagugcccc      300
gggaggucuc guagaccgug caggaauu                                         328

<210> SEQ ID NO 74
<211> LENGTH: 325
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(325)
<223> OTHER INFORMATION: pBluescript II SK (+) HCV 5a 325b

<400> SEQUENCE: 74
gggcgaauug gguaccucac uccccuguga ggaacuacug ucuucacgca gaaagcgucu       60
agccauggcg uuaguaugag ugucgaacag ccuccaggac ccccccuccc gggagagcca      120
uaguggucug cggaaccggu gaguacaccg gaauugccgg gacgaccggg uccuuucuug      180
gauaaacccg cucaaugccc ggagauuugg gcgugccccc gcgagacugc uagccgagua      240 guguugggguc gcgaaaggcc uuguggu acu gccugauagg gugcuugcga gugccccggg   300
aggucucgua gaccgugcag gaauu                                            325

<210> SEQ ID NO 75
<211> LENGTH: 9401
<212> TYPE: DNA
<213> ORGANISM: Hepatitis C virus
<220> FEATURE:
<221> NAME/KEY: misc_feature
<222> LOCATION: (1)..(9401)
<223> OTHER INFORMATION: HCV 1a mRNA genome sequence
<300> PUBLICATION INFORMATION:
<308> DATABASE ACCESSION NUMBER: M62321
<309> DATABASE ENTRY DATE: 2007-09-05
<313> RELEVANT RESIDUES IN SEQ ID NO: (1)..(9401)

<400> SEQUENCE: 75
gccagccccc tgatggggggc gacactccac catgaatcac tcccctgtga ggaactactg       60
tcttcacgca gaaagcgtct agccatggcg ttagtatgag tgtcgtgcag cctccaggac      120 ccccccctccc gggagagcca tagtggtctg cggaaccggt gagtacaccg gaattgccag      180
gacgaccggg tcctttcttg gatcaacccg ctcaatgcct ggagatttgg gcgtgccccc      240

```
gcaagactgc tagccgagta gtgttgggtc gcgaaaggcc ttgtggtact gcctgatagg      300
gtgcttgcga gtgccccggg aggtctcgta gaccgtgcac catgagcacg aatcctaaac      360
ctcaaaaaaa aaacaaacgt aacaccaacc gtcgcccaca ggacgtcaag ttcccgggtg      420
gcggtcagat cgttggtgga gtttacttgt tgccgcgcag gggccctaga ttgggtgtgc      480
gcgcgacgag aaagacttcc gagcggtcgc aacctcgagg tagacgtcag cctatcccca      540
aggctcgtcg gcccgagggc aggacctggg ctcagcccgg gtaccttgg cccctctatg       600 gcaatgaggg ctgcgggtgg gcgggatggc tcctgtctcc ccgtggctct cggcctagct      660
ggggccccac agaccccgg cgtaggtcgc gcaatttggg taaggtcatc gatacccta       720 cgtgcggctt cgccgacctc atggggtaca taccgctcgt cggcgcccct cttggaggcg      780
ctgccagggc cctggcgcat ggcgtccggg ttctggaaga cggcgtgaac tatgcaacag      840
ggaaccttcc tggttgctct ttctctatct tccttctggc cctgctctct tgcttgactg      900
tgcccgcttc ggcctaccaa gtgcgcaact ccacggggct ttaccacgtc accaatgatt      960
gccctaactc gagtattgtg tacgaggcgg ccgatgccat cctgcacact ccggggtgcg     1020
tcccttgcgt tcgtgagggc aacgcctcga ggtgttgggt ggcgatgacc cctacggtgg     1080
ccaccaggga tggcaaactc cccgcgacgc agcttcgacg tcacatcgat ctgcttgtcg     1140
ggagcgccac cctctgttcg gccctctacg tgggggacct atgcgggtct gtctttcttg     1200
tcggccaact gttcaccttc tctcccaggc gccactggac gacgcaaggt tgcaattgct     1260
ctatctatcc cggccatata acgggtcacc gcatggcatg ggatatgatg atgaactggt     1320
cccctacgac ggcgttggta atggctcagc tgctccggat cccacaagcc atcttggaca     1380
tgatcgctgg tgctcactgg ggagtcctgg cgggcatagc gtatttctcc atggtgggga     1440
actgggcgaa ggtcctggta gtgctgctgc tatttgccgg cgtcgacgcg gaaacccacg     1500
tcaccggggg aagtgccggc cacactgtgt ctggatttgt tagcctcctc gcaccaggcg     1560
ccaagcagaa cgtccagctg atcaacacca acggcagttg gcacctcaat agcacggccc     1620
tgaactgcaa tgatagcctc aacaccggct ggttggcagg gcttttctat caccacaagt     1680
tcaactcttc aggctgtcct gagaggctag ccagctgccg accccttacc gattttgacc     1740
agggctgggg ccctatcagt tatgccaacg gaagcggccc cgaccagcgc ccctactgct     1800
ggcactaccc cccaaaacct tgcggtattg tgcccgcgaa gagtgtgtgt ggtccggtat     1860
attgcttcac tcccagcccc gtggtggtgg gaacgaccga caggtcgggc gcgcccacct     1920
acagctgggg tgaaaatgat acggacgtct tcgtccttaa caataccagg ccaccgctgg     1980
gcaattggtt cggttgtacc tggatgaact caactggatt caccaaagtg tgcggagcgc     2040
ctccttgtgt catcggaggg gcgggcaaca acacccctgca ctgccccact gattgcttcc     2100
gcaagcatcc ggacgccaca tactctcggt gcggctccgg tccctggatc acacccaggt     2160
gcctggtcga ctaccgtat aggctttggc attatccttg taccatcaac tacaccatat      2220
ttaaaatcag gatgtacgtg ggaggggtcg aacacaggct ggaagctgcc tgcaactgga     2280
cgcggggcga acgttgcgat ctggaagaca gggacaggtc cgagctcagc ccgttactgc     2340
tgaccactac acagtggcag gtcctcccgt gttccttcac aacccctacca gccttgtcca     2400 ccggcctcat ccacctccac cagaacattg tggacgtgca gtacttgtac ggggtgggt      2460 caagcatcgc gtcctgggcc attaagtggg agtacgtcgt tctcctgttc cttctgcttg     2520
cagacgcgcg cgtctgctcc tgcttgtgga tgatgcact catatcccaa gcggaggcgg      2580
ctttggagaa cctcgtaata cttaatgcag catccctggc cgggacgcac ggtcttgtat     2640
```

```
ccttcctcgt gttcttctgc tttgcatggt atttgaaggg taagtgggtg cccggagcgg   2700
tctacacctt ctacgggatg tggcctctcc tcctgctcct gttggcgttg ccccagcggg   2760
cgtacgcgct ggacacggag gtggccgcgt cgtgtggcgg tgttgttctc gtcgggttga   2820
tggcgctgac tctgtcacca tattacaagc gctatatcag ctggtgcttg tggtggcttc   2880
agtattttct gaccagagtg gaagcgcaac tgcacgtgtg gattccccc ctcaacgtcc    2940
gagggggcg cgacgccgtc atcttactca tgtgtgctgt acacccgact ctggtatttg    3000
acatcaccaa attgctgctg gccgtcttcg accccttg gattcttcaa gccagtttgc     3060
ttaaagtacc ctactttgtg cgcgtccaag gccttctccg gttctgcgcg ttagcgcgga   3120
agatgatcgg aggccattac gtgcaaatgg tcatcattaa gttaggggcg cttactggca   3180
cctatgttta taaccatctc actcctcttc gggactgggc gcacaacggc ttgcgagatc   3240
tggccgtggc tgtagagcca gtcgtcttct cccaaatgga gaccaagctc atcacgtggg   3300
gggcagatac cgccgcgtgc ggtgacatca tcaacggctt gcctgtttcc gcccgcaggg   3360
gccgggagat actgctcggg ccagccgatg gaatggtctc caaggggtgg aggttgctgg   3420
cgcccatcac ggcgtacgcc cagcagacaa ggggcctcct agggtgcata atcaccagcc   3480
taactggccg ggacaaaaac caagtggagg gtgaggtcca gattgtgtca actgctgccc   3540
aaaccttcct ggcaacgtgc atcaatgggg tgtgctggac tgtctaccac ggggccggaa   3600
cgaggaccat cgcgtcaccc aagggtcctg tcatccagat gtataccaat gtagaccaag   3660
accttgtggg ctggccccgct ccgcaaggta gccgctcatt gacaccctgc acttgcggct   3720
cctcggacct ttacctggtc acgaggcacg ccgatgtcat tcccgtgcgc cggcggggtg   3780
atagcagggg cagcctgctg tcgccccggc ccatttccta cttgaaaggc tcctcggggg   3840
gtccgctgtt gtgccccgcg gggcacgccg tgggcatatt tagggccgcg gtgtgcaccc   3900
gtggagtggc taaggcggtg gactttatcc ctgtggagaa cctagagaca accatgaggt   3960
ccccggtgtt cacggataac tcctctccac cagtagtgcc ccagagcttc caggtggctc   4020
acctccatgc tcccacaggc agcggcaaaa gcaccaaggt cccggctgca tatgcagctc   4080
agggctataa ggtgctagta ctcaacccct ctgttgctgc aacactgggc tttggtgctt   4140
acatgtccaa ggctcatggg atcgatccta acatcaggac cggggtgaga acaattacca   4200
ctggcagccc catcacgtac tccacctacg gcaagttcct tgccgacggc gggtgctcgg   4260
ggggcgctta tgacataata atttgtgacg agtgccactc cacggatgcc acatccatct   4320
tgggcatcgg cactgtccctt gaccaagcag agactgcggg ggcgagactg gttgtgctcg   4380
ccaccgccac ccctccgggc tccgtcactg tgccccatcc caacatcgag gaggttgctc   4440
tgtccaccac cggagagatc ccttttttacg gcaaggctat ccccctcgaa gtaatcaagg   4500
gggggagaca tctcatcttc tgtcattcaa agaagaagtg cgacgaactc gccgcaaagc   4560
tggtcgcatt gggcatcaat gccgtggcct actaccgcgg tcttgacgtg tccgtcatcc   4620
cgaccagcgg cgatgttgtc gtcgtggcaa ccgatgccct catgaccggc tataccggcg   4680
acttcgactc ggtgatagac tgcaatacgt gtgtcaccca gacagtcgat ttcagccttg   4740
accctacctt caccattgag acaatcacgc tcccccagga tgctgtctcc cgcactcaac   4800
gtcggggcag gactggcagg gggaagccag gcatctacag atttgtggca ccgggggagc   4860
gccctccgg catgttcgac tcgtccgtcc tctgtgagtg ctatgacgca ggctgtgctt   4920
ggtatgagct cacgcccgcc gagactacag ttaggctacg agcgtacatg aacaccccgg   4980
```

```
ggcttcccgt gtgccaggac catcttgaat tttgggaggg cgtctttaca ggcctcactc    5040
atatagatgc ccactttcta tcccagacaa agcagagtgg ggagaacctt ccttacctgg    5100
tagcgtacca agccaccgtg tgcgctaggg ctcaagcccc tcccccatcg tgggaccaga    5160
tgtggaagtg tttgattcgc ctcaagccca ccctccatgg gccaacaccc ctgctataca    5220
gactgggcgc tgttcagaat gaaatcaccc tgacgcaccc agtcaccaaa tacatcatga    5280
catgcatgtc ggccgacctg gaggtcgtca cgagcacctg ggtgctcgtt ggcggcgtcc    5340
tggctgcttt ggccgcgtat tgcctgtcaa caggctgcgt ggtcatagtg ggcagggtcg    5400
tcttgtccgg gaagccggca atcataccta acagggaagt cctctaccga gagttcgatg    5460
agatggaaga gtgctctcag cacttaccgt acatcgagca agggatgatg ctcgccgagc    5520
agttcaagca gaaggccctc ggcctcctgc agaccgcgtc ccgtcaggca gaggttatcg    5580
cccctgctgt ccagaccaac tggcaaaaac tcgagacctt ctgggcgaag catatgtgga    5640
acttcatcag tgggatacaa tacttggcgg cttgtcaac gctgcctggt aaccccgcca    5700
ttgcttcatt gatggctttt acagctgctg tcaccagccc actaaccact agccaaaccc    5760
tcctcttcaa catattgggg gggtgggtgg ctgcccagct cgccgccccc ggtgccgcta    5820
ctgcctttgt gggcgctggc ttagctgcg ccgccatcgg cagtgttgga ctggggaagg    5880
tcctcataga catccttgca gggtatggcg cgggcgtggc gggagctctt gtggcattca    5940
agatcatgag cggtgaggtc ccctccacgg aggacctggt caatctactg cccgccatcc    6000
tctcgcccgg agccctcgta gtcggcgtgg tctgtgcagc aatactgcgc cggcacgttg    6060
gcccgggcga gggggcagtg cagtggatga accggctgat agccttcgcc tcccggggga    6120
accatgtttc ccccacgcac tacgtgccgg agagcgatgc agctgcccgc gtcactgcca    6180
tactcagcag cctcactgta acccagctcc tgaggcgact gcaccagtgg ataagctcgg    6240
agtgtaccac tccatgctcc ggttcctggc taagggacat ctgggactgg atatgcgagg    6300
tgttgagcga ctttaagacc tggctaaaag ctaagctcat gccacagctg cctgggatcc    6360
cctttgtgtc ctgccagcgc gggtataagg gggtctggcg agtggacggc atcatgcaca    6420
ctcgctgcca ctgtggagct gagatcactg gacatgtcaa aaacgggacg atgaggatcg    6480
tcggtcctag gacctgcagg aacatgtgga gtgggacctt ccccattaat gcctacacca    6540
cgggcccctg tacccccctt cctgcgccga actacacgtt cgcgctatgg agggtgtctg    6600
cagaggaata tgtggagata aggcaggtgg gggacttcca ctacgtgacg ggtatgacta    6660
ctgacaatct caaatgcccg tgccaggtcc catcgcccga ttttcaca gaattggacg    6720 gggtgcgcct acataggttt gcgccccct gcaagccctt gctgcgggag gaggtatcat    6780
tcagagtagg actccacgaa tacccggtag ggtcgcaatt accttgcgag cccgaaccgg    6840
acgtggccgt gttgacgtcc atgctcactg atcctccca tataacagca gaggcggccg    6900
ggcgaaggtt ggcgagggga tcacccccct ctgtggccag ctcctcggct agccagctat    6960
ccgctccatc tctcaaggca acttgcaccg ctaaccatga ctcccctgat gctgagctca    7020
tagaggccaa cctcctatgg aggcaggaga tgggcggcaa catcaccagg gttgagtcag    7080
aaaacaaagt ggtgattctg gactccttcg atccgcttgt ggcggaggag gacgagcggg    7140
agatctccgt acccgcagaa atcctgcgga agtctcggag attcgcccag gccctgcccg    7200
tttgggcgcg gccggactat aacccccgc tagtggagac gtggaaaaag cccgactacg    7260
aaccacctgt ggtccatggc tgtccgcttc cacctccaaa gtcccctcct gtgcctccgc    7320
ctcggaagaa gcggacggtg gtcctcactg aatcaaccct atctactgcc ttggccgagc    7380
```

```
tcgccaccag aagctttggc agctcctcaa cttccggcat tacgggcgac aatacgacaa    7440
catcctctga gcccgcccct tctggctgcc ccccgactc cgacgctgag tcctattcct    7500
ccatgccccc cctggagggg gagcctgggg atccggatct tagcgacggg tcatggtcaa    7560
cggtcagtag tgaggccaac gcggaggatg tcgtgtgctg ctcaatgtct tactcttgga    7620
caggcgcact cgtcaccccg tgcgccgcgg aagaacagaa actgcccatc aatgcactaa    7680
gcaactcgtt gctacgtcac cacaatttgg tgtattccac cacctcacgc agtgcttgcc    7740
aaaggcagaa gaaagtcaca tttgacagac tgcaagttct ggacagccat taccaggacg    7800
tactcaagga ggttaaagca gcggcgtcaa aagtgaaggc taacttgcta tccgtagagg    7860
aagcttgcag cctgacgccc ccacactcag ccaaatccaa gtttggttat ggggcaaaag    7920
acgtccgttg ccatgccaga aaggccgtaa cccacatcaa ctccgtgtgg aaagaccttc    7980
tggaagacaa tgtaacacca atagacacta ccatcatggc taagaacgag gttttctgcg    8040
ttcagcctga aagggggggt cgtaagccag ctcgtctcat cgtgttcccc gatctgggcg    8100
tgcgcgtgtg cgaaaagatg gctttgtacg acgtggttac aaagctcccc ttggccgtga    8160
tgggaagctc ctacggattc caatactcac caggacagcg ggttgaattc ctcgtgcaag    8220
cgtggaagtc caagaaaacc ccaatggggt tctcgtatga tacccgctgc tttgactcca    8280
cagtcactga gagcgacatc cgtacggagg aggcaatcta ccaatgttgt gacctcgacc    8340
cccaagcccg cgtggccatc aagtccctca ccgagaggct ttatgttggg ggccctctta    8400
ccaattcaag gggggagaac tgcggctatc gcaggtgccg cgcgagcggc gtactgacaa    8460
ctagctgtgg taacaccctc acttgctaca tcaaggcccg ggcagcctgt cgagccgcag    8520
ggctccagga ctgcaccatg ctcgtgtgtg cgacgacttt agtcgttatc tgtgaaagcg    8580
cgggggtcca ggaggacgcg gcgagcctga gagccttcac ggaggctatg accaggtact    8640
ccgccccccc tggggacccc ccacaaccag aatacgactt ggagctcata acatcatgct    8700
cctccaacgt gtcagtcgcc cacgacggcg ctggaaagag ggtctactac ctcacccgtg    8760
accctacaac cccccctcgcg agagctgcgt gggagacagc aagacacact ccagtcaatt    8820
cctggctagg caacataatc atgtttgccc ccacactgtg ggcgaggatg atactgatga    8880
cccatttctt tagcgtcctt atagccaggg accagcttga acaggccctc gattgcgaga    8940
tctacggggc ctgctactcc atagaaccac ttgatctacc tccaatcatt caaagactcc    9000
atggcctcag cgcatttttca ctccacagtt actctccagg tgaaattaat agggtggccg    9060
catgcctcag aaaacttggg gtaccgcct tgcgagcttg gagacaccgg gccggagcc    9120 tccgcgctag gcttctggcc agaggaggca gggctgccat atgtggcaag tacctcttca    9180
actgggcagt aagaacaaag ctcaaactca ctccaatagc ggccgctggc cagctggact    9240
tgtccggctg gttcacggct ggctacagcg ggggagacat ttatcacagc gtgtctcatg    9300
cccggccccg ctggatctgg ttttgcctac tcctgcttgc tgcagggggta ggcatctacc    9360 tcctccccaa ccgatgaagg ttggggtaaa cactccggcc t                         9401
```

<210> SEQ ID NO 76
<211> LENGTH: 22
<212> TYPE: DNA
<213> ORGANISM: Hepatitis C virus
<220> FEATURE:
<221> NAME/KEY: misc_feature
<222> LOCATION: (1)..(22)
<223> OTHER INFORMATION: HCV non-T7 primer

```
<400> SEQUENCE: 76
atttgggcgt gcccccgcaa ga                                              22

<210> SEQ ID NO 77
<211> LENGTH: 22
<212> TYPE: DNA
<213> ORGANISM: Hepatitis C virus
<220> FEATURE:
<221> NAME/KEY: misc_feature
<222> LOCATION: (1)..(22)
<223> OTHER INFORMATION: HCV non-T7 primer

<400> SEQUENCE: 77
atttgggcgt gcccccgcga ga                                              22

<210> SEQ ID NO 78
<211> LENGTH: 20
<212> TYPE: DNA
<213> ORGANISM: Hepatitis C virus
<220> FEATURE:
<221> NAME/KEY: misc_feature
<222> LOCATION: (1)..(20)
<223> OTHER INFORMATION: HCV non-T7 primer

<400> SEQUENCE: 78
ctagccgagt agtgttgggt                                                 20

<210> SEQ ID NO 79
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV non-T7 primer

<400> SEQUENCE: 79
agtagtgttg ggtcgcgaaa ggccttg                                         27

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(20)
<223> OTHER INFORMATION: HCV non-T7 primer

<400> SEQUENCE: 80
gaggaactac tgtcttcacg                                                 20

<210> SEQ ID NO 81
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV non-T7 primer

<400> SEQUENCE: 81
ggaactactg tcttcacgcg gaaagcg                                         27
```

<210> SEQ ID NO 82
<211> LENGTH: 29
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(29)
<223> OTHER INFORMATION: HCV non-T7 primer

<400> SEQUENCE: 82
gaggaactac tgtcttcacg cggaaagcg                                   29

<210> SEQ ID NO 83
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV non-T7 primer

<400> SEQUENCE: 83
gcgaaaggcc ttgtggtact gcctgat                                     27

<210> SEQ ID NO 84
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV non-T7 primer

<400> SEQUENCE: 84
ggccttgtgg tactgcctga tagggtg                                     27

<210> SEQ ID NO 85
<211> LENGTH: 19
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(19)
<223> OTHER INFORMATION: HCV non-T7 primer

<400> SEQUENCE: 85
tgtcttcacg cggaaagcg                                              19

<210> SEQ ID NO 86
<211> LENGTH: 22
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(22)
<223> OTHER INFORMATION: HCV non-T7 primer

<400> SEQUENCE: 86
atttgggcgt gcccccgcaa ga					22

<210> SEQ ID NO 87
<211> LENGTH: 22
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(22)
<223> OTHER INFORMATION: HCV non-T7 primer

<400> SEQUENCE: 87
atttgggcgt gcccccgcga ga					22

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(20)
<223> OTHER INFORMATION: HCV non-T7 primer

<400> SEQUENCE: 88
ctagccgagt agtgttgggt					20

<210> SEQ ID NO 89
<211> LENGTH: 25
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(25)
<223> OTHER INFORMATION: HCV non-T7 primer

<400> SEQUENCE: 89
tagccgagta gtgttgggtc gcgaa					25

<210> SEQ ID NO 90
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV non-T7 primer

<400> SEQUENCE: 90
agtagtgttg ggtcgcgaaa ggccttg					27

<210> SEQ ID NO 91
<211> LENGTH: 28
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(28)
<223> OTHER INFORMATION: HCV non-T7 primer

<400> SEQUENCE: 91

```
gttgggtcgc gaaaggcctt gtggtact                                              28

<210> SEQ ID NO 92
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV non-T7 primer

<400> SEQUENCE: 92
gcgaaaggcc ttgtggtact gcctgat                                               27

<210> SEQ ID NO 93
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV non-T7 primer

<400> SEQUENCE: 93
ggccttgtgg tactgcctga tagggtg                                               27

<210> SEQ ID NO 94
<211> LENGTH: 29
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(29)
<223> OTHER INFORMATION: HCV non-T7 primer

<400> SEQUENCE: 94
gaggaacttc tgtcttcacg cggaaagcg                                             29

<210> SEQ ID NO 95
<211> LENGTH: 19
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(19)
<223> OTHER INFORMATION: HCV non-T7 primer

<400> SEQUENCE: 95
tgtcttcacg cggaaagcg                                                        19

<210> SEQ ID NO 96
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV non-T7 primer
```

<400> SEQUENCE: 96
ggaacttctg tcttcacgca gaaagcg 27

<210> SEQ ID NO 97
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV non-T7 primer
<220> FEATURE:
<221> NAME/KEY: misc_feature
<222> LOCATION: (20)..(20)
<223> OTHER INFORMATION: Position 20 occupied by inosine

<400> SEQUENCE: 97
ggaacttctg tcttcacgcn gaaagcg 27

<210> SEQ ID NO 98
<211> LENGTH: 19
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(19)
<223> OTHER INFORMATION: HCV non-T7 primer

<400> SEQUENCE: 98
tgtcttcacg cagaaagcg 19

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(20)
<223> OTHER INFORMATION: HCV non-T7 primer

<400> SEQUENCE: 99
gaggaacttc tgtcttcacg 20

<210> SEQ ID NO 100
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV non-T7 primer

<400> SEQUENCE: 100
ggaactactg tcttcacgca gaaagcg 27

<210> SEQ ID NO 101
<211> LENGTH: 25
<212> TYPE: DNA
<213> ORGANISM: Artificial Sequence
<220> FEATURE:
<223> OTHER INFORMATION: Synthetic Oligomer

```
<220> FEATURE:
<221> NAME/KEY: misc_feature
<222> LOCATION: (1)..(25)
<223> OTHER INFORMATION: HCV non-T7 primer

<400> SEQUENCE: 101
tagcctagta gcgttgggtt gcgaa                                          25

<210> SEQ ID NO 102
<211> LENGTH: 26
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(26)
<223> OTHER INFORMATION: HCV non-T7 primer

<400> SEQUENCE: 102
tagcctagta gcgttgggtt gcgaac                                         26

<210> SEQ ID NO 103
<211> LENGTH: 25
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(25)
<223> OTHER INFORMATION: HCV non-T7 primer

<400> SEQUENCE: 103
tagccgagta gtgttgggtt gcgaa                                          25

<210> SEQ ID NO 104
<211> LENGTH: 25
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(25)
<223> OTHER INFORMATION: HCV non-T7 primer

<400> SEQUENCE: 104
tagcctagta gtgttgggtc gcgaa                                          25

<210> SEQ ID NO 105
<211> LENGTH: 25
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(25)
<223> OTHER INFORMATION: HCV non-T7 primer

<400> SEQUENCE: 105
tagccgagta gcgttgggtc gcgaa                                          25

<210> SEQ ID NO 106
<211> LENGTH: 25
<212> TYPE: DNA
<213> ORGANISM: Artificial Sequence
<220> FEATURE:
```

```
<223> OTHER INFORMATION: Synthetic Oligomer
<220> FEATURE:
<221> NAME/KEY: misc_feature
<222> LOCATION: (1)..(25)
<223> OTHER INFORMATION: HCV non-T7 primer

<400> SEQUENCE: 106
tagccgagta gcgttgggtt gcgaa                                          25

<210> SEQ ID NO 107
<211> LENGTH: 25
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(25)
<223> OTHER INFORMATION: HCV non-T7 primer

<400> SEQUENCE: 107
tagccgagta gtgctgtgtc gcgaa                                          25

<210> SEQ ID NO 108
<211> LENGTH: 68
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(68)
<223> OTHER INFORMATION: HCV T7 promoter primer

<400> SEQUENCE: 108
aatttaatac gactcactat agggagacct ggaggctgca cgacactcat actaacgcca    60
tggctaga                                                             68

<210> SEQ ID NO 109
<211> LENGTH: 67
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(67)
<223> OTHER INFORMATION: HCV T7 promoter primer

<400> SEQUENCE: 109
aatttaatac gactcactat agggagacct ggaggctgca cgacactcat actaacgcca    60
tggctag                                                              67

<210> SEQ ID NO 110
<211> LENGTH: 66
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(66)
<223> OTHER INFORMATION: HCV T7 promoter primer

<400> SEQUENCE: 110
aatttaatac gactcactat agggagacct ggaggctgca cgacactcat actaacgcca    60
tggcta                                                               66
```

<210> SEQ ID NO 111
<211> LENGTH: 65
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(65)
<223> OTHER INFORMATION: HCV T7 promoter primer

<400> SEQUENCE: 111
aatttaatac gactcactat agggagacct ggaggctgca cgacactcat actaacgcca    60
tggct                                                                65

<210> SEQ ID NO 112
<211> LENGTH: 64
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(64)
<223> OTHER INFORMATION: HCV T7 promoter primer

<400> SEQUENCE: 112
aatttaatac gactcactat agggagacct ggaggctgca cgacactcat actaacgcca    60
tggc                                                                 64

<210> SEQ ID NO 113
<211> LENGTH: 63
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(63)
<223> OTHER INFORMATION: HCV T7 promoter primer

<400> SEQUENCE: 113
aatttaatac gactcactat agggagacct ggaggctgca cgacactcat actaacgcca    60
tgg                                                                  63

<210> SEQ ID NO 114
<211> LENGTH: 60
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(60)
<223> OTHER INFORMATION: HCV T7 promoter primer

<400> SEQUENCE: 114
aatttaatac gactcactat agggagacct ggaggctgca cgacactcat actaacgcca    60

<210> SEQ ID NO 115
<211> LENGTH: 59
<212> TYPE: DNA
<213> ORGANISM: Artificial Sequence
<220> FEATURE:
<223> OTHER INFORMATION: Synthetic Oligomer
<220> FEATURE:

```
<221> NAME/KEY: misc_feature
<222> LOCATION: (1)..(59)
<223> OTHER INFORMATION: HCV T7 promoter primer

<400> SEQUENCE: 115
aatttaatac gactcactat agggagacct ggaggctgca cgacactcat actaacgcc      59

<210> SEQ ID NO 116
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(58)
<223> OTHER INFORMATION: HCV T7 promoter primer
<220> FEATURE:
<221> NAME/KEY: misc_feature
<222> LOCATION: (39)..(39)
<223> OTHER INFORMATION: Position 39 occupied by inosine
<220> FEATURE:
<221> NAME/KEY: misc_feature
<222> LOCATION: (42)..(42)
<223> OTHER INFORMATION: Position 42 occupied by inosine
<220> FEATURE:
<221> NAME/KEY: misc_feature
<222> LOCATION: (55)..(55)
<223> OTHER INFORMATION: Position 55 occupied by inosine

<400> SEQUENCE: 116
aatttaatac gactcactat agggagacct ggaggctgna cnacactcat actancgc       58

<210> SEQ ID NO 117
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(58)
<223> OTHER INFORMATION: HCV T7 promoter primer

<400> SEQUENCE: 117
aatttaatac gactcactat agggagacct ggaggctgca caacactcat actaacgc       58

<210> SEQ ID NO 118
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(58)
<223> OTHER INFORMATION: HCV T7 promoter primer

<400> SEQUENCE: 118
aatttaatac gactcactat agggagacct ggaggctgca cgacactcat actagcgc       58

<210> SEQ ID NO 119
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(58)
<223> OTHER INFORMATION: HCV T7 promoter primer
```

<220> FEATURE:
<221> NAME/KEY: misc_feature
<222> LOCATION: (42)..(42)
<223> OTHER INFORMATION: Position 42 occupied by inosine

<400> SEQUENCE: 119
aatttaatac gactcactat agggagacct ggaggctgca cnacactcat actaacgc    58

<210> SEQ ID NO 120
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(58)
<223> OTHER INFORMATION: HCV T7 promoter primer
<220> FEATURE:
<221> NAME/KEY: misc_feature
<222> LOCATION: (55)..(55)
<223> OTHER INFORMATION: Position 55 occupied by inosine

<400> SEQUENCE: 120
aatttaatac gactcactat agggagacct ggaggctgca cgacactcat actancgc    58

<210> SEQ ID NO 121
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(58)
<223> OTHER INFORMATION: HCV T7 promoter primer
<220> FEATURE:
<221> NAME/KEY: misc_feature
<222> LOCATION: (39)..(39)
<223> OTHER INFORMATION: Position 39 occupied by inosine

<400> SEQUENCE: 121
aatttaatac gactcactat agggagacct ggaggctgna cgacactcat actaacgc    58

<210> SEQ ID NO 122
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(58)
<223> OTHER INFORMATION: HCV T7 promoter primer

<400> SEQUENCE: 122
aatttaatac gactcactat agggagacct ggaggttgta caacgctcat actaacgc    58

<210> SEQ ID NO 123
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(58)
<223> OTHER INFORMATION: HCV T7 promoter primer

<400> SEQUENCE: 123
aatttaatac gactcactat agggagacct ggaggctgta cgacactcat actaacgc      58

<210> SEQ ID NO 124
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(58)
<223> OTHER INFORMATION: HCV T7 promoter primer

<400> SEQUENCE: 124
aatttaatac gactcactat agggagacct ggaggctgta caacactcat actaacgc      58

<210> SEQ ID NO 125
<211> LENGTH: 57
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(57)
<223> OTHER INFORMATION: HCV T7 promoter primer

<400> SEQUENCE: 125
aatttaatac gactcactat agggagacct ggaggctgca cgacactcat actaacg       57

<210> SEQ ID NO 126
<211> LENGTH: 54
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(57)
<223> OTHER INFORMATION: HCV T7 promoter primer

<400> SEQUENCE: 126
aatttaatac gactcactat agggagacct ggaggctgca caacactcat acta          54

<210> SEQ ID NO 127
<211> LENGTH: 54
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(54)
<223> OTHER INFORMATION: HCV T7 promoter primer

<400> SEQUENCE: 127
aatttaatac gactcactat agggagacct ggaggttgta caacgctcat acta          54

<210> SEQ ID NO 128
<211> LENGTH: 54
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(54)
<223> OTHER INFORMATION: HCV T7 promoter primer

<400> SEQUENCE: 128
aatttaatac gactcactat agggagacct ggaggctgta cgacactcat acta          54

<210> SEQ ID NO 129
<211> LENGTH: 48
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(48)
<223> OTHER INFORMATION: HCV T7 promoter primer

<400> SEQUENCE: 129
aatttaatac gactcactat agggagacct ggaggctgca cgacactc               48

<210> SEQ ID NO 130
<211> LENGTH: 48
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(48)
<223> OTHER INFORMATION: HCV T7 promoter primer

<400> SEQUENCE: 130
aatttaatac gactcactat agggagacct ggaggctgta caacactc               48

<210> SEQ ID NO 131
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(58)
<223> OTHER INFORMATION: HCV T7 promoter primer

<400> SEQUENCE: 131
aatttaatac gactcactat agggagagtt ccgcagacca ctatggctct cccgggag    58

<210> SEQ ID NO 132
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(58)
<223> OTHER INFORMATION: HCV T7 promoter primer

<400> SEQUENCE: 132
aatttaatac gactcactat agggagatca ccggttccgc agaccactat ggctctcc    58

<210> SEQ ID NO 133
<211> LENGTH: 52
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(52)
<223> OTHER INFORMATION: HCV T7 promoter primer

<400> SEQUENCE: 133
aatttaatac gactcactat agggagaggt tccgcagacc actatggctc tc        52

<210> SEQ ID NO 134
<211> LENGTH: 49
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(49)
<223> OTHER INFORMATION: HCV T7 promoter primer

<400> SEQUENCE: 134
aatttaatac gactcactat agggagagtt ccgcagacca ctatggctc            49

<210> SEQ ID NO 135
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(51)
<223> OTHER INFORMATION: HCV T7 promoter primer; HCV-1a 139-162(-)

<400> SEQUENCE: 135
aatttaatac gactcactat agggagacac cggttccgca gaccactatg g         51

<210> SEQ ID NO 136
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(51)
<223> OTHER INFORMATION: HCV T7 promoter primer; HCV-1a 143-166(-)

<400> SEQUENCE: 136
aatttaatac gactcactat agggagatac tcaccggttc cgcagaccac t         51

<210> SEQ ID NO 137
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(51)
<223> OTHER INFORMATION: HCV T7 promoter primer; HCV-1a; 144-167(-)

<400> SEQUENCE: 137
aatttaatac gactcactat agggagagta ctcaccggtt ccgcagacca c         51

<210> SEQ ID NO 138
<211> LENGTH: 57
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(57)
<223> OTHER INFORMATION: HCV T7 promoter primer; HCV-1a 146-175(-)

<400> SEQUENCE: 138
aatttaatac gactcactat agggagaatt ccggtgtact caccggttcc gcagacc    57

<210> SEQ ID NO 139
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(51)
<223> OTHER INFORMATION: HCV T7 promoter primer; HCV-1a 149-172(-)

<400> SEQUENCE: 139
aatttaatac gactcactat agggagaccg gtgtactcac cggttccgca g    51

<210> SEQ ID NO 140
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(58)
<223> OTHER INFORMATION: HCV T7 promoter primer; DNA HCV(-) 303-333

<400> SEQUENCE: 140
aatttaatac gactcactat agggagaact cgcaagcacc ctatcaggca gtaccaca    58

<210> SEQ ID NO 141
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(53)
<223> OTHER INFORMATION: HCV T7 promoter primer; DNA HCV(-) 308-333

<400> SEQUENCE: 141
aatttaatac gactcactat agggagaact cgcaagcacc ctatcaggca gta    53

<210> SEQ ID NO 142
<211> LENGTH: 57
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(57)
<223> OTHER INFORMATION: HCV T7 promoter primer; DNA HCV(-) 316-345

<400> SEQUENCE: 142
aatttaatac gactcactat agggagaacc tcccggggca ctcgcaagca ccctatc    57

<210> SEQ ID NO 143
<211> LENGTH: 55
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(55)

<223> OTHER INFORMATION: HCV T7 promoter primer; DNA HCV(-) 327-354

<400> SEQUENCE: 143
aatttaatac gactcactat agggagagtc tacgagacct cccggggcac tcgca    55

<210> SEQ ID NO 144
<211> LENGTH: 54
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(54)
<223> OTHER INFORMATION: HCV T7 promoter primer; DNA HCV(-) 329-355

<400> SEQUENCE: 144
aatttaatac gactcactat agggagaggt ctacgagacc tcccgggca ctcg    54

<210> SEQ ID NO 145
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(53)
<223> OTHER INFORMATION: HCV T7 promoter primer; DNA HCV(-) 333-360

<400> SEQUENCE: 145
aatttaatac gactcactat agggagacac ggtctacgag acctcccggg gca    53

<210> SEQ ID NO 146
<211> LENGTH: 55
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(55)
<223> OTHER INFORMATION: HCV T7 promoter primer; DNA T7A HCV0263(-)
<220> FEATURE:
<221> NAME/KEY: misc_feature
<222> LOCATION: (48)..(48)
<223> OTHER INFORMATION: Position 48 occupied by inosine

<400> SEQUENCE: 146
aatttaatac gactcactat agggagaagt accacaaggc ctttcgcnac ccaac    55

<210> SEQ ID NO 147
<211> LENGTH: 44
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(44)
<223> OTHER INFORMATION: HCV T7 promoter primer; DNA HCV(-) 89-108

<400> SEQUENCE: 147
aatttaatac gactcactat agggagagac actcatacta acgc    44

<210> SEQ ID NO 148
<211> LENGTH: 22
<212> TYPE: DNA
<213> ORGANISM: Artificial Sequence -continued
<220> FEATURE:
<223> OTHER INFORMATION: Synthetic Oligomer
<220> FEATURE:
<221> NAME/KEY: misc_feature
<222> LOCATION: (1)..(22)
<223> OTHER INFORMATION: HCV Torch 80-96 5F3D

<400> SEQUENCE: 148
cuagccaugg cguuagugcu ag                                        22

<210> SEQ ID NO 149
<211> LENGTH: 21
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(21)
<223> OTHER INFORMATION: HCV Torch 81-96 5F3D_93C

<400> SEQUENCE: 149
uagcccuggc guuaguggcu a                                         21

<210> SEQ ID NO 150
<211> LENGTH: 19
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(19)
<223> OTHER INFORMATION: HCV Torch 81-94 5F3D

<400> SEQUENCE: 150
uagccauggc guuaggcua                                            19

<210> SEQ ID NO 151
<211> LENGTH: 20
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(20)
<223> OTHER INFORMATION: HCV Torch 80-94 5F3D

<400> SEQUENCE: 151
cuagccaugg cguuagcuag                                           20

<210> SEQ ID NO 152
<211> LENGTH: 23
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(23)
<223> OTHER INFORMATION: HCV Torch 292-309 5F3D

<400> SEQUENCE: 152
gcgaaaggcc uugugguauu cgc                                       23

<210> SEQ ID NO 153
<211> LENGTH: 21
<212> TYPE: DNA

```
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(21)
<223> OTHER INFORMATION: HCV Torch 325-340 5F3D

<400> SEQUENCE: 153
cuugcgagug ccccgggcaa g                                              21

<210> SEQ ID NO 154
<211> LENGTH: 21
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(21)
<223> OTHER INFORMATION: HCV Torch 321-336 5F3D

<400> SEQUENCE: 154
ggugcuugcg agugccgcac c                                              21

<210> SEQ ID NO 155
<211> LENGTH: 21
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(21)
<223> OTHER INFORMATION: HCV Torch 316-331 5F3D

<400> SEQUENCE: 155
gauagggugc uugcgacuau c                                              21

<210> SEQ ID NO 156
<211> LENGTH: 21
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(21)
<223> OTHER INFORMATION: HCV Torch 314-329 5F3D

<400> SEQUENCE: 156
cugauagggu gcuugcauca g                                              21

<210> SEQ ID NO 157
<211> LENGTH: 21
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(21)
<223> OTHER INFORMATION: HCV Torch 310-325 5F3D

<400> SEQUENCE: 157
cugccugaua ggguugcggca g                                             21

<210> SEQ ID NO 158
<211> LENGTH: 21
```

```
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(21)
<223> OTHER INFORMATION: HCV Torch 307-322 5F3D

<400> SEQUENCE: 158
guacugccug auagggagua c                                              21

<210> SEQ ID NO 159
<211> LENGTH: 21
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(21)
<223> OTHER INFORMATION: HCV Torch 306-321 5F3D

<400> SEQUENCE: 159
gguacugccu gauaggguac c                                              21

<210> SEQ ID NO 160
<211> LENGTH: 20
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(20)
<223> OTHER INFORMATION: HCV Torch 300-314 5F3D

<400> SEQUENCE: 160
ccuuguggua cugcccaagg                                                20

<210> SEQ ID NO 161
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(45)
<223> OTHER INFORMATION: Target capture oligomer; HCV0168-186(-) dT3dA30
<220> FEATURE:
<221> NAME/KEY: misc_feature
<222> LOCATION: (20)..(45)
<223> OTHER INFORMATION: Immobilized probe-binding region: Tail

<400> SEQUENCE: 161
auuccggugu acucaccggt ttaaaaaaaa aaaaaaaaa aaaaa                      45

<210> SEQ ID NO 162
<211> LENGTH: 44
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(44)
<223> OTHER INFORMATION: Target capture oligomer; HCV0157-174(-) dT3dA30
<220> FEATURE:
<221> NAME/KEY: misc_feature
<222> LOCATION: (19)..(44)
```

<223> OTHER INFORMATION: Immobilized probe-binding region: Tail

<400> SEQUENCE: 162
ucaccgguuc cgcagaccut taaaaaaaaa aaaaaaaaaa aaaa                         44

<210> SEQ ID NO 163
<211> LENGTH: 46
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(46)
<223> OTHER INFORMATION: Target capture oligomer; HCV0154-173(-) dT3dA30
<220> FEATURE:
<221> NAME/KEY: misc_feature
<222> LOCATION: (21)..(46)
<223> OTHER INFORMATION: Immobilized probe-binding region: Tail

<400> SEQUENCE: 163
caccgguucc gcagaccacu tttaaaaaaa aaaaaaaaaa aaaaaa                       46

<210> SEQ ID NO 164
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(45)
<223> OTHER INFORMATION: Target capture oligomer; HCV0143-161(-) dT3dA30
<220> FEATURE:
<221> NAME/KEY: misc_feature
<222> LOCATION: (20)..(45)
<223> OTHER INFORMATION: Immobilized probe-binding region: Tail

<400> SEQUENCE: 164
agaccacuau ggcucuccct ttaaaaaaaa aaaaaaaaaa aaaaa                        45

<210> SEQ ID NO 165
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(45)
<223> OTHER INFORMATION: Target capture oligomer; HCV0141-159(-) dT3dA30
<220> FEATURE:
<221> NAME/KEY: misc_feature
<222> LOCATION: (20)..(45)
<223> OTHER INFORMATION: Immobilized probe-binding region: Tail

<400> SEQUENCE: 165
accacuaugg cucucccggt ttaaaaaaaa aaaaaaaaaa aaaaa                        45

<210> SEQ ID NO 166
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV-1a NT7 A clone

<400> SEQUENCE: 166
ggaactaatg tcttcacgca gaaagcg                                27

<210> SEQ ID NO 167
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 C-T-A-A clone

<400> SEQUENCE: 167
gcgttagtat gagcgttgta caacctccag g                           31

<210> SEQ ID NO 168
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 T-A

<400> SEQUENCE: 168
gcgttagtat gagtgttgta cagcctccag g                           31

<210> SEQ ID NO 169
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 A-A

<400> SEQUENCE: 169
acgttagtat gagtgtcgta cagcctccag g                           31

<210> SEQ ID NO 170
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV-1a NT7  T-T-A

<400> SEQUENCE: 170
ggaattactg ttttaacgca gaaagcg                                27

<210> SEQ ID NO 171
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV-5a NT7 T

<400> SEQUENCE: 171
ggaactactt tcttcacgca gaaagcg                                                 27

<210> SEQ ID NO 172
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV-5a NT7 C-C

<400> SEQUENCE: 172
ggaaccactg tcctcacgca gaaagcg                                                 27

<210> SEQ ID NO 173
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV-1a NT7 T

<400> SEQUENCE: 173
ggaactactg tcttcacgca gaaagtg                                                 27

<210> SEQ ID NO 174
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 T-C

<400> SEQUENCE: 174
gcgttagtat gagtgttgca cagcctccag g                                            31

<210> SEQ ID NO 175
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 A-C-G

<400> SEQUENCE: 175
gcgttaatac gagtgtcgtg cagcctccag g                                            31

<210> SEQ ID NO 176
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 C-C-C-G

<400> SEQUENCE: 176
gcgttaccac gagtgtcgtg cagcctccag g                               31

<210> SEQ ID NO 177
<211> LENGTH: 16
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(16)
<223> OTHER INFORMATION: HCV-1a Tch A-C

<400> SEQUENCE: 177
taaccctggc gttagt                                                16

<210> SEQ ID NO 178
<211> LENGTH: 16
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(16)
<223> OTHER INFORMATION: HCV-1a Tch C

<400> SEQUENCE: 178
tagccctggc gttagt                                                16

<210> SEQ ID NO 179
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV-1a NT EF424625

<400> SEQUENCE: 179
ggaactattg tcttcacgca gaaagcg                                    27

<210> SEQ ID NO 180
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV-1a NT DQ295833

<400> SEQUENCE: 180
ggtactactg tcttcacgca gaaagcg                                    27

<210> SEQ ID NO 181
<211> LENGTH: 33
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(33)

<223> OTHER INFORMATION: HCV-1a T7 DQ295833

<400> SEQUENCE: 181
gcagttagta tagagtgtcg tacagcctcc agg                                    33

<210> SEQ ID NO 182
<211> LENGTH: 19
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(19)
<223> OTHER INFORMATION: HCV-1a TCO DQ295833

<400> SEQUENCE: 182
aaggtgcttg cgagtcgcc                                                    19

<210> SEQ ID NO 183
<211> LENGTH: 17
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(17)
<223> OTHER INFORMATION: HCV-1a Tch AJ621232

<400> SEQUENCE: 183
tagcccctgg cgttagt                                                      17

<210> SEQ ID NO 184
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV-1a NT EU360317

<400> SEQUENCE: 184
ggaactgctg tcttcccgca gaaagcg                                           27

<210> SEQ ID NO 185
<211> LENGTH: 25
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(25)
<223> OTHER INFORMATION: HCV-3a NT AJ621233

<400> SEQUENCE: 185
gaacttttgt tttcacggaa aagcg                                             25

<210> SEQ ID NO 186
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature

```
<222> LOCATION: (1)..(31)
<223> OTHER INFORMATION: HCV-1a T7 FJ696476

<400> SEQUENCE: 186
gcgtctgtat gagtttcggg cagcctccag g                                31

<210> SEQ ID NO 187
<211> LENGTH: 16
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(16)
<223> OTHER INFORMATION: HCV-1a Tch FJ696480

<400> SEQUENCE: 187
tagccatggc gctagt                                                 16

<210> SEQ ID NO 188
<211> LENGTH: 16
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(16)
<223> OTHER INFORMATION: HCV-1a Tch FJ696498

<400> SEQUENCE: 188
tagccatggc gcttgt                                                 16

<210> SEQ ID NO 189
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 FJ696503

<400> SEQUENCE: 189
gcgcttttat gagcgtcgtg cagcctccag g                                31

<210> SEQ ID NO 190
<211> LENGTH: 16
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(16)
<223> OTHER INFORMATION: HCV-1a Tch EU360323

<400> SEQUENCE: 190
tagccatggc gtcagt                                                 16

<210> SEQ ID NO 191
<211> LENGTH: 16
<212> TYPE: DNA
<213> ORGANISM: Artificial Sequence
<220> FEATURE:
<223> OTHER INFORMATION: Synthetic Oligomer
<220> FEATURE:
```

```
<221> NAME/KEY: misc_feature
<222> LOCATION: (1)..(16)
<223> OTHER INFORMATION: HCV-3a Tch FJ696423

<400> SEQUENCE: 191
tagctatggc gttagt                                                        16

<210> SEQ ID NO 192
<211> LENGTH: 32
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(32)
<223> OTHER INFORMATION: HCV-1a T7 AJ621237

<400> SEQUENCE: 192
gcgttatcca cgagtgtcgt gcagcctcca gg                                      32

<210> SEQ ID NO 193
<211> LENGTH: 19
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(19)
<223> OTHER INFORMATION: HCV-1a TCO DQ071885

<400> SEQUENCE: 193
agggtgcgtg caagtgccc                                                     19

<210> SEQ ID NO 194
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 FJ696420

<400> SEQUENCE: 194
gcgttagtac gagtgtcgtg caccctctag g                                       31

<210> SEQ ID NO 195
<211> LENGTH: 16
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(16)
<223> OTHER INFORMATION: HCV-1a Tch GU451220

<400> SEQUENCE: 195
tagtgctggc gttagt                                                        16

<210> SEQ ID NO 196
<211> LENGTH: 19
<212> TYPE: DNA
<213> ORGANISM: Artificial Sequence
<220> FEATURE:
<223> OTHER INFORMATION: Synthetic Oligomer
```

```
<220> FEATURE:
<221> NAME/KEY: misc_feature
<222> LOCATION: (1)..(19)
<223> OTHER INFORMATION: HCV-1a TCO EU360321

<400> SEQUENCE: 196
aggttgcttg cgagtgccc                                                        19

<210> SEQ ID NO 197
<211> LENGTH: 19
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(19)
<223> OTHER INFORMATION: HCV-3a TCO HM043011

<400> SEQUENCE: 197
agggcgcttg cgagtgccc                                                        19

<210> SEQ ID NO 198
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV-1a NT DQ295833

<400> SEQUENCE: 198
ggtactactg tcttcacgca gaaagcg                                               27

<210> SEQ ID NO 199
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 FJ696429 E(12)

<400> SEQUENCE: 199
gcgttagtat gagtgtcgtg cagcctccaa g                                          31

<210> SEQ ID NO 200
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 FJ696458 G(10)

<400> SEQUENCE: 200
gcgctagtat gagtgtcgtg cagcctccag g                                          31

<210> SEQ ID NO 201
<211> LENGTH: 31
<212> TYPE: DNA
<213> ORGANISM: Artificial Sequence
<220> FEATURE:
```

<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 FJ696439 I(4)

<400> SEQUENCE: 201
gcgttagtat gaatgtcgtg cagcctccag g        31

<210> SEQ ID NO 202
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 FJ696473 J(3)

<400> SEQUENCE: 202
gcgtcagtat gagtgtcgtg cagcctccag g        31

<210> SEQ ID NO 203
<211> LENGTH: 30
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(30)
<223> OTHER INFORMATION: HCV-1a T7 AJ621233 K(2)

<400> SEQUENCE: 203
gcgttagacg agtgtcgtgc agcctccagg         30

<210> SEQ ID NO 204
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 DQ071885 L(2)

<400> SEQUENCE: 204
gcgttagtat gagtgtcgtg cagcctccat g        31

<210> SEQ ID NO 205
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 AJ621234 M(2)

<400> SEQUENCE: 205
gcgttagtac gagtgtcgtg cagcatccag g        31

<210> SEQ ID NO 206
<211> LENGTH: 31
<212> TYPE: DNA
<213> ORGANISM: Artificial Sequence

```
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 FJ696431 N(2)

<400> SEQUENCE: 206
gcgttagtat gagagtcgtg cagcctccag g                                    31

<210> SEQ ID NO 207
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 EU360320 O(2)

<400> SEQUENCE: 207
gcgttagtat gagtgacgtg cagcctccag g                                    31

<210> SEQ ID NO 208
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 FJ696486

<400> SEQUENCE: 208
gcgctagtat gagcgtcgtg cagcctccag g                                    31

<210> SEQ ID NO 209
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 FJ696498

<400> SEQUENCE: 209
gcgcttgtat gagtgtcgtg cagcctccag g                                    31

<210> SEQ ID NO 210
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 FJ696503 mod

<400> SEQUENCE: 210
gcgtttttat gagcgtcgtg cagcctccag g                                    31

<210> SEQ ID NO 211
<211> LENGTH: 32
<212> TYPE: DNA
```

<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(32)
<223> OTHER INFORMATION: HCV-1a T7 AJ621237 mod

<400> SEQUENCE: 211
gcgttatcca tgagtgtcgt gcagcctcca gg                          32

<210> SEQ ID NO 212
<211> LENGTH: 31
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(31)
<223> OTHER INFORMATION: HCV-1a T7 FJ696428

<400> SEQUENCE: 212
gcgttagtat gagagtcgtg cagccccag g                            31

<210> SEQ ID NO 213
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(27)
<223> OTHER INFORMATION: HCV-3a NT FJ790793 F(2)

<400> SEQUENCE: 213
ggaatttctg tcttcacgcg gaaagcg                                27

<210> SEQ ID NO 214
<211> LENGTH: 19
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(19)
<223> OTHER INFORMATION: HCV-1a TCO EU360322 H(2)

<400> SEQUENCE: 214
agggtgcttg cgaatgccc                                         19

<210> SEQ ID NO 215
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(27)
<223> OTHER INFORMATION: HCV non-T7 primer

<400> SEQUENCE: 215
ggaacttctg tcttcacgca gaaagcg                                27

<210> SEQ ID NO 216
<211> LENGTH: 24

```
<212> TYPE: RNA
<213> ORGANISM: Artificial Sequence
<220> FEATURE:
<223> OTHER INFORMATION: HCV torch
<220> FEATURE:
<221> NAME/KEY: misc_feature
<222> LOCATION: (1)..(25)
<223> OTHER INFORMATION: Molecular torch hybridization probe
<220> FEATURE:
<221> NAME/KEY: misc_feature
<222> LOCATION: (19)..(20)
<223> OTHER INFORMATION: Non-nucleotide C9 linker located between base
      positions 19-20

<400> SEQUENCE: 216
cuagccaugg cguuaguaug cuag                                              24

<210> SEQ ID NO 217
<211> LENGTH: 25
<212> TYPE: RNA
<213> ORGANISM: Artificial Sequence
<220> FEATURE:
<223> OTHER INFORMATION: HCV torch
<220> FEATURE:
<221> NAME/KEY: misc_feature
<222> LOCATION: (1)..(26)
<223> OTHER INFORMATION: Molecular torch hybridization probe
<220> FEATURE:
<221> NAME/KEY: misc_feature
<222> LOCATION: (20)..(21)
<223> OTHER INFORMATION: Non-nucleotide C9 linker located between base
      positions 20-21

<400> SEQUENCE: 217
gcuagccaug gcguuaguau cuagc                                             25

<210> SEQ ID NO 218
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(48)
<223> OTHER INFORMATION: HCV T7 promoter primer

<400> SEQUENCE: 218
aatttaatac gactcactat agggagacct ggaggctgca cgacactc                    48

<210> SEQ ID NO 219
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(48)
<223> OTHER INFORMATION: HCV T7 promoter primer
<220> FEATURE:
<221> NAME/KEY: misc_feature
<222> LOCATION: (39)..(39)
<223> OTHER INFORMATION: Position 39 occupied by inosine

<400> SEQUENCE: 219
aatttaatac gactcactat agggagacct ggaggctgna cgacactc                    48

<210> SEQ ID NO 220
<211> LENGTH: 58
<212> TYPE: DNA
```

```
<213> ORGANISM: Artificial Sequence
<220> FEATURE:
<223> OTHER INFORMATION: Primer
<220> FEATURE:
<221> NAME/KEY: misc_feature
<222> LOCATION: (1)..(58)
<223> OTHER INFORMATION: HCV T7 promoter priimer
<220> FEATURE:
<221> NAME/KEY: misc_feature
<222> LOCATION: (1)..(58)
<223> OTHER INFORMATION: HCV T7 89-119 (-); or DNA, HCV(-)89-119 T7_3 ;
      or DNA, HCV(-)89-119 T7

<400> SEQUENCE: 220
aatttaatac gactcactat agggagacct ggaggctgca cgacactcat actaacgc          58

<210> SEQ ID NO 221
<211> LENGTH: 33
<212> TYPE: DNA
<213> ORGANISM: Artificial Sequence
<220> FEATURE:
<223> OTHER INFORMATION: In vitro transcript mutant
<220> FEATURE:
<221> NAME/KEY: misc_feature
<222> LOCATION: (1)..(33)
<223> OTHER INFORMATION: HCV-1a T7-NT7 DQ295833

<400> SEQUENCE: 221
gcagttagta tagagtgtcg tacagcctcc agg                                    33

<210> SEQ ID NO 222
<211> LENGTH: 54
<212> TYPE: DNA
<213> ORGANISM: Artificial Sequence
<220> FEATURE:
<223> OTHER INFORMATION: T7 promoter-primer
<220> FEATURE:
<221> NAME/KEY: misc_feature
<222> LOCATION: (1)..(54)
<223> OTHER INFORMATION: HCV T7 93-119 (-) _ti primer
<220> FEATURE:
<221> NAME/KEY: modified_base
<222> LOCATION: (39)..(39)
<223> OTHER INFORMATION: Position 39 occupied by inosine

<400> SEQUENCE: 222
aatttaatac gactcactat agggagacct ggaggctgnt cgacactcat acta             54

<210> SEQ ID NO 223
<211> LENGTH: 54
<212> TYPE: DNA
<213> ORGANISM: Artificial Sequence
<220> FEATURE:
<223> OTHER INFORMATION: T7 promoter-primer
<220> FEATURE:
<221> NAME/KEY: misc_feature
<222> LOCATION: (1)..(54)
<223> OTHER INFORMATION: HCV T7 93-119 (-) _i
<220> FEATURE:
<221> NAME/KEY: misc_feature
<222> LOCATION: (39)..(39)
<223> OTHER INFORMATION: Position 39 occupied by inosine

<400> SEQUENCE: 223
aatttaatac gactcactat agggagacct ggaggctgna cgacactcat acta             54

<210> SEQ ID NO 224
<211> LENGTH: 100
<212> TYPE: RNA
<213> ORGANISM: Hepatitis C virus
<220> FEATURE:
```

<221> NAME/KEY: misc_feature
<222> LOCATION: (1)..(100)
<223> OTHER INFORMATION: HCV 1A gp ivt_1 transcript

<400> SEQUENCE: 224
ugaggaacua cugucuucac gcagaaagcg ucuagccaug gcguuaguau gaguguucgug    60 cagccuccag gacccccccu cccgggagag ccauaguggu                          100

<210> SEQ ID NO 225
<211> LENGTH: 100
<212> TYPE: RNA
<213> ORGANISM: Hepatitis C virus
<220> FEATURE:
<221> NAME/KEY: misc_feature
<222> LOCATION: (1)..(100)
<223> OTHER INFORMATION: HCV 2b Transcript IA, and HCV 6a Transcript IA

<400> SEQUENCE: 225
ugaggaacua cugucuucac gcagaaagcg ucuagccaug gcguuaguau gaguguucgua    60 cagccuccag gccccccccu cccgggagag ccauaguggu                          100

<210> SEQ ID NO 226
<211> LENGTH: 100
<212> TYPE: DNA
<213> ORGANISM: Hepatitis C virus
<220> FEATURE:
<221> NAME/KEY: misc_feature
<222> LOCATION: (1)..(100)
<223> OTHER INFORMATION: HCV 3a IVT PCR sequence (consensus)

<400> SEQUENCE: 226
tgaggaactt ctgtcttcac gcggaaagcg cctagccatg gcgttagtac gagtgtcgtg    60
cagcctccag gccccccct cccgggagag ccatagtggt                           100

<210> SEQ ID NO 227
<211> LENGTH: 100
<212> TYPE: RNA
<213> ORGANISM: Hepatitis C virus
<220> FEATURE:
<221> NAME/KEY: misc_feature
<222> LOCATION: (1)..(100)
<223> OTHER INFORMATION: HCV-3a IVT sequence IA

<400> SEQUENCE: 227
ugaggaacuu cugucuucac gcggaaagcg ccuagccaug gcguuaguac gaguguucgug    60 cagccuccag gccccccccu cccgggagag ccauaguggu                          100

<210> SEQ ID NO 228
<211> LENGTH: 100
<212> TYPE: RNA
<213> ORGANISM: Hepatitis C virus
<220> FEATURE:
<221> NAME/KEY: misc_feature
<222> LOCATION: (1)..(100)
<223> OTHER INFORMATION: HCV 3b Transcript IA pBlu_1

<400> SEQUENCE: 228
ugaggaacuu cugucuucac gcggaaagcg ucuagccaug gcguuaguac gaguguucgug    60 cagccuccag gccccccccu cccgggagag ccauaguggu                          100

<210> SEQ ID NO 229
<211> LENGTH: 100
<212> TYPE: RNA
<213> ORGANISM: Hepatitis C virus

```
<220> FEATURE:
<221> NAME/KEY: misc_feature
<222> LOCATION: (1)..(100)
<223> OTHER INFORMATION: HCV 4h Transcript IA_1

<400> SEQUENCE: 229
ugaggaacua cugucuucac gcagaaagcg ucuagccaug gcguuaguau gaguguugug      60
cagccuccag gaucccccu cccgggagag ccauagguggu                           100

<210> SEQ ID NO 230
<211> LENGTH: 100
<212> TYPE: RNA
<213> ORGANISM: Hepatitis C virus
<220> FEATURE:
<221> NAME/KEY: misc_feature
<222> LOCATION: (1)..(100)
<223> OTHER INFORMATION: HCV 5a Transcript IA

<400> SEQUENCE: 230
ugaggaacua cugucuucac gcagaaagcg ucuagccaug gcguuaguau gagugucgaa      60
cagccuccag gaccccccu cccgggagag ccauagguggu                           100

<210> SEQ ID NO 231
<211> LENGTH: 107
<212> TYPE: RNA
<213> ORGANISM: Hepatitis C virus
<220> FEATURE:
<221> NAME/KEY: misc_feature
<222> LOCATION: (1)..(107)
<223> OTHER INFORMATION: HCV 1A gp ivt_1 transcript, and HCV 6a gp ivt
      transcript

<400> SEQUENCE: 231
uccccuguga ggaacuacug ucuucacgca gaaagcgucu agccauggcg uuaguaugag      60
ugucgugcag ccuccaggac ccccccuccc gggagagcca uagggu                    107

<210> SEQ ID NO 232
<211> LENGTH: 107
<212> TYPE: RNA
<213> ORGANISM: Hepatitis C virus
<220> FEATURE:
<221> NAME/KEY: misc_feature
<222> LOCATION: (1)..(107)
<223> OTHER INFORMATION: HCV 2B gp ivt_1 transcript

<400> SEQUENCE: 232
uccccuguga ggaacuacug ucuucacgca gaaagcgucu agccauggcg uuaguaugag      60
ugucguacag ccuccaggcc ccccccuccc gggagagcca uagggu                    107

<210> SEQ ID NO 233
<211> LENGTH: 107
<212> TYPE: RNA
<213> ORGANISM: Hepatitis C virus
<220> FEATURE:
<221> NAME/KEY: misc_feature
<222> LOCATION: (1)..(107)
<223> OTHER INFORMATION: HCV 3A gp ivt transcript

<400> SEQUENCE: 233
gcccuuguga ggaacuucug ucuucacgcg gaaagcgccu agccauggcg uuaguacgag      60
ugucgugcag ccuccaggcc ccccccuccc gggagagcca uagggu                    107

<210> SEQ ID NO 234
<211> LENGTH: 107
```

<212> TYPE: RNA
<213> ORGANISM: Hepatitis C virus
<220> FEATURE:
<221> NAME/KEY: misc_feature
<222> LOCATION: (1)..(107)
<223> OTHER INFORMATION: HCV 3b Transcript IA pBlu

<400> SEQUENCE: 234
uccccuguga ggaacuucug ucuucacgcg gaaagcgucu agccauggcg uuaguacgag 60
ugucgugcag ccuccaggcc ccccccuccc gggagagcca uaguggu 107

<210> SEQ ID NO 235
<211> LENGTH: 107
<212> TYPE: RNA
<213> ORGANISM: Hepatitis C virus
<220> FEATURE:
<221> NAME/KEY: misc_feature
<222> LOCATION: (1)..(107)
<223> OTHER INFORMATION: HCV 4h gp ivt transcript

<400> SEQUENCE: 235
uccccuguga ggaacuacug ucuucacgca gaaagcgucu agccauggcg uuaguaugag 60
uguugugcag ccuccaggau ccccccuccc gggagagcca uaguggu 107

<210> SEQ ID NO 236
<211> LENGTH: 87
<212> TYPE: RNA
<213> ORGANISM: Hepatitis C virus
<220> FEATURE:
<221> NAME/KEY: misc_feature
<222> LOCATION: (1)..(87)
<223> OTHER INFORMATION: PHW201_08_fwd (5a subtype)_1

<400> SEQUENCE: 236
ucuucacgca gaaagcgucu agccauggcg uuaguaugag ugucgaacag ccuccaggac 60
ccccccuccc gggagagcca uaguggu 87

<210> SEQ ID NO 237
<211> LENGTH: 62
<212> TYPE: DNA
<213> ORGANISM: Artificial Sequence
<220> FEATURE:
<223> OTHER INFORMATION: T7 promoter-primer
<220> FEATURE:
<221> NAME/KEY: misc_feature
<222> LOCATION: (1)..(62)
<223> OTHER INFORMATION: HCV T7 85-119 (-)

<400> SEQUENCE: 237
aatttaatac gactcactat agggagacct ggaggctgca cgacactcat actaacgcca 60
tg 62

<210> SEQ ID NO 238
<211> LENGTH: 45
<212> TYPE: DNA
<213> ORGANISM: Artificial Sequence
<220> FEATURE:
<223> OTHER INFORMATION: HCV Target Capture Oligonucleotide (TCO)
<220> FEATURE:
<221> NAME/KEY: misc_feature
<222> LOCATION: (1)..(45)
<223> OTHER INFORMATION: HCV 0297(-)dT3dA30_5_1

<400> SEQUENCE: 238
gggcacucgc aagcacccut ttaaaaaaaa aaaaaaaaaa aaaaa 45

<210> SEQ ID NO 239
<211> LENGTH: 66
<212> TYPE: DNA
<213> ORGANISM: Hepatitis C virus
<220> FEATURE:
<221> NAME/KEY: misc_feature
<222> LOCATION: (1)..(66)
<223> OTHER INFORMATION: Combined T7 NT torch HCV not real_1 US5

<400> SEQUENCE: 239
ggaacttctg tcttcacgcg gaaagcguag ccauggcguu aguaugagug tcgtgcagcc    60
tccagg    66

<210> SEQ ID NO 240
<211> LENGTH: 78
<212> TYPE: DNA
<213> ORGANISM: Hepatitis C virus
<220> FEATURE:
<221> NAME/KEY: misc_feature
<222> LOCATION: (1)..(78)
<223> OTHER INFORMATION: HCV 1a plasmid_Mfg_M/N 400602

<400> SEQUENCE: 240
cccctgtgag gaactactgt cttcacgcag aaagcgtcta gccatggcgt tagtatgagt    60
gtcgtacagc ctccagga    78

<210> SEQ ID NO 241
<211> LENGTH: 72
<212> TYPE: RNA
<213> ORGANISM: Hepatitis C virus
<220> FEATURE:
<221> NAME/KEY: misc_feature
<222> LOCATION: (1)..(72)
<223> OTHER INFORMATION: HCV 1a Transcript_E0

<400> SEQUENCE: 241
ugaggaacua cugucuucac gcagaaagcg ucuagccaug gcguuaguau gagugucgug    60
cagccuccag ga    72

<210> SEQ ID NO 242
<211> LENGTH: 72
<212> TYPE: RNA
<213> ORGANISM: Hepatitis C virus
<220> FEATURE:
<221> NAME/KEY: misc_feature
<222> LOCATION: (1)..(72)
<223> OTHER INFORMATION: HCV 2b Transcript_E0; and pBS(+)HCV-6a IVT
      sequence

<400> SEQUENCE: 242
ugaggaacua cugucuucac gcagaaagcg ucuagccaug gcguuaguau gagugucgua    60
cagccuccag gc    72

<210> SEQ ID NO 243
<211> LENGTH: 78
<212> TYPE: RNA
<213> ORGANISM: Hepatitis C virus
<220> FEATURE:
<221> NAME/KEY: misc_feature
<222> LOCATION: (1)..(78)
<223> OTHER INFORMATION: pBS(+)GCV-3a V2 IVT sequence

<400> SEQUENCE: 243
agcuugugag gaacuucugu cuucacgcgg aaagcgccua gccauggcgu uaguacgagu    60
gucgugcagc cuccaggc                                                   78

<210> SEQ ID NO 244
<211> LENGTH: 72
<212> TYPE: RNA
<213> ORGANISM: Hepatitis C virus
<220> FEATURE:
<221> NAME/KEY: misc_feature
<222> LOCATION: (1)..(72)
<223> OTHER INFORMATION: pBS(+)HCV-3b IVT sequence

<400> SEQUENCE: 244
ugaggaacuu cugucuucac gcggaaagcg ucuagccaug gcguuaguac gagugucgug    60
cagccuccag gc                                                         72

<210> SEQ ID NO 245
<211> LENGTH: 72
<212> TYPE: RNA
<213> ORGANISM: Hepatitis C virus
<220> FEATURE:
<221> NAME/KEY: misc_feature
<222> LOCATION: (1)..(72)
<223> OTHER INFORMATION: pBS(+)HCV-4h IVT sequence

<400> SEQUENCE: 245
ugaggaacua cugucuucac gcagaaagcg ucuagccaug gcguuaguau gaguguugug    60
cagccuccag ga                                                         72

<210> SEQ ID NO 246
<211> LENGTH: 72
<212> TYPE: RNA
<213> ORGANISM: Hepatitis C virus
<220> FEATURE:
<221> NAME/KEY: misc_feature
<222> LOCATION: (1)..(72)
<223> OTHER INFORMATION: pBS(+)HCV-5a IVT sequence

<400> SEQUENCE: 246
ugaggaacua cugucuucac gcagaaagcg ucuagccaug gcguuaguau gagugucgaa    60
cagccuccag ga                                                         72

<210> SEQ ID NO 247
<211> LENGTH: 77
<212> TYPE: DNA
<213> ORGANISM: Hepatitis C virus
<220> FEATURE:
<221> NAME/KEY: misc_feature
<222> LOCATION: (1)..(77)
<223> OTHER INFORMATION: HCV 1a plasmid_Mfg_M/N 400602

<400> SEQUENCE: 247
ctgtgaggaa ctactgtctt cacgcagaaa gcgtctagcc atggcgttag tatgagtgtc    60
gtacagcctc caggacc                                                    77

<210> SEQ ID NO 248
<211> LENGTH: 74
<212> TYPE: RNA
<213> ORGANISM: Hepatitis C virus
<220> FEATURE:
<221> NAME/KEY: misc_feature
<222> LOCATION: (1)..(74)
<223> OTHER INFORMATION: HCV 1a Transcript_EO

<400> SEQUENCE: 248
ugaggaacua cugucuucac gcagaaagcg ucuagccaug gcguuaguau gagugucgug    60

```
cagccuccag gacc                                                         74

<210> SEQ ID NO 249
<211> LENGTH: 74
<212> TYPE: RNA
<213> ORGANISM: Hepatitis C virus
<220> FEATURE:
<221> NAME/KEY: misc_feature
<222> LOCATION: (1)..(74)
<223> OTHER INFORMATION: HCV 2b Transcript_EO

<400> SEQUENCE: 249
ugaggaacua cugucuucac gcagaaagcg ucuagccaug gcguuaguau gagugucgua       60
cagccuccag gccc                                                         74

<210> SEQ ID NO 250
<211> LENGTH: 77
<212> TYPE: RNA
<213> ORGANISM: Hepatitis C virus
<220> FEATURE:
<221> NAME/KEY: misc_feature
<222> LOCATION: (1)..(77)
<223> OTHER INFORMATION: pBS(+)GCV-3a V2 IVT sequence

<400> SEQUENCE: 250
uugugaggaa cuucugucuu cacgcggaaa gcgccuagcc auggcguuag uacgaguguc       60
gugcagccuc caggccc                                                      77

<210> SEQ ID NO 251
<211> LENGTH: 74
<212> TYPE: RNA
<213> ORGANISM: Hepatitis C virus
<220> FEATURE:
<221> NAME/KEY: misc_feature
<222> LOCATION: (1)..(74)
<223> OTHER INFORMATION: pBS(+)HCV-3b IVT sequence

<400> SEQUENCE: 251
ugaggaacuu cugucuucac gcggaaagcg ucuagccaug gcguuaguac gagugucgug       60
cagccuccag gccc                                                         74

<210> SEQ ID NO 252
<211> LENGTH: 74
<212> TYPE: RNA
<213> ORGANISM: Hepatitis C virus
<220> FEATURE:
<221> NAME/KEY: misc_feature
<222> LOCATION: (1)..(74)
<223> OTHER INFORMATION: pBS(+)HCV-4h IVT sequence

<400> SEQUENCE: 252
ugaggaacua cugucuucac gcagaaagcg ucuagccaug gcguuaguau gaguguugug       60
cagccuccag gauc                                                         74

<210> SEQ ID NO 253
<211> LENGTH: 74
<212> TYPE: RNA
<213> ORGANISM: Hepatitis C virus
<220> FEATURE:
<221> NAME/KEY: misc_feature
<222> LOCATION: (1)..(74)
<223> OTHER INFORMATION: pBS(+)HCV-5a IVT sequence

<400> SEQUENCE: 253
```
ugaggaacua cugucuucac gcagaaagcg ucuagccaug gcguuaguau gagugucgaa        60
cagccuccag gacc                                                          74

<210> SEQ ID NO 254
<211> LENGTH: 75
<212> TYPE: RNA
<213> ORGANISM: Hepatitis C virus
<220> FEATURE:
<221> NAME/KEY: misc_feature
<222> LOCATION: (1)..(75)
<223> OTHER INFORMATION: pBS(+)HCV-6a IVT sequence

<400> SEQUENCE: 254
ugaggaacua cugucuucac gcagaaagcg ucuagccaug gcguuaguau gagugucgua        60
cagccuccag guccc                                                         75

<210> SEQ ID NO 255
<211> LENGTH: 77
<212> TYPE: DNA
<213> ORGANISM: Hepatitis C virus
<220> FEATURE:
<221> NAME/KEY: misc_feature
<222> LOCATION: (1)..(77)
<223> OTHER INFORMATION: HCV-1a T7 CTT FJ696420

<400> SEQUENCE: 255
ctgtgaggaa ctactgtctt cacgcagaaa gcgtctagcc atggcgttag tacgagtgtc        60
gtgcaccctc taggacc                                                       77

<210> SEQ ID NO 256
<211> LENGTH: 77
<212> TYPE: DNA
<213> ORGANISM: Hepatitis C virus
<220> FEATURE:
<221> NAME/KEY: misc_feature
<222> LOCATION: (1)..(77)
<223> OTHER INFORMATION: HCV-1a T7 CTTC FJ696503

<400> SEQUENCE: 256
ctgtgaggaa ctactgtctt cacgcagaaa gcgtctagcc atggcgcttt tatgagcgtc        60
gtgcagcctc caggacc                                                       77

<210> SEQ ID NO 257
<211> LENGTH: 77
<212> TYPE: RNA
<213> ORGANISM: Hepatitis C virus
<220> FEATURE:
<221> NAME/KEY: misc_feature
<222> LOCATION: (1)..(77)
<223> OTHER INFORMATION: HCV-5a NT7 C-C IVT sequence

<400> SEQUENCE: 257
cugugaggaa ccacuguccu cacgcagaaa gcgucuagcc auggcguuag uaugaguguc        60
gaacagccuc caggacc                                                       77

<210> SEQ ID NO 258
<211> LENGTH: 77
<212> TYPE: DNA
<213> ORGANISM: Hepatitis C virus
<220> FEATURE:
<221> NAME/KEY: misc_feature
<222> LOCATION: (1)..(77)
<223> OTHER INFORMATION: HCV-3a NT TTCA AJ621233

<400> SEQUENCE: 258

```
uugugaggaa cuuuugullll cacggagaaa gcgccuagcc auggcguuag uacgagugUC    60
gugcagccuc caggccc                                                    77
```

<210> SEQ ID NO 259
<211> LENGTH: 77
<212> TYPE: RNA
<213> ORGANISM: Hepatitis C virus
<220> FEATURE:
<221> NAME/KEY: misc_feature
<222> LOCATION: (1)..(77)
<223> OTHER INFORMATION: HCV-5a NT7 T IVT sequence

<400> SEQUENCE: 259

```
cugugaggaa cuacuuucuu cacgcagaaa gcgucuagcc auggcguuag uaugagugUC    60
gaacagccuc caggacc                                                    77
```

<210> SEQ ID NO 260
<211> LENGTH: 77
<212> TYPE: RNA
<213> ORGANISM: Hepatitis C virus
<220> FEATURE:
<221> NAME/KEY: misc_feature
<222> LOCATION: (1)..(77)
<223> OTHER INFORMATION: HCV-1a NT7 T-T-A IVT sequence

<400> SEQUENCE: 260

```
cugugaggaa uuacuguuuu aacgcagaaa gcgucuagcc auggcguuag uaugagugUC    60
guacagccuc caggacc                                                    77
```

<210> SEQ ID NO 261
<211> LENGTH: 77
<212> TYPE: RNA
<213> ORGANISM: Hepatitis C virus
<220> FEATURE:
<221> NAME/KEY: misc_feature
<222> LOCATION: (1)..(77)
<223> OTHER INFORMATION: HCV 1a T7 C-T-A-A IVT sequence

<400> SEQUENCE: 261

```
cugugaggaa cuacugucuu cacgcagaaa gcgucuagcc auggcguuag uaugagcguu    60
guacaaccuc caggacc                                                    77
```

<210> SEQ ID NO 262
<211> LENGTH: 77
<212> TYPE: DNA
<213> ORGANISM: Hepatitis C virus
<220> FEATURE:
<221> NAME/KEY: misc_feature
<222> LOCATION: (1)..(77)
<223> OTHER INFORMATION: HCV-1a T7 CTTG FJ696476

<400> SEQUENCE: 262

```
ctgtgaggaa ctactgtctt cacgcagaaa gcgtctagcc atggcgtctg tatgagtttc    60
gggcagcctc caggacc                                                    77
```

<210> SEQ ID NO 263
<211> LENGTH: 77
<212> TYPE: RNA
<213> ORGANISM: Hepatitis C virus
<220> FEATURE:
<221> NAME/KEY: misc_feature
<222> LOCATION: (1)..(77)
<223> OTHER INFORMATION: HCV 1a T7 T-C IVT sequence

```
<400> SEQUENCE: 263
cugugaggaa cuacugucuu cacgcagaaa gcgucuagcc auggcguuag uaugagiguu    60 gcacagccuc caggacc                                                  77

<210> SEQ ID NO 264
<211> LENGTH: 78
<212> TYPE: DNA
<213> ORGANISM: Hepatitis C virus
<220> FEATURE:
<221> NAME/KEY: misc_feature
<222> LOCATION: (1)..(78)
<223> OTHER INFORMATION: HCV-1a tch CC AJ621232

<400> SEQUENCE: 264
ctgtgaggaa ctactgtctt cacgcagaaa gcgtctagcc cctggcgtta gtatgagtgt    60
cgtacagcct ccaggacc                                                  78

<210> SEQ ID NO 265
<211> LENGTH: 77
<212> TYPE: RNA
<213> ORGANISM: Hepatitis C virus
<220> FEATURE:
<221> NAME/KEY: misc_feature
<222> LOCATION: (1)..(77)
<223> OTHER INFORMATION: HCV 1a Tch C IVT sequence

<400> SEQUENCE: 265
cugugaggaa cuacugucuu cacgcagaaa gcgucuagcc cuggcguuag uaugaguguc    60
guacagccuc caggacc                                                  77

<210> SEQ ID NO 266
<211> LENGTH: 77
<212> TYPE: DNA
<213> ORGANISM: Hepatitis C virus
<220> FEATURE:
<221> NAME/KEY: misc_feature
<222> LOCATION: (1)..(77)
<223> OTHER INFORMATION: HCV-1a tch TGC GU451220

<400> SEQUENCE: 266
ctgtgaggaa ctactgtctt cacgcagaaa gcgtctagtg ctggcgttag tatgagtgtc    60
gtacagcctc caggacc                                                  77

<210> SEQ ID NO 267
<211> LENGTH: 79
<212> TYPE: DNA
<213> ORGANISM: Hepatitis C virus
<220> FEATURE:
<221> NAME/KEY: misc_feature
<222> LOCATION: (1)..(79)
<223> OTHER INFORMATION: HCV-1a T76NT6TCO AAA DQ295833

<400> SEQUENCE: 267
ctgtgaggta ctactgtctt cacgcagaaa gcgtctagcc atggcagtta gtatagagtg    60
tcgtacagcc tccaggacc                                                 79

<210> SEQ ID NO 268
<211> LENGTH: 40
<212> TYPE: DNA
<213> ORGANISM: Artificial Sequence
<220> FEATURE:
<223> OTHER INFORMATION: A40 synthetic sequence
```

<220> FEATURE:
<221> NAME/KEY: misc_feature
<222> LOCATION: (1)..(40)
<223> OTHER INFORMATION: Poly(dA) sequence

<400> SEQUENCE: 268
aaaaaaaaaa aaaaaaaaaa aaaaaaaaaa aaaaaaaaaa 40

<210> SEQ ID NO 269
<211> LENGTH: 105
<212> TYPE: RNA
<213> ORGANISM: Hepatitis C virus
<220> FEATURE:
<221> NAME/KEY: misc_feature
<222> LOCATION: (1)..(105)
<223> OTHER INFORMATION: HCV 1A gp ivt_1

<400> SEQUENCE: 269
ccugugagga acuacugucu ucacgcagaa agcgucuagc cauggcguua guaugagugu 60
cgugcagccu ccaggacccc cccucccggg agagccauag ugguc 105

<210> SEQ ID NO 270
<211> LENGTH: 105
<212> TYPE: RNA
<213> ORGANISM: Hepatitis C virus
<220> FEATURE:
<221> NAME/KEY: misc_feature
<222> LOCATION: (1)..(105)
<223> OTHER INFORMATION: HCV 2b Transcript IA

<400> SEQUENCE: 270
ccugugagga acuacugucu ucacgcagaa agcgucuagc cauggcguua guaugagugu 60
cguacagccu ccaggccccc cccucccggg agagccauag ugguc 105

<210> SEQ ID NO 271
<211> LENGTH: 105
<212> TYPE: RNA
<213> ORGANISM: Hepatitis C virus
<220> FEATURE:
<221> NAME/KEY: misc_feature
<222> LOCATION: (1)..(105)
<223> OTHER INFORMATION: HCV 3a IVT sequence IA

<400> SEQUENCE: 271
cuugugagga acuucugucu ucacgcggaa agcgccuagc cauggcguua guacgagugu 60
cgugcagccu ccaggccccc cccucccggg agagccauag ugguc 105

<210> SEQ ID NO 272
<211> LENGTH: 105
<212> TYPE: RNA
<213> ORGANISM: Hepatitis C virus
<220> FEATURE:
<221> NAME/KEY: misc_feature
<222> LOCATION: (1)..(105)
<223> OTHER INFORMATION: HCV 3b Transcript IA pBlu_1

<400> SEQUENCE: 272
ccugugagga acuucugucu ucacgcggaa agcgucuagc cauggcguua guacgagugu 60
cgugcagccu ccaggccccc cccucccggg agagccauag ugguc 105

<210> SEQ ID NO 273
<211> LENGTH: 105
<212> TYPE: RNA
<213> ORGANISM: Hepatitis C virus

```
<220> FEATURE:
<221> NAME/KEY: misc_feature
<222> LOCATION: (1)..(105)
<223> OTHER INFORMATION: HCV 4h Transcript IA_1

<400> SEQUENCE: 273
ccugugagga acuacugucu ucacgcagaa agcgucuagc cauggcguua guaugagugu      60
ugugcagccu ccaggauccc cccucccggg agagccauag gguc                     105

<210> SEQ ID NO 274
<211> LENGTH: 105
<212> TYPE: RNA
<213> ORGANISM: Hepatitis C virus
<220> FEATURE:
<221> NAME/KEY: misc_feature
<222> LOCATION: (1)..(105)
<223> OTHER INFORMATION: HCV 5a Transcript IA

<400> SEQUENCE: 274
ccugugagga acuacugucu ucacgcagaa agcgucuagc cauggcguua guaugagugu      60
cgaacagccu ccaggacccc cccucccggg agagccauag gguc                     105

<210> SEQ ID NO 275
<211> LENGTH: 105
<212> TYPE: RNA
<213> ORGANISM: Hepatitis C virus
<220> FEATURE:
<221> NAME/KEY: misc_feature
<222> LOCATION: (1)..(105)
<223> OTHER INFORMATION: HCV 6a Transcript IA

<400> SEQUENCE: 275
ccugugagga acuacugucu ucacgcagaa agcgucuagc cauggcguua guaugagugu      60
cguacagccu ccaggccccc cccucccggg agagccauag gguc                     105
```

COMPOSITIONS AND METHODS FOR DETECTING OR QUANTIFYING HEPATITIS C VIRUS

CROSS-REFERENCE TO RELATED APPLICATIONS

This application claims the benefit of U.S. Provisional Application No. 62/410,188, filed Oct. 19, 2016, the contents of which are hereby incorporated by reference herein.

SEQUENCE LISTING

The present application is filed with a Sequence Listing in electronic format. The Sequence Listing is provided as a file entitled "DIA.0024 SeqLst_6.16.20.prj (1)_5T25" created on Jun. 18, 2020, which is 113,424 bytes in size. The information in the electronic format of the sequence listing is incorporated herein by reference in its entirety.

INTRODUCTION

This disclosure relates to compositions, kits, and methods useful for the detection and quantification of Hepatitis C Virus nucleic acid.

SUMMARY

Hepatitis C Virus (HCV) can cause acute and chronic disease, with infected individuals being at risk of liver cirrhosis and cancer. Approximately 130-150 million individuals worldwide are estimated to be infected, with approximately 700 thousand deaths per year attributable to hepatitis C-related liver disease according to the July 2016 WHO Hepatitis C Fact Sheet. Transmission of HCV can occur through typical routes for bloodborne viruses including transfusion and use of contaminated needles or medical equipment. Sexual and mother-to-infant transmission are also known to occur.

HCV is a positive-sense single stranded RNA (ssRNA) virus. Its distribution is worldwide, with seven genotypes and multiple subtypes known. Antiviral therapy can be effective against HCV, but reliable and sensitive nucleic acid-based detection and quantification is complicated by marked genetic heterogeneity among the different genotypes. See, e.g., Ohno O, Mizokami M, Wu R R, Saleh M G, Ohba K, Onto E, Mukaide M, Williams R, Lau J Y, et al. (1997), "New hepatitis C virus (HCV) genotyping system that allows for identification of HCV genotypes 1a, 1b, 2a, 2b, 3a, 3b, 4, 5a, and 6a," *J Clin Microbiol.* 35 (1): 201-7, PMCID: PMC229539. Quantification can be useful, e.g., in monitoring viral load before, during, or after antiviral therapy, or in assessing severity of infection.

Accordingly, there is a need for sensitive detection and quantification of HCV irrespective of genotype. Compositions, kits, and methods are provided herein to meet this need, provide other benefits, or at least provide the public with a useful choice.

In some embodiments, a composition or kit is provided comprising at least first and second amplification oligomers, wherein: the first amplification oligomer comprises a target-hybridizing sequence comprising at least 10 contiguous nucleotides of SEQ ID NO: 2, including at least one of positions 5, 7, 12, and 15 of SEQ ID NO: 2; and the second amplification oligomer comprises a target-hybridizing sequence comprising at least 10 contiguous nucleotides of SEQ ID NO: 3 including at least one of positions 5, 7, 12, and 15 of SEQ ID NO: 3; and the target-hybridizing sequences of the first and second amplification oligomers each comprise at least about 14 contiguous nucleotides of Hepatitis C virus sequence. In some embodiments, the composition or kit further comprises a third amplification oligomer, wherein the third amplification oligomer comprises at least about 14 contiguous nucleotides of antisense Hepatitis C virus sequence and is configured to specifically hybridize downstream of HCV genomic position 78.

In some embodiments, a method is provided of detecting Hepatitis C virus nucleic acid in a sample, comprising: contacting the sample with at least first, second, and third amplification oligomers, thereby forming a composition, performing a nucleic acid amplification reaction in the composition which produces one or more amplicons in the presence of a Hepatitis C virus nucleic acid, and detecting the amplicon, wherein: the first amplification oligomer comprises a target-hybridizing sequence comprising at least 10 contiguous nucleotides of SEQ ID NO: 2, including at least one of positions 5, 7, 12, and 15 of SEQ ID NO: 2; the second amplification oligomer comprises a target-hybridizing sequence comprising at least 10 contiguous nucleotides of SEQ ID NO: 3 including at least one of positions 5, 7, 12, and 15 of SEQ ID NO: 3; the third amplification oligomer comprises at least about 14 contiguous nucleotides of antisense Hepatitis C virus sequence and is configured to specifically hybridize to downstream of HCV genomic position 78; the target-hybridizing sequences of the first and second amplification oligomers each comprise at least about 14 contiguous nucleotides of Hepatitis C virus sequence; and the one or more amplicons are produced through extension of the first and third amplification oligomers or second and third amplification oligomers in the presence of the Hepatitis C virus nucleic acid.

In some embodiments, a composition or kit is provided comprising at least first and second capture oligomers, wherein: the first capture oligomer comprises a target-hybridizing sequence comprising at least 10 contiguous nucleotides of SEQ ID NO: 54; and the second capture oligomer comprises a target-hybridizing sequence comprising at least 10 contiguous nucleotides of SEQ ID NO: 55; and the target-hybridizing sequences of the first and second capture oligomers each comprise at least about 14 contiguous nucleotides of Hepatitis C virus sequence.

In some embodiments, a method of isolating Hepatitis C virus nucleic acid from a sample is provided, comprising: contacting the sample with at least first and second capture oligomers under conditions permissive for annealing of the first and second capture oligomers to the Hepatitis C virus nucleic acid, thereby forming at least one complex of Hepatitis C virus nucleic acid and a capture oligomer; and isolating the at least one complex, thereby providing a composition comprising the complex; wherein: the first capture oligomer comprises a target-hybridizing sequence comprising at least 10 contiguous nucleotides of SEQ ID NO: 54; and the second capture oligomer comprises a target-hybridizing sequence comprising at least 10 contiguous nucleotides of SEQ ID NO: 55; and the target-hybridizing sequences of the first and second capture oligomers each comprise at least about 14 contiguous nucleotides of Hepatitis C virus sequence.

In some embodiments, a composition or kit further comprises an initial amplification oligomer comprising at least 10 contiguous nucleotides of SEQ ID NO: 6.

In some embodiments, a composition or kit further comprises a probe oligomer comprising at least 10 contiguous nucleotides of SEQ ID NO: 13 and at least about 14 contiguous nucleotides of Hepatitis C virus sequence.

In some embodiments, the initial amplification oligomer and probe oligomer anneal to at least one common position in an HCV nucleic acid.

In some embodiments, a kit or composition is provided comprising an initial amplification oligomer and a probe oligomer, wherein: the initial amplification oligomer comprises at least 10 contiguous nucleotides of SEQ ID NO: 6; the probe oligomer comprises at least 10 contiguous nucleotides of SEQ ID NO: 13; the initial amplification oligomer and probe oligomer each comprise at least about 14 contiguous nucleotides of Hepatitis C virus sequence; and the initial amplification oligomer and probe oligomer anneal to at least one common position in an HCV nucleic acid.

In some embodiments, a kit or composition further comprises at least 1, 2, or 3 of: a first amplification oligomer comprising a target-hybridizing sequence comprising at least about 14 contiguous nucleotides of Hepatitis C virus sequence that is configured to specifically hybridize upstream of HCV genomic position 81; a second amplification oligomer different from the first amplification oligomer comprising at least about 14 contiguous nucleotides of Hepatitis C virus sequence that is configured to specifically hybridize upstream of HCV genomic position 81; and a third amplification oligomer different from the initial amplification oligomer comprising at least about 14 contiguous nucleotides of antisense Hepatitis C virus sequence that is configured to specifically hybridize downstream of HCV genomic position 90.

In some embodiments, a kit or composition further comprises one or more capture oligomers comprising at least about 14 contiguous nucleotides of antisense Hepatitis C virus sequence.

In some embodiments, a method of detecting Hepatitis C virus nucleic acid in a sample is provided, comprising: contacting the sample with one or more capture oligomers and an initial amplification oligomer, thereby associating at least one capture oligomer and amplification oligomer with HCV nucleic acid if present; removing initial amplification oligomer not associated with the HCV nucleic acid; performing an extension reaction that extends initial amplification oligomer associated with HCV nucleic acid if present; performing an amplification reaction with the extended initial amplification oligomer as template if present, thereby producing an amplicon; and detecting the presence or absence of the amplicon using a probe oligomer; wherein the initial amplification oligomer comprises at least 10 contiguous nucleotides of SEQ ID NO: 6; the probe oligomer comprises at least 10 contiguous nucleotides of SEQ ID NO: 13 and is configured to specifically hybridize to the amplicon if present; the initial amplification oligomer and probe oligomer each comprise at least about 14 contiguous nucleotides of Hepatitis C virus sequence; and the initial amplification oligomer and probe oligomer anneal to at least one common position in an HCV nucleic acid.

In some embodiments, performing the amplification reaction comprises: adding (i) at least one of first and second amplification oligomers that anneal to the template or amplicon upstream of the probe oligomer and (ii) a third amplification oligomer that is configured to specifically hybridize to the template or amplicon downstream of the probe oligomer; and if the template is present, extending the first and second amplification oligomers.

An initial amplification oligomer is provided comprising a promoter and a 3'-terminal target-hybridizing sequence, wherein the target-hybridizing sequence comprises at least 10 contiguous nucleotides of SEQ ID NO: 6 and at least about 14 contiguous nucleotides of Hepatitis C virus sequence.

In some embodiments, the initial amplification oligomer comprises a T7 promoter. In some embodiments, the initial amplification oligomer comprises the sequence of SEQ ID NO: 8, 9, 10, or 11. In some embodiments, the initial amplification oligomer is configured to specifically hybridize to positions comprising at least 1, 2, 3, 4, 5, 6, 7, 8, 9, 10, 11, or 12 of HCV genomic positions 81-92. In some embodiments, the initial amplification oligomer is configured to specifically hybridize to positions comprising at least 1, 2, 3, 4, 5, 6, 7, 8, or 9 of HCV genomic positions 81-89.

A probe oligomer is provided comprising at least 10 contiguous nucleotides of SEQ ID NO: 13 and at least about 14 contiguous nucleotides of Hepatitis C virus sequence.

In some embodiments, the probe oligomer is configured to specifically hybridize to positions comprising at least 6, 7, 8, 9, 10, 11, or 12 of HCV genomic positions 81-92. In some embodiments, the probe oligomer is configured to specifically hybridize to positions comprising at least 11, 12, 13, 14, 15, or 16 of HCV genomic positions 81-96.

In some embodiments, the first amplification oligomer comprises at least 10 contiguous nucleotides of SEQ ID NO: 2.

In some embodiments, the second amplification oligomer comprises at least 10 contiguous nucleotides of SEQ ID NO: 3.

In some embodiments, the third amplification oligomer does not anneal downstream of an HCV genomic position selected from position 120, 125, 130, 135, 140, 145, or 150 in at least one HCV type. In some embodiments, the at least one HCV type includes one or more of HCV types 1a, 1b, 2b, 3b, 4b, 5a, and 6a.

In some embodiments, the third amplification oligomer is configured to specifically hybridize to a site comprising at least one of HCV genomic positions 80-119. In some embodiments, the third amplification oligomer comprises a target-hybridizing sequence comprising at least 10 contiguous nucleotides of SEQ ID NO: 6 or 7. In some embodiments, the third amplification oligomer comprises a target-hybridizing sequence comprising at least one, two, three, or four of SEQ ID NOs: 33-37. In some embodiments, the third amplification oligomer comprises at least 11, 12, 13, 14, 15, 16, 17, 18, 19, 20, 21, 22, 23, 24, 25, 26, 27, 28, 29, 30, or 31 contiguous nucleotides of SEQ ID NO: 7. In some embodiments, the third amplification oligomer comprises the sequence of SEQ ID NO: 7. In some embodiments, the third amplification oligomer comprises the sequence of at least one, two, three, four, or five of SEQ ID NOs: 42-47. In some embodiments, the third amplification oligomer comprises the sequence of SEQ ID NO: 5.

In some embodiments, the first amplification oligomer comprises a target-hybridizing sequence comprising at least one, two, three, or four of SEQ ID NOs: 23-27. In some embodiments, the first amplification oligomer comprises at least 11, 12, 13, 14, 15, 16, 17, 18, 19, 20, 21, 22, 23, 24, 25, or 26 contiguous nucleotides of SEQ ID NO: 2. In some embodiments, the first amplification oligomer comprises the sequence of SEQ ID NO: 2.

In some embodiments, the second amplification oligomer comprises a target-hybridizing sequence comprising at least one, two, three, or four of SEQ ID NOs: 28-32. In some embodiments, the second amplification oligomer comprises at least 11, 12, 13, 14, 15, 16, 17, 18, 19, 20, 21, 22, 23, 24, 25, or 26 contiguous nucleotides of SEQ ID NO: 3. In some embodiments, the second amplification oligomer comprises the sequence of SEQ ID NO: 3.

In some embodiments, the first and second amplification oligomers are present in relative molar amounts (first: second) ranging from about 8.5:1.5 to about 1.5:8.5, about 7.5:2.5 to about 2.5:7.5, about 8:2 to about 7:3, about 7:3 to about 6:4, about 6:4 to about 5:5, about 5:5 to about 4:6, about 4:6 to about 3:7, or about 3:7 to about 2:8. In some embodiments, the first and second amplification oligomers are present in relative molar amounts (first:second) ranging from about 6:4 to about 1.5:8.5, about 4:6 to about 6:4, or about 4.5:5.5 to about 5.5:4.5.

In some embodiments, the initial amplification oligomer comprises a target-hybridizing sequence comprising at least one, two, three, four, five, six, or seven of SEQ ID NOs: 33-41. In some embodiments, the initial amplification oligomer comprises at least 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 contiguous nucleotides of SEQ ID NO: 6. In some embodiments, the initial amplification oligomer comprises the sequence of SEQ ID NO: 6. In some embodiments, the initial amplification oligomer comprises the sequence of at least one, two, three, four, or five of SEQ ID NOs: 42-47. In some embodiments, the initial amplification oligomer comprises the sequence of SEQ ID NO: 4.

In some embodiments, the probe oligomer comprises a target-hybridizing sequence comprising at least one or two of SEQ ID NOs: 50-52. In some embodiments, the probe oligomer comprises the sequence of SEQ ID NO: 48 or 49. In some embodiments, the probe oligomer comprises at least 11, 12, 13, 14, or 15 contiguous nucleotides of SEQ ID NO: 12. In some embodiments, the probe oligomer comprises a target-hybridizing sequence comprising at least 11, 12, 13, 14, or 15 contiguous nucleotides of SEQ ID NO: 13. In some embodiments, the probe oligomer comprises a first self-complementary region at its 5' end and a second self-complementary region at its 3' end. In some embodiments, the self-complementary regions can hybridize to form about 4 to 7 Watson-Crick or wobble base pairs. In some embodiments, the self-complementary regions can hybridize to form about 5 Watson-Crick or wobble base pairs. In some embodiments, the probe oligomer comprises the sequence of SEQ ID NO: 12. In some embodiments, the probe oligomer comprises a target-hybridizing sequence comprising the sequence of SEQ ID NO: 13. In some embodiments, the probe oligomer comprises a non-nucleotide detectable label. In some embodiments, the non-nucleotide detectable label is a fluorescent label. In some embodiments, the probe oligomer comprises a quencher. In some embodiments, the non-nucleotide detectable label is a fluorescent label and the quencher absorbs fluorescence to a greater extent when the probe is free than when the probe is annealed to a target nucleic acid. In some embodiments, the fluorescent label is FAM, HEX, or acridine. In some embodiments, the quencher is DABCYL or ROX. In some embodiments, the fluorescent label is attached to the 5'-terminus of the probe oligomer and the quencher is attached to the 3'-terminus of the probe oligomer, or the fluorescent label is attached to the 3'-terminus of the probe oligomer and the quencher is attached to the 5'-terminus of the probe oligomer. In some embodiments, at least about half, at least about 90%, or all of the sugars in the probe oligomer are 2'-O-methyl-ribose.

In some embodiments, a first capture oligomer is present comprising a target-hybridizing sequence comprising at least 10, 11, 12, 13, 14, 15, 16, 17, or 18 contiguous nucleotides of SEQ ID NO: 54. In some embodiments, the target-hybridizing sequence of the first capture oligomer comprises at least one or two of SEQ ID NOs: 57-59. In some embodiments, the first capture oligomer comprises the sequence of SEQ ID NO: 54. In some embodiments, the first capture oligomer comprises the sequence of SEQ ID NO: 16.

In some embodiments, a second capture oligomer is present comprising a target-hybridizing sequence comprising at least 10, 11, 12, 13, 14, 15, 16, or 17 contiguous nucleotides of SEQ ID NO: 55. In some embodiments, the target-hybridizing sequence of the second capture oligomer comprises at least one or two of SEQ ID NOs: 60-62. In some embodiments, the second capture oligomer comprises the sequence of SEQ ID NO: 55. In some embodiments, the second capture oligomer comprises the sequence of SEQ ID NO: 17.

In some embodiments, at least one capture oligomer further comprises a non-nucleotide affinity label. In some embodiments, at least one capture oligomer further comprises a non-HCV sequence. In some embodiments, the first and second capture oligomers further comprise a non-HCV sequence. In some embodiments, at least one or two capture oligomers further comprise a poly-N sequence. In some embodiments, the poly-N sequence is a poly-A or poly-T sequence. In some embodiments, at least one or two capture oligomers comprise the sequence of SEQ ID NO: 21 or SEQ ID NO: 22.

In some embodiments, a kit or composition comprises at least one amplification oligomer that is a promoter-primer. In some embodiments, the third amplification oligomer is a promoter-primer. In some embodiments, one or more of the promoter-primers comprises a T7 promoter located 5' of the target-hybridizing sequence. In some embodiments, one or more promoter-primers comprises the sequence of SEQ ID NO: 8, 9, 10, or 11.

In some embodiments, at least one amplification oligomer comprises a non-nucleotide detectable label.

In some embodiments, the initial amplification and probe oligomers each anneal to at least 1, 2, 3, 4, 5, 6, 7, 8, or 9 of positions 86-95 in an HCV genome or the complement thereof.

In some embodiments, a composition further comprises HCV nucleic acid.

In some embodiments, a composition or kit further comprises at least one DNA polymerase. In some embodiments, the DNA polymerase is a reverse transcriptase. In some embodiments, the DNA polymerase is thermophilic. In some embodiments, the DNA polymerase is mesophilic.

In some embodiments, composition or kit further comprises an RNA polymerase. In some embodiments, the RNA polymerase is T7 RNA polymerase.

In some embodiments, a composition or kit further comprises at least one, at least two, or each of Mg2+, a buffer, and dNTPs.

In some embodiments, a composition or kit further comprises rNTPs.

In some embodiments, a composition or kit further comprises a first control amplification oligomer and a second control amplification oligomer that do not hybridize specifically to HCV. In some embodiments, the first control amplification oligomer comprises at least 10, 11, 12, 13, 14, 15, 16, 17, 18, or 19 contiguous nucleotides of the sequence of SEQ ID NO: 18. In some embodiments, the second control amplification oligomer comprises at least 10, 11, 12, 13, 14, 15, 16, 17, 18, 19, 20, 21, or 22 contiguous nucleotides of the sequence of SEQ ID NO: 56. In some embodiments, the first control amplification oligomer or the second control amplification oligomer is a promoter-primer.

In some embodiments, a composition or kit further comprises at least one control probe oligomer capable of hybridizing specifically to an amplicon produced from the first and second control amplification oligomers. In some embodiments, the control probe oligomer comprises at least 10, 11, 12, 13, 14, 15, 16, 17, 18, 19, 20, 21, 22, or 23 contiguous nucleotides of the sequence of SEQ ID NO: 20.

In some embodiments, one, two, three, or more target-hybridizing sequences (e.g., of amplification oligomers, capture oligomers, or probe oligomers) comprise at least about 15, 16, 17, 18, 19, 20, 21, 22, 23, 24, or 25 contiguous nucleotides of Hepatitis C virus sequence.

In some embodiments, a method further comprises performing a linear amplification wherein at least one amplification oligomer is extended. In some embodiments, prior to the linear amplification, the amplification oligomer is associated with a complex of HCV nucleic acid and a capture oligomer and the complex is associated with a solid support, and the method comprises washing the solid support. In some embodiments, the solid support is a population of microbeads. In some embodiments, the microbeads of the population are magnetic. In some embodiments, following the washing step, the method comprises adding one or more additional amplification oligomers oppositely oriented to an amplification oligomer associated with the complex of HCV nucleic acid and the capture oligomer. In some embodiments, one or more oppositely oriented additional amplification oligomer is a promoter-primer. In some embodiments, one or more oppositely oriented additional amplification oligomer is not a promoter-primer. In some embodiments, one or more oppositely oriented additional amplification oligomer includes a first amplification oligomer as disclosed herein. In some embodiments, the one or more oppositely oriented additional amplification oligomer includes a second amplification oligomer as disclosed herein.

In some embodiments, a method further comprises performing an exponential amplification following a linear amplification. In some embodiments, the exponential amplification comprises extending a third amplification oligomer as disclosed herein. In some embodiments, the exponential amplification is isothermal amplification. In some embodiments, the isothermal amplification is transcription-mediated amplification.

In some embodiments, a method further comprises quantifying at least one amplicon produced by the method. In some embodiments, the amplicon is quantified in real time.

In some embodiments, a composition is aqueous, frozen, or lyophilized.

In some embodiments, a composition further comprises an extension product of an initial amplification oligomer, the extension product comprising a sequence of an initial amplification oligomer comprising a promoter and a 3'-terminal terminal target hybridizing sequence, wherein the target-hybridizing sequence comprises at least 10 contiguous nucleotides of SEQ ID NO: 6 and at least about 14 contiguous nucleotides of Hepatitis C virus sequence and at least 1, 2, 3, 4, 5, 10, 15, or 20 additional 3'-terminal nucleotides of Hepatitis C nucleic acid sequence.

Section headings are provided for the convenience of the reader and do not limit the scope of the disclosure.

BRIEF DESCRIPTION OF THE DRAWINGS

FIG. 2A presents results obtained using HCV genotype 1a. FIG. 2B presents results obtained using HCV genotype 2b. FIG. 2C presents results obtained using HCV genotype 3b. FIG. 2D presents results obtained using HCV genotype 4h. FIG. 2E presents results obtained using HCV genotype 3a. FIG. 2F presents results obtained using HCV genotype 5a. FIG. 2G presents results obtained using HCV genotype 6a. In these experiments, genotype 1a showed distinct groupings of traces for the three concentrations, but at the lowest concentration ($10^2$ copies/ml), other genotypes either failed to amplify (2a) or showed heterogeneous emergence times (3b, 4h, 3a, 5a, 6a).

In FIG. 4C, the curves for genotypes 1a and 3a substantially overlapped.

FIG. 7A-7D show side-by-side comparisons of HCV torch 68-86 versus HCV torch 80-98 5st a with the indicated genotypes at $10^2$, $10^4$, and $10^7$ copies/ml. FIGS. 7A-7B present results obtained using the HCV torch 68-86(+) (having two 3a mismatches) during amplification and detection of HCV genotypes 1a and 3a, respectively. FIGS. 7C-7D present results obtained using the HCV torch 80-98 5st a(+) (having no mismatches) during amplification and detection of HCV genotypes 1a and 3a, respectively. Arrows indicate traces for the $10^2$ copies/ml condition.

FIG. 11 shows an alignment of T7 primers against HCV genotypes. The aligned sequences in order from top to bottom are SEQ ID NOs: 100, 2, 12, 5, 222, 223, 224, 225, 226, 227, 228, 229, 230, and 225.

FIG. 20 shows HCV genotype quantification for various genotypes versus HCV 1a with an exemplary oligomer set.

FIGS. 22A and 22B show in vitro transcript HCV mutant testing with initial assay feasibility oligomer system log difference for all tested mutants (FIG. 23A) and log difference c/ml of mutants with >0.4 log c/ml divergence from expected target (FIG. 23B).

FIG. 23 shows a sequence alignment with the 13 HCV mutants that under quantified by >0.4 log c/mL. The aligned sequences in order from top to bottom are SEQ ID NOs: 2, 220, none, 12, 239, 247, 248, 249, 250, 251, 252, 253, 254, 255, 256, 257, 258, 259, 260, 261, 262, 263, 264, 265, 266, and 267. The target-hybridizing sequence for the HCV0297 (−)dT3dA30 target capture oligonucleotide (SEQ ID NO: 16) (third entry in the alignment) falls outside the sequence presented in the figure.

DETAILED DESCRIPTION

A. Definitions

Figure 1:
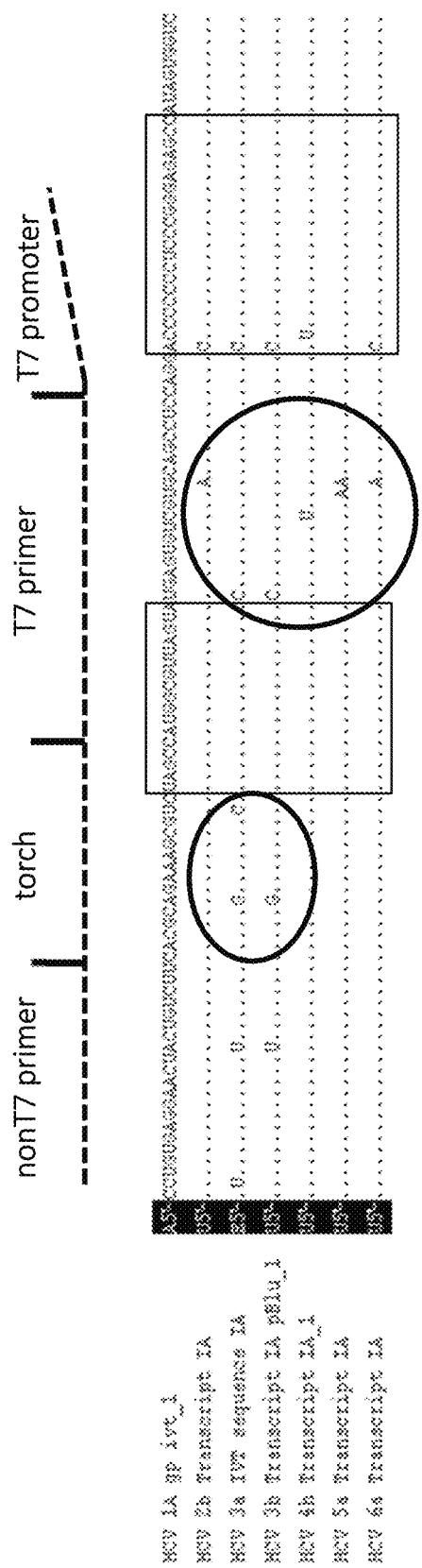
FIG. 1 shows alignment of HCV sequences and indicates regions bound by amplification and probe oligomers. In this and subsequent alignments, dots indicate matches to the reference sequence (here, the HCV 1a transcript (SEQ ID NO: 269)), dashes indicate gaps, carets indicate complementary positions, and mismatches are shown as the mismatching base. The ovals highlight certain mismatches relative to genotype 1a. The left box indicates a region where no mismatches were observed in the listed genotypes (1a, 2b, 3a, 3b, 4h, 5a, and 6a (SEQ ID NOs: 269, 270, 271, 272, 273, 274, and 275, respectively)). The right box indicates a G+C-rich region.
Figure 2A:
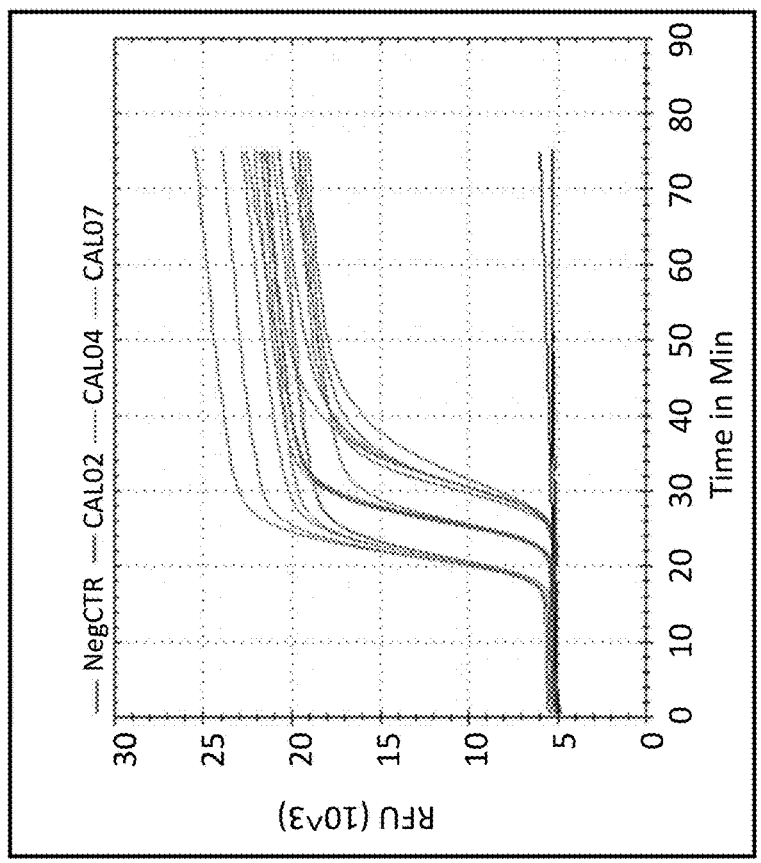
FIG. 2A-2G show amplification kinetics for various HCV genotypes at three concentrations.
Figure 2B:
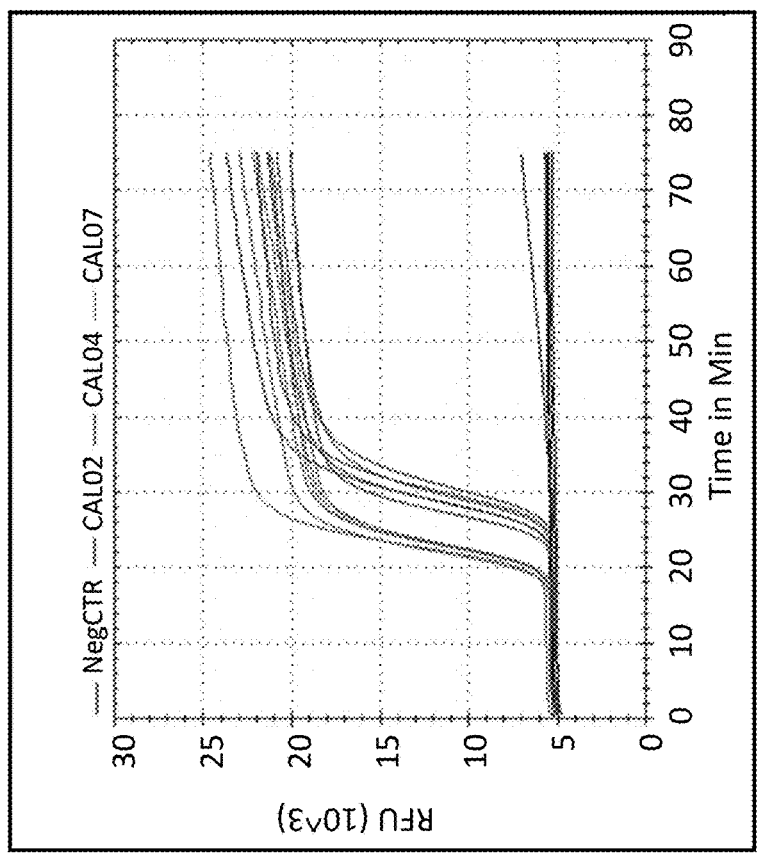
Figure 2C:
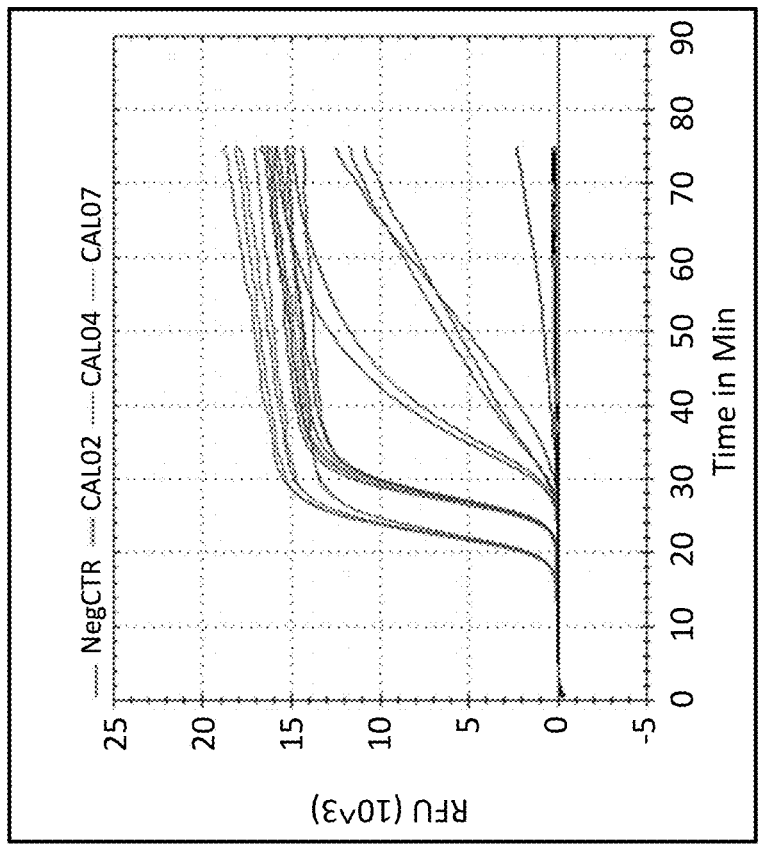
Figure 2D:
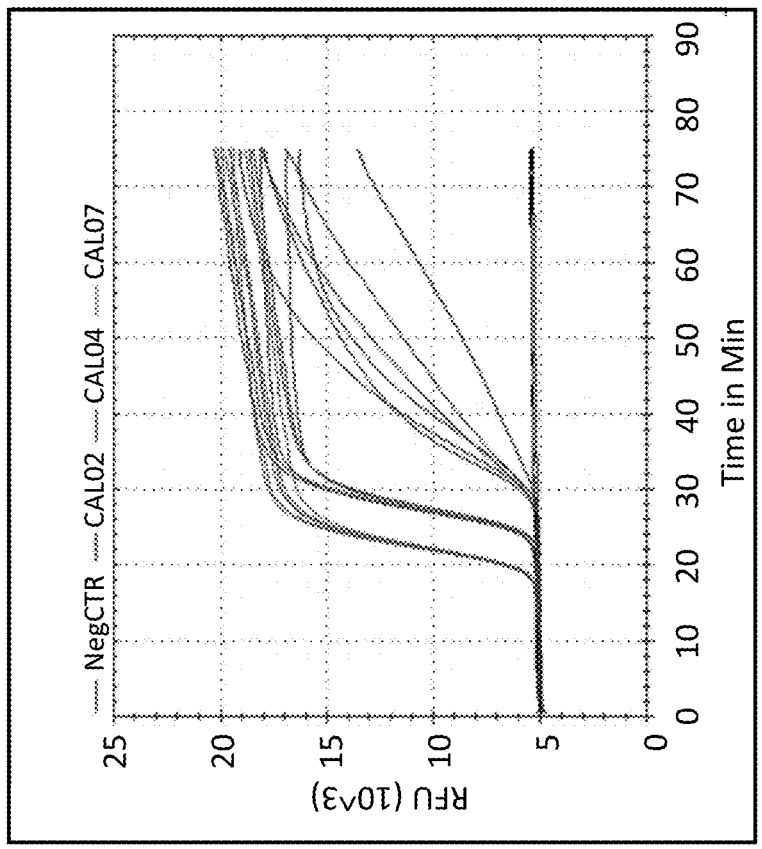
Figure 2E:
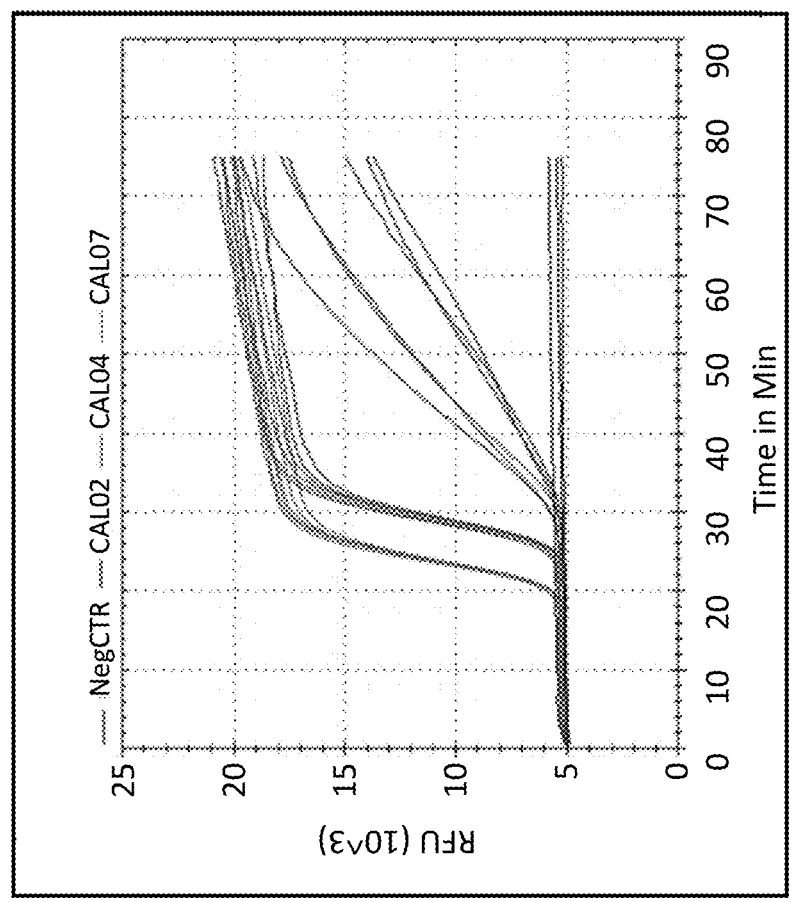
Figure 2G:
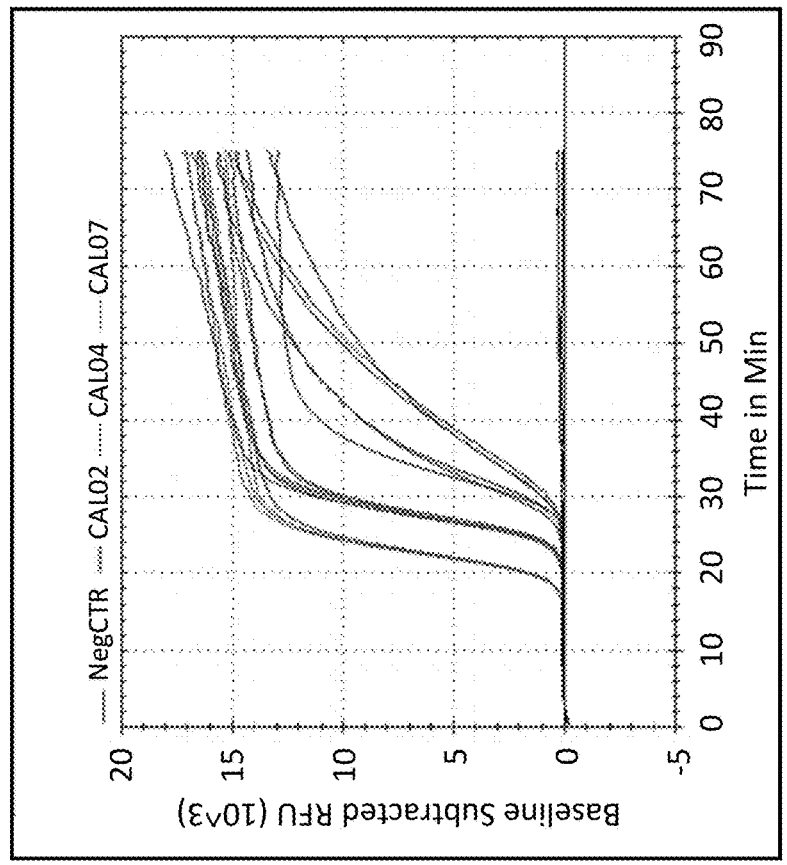
Figure 2F:
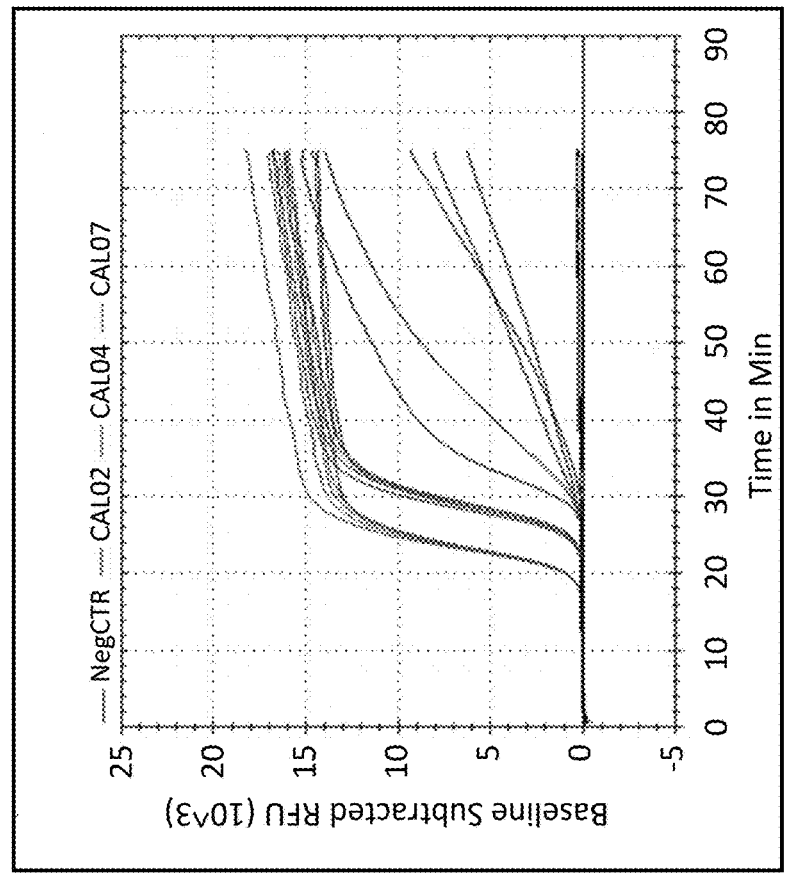
Figure 3:
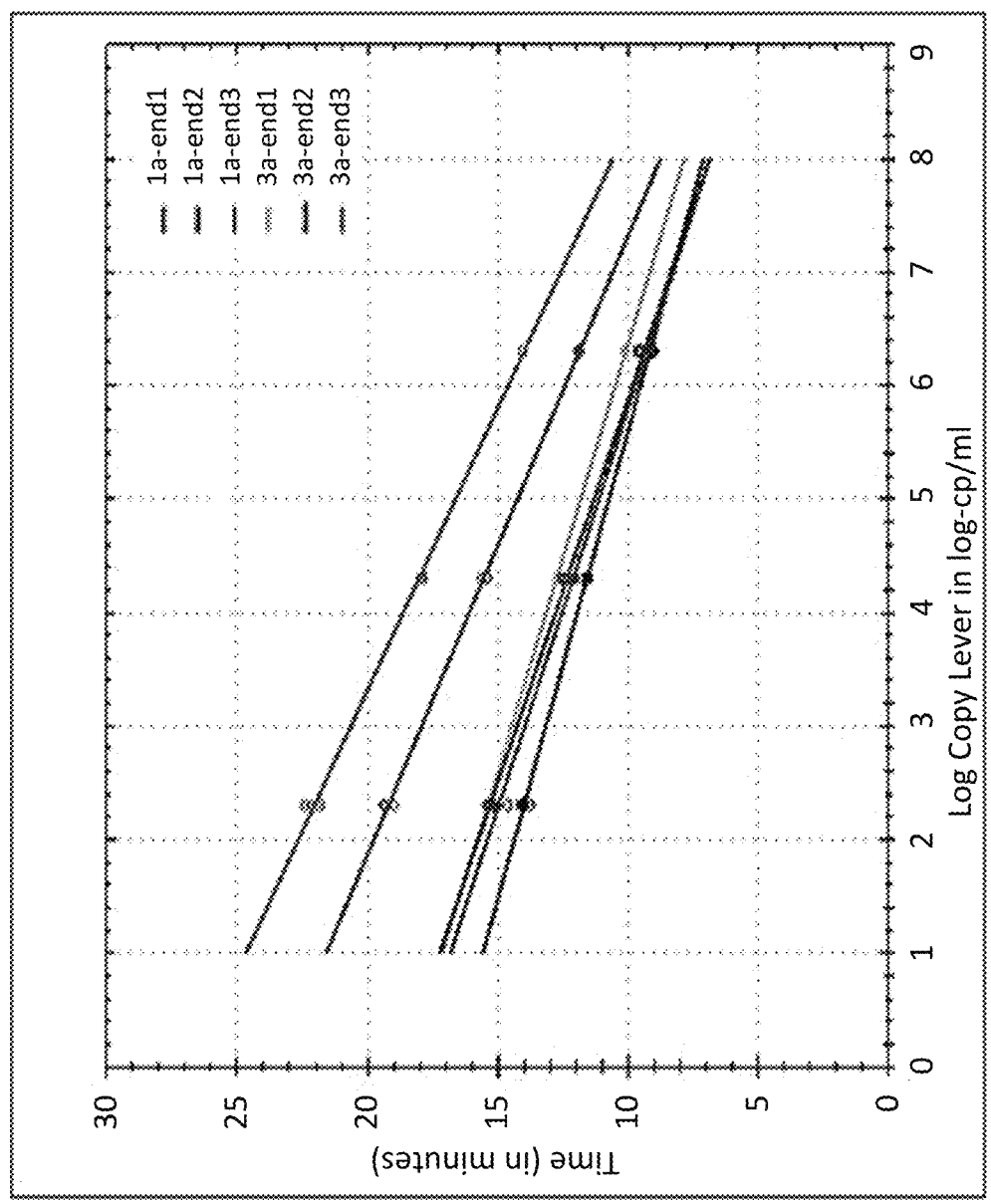
FIG. 3 shows calibration curves for genotypes 1a and 3a using different NT7 primers.
Figure 4A:
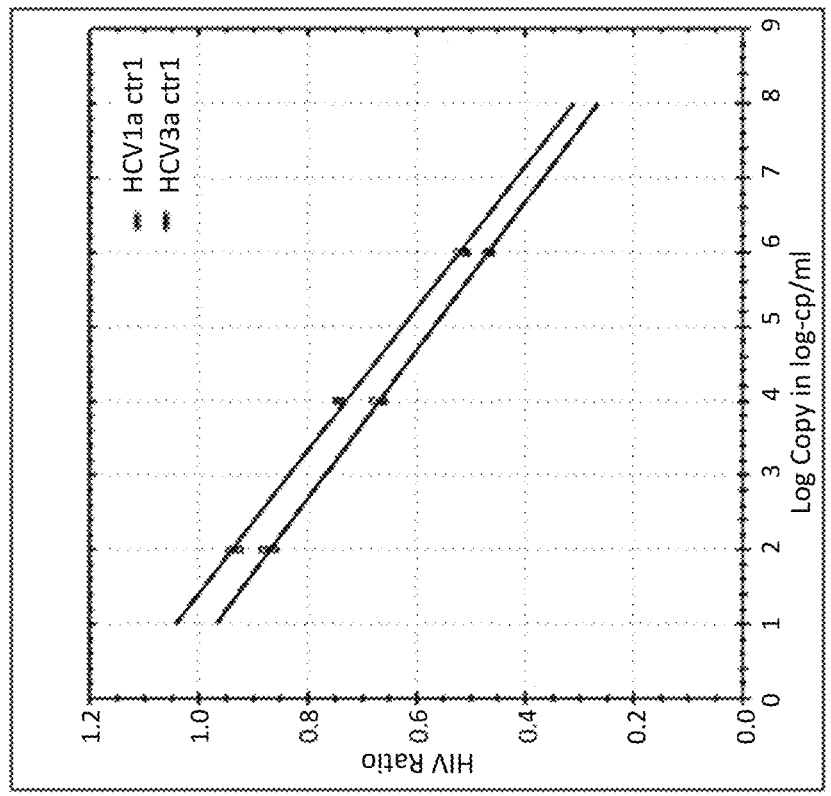
FIGS. 4A, 4B, and 4C show genotype quantitation with different NT7 primers (HCV 52-78, matching genotype 1a sequence, in FIG. 4A; HCV 52-78tg, matching genotype 3a sequence, in FIG. 4B; or a 50:50 mixture of HCV 52-78 and HCV 52-78tg in FIG. 4C). Arrows indicate the curve for genotype 1A in FIGS. 4A and 4B.
Figure 4B:
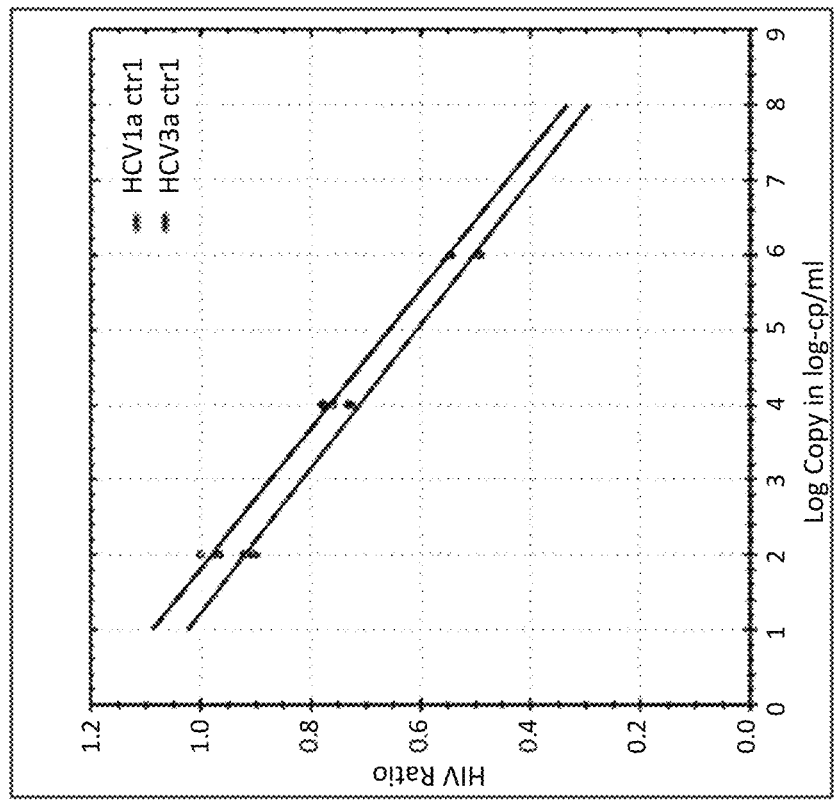
Figure 4C:
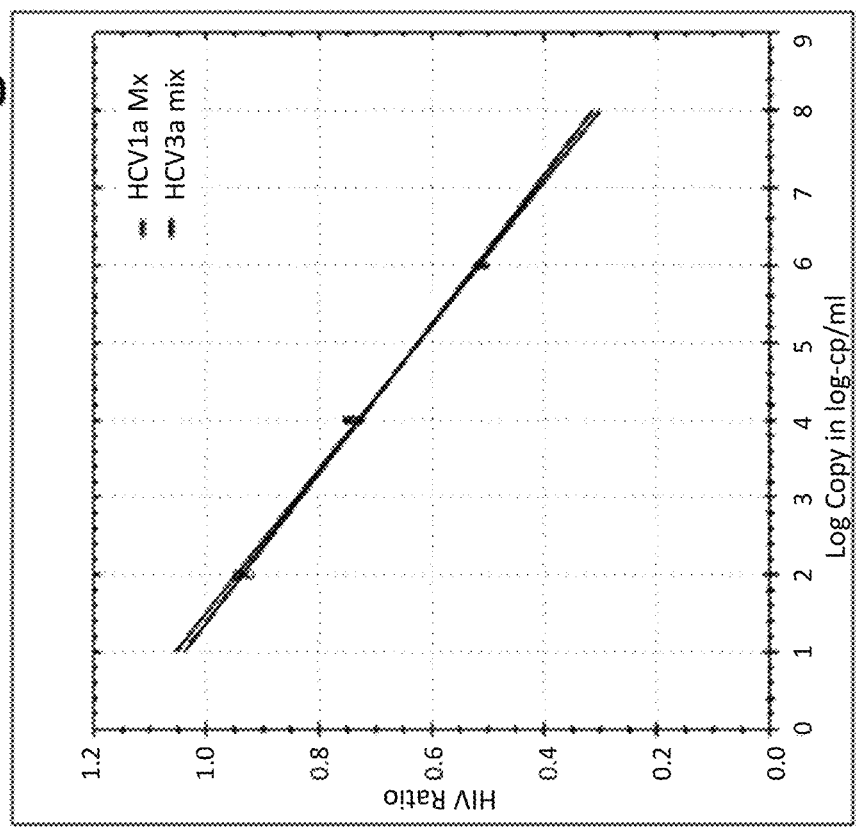
Figures 5A, 5B:
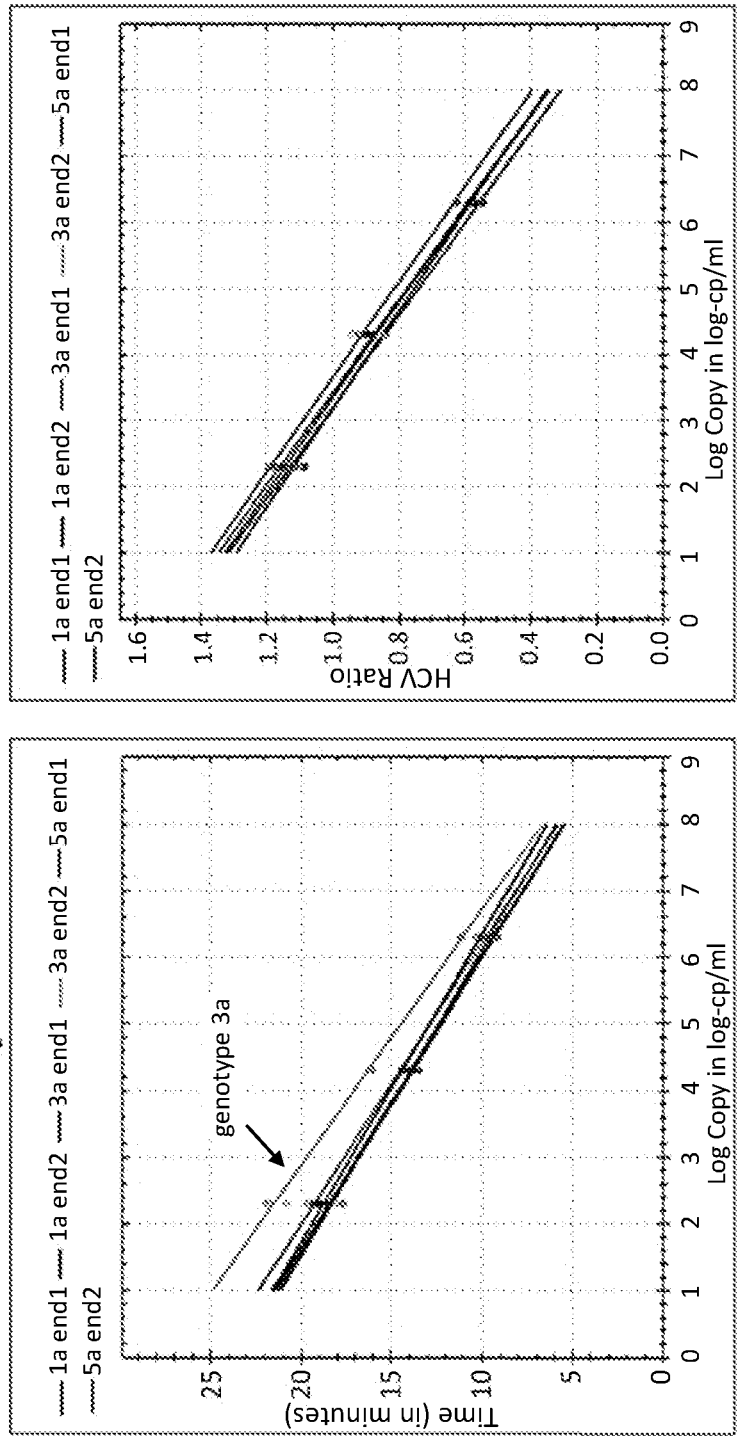
FIGS. 5A and 5B show results across multiple HCV genotypes for nonT7 primers 52-78t only (FIG. 5A; arrow indicates genotype 3a) and 52-78tg only (FIG. 5B).
Figure 6:
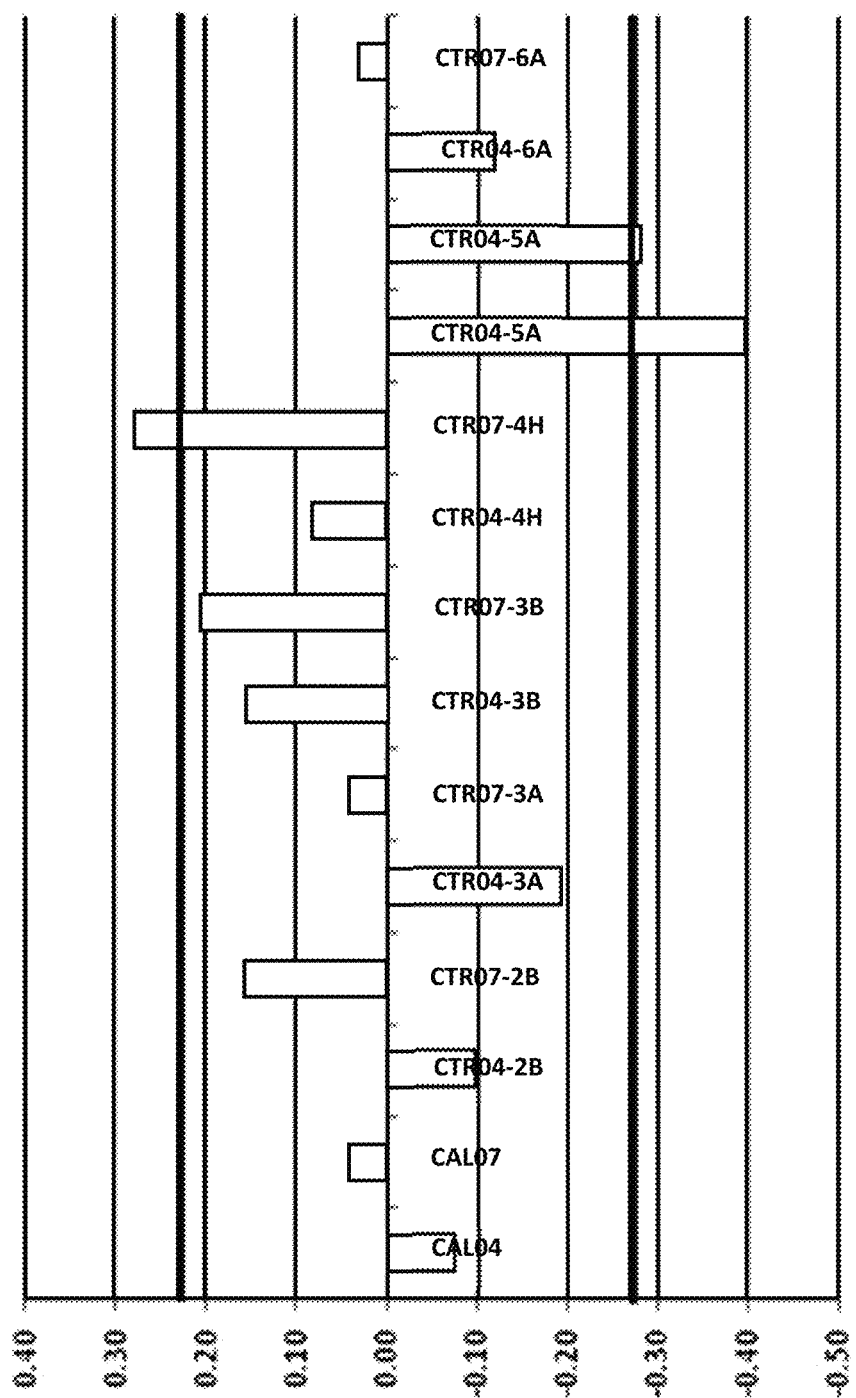
FIG. 6 shows log difference from target (LogDiff) for quantitation assays with various genotypes. The genotypes are presented from left to right in the order 1a, 2b, 3a, 3b, 4h, 5a, 6a, with each genotype having two bars reflecting $10^4$ (left) and $10^7$ (right) copies/ml conditions.
Figure 7C:
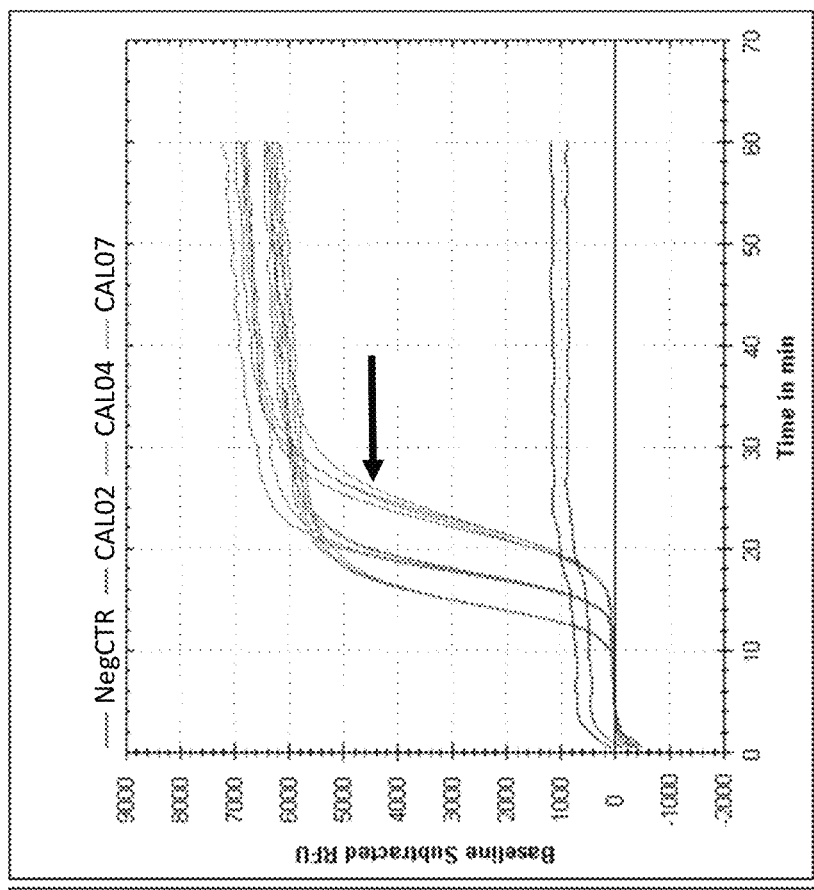
Figure 7D:
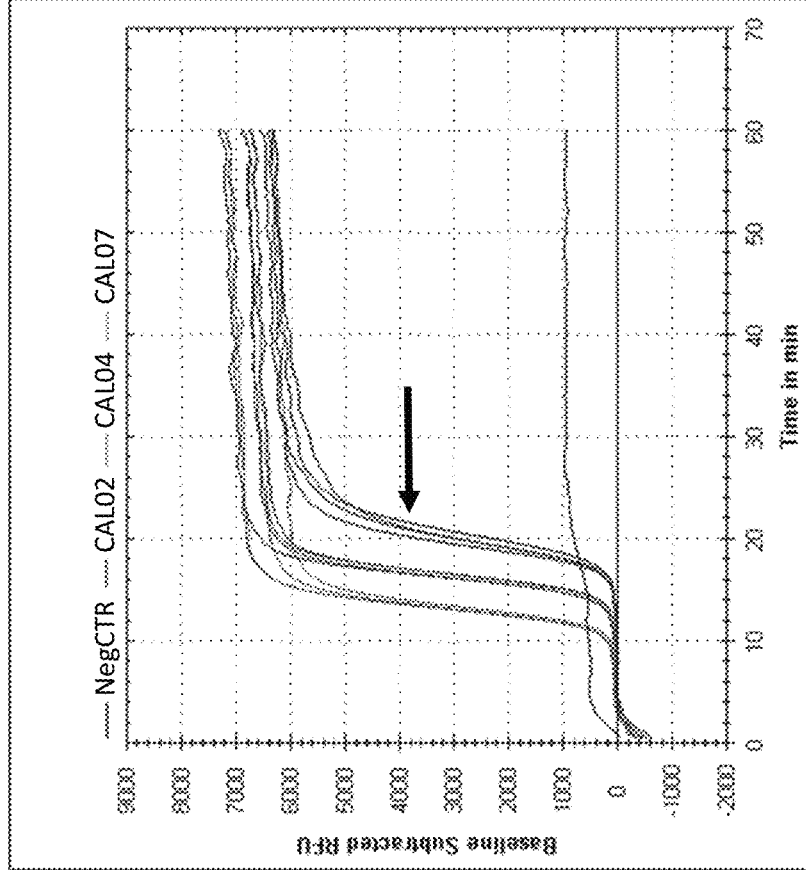
Figure 8:
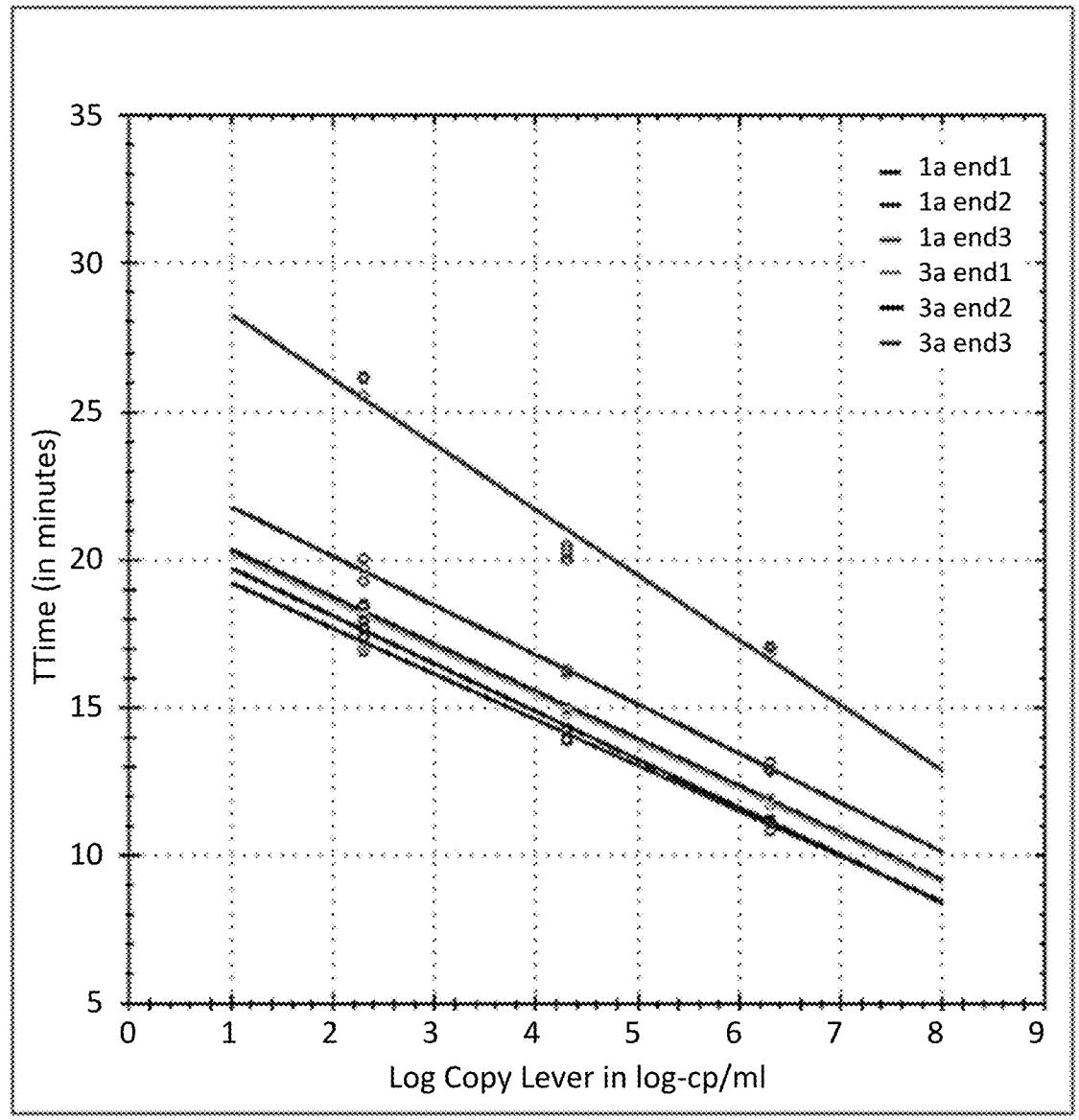
FIG. 8 shows calibration curves with different HCV torches and T7 oligomers. The straight arrow indicates the curve for genotype 3a, T7 95-119, torch 68-86. The curved arrow indicates the curve for genotype 1a, T7 95-119, torch 68-86.
Figure 9:
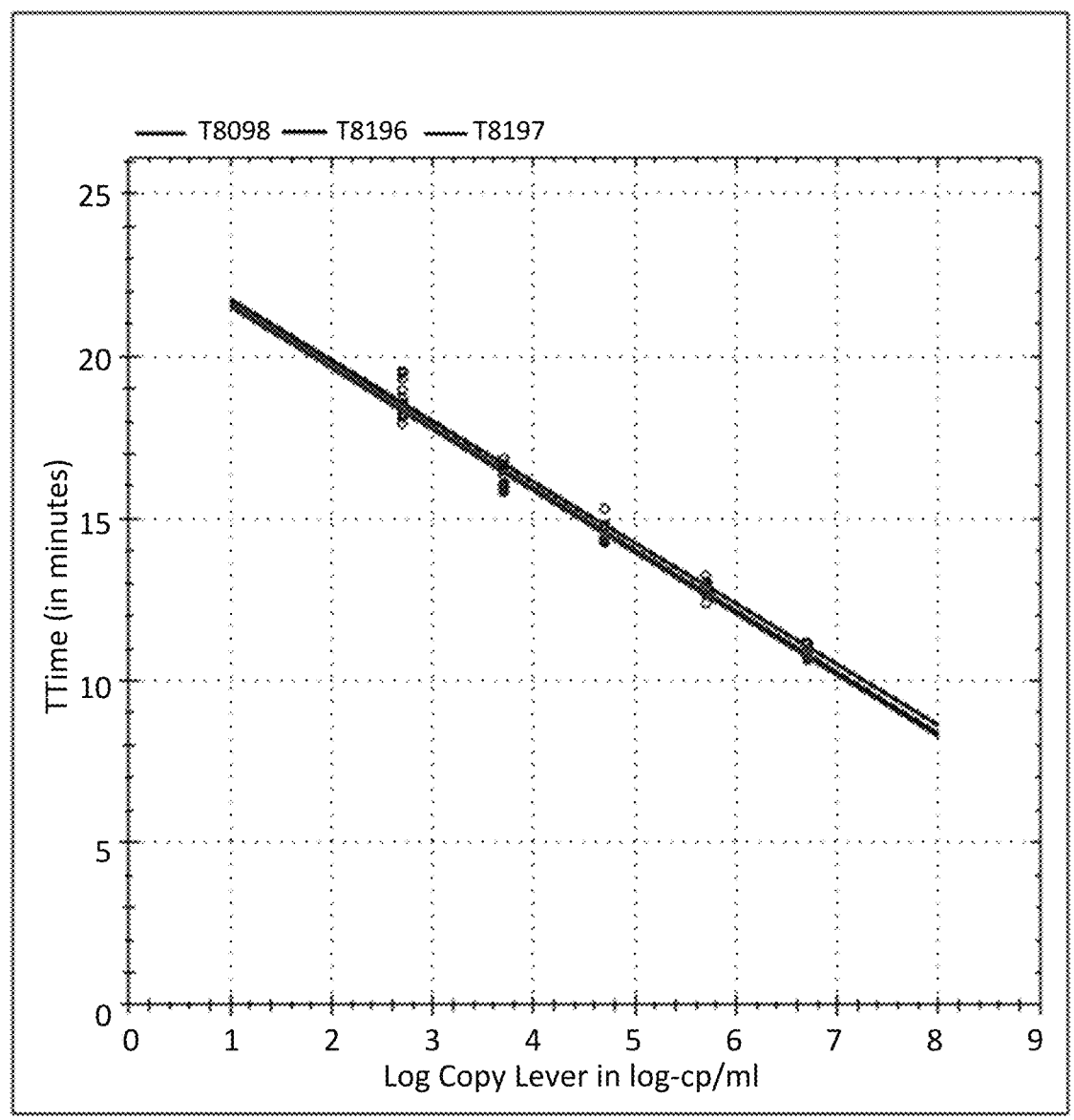
FIG. 9 shows calibration curves for HCV torches 81-96, 81-97, and 80-98.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "an oligomer" includes a plurality of oligomers and the like.

It will be appreciated that there is an implied "about" prior to the temperatures, concentrations, times, etc. discussed in the present disclosure, such that slight and insubstantial deviations are within the scope of the present teachings herein. In general, the term "about" indicates insubstantial variation in a quantity of a component of a composition not having any significant effect on the activity or stability of the composition. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

"Sample" includes any specimen that may contain hepatitis C virus (HCV) or components thereof, such as nucleic acids or fragments of nucleic acids. Samples include "biological samples" which include any tissue or material derived from a living or dead human that may contain HCV or target nucleic acid derived therefrom, including, e.g., peripheral blood, plasma, serum, lymph node, gastrointestinal tissue (e.g., liver), or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see, e.g., International Patent Application Pub. No. WO 95/32305), phosphorothioate linkages, methylphosphonate linkages, or combinations thereof Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., The Biochemistry of the Nucleic Acids 5-36, Adams et al., ed., 11th ed., 1992; Abraham et al., 2007, BioTechniques 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo [3,4-d]pyrimidine; U.S. Pat. Nos. 5,378,825, 6,949,367 and International Patent Application Pub. No. WO 93/13121, each incorporated by reference herein). Nucleic acids may include "abasic" residues in which the backbone does not include a nitrogenous base for one or more residues (see. e.g., U.S. Pat. No. 5,585,481, incorporated by reference herein). A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., Biochemistry 43:13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well-known in the art although nucleic acids may be purified from natural sources using routine techniques.

A sequence is a "Hepatitis C virus sequence" if it or its complement occurs in, is at least about 90% or at least about 95% identical to, or contains no more than one mismatch relative to any genotype, subtype, or isolate of HCV, thereto, such that, for example, "14 contiguous nucleotides of Hepatitis C virus sequence" refers to a 14-mer that matches at least 13 out of 14 positions of a genotype, subtype, or isolate of HCV, or the complement thereof. The presence of a U is considered equivalent to a T and vice versa for purposes of determining whether a sequence qualifies as a Hepatitis C virus sequence. The target-hybridizing regions of exemplary oligomers disclosed herein, the HCV-derived sequence of in vitro transcripts disclosed herein, and subsequences thereof are also considered Hepatitis C virus sequence. Thus, examples of Hepatitis C virus sequence include SEQ ID NOs: 1-3, 6-7, 13-14, 23-41, 48, 50-52, 54-62, and 76-107; the HCV sequence fragments of SEQ ID NO: 166-214 and 221 and the HCV sequences indicated by the accession numbers in Table 5; the transcript sequences of SEQ ID NOs: 63-74, excluding any non-HCV component (e.g., TOPO or pBlueScript® vector sequence that may be present in the transcript); the target-hybridizing regions of T7 amplification oligomers of SEQ ID NOs: 108-147 (excluding non-HCV sequence such as T7 promoter regions, e.g., as in SEQ ID NO: 11); the target-hybridizing regions of capture oligomers of SEQ ID NOs: 161-165 (excluding non-HCV sequence such as artificial regions, e.g., as in SEQ ID NO: 21). In some embodiments, the genotype, subtype, or isolate of HCV referred to above is a known genotype, subtype, or isolate of HCV, e.g., which is present in a sequence database or publication available at the date of this disclosure.

When an oligomer comprises, e.g., "at least 10 contiguous nucleotides of" a specified SEQ ID NO and "at least about 14 contiguous nucleotides of Hepatitis C virus sequence," the same nucleotides can be counted toward both (i) and (ii), e.g., the at least 14 contiguous nucleotides of Hepatitis C virus sequence can comprise any or all of the at least 10 contiguous nucleotides of the specified SEQ ID NO, to the extent consistent with the foregoing definition of Hepatitis C virus sequence. Similarly, an "oligomer comprises a target-hybridizing sequence comprising at least two" (or more) of a plurality of specified SEQ ID NOs if each of the sequence of the SEQ ID NOs is present, regardless of whether they overlap. Thus, as a simplified example, CAT comprises both CA and AT.

For two molecules to "anneal to at least N common position(s)" means that the molecules have hybridization sites that overlap by N or more nucleotides on the same or opposite strands of a target nucleic acid, e.g., an HCV nucleic acid. For example, a first oligomer that is configured to specifically hybridize to positions 81-96 and a second oligomer that is configured to specifically hybridize to positions 93-119 anneal to four common positions (93, 94, 95, and 96) regardless of whether (i) they both anneal to the same strand or (ii) one is configured to specifically hybridize to the sense or (+) strand and the other is configured to specifically hybridize to the antisense or (−) strand.

The term "polynucleotide" as used herein denotes a nucleic acid chain. Throughout this application, nucleic acids are designated by the 5'-terminus to the 3'-terminus. Synthetic nucleic acids, e.g., DNA, RNA, DNA/RNA chimerics, (including when non-natural nucleotides or analogues are included therein), are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar, and a nitrogenous base (also referred to herein as "nucleobase"). The 5-carbon sugar found in RNA is ribose. In DNA, the 5-carbon sugar is 2'-deoxyribose. The term also includes analogs of such subunits, such as a methoxy group at the 2' position of the ribose (also referred to herein as "2'-O-Me" or "2'-methoxy"). As used herein, methoxy oligonucleotides containing "T" residues have a methoxy group at the 2' position of the ribose moiety, and a uracil at the base position of the nucleotide.

A "non-nucleotide unit" as used herein is a unit that does not significantly participate in hybridization of a polymer. Such units do not, for example, participate in any significant hydrogen bonding with a nucleotide, and would exclude units having as a component one of the five nucleotide bases or analogs thereof.

A "target nucleic acid" as used herein is a nucleic acid comprising a target sequence to be amplified. Target nucleic acids may be DNA or RNA as described herein, and may be either single-stranded or double-stranded. The target nucleic acid may include other sequences besides the target sequence, which may not be amplified.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during an amplification processes (e.g., TMA). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands.

"Target-hybridizing sequence" is used herein to refer to the portion of an oligomer that is configured to hybridize with a target nucleic acid sequence. In some embodiments, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to various genotypes of HCV. It is understood that other reasons exist for configuring a target-hybridizing sequence to have less than 100% complementarity to a target nucleic acid.

The term "targets a sequence" as used herein in reference to a region of HCV nucleic acid refers to a process whereby an oligonucleotide hybridizes to the target sequence in a manner that allows for amplification and detection as described herein. In one preferred embodiment, the oligonucleotide is complementary with the targeted HCV nucleic acid sequence and contains no mismatches. In another preferred embodiment, the oligonucleotide is complementary but contains 1, 2, 3, 4, or 5 mismatches with the targeted HCV nucleic acid sequence. In some embodiments, the oligonucleotide that hybridizes to the HCV nucleic acid sequence includes at least 10 to as many as 50 nucleotides complementary to the target sequence. It is understood that at least 10 and as many as 50 is an inclusive range such that 10, 50 and each whole number there between are included. In some embodiments, the oligomer specifically hybridizes to the target sequence.

The term "configured to" denotes an actual arrangement of the polynucleotide sequence configuration of a referenced oligonucleotide target-hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an amplification oligonucleotide, detection probe, or other oligonucleotide is designed to have a polynucleotide sequence that could target a sequence of the referenced HCV target region. Such an oligonucleotide is not limited to targeting that sequence only, but is rather useful as a composition, in a kit, or in a method for targeting a HCV target nucleic acid. The oligonucleotide is designed to function as a component of an assay for amplification and detection of HCV from a sample, and therefore is designed to target HCV in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined.

"Upstream" refers to a location closer to the 5' end of the (+) strand (or the 3' end of the (−) strand) than a given position. "Downstream" refers to a location closer to the 3' end of the (+) strand (or the 5' end of the (−) strand) than a given position.

The term "fragment," as used herein in reference to the targeted HCV nucleic acid, refers to a piece of contiguous nucleic acid. In certain embodiments, the fragment includes contiguous nucleotides from an HCV RNA corresponding to SEQ ID NO: 1, wherein the number of contiguous nucleotides in the fragment are less than that for the entire sequence corresponding to SEQ ID NO:1.

The term "region," as used herein, refers to a portion of a nucleic acid wherein said portion is smaller than the entire nucleic acid. For example, when the nucleic acid in reference is an oligonucleotide promoter primer, the term "region" may be used to refer to the smaller promoter portion of the entire oligonucleotide. Similarly, and also as example only, when the nucleic acid is an HCV RNA, the term "region" may be used to refer to a smaller area of the nucleic acid, wherein the smaller area is targeted by one or more oligonucleotides of the disclosure. As another non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods.

The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., a fluorophore).

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA or DNA equivalent thereof as well as DNA/RNA chimerics thereof, and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In some embodiments, the percentage is from 100% to about 85%. In some embodiments, this percentage is from 100% to about 90%, e.g., from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

As used herein, the phrase "or its complement, or an RNA equivalent or DNA/RNA chimeric thereof," with reference to a DNA sequence, includes (in addition to the referenced DNA sequence) the complement of the DNA sequence, an RNA equivalent of the referenced DNA sequence, an RNA equivalent of the complement of the referenced DNA sequence, a DNA/RNA chimeric of the referenced DNA sequence, and a DNA/RNA chimeric of the complement of the referenced DNA sequence.

Similarly, the phrase "or its complement, or a DNA equivalent or DNA/RNA chimeric thereof," with reference to an RNA sequence, includes (in addition to the referenced RNA sequence) the complement of the RNA sequence, a DNA equivalent of the referenced RNA sequence, a DNA equivalent of the complement of the referenced RNA sequence, a DNA/RNA chimeric of the referenced RNA sequence, and a DNA/RNA chimeric of the complement of the referenced RNA sequence.

As used herein, a "blocking moiety" is a substance used to "block" the 3'-terminus of an oligonucleotide or other nucleic acid so that it cannot be efficiently extended by a nucleic acid polymerase. Oligomers not intended for extension by a nucleic acid polymerase may include a blocker group that replaces the 3' OH to prevent enzyme-mediated extension of the oligomer in an amplification reaction. For example, blocked amplification oligomers and/or detection probes present during amplification may not have functional 3' OH and instead include one or more blocking groups located at or near the 3' end. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. In some embodiments, the 5' region of an amplification oligonucleotide may include a promoter sequence that is non-complementary to the target nucleic acid (which may be referred to as a "promoter primer"). Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions, and which is modified to prevent the initiation of DNA synthesis from its 3'-terminus. The "first region" of a promoter provider oligonucleotide comprises a base sequence that hybridizes to a DNA template, where the hybridizing sequence is situated 3', but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, In some embodiments comprising a blocking moiety at its 3'-terminus as described above. As referred to herein, a "T7 Provider" is a blocked promoter provider oligonucleotide that provides an oligonucleotide sequence that is recognized by T7 RNA polymerase.

A "terminating oligonucleotide" is an oligonucleotide comprising a base sequence that is substantially complementary to a sequence within the target nucleic acid in the vicinity of the 5'-end of the target region, so as to "terminate" primer extension of a nascent nucleic acid that includes a priming oligonucleotide, thereby providing a defined 3'-end for the nascent nucleic acid strand. A terminating oligonucleotide is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more 2'-O-ME ribonucleotides. These modified nucleotides have demonstrated higher thermal stability of complementary duplexes. The 2'-O-ME ribonucleotides also function to increase the resistance of oligonucleotides to exonucleases, thereby increasing the half-life of the modified oligonucleotides. (See, e.g., Majlessi et al., Nucleic Acids Res. 26:2224-9, 1988, incorporated by reference herein.) Other modifications as described elsewhere herein may be utilized in addition to or in place of 2'-O-Me ribonucleotides. For example, a terminating oligonucleotide may comprise PNA or an LNA. (See. e.g., Petersen et al., J. Mol. Recognit. 13:44-53, 2000, incorporated by reference herein.) A terminating oligonucleotide of the present disclosure typically includes a blocking moiety at its 3'-terminus to prevent extension. A terminating oligonucleotide may also comprise a protein or peptide joined to the oligonucleotide so as to terminate further extension of a nascent nucleic acid chain by a polymerase. A terminating oligonucleotide of the present disclosure is typically at least 10 bases in length, and may extend up to 15, 20, 25, 30, 35, 40, 50 or more nucleotides in length. While a terminating oligonucleotide typically or necessarily includes a 3'-blocking moiety, "3'-blocked" oligonucleotides are not necessarily terminating oligonucleotides.

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (see. e.g., U.S. Pat. No. 4,786,600, incorporated by reference herein). PCR amplification uses a DNA polymerase, pairs of primers, and thermal cycling to synthesize multiple copies of two complementary strands of dsDNA or from a cDNA (see. e.g., U.S. Pat. Nos. 4,683,195; 4,683,202; and 4,800,159; each incorporated by reference herein). LCR amplification uses four or more different oligonucleotides to amplify a target and its complementary strand by using multiple cycles of hybridization, ligation, and denaturation (see. e.g., U.S. Pat. Nos. 5,427,930 and 5,516,663, each incorporated by reference herein). SDA uses a primer that contains a recognition site for a restriction endonuclease and an endonuclease that nicks one strand of a hemimodified DNA duplex that includes the target sequence, whereby amplification occurs in a series of primer extension and strand displacement steps (see. e.g., U.S. Pat. Nos. 5,422,252; 5,547,861; and 5,648,211; each incorporated by reference herein).

As used herein, the term "linear amplification" refers to an amplification mechanism that is designed to produce an increase in the target nucleic acid linearly proportional to the amount of target nucleic acid in the reaction. For instance, multiple RNA copies can be made from a DNA target using a transcription-associated reaction, where the increase in the number of copies can be described by a linear factor (e.g., starting copies of template×100). In some embodiments, a first phase linear amplification in a multiphase amplification procedure increases the starting number of target nucleic acid strands or the complements thereof by at least 10 fold, e.g., by at least 100 fold, or by 10 to 1,000 fold before the second phase amplification reaction is begun. An example of a linear amplification system is "T7-based Linear Amplification of DNA" (TLAD; see Liu et al., BMC Genomics, 4: Art. No. 19, May 9, 2003). Other methods are known, e.g., from U.S. Pat. No. 9,139,870, or disclosed herein. Accordingly, the term "linear amplification" refers to an amplification reaction which does not result in the exponential amplification of a target nucleic acid sequence. The term "linear amplification" does not refer to a method that simply makes a single copy of a nucleic acid strand, such as the transcription of an RNA molecule into a single cDNA molecule as in the case of reverse transcription (RT)-PCR.

As used herein, the term "exponential amplification" refers to nucleic acid amplification that is designed to produce an increase in the target nucleic acid geometrically proportional to the amount of target nucleic acid in the reaction. For example, PCR produces one DNA strand for every original target strand and for every synthesized strand present. Similarly, transcription-associated amplification produces multiple RNA transcripts for every original target strand and for every subsequently synthesized strand. The amplification is exponential because the synthesized strands are used as templates in subsequent rounds of amplification. An amplification reaction need not actually produce exponentially increasing amounts of nucleic acid to be considered exponential amplification, so long as the amplification reaction is designed to produce such increases.

"Transcription-associated amplification" or "transcription-mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, e.g., a T7 promoter, and optionally may include one or more other oligonucleotides. When a T7 promoter-containing oligomer is used, it may be referred to as a "T7 primer" or "T7 oligomer"; other primers/oligomers may be referred to as "non-T7" or "NT7" primers/oligomers. TMA methods and single-primer transcription-associated amplification methods are embodiments of amplification methods used for detection of HCV target sequences as described herein. Variations of transcription-associated amplification are well-known in the art as previously disclosed in detail (see. e.g., U.S. Pat. Nos. 4,868,105; 5,124,246; 5,130,238; 5,399,491; 5,437,990; 5,554,516; and 7,374,885; and International Patent Application Pub. Nos. WO 88/01302; WO 88/10315; and WO 95/03430; each incorporated by reference herein). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored through real-time detection.

The term "amplicon" or "amplification product" as used herein refers to the nucleic acid molecule generated during an amplification procedure that is complementary or homologous to a sequence contained within the target sequence. The complementary or homologous sequence of an amplicon is sometimes referred to herein as a "target-specific sequence." Amplicons generated using the amplification oligomers of the current disclosure may comprise non-target specific sequences. Amplicons can be double-stranded or single-stranded and can include DNA, RNA, or both. For example, DNA-dependent RNA polymerase transcribes single-stranded amplicons from double-stranded DNA during transcription-mediated amplification procedures. These single-stranded amplicons are RNA amplicons and can be either strand of a double-stranded complex, depending on how the amplification oligomers are configured. Thus, amplicons can be single-stranded RNA. RNA-dependent DNA polymerases synthesize a DNA strand that is complementary to an RNA template. Thus, amplicons can be double-stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double-stranded DNA. RNA-dependent RNA polymerases synthesize RNA from an RNA template. Thus, amplicons can be double-stranded RNA. DNA-dependent RNA polymerases synthesize RNA from double-stranded DNA templates, also referred to as transcription. Thus, amplicons can be single stranded RNA. Amplicons and methods for generating amplicons are known to those skilled in the art. For convenience herein, a single strand of RNA or a single strand of DNA may represent an amplicon generated by an amplification oligomer combination of the current disclosure. Such representation is not meant to limit the amplicon to the representation shown. Skilled artisans in possession of the instant disclosure will use amplification oligomers and polymerase enzymes to generate any of the numerous types of amplicons, all within the spirit and scope of the current disclosure.

A "non-target-specific sequence," as is used herein refers to a region of an oligomer sequence, wherein said region does not stably hybridize with a target sequence under standard hybridization conditions. Oligomers with non-target-specific sequences include, but are not limited to, promoter primers and molecular beacons. An amplification oligomer may contain a sequence that is not complementary to the target or template sequence; for example, the 5' region of a primer may include a promoter sequence that is non-complementary to the target nucleic acid (referred to as a "promoter primer"). Those skilled in the art will understand that an amplification oligomer that functions as a primer may be modified to include a 5' promoter sequence, and thus function as a promoter primer. Similarly, a promoter primer may be modified by removal of, or synthesis without, a promoter sequence and still function as a primer. A 3' blocked amplification oligomer may provide a promoter sequence and serve as a template for polymerization (referred to as a "promoter provider"). Thus, an amplicon that is generated by an amplification oligomer member such as a promoter primer will comprise a target-specific sequence and a non-target-specific sequence.

"Detection probe," "detection oligonucleotide," "probe oligomer," and "detection probe oligomer" are used interchangeably to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Detection probes may be DNA, RNA, analogs thereof or combinations thereof (e.g., DNA/RNA chimerics) and they may be labeled or unlabeled. Detection probes may further include alternative backbone linkages such as, e.g., 2'-O-methyl linkages. A detection probe's "target sequence" generally refers to a smaller nucleic acid sequence region within a larger nucleic acid sequence that hybridizes specifically to at least a portion of a probe oligomer by standard base pairing. A detection probe may comprise target-specific sequences and other sequences that contribute to the three-dimensional conformation of the probe (see. e.g., U.S. Pat. Nos. 5,118,801; 5,312,728; 6,849,412; 6,835,542; 6,534,274; and 6,361,945; and US Patent Application Pub. No. 20060068417; each incorporated by reference herein).

By "stable" or "stable for detection" is meant that the temperature of a reaction mixture is at least 2° C. below the melting temperature of a nucleic acid duplex.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (see. e.g., U.S.

Pat. Nos. 5,283,174; 5,656,207; and 5,658,737; each incorporated by reference herein). Labels include chemiluminescent compounds, e.g., acridinium ester ("AE") compounds that include standard AE and derivatives (see. e.g., U.S. Pat. Nos. 5,656,207; 5,658,737; and 5,639,604; each incorporated by reference herein). Synthesis and methods of attaching labels to nucleic acids and detecting labels are well known. (See. e.g., Sambrook et al. Molecular Cloning. A Laboratory Manual, 2nd ed. (Cold Spring Harbor Laboratory Press, Cold Spring Harbor, N Y, 1989), Chapter 10, incorporated by reference herein. See also U.S. Pat. Nos. 5,658,737; 5,656,207; 5,547,842; 5,283,174; and 4,581,333; each incorporated by reference herein). More than one label, and more than one type of label, may be present on a particular probe, or detection may use a mixture of probes in which each probe is labeled with a compound that produces a detectable signal (see. e.g., U.S. Pat. Nos. 6,180,340 and 6,350,579, each incorporated by reference herein).

"Capture probe," "capture oligonucleotide," "capture oligomer," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. Another embodiment of a capture oligomer uses a target-sequence binding region that includes random or non-random poly-GU, poly-GT, or poly U sequences to bind non-specifically to a target nucleic acid and link it to an immobilized probe on a support.

As used herein, an "immobilized oligonucleotide," "immobilized probe," "immobilized binding partner," "immobilized oligomer," or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size+ 5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or two different regions of the same single-stranded nucleic acid, have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g., G:C, A:T, or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues, including abasic residues, that are not complementary. Sufficiently complementary contiguous sequences typically are at least 80%, or at least 90%, complementary to a sequence to which an oligomer is intended to specifically hybridize. Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" or "Watson-Crick" hydrogen-bonded base pairs with an analogous sequence of nucleotides of the other single-stranded region, such that A is paired with U or T and C is paired with G, the nucleotides sequences are "completely" complementary (see. e.g., Sambrook et al., Molecular Cloning. A Laboratory Manual, 2nd ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein). It is understood that ranges for percent identity are inclusive of all whole and partial numbers (e.g., at least 90% includes 90, 91, 93.5, 97.687, etc.). Reference to "the complement" of a particular sequence generally indicates a completely complementary sequence unless the context indicates otherwise.

"Wobble" base pairs refer to a pairing of a G to either a U or a T.

By "preferentially hybridize" or "specifically hybridize" is meant that under stringent hybridization assay conditions, probes hybridize to their target sequences, or replicates thereof, to form stable probe:target hybrids, while at the same time formation of stable probe:non-target hybrids is minimized. Thus, a probe hybridizes to a target sequence or replicate thereof to a sufficiently greater extent than to a non-target sequence, to enable one having ordinary skill in the art to accurately detect or quantitate RNA replicates or complementary DNA (cDNA) of the target sequence formed during the amplification. Appropriate hybridization conditions are well-known in the art, may be predicted based on sequence composition, or can be determined by using routine testing methods (see. e.g., Sambrook et al., Molecular Cloning A Laboratory Manual, 2nd ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein).

By "nucleic acid hybrid," "hybrid," or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

"Sample preparation" refers to any steps or method that treats a sample for subsequent amplification and/or detection of HCV nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. "Separating" or "purifying" does not connote any degree of purification. Typically, separating or purifying removes at least 70%, or at least 80%, or at least 95% of the target nucleic acid from other sample components.

As used herein, a "DNA-dependent DNA polymerase" is an enzyme that synthesizes a complementary DNA copy from a DNA template. Examples are DNA polymerase I from E. coli, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from E. coli and bacteriophages T7, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

"Thermophilic" indicates that an enzyme, e.g., a polymerase, exhibits optimal activity at a temperature greater than about 45° C., e.g., at a temperature in the range from about 50° C. to 99° C. In some embodiments, a thermophilic enzyme does not lose more than 50% of its activity upon incubation for 20 minutes at 60° C. In some embodiments, a thermophilic enzyme is obtained or derived from a thermophilic organism, e.g., an organism whose optimal growth temperature is greater than or equal to about 45° C., e.g., greater than or equal to about 50° C.

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes possessing the same or similar activity as RNAse H may also be used. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes that selectively degrade RNA target sequences or RNA products of the present disclosure will be readily apparent to those of ordinary skill in the art.

As used herein, a "standard curve" is a representation that relates (1) a pre-amplification amount of a polynucleotide, and (2) some time-dependent indicia of a post-amplification amount of a corresponding amplicon. For example, a standard curve can be a graph having known numbers of input template molecules plotted on the x-axis, and a time value required for the amplification reaction to achieve some level of detectable amplicon production plotted on the y-axis. Standard curves typically are produced using control polynucleotide standards containing known numbers of polynucleotide templates. Standard curves can be stored in electronic form or can be represented graphically. The pre-amplification amount of an analyte polynucleotide in a test sample can be determined by comparing a measured time-dependent value obtained for the test sample with a standard curve, as will be familiar to those having an ordinary level of skill in the art.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

As used herein, the terms "relative light unit" ("RLU") and "relative fluorescence unit" ("RFU") represent arbitrary units of measurement indicating the relative number of photons emitted by the sample at a given wavelength or band of wavelengths. A measurement of RLU or RFU varies with the characteristics of the detector used for the measurement.

As used herein, the terms "TTime," "emergence time," and "time of emergence" are interchangeable and represent the threshold time or time of emergence of signal in a real-time plot of the assay data. TTime values estimate the time at which a particular threshold indicating amplicon production is passed in a real-time amplification reaction. TTime and an algorithm for calculating and using TTime values are described in Light et al., U.S. Pub. No. 2006/0276972, paragraphs [0517] through [0538], the disclosure of which is incorporated by reference herein. A curve fitting procedure is applied to normalized and background-adjusted data. The curve fit is performed for only a portion of the data between a predetermined low bound and high bound. The goal, after finding the curve that fits the data, is to estimate the time corresponding to the point at which the curve or a projection thereof intersects a predefined threshold value. In one embodiment, the threshold for normalized data is 0.11. The high and low bounds are determined empirically as that range over which curves fit to a variety of control data sets exhibit the least variability in the time associated with the given threshold value. For example, in one embodiment, the low bound is 0.04 and the high bound is 0.36. The curve is fit for data extending from the first data point below the low bound through the first data point past the high bound. Next, there is made a determination whether the slope of the fit is statistically significant. For example, if the p value of the first order coefficient is less than 0.05, the fit is considered significant, and processing continues. If not, processing stops. Alternatively, the validity of the data can be determined by the $R^2$ value. The slope m and intercept b of the linear curve y=mx+b are determined for the fitted curve. With that information, TTime can be determined as follows: TTime=(Threshold−b)/m.

Unless otherwise indicated, oligomer sequences appearing in tables below follow the conventions that lower case letters indicate 2'-O-methyl RNA for oligomers or RNA for viral sequences, and upper case letters indicate DNA. "(c9)" indicates a —(CH$_2$)$_9$— linker. In vitro transcript (IVT) sequences are RNA unless otherwise indicated.

References, particularly in the claims, to "the sequence of SEQ ID NO: X" refer to the base sequence of the corresponding sequence listing entry and do not require identity of the backbone (e.g., RNA, 2'-O-Me RNA, or DNA) unless otherwise indicated. Furthermore, T and U residues are to be considered interchangeable for purposes of sequence listing entries unless otherwise indicated, e.g., a sequence can be considered identical to SEQ ID NO: 2 regardless of whether the residue at the sixth position is a T or a U.

B. Oligomers, Compositions, and Kits

The present disclosure provides oligomers, compositions, and kits, useful for amplifying, detecting, or quantifying HCV from a sample.

In some embodiments, amplification oligomers are provided. Amplification oligomers generally comprise a target-hybridizing region, e.g., configured to hybridize specifically to an HCV nucleic acid. While oligomers of different lengths and base composition may be used for amplifying HCV nucleic acids, in some embodiments oligomers in this disclosure have target-hybridizing regions from 10 to 60 bases in length, between 14 and 50 bases in length, or between 15 and 40 bases in length. In some embodiments, an initial amplification oligomer is used having a relatively long target hybridizing region such as about 30-50 nucleotides, e.g., 35-45, and at a later stage amplification oligomers with shorter target-hybridizing regions are used, e.g., about 14-35 nucleotides, such as about 15-30 nt.

In certain embodiments, an amplification oligomer as described herein is a promoter primer further comprising a promoter sequence located 5' to the target-hybridizing sequence and which is non-complementary to the HCV target nucleic acid. For example, in some embodiments of an oligomer combination as described herein for amplification of an HCV target region, an amplification oligomer as described above in (b) (e.g., an amplification oligomer comprising or consisting of an antisense target-hybridizing sequence as shown in Table 1) is a promoter primer further comprising a 5' promoter sequence. In particular embodiments, the promoter sequence is a T7 RNA polymerase promoter sequence such as, for example, a T7 promoter sequence having the sequence shown in SEQ ID NO:8. In specific variations, a promoter primer comprises the non-HCV sequence including a T7 promoter shown in one of SEQ ID NOs:9, SEQ ID NO:10, or, In some embodiments, SEQ ID NO:11. Alternatively, an amplification oligomer can be a promoter provider.

In some embodiments, an amplification oligomer is not a promoter primer or does not comprise a promoter sequence. For example, in PCR-based approaches the primers are generally not promoter primers, and in TMA-based approaches at least one primer that is not a promoter primer is typically used (while at least one promoter primer is also used).

In some embodiments, a first amplification oligomer is provided which is a forward amplification oligomer, i.e., it is configured to hybridize specifically to (−) strand HCV nucleic acid and its target-hybridizing sequence corresponds to the "sense" sequence of HCV.

In some embodiments, the target sequence of the first amplification oligomer comprises position 65 of an HCV genomic nucleic acid such as SEQ ID NO: 75, e.g., positions 64-66, 63-67, 62-68, 61-69, 60-70, 59-71, 58-72, 57-73, 56-74, 55-75, 54-76, 53-77, or 52-78. In some embodiments, the first amplification oligomer comprises a sequence having up to 1 or 2 mismatches relative to SEQ ID NO: 2. In some embodiments, the first amplification oligomer comprises a sequence having up to 1 or 2 mismatches relative to SEQ ID NO: 3 or 215. In some embodiments, the first amplification oligomer comprises a sequence having up to 1 or 2 mismatches relative to one of SEQ ID NOs: 76-107. Various embodiments of the first amplification oligomer, including with respect to its sequence, are disclosed in the summary above, any of which can be combined to the extent feasible with the features discussed above in this section.

In some embodiments, a second amplification oligomer is provided which is an additional forward amplification oligomer different from the first amplification oligomer. As described in the examples, using a second forward amplification oligomer can improve the relative accuracy of quantification of HCV nucleic acid despite sequence variation between genotypes.

In some embodiments, the target sequence of the second amplification oligomer comprises position 65 of an HCV genomic nucleic acid such as SEQ ID NO: 75, e.g., positions 64-66, 63-67, 62-68, 61-69, 60-70, 59-71, 58-72, 57-73, 56-74, 55-75, 54-76, 53-77, or 52-78. In some embodiments, the second amplification oligomer comprises a sequence having up to 1 or 2 mismatches relative to SEQ ID NO: 3. In some embodiments, the second amplification oligomer comprises a sequence having up to 1 or 2 mismatches relative to SEQ ID NO: 2 or 215. In some embodiments, the first amplification oligomer comprises a sequence having up to 1 or 2 mismatches relative to one of SEQ ID NOs: 76-107. Various embodiments of the second amplification oligomer, including with respect to its sequence, are disclosed in the summary above, any of which can be combined to the extent feasible with the features discussed above in this section.

It should be noted that when only one forward amplification oligomer is used, it can have the features attributed either to a first or a second amplification oligomer herein. This note applies mutatis mutandis to other instances where ordinal numerals are used, e.g., if only one capture oligomer is used, it can have the features attributed either to a first or a second capture oligomer herein.

In some embodiments, a third amplification oligomer is provided which is a reverse amplification oligomer, i.e., it is configured to hybridize specifically to (+) strand HCV nucleic acid and its target-hybridizing sequence corresponds to the "antisense" sequence of HCV.

In some embodiments, the target sequence of the third amplification oligomer comprises position 106 of an HCV genomic nucleic acid such as SEQ ID NO: 75, e.g., positions 105-107, 104-108, 103-109, 102-110, 101-111, 100-112, 99-113, 98-114, 97-115, 96-116, 95-117, 94-118, or 93-119. In some embodiments, the third amplification oligomer comprises a sequence having up to 1 or 2 mismatches relative to SEQ ID NO: 7. In some embodiments, the third amplification oligomer comprises a sequence of SEQ ID NO: 218 or 219, or a sequence having up to 1 or 2 mismatches relative thereto. In some embodiments, the third amplification oligomer comprises a sequence of SEQ ID NO: 147 or 220 or a sequence having up to 1 or 2 mismatches relative thereto. In some embodiments, the third amplification oligomer comprises a target-hybridizing sequence comprising the complement of positions N-119 of SEQ ID NO: 75, where N is 87, 88, 89, 90, 91, 92, 93, 94, or 95 or a sequence having up to 1 or 2 mismatches relative thereto, e.g., one of SEQ ID NOs: 114-128.

Various embodiments of the third amplification oligomer, including with respect to its sequence, are disclosed in the summary above, any of which can be combined to the extent feasible with the features discussed above in this section.

It should be noted that the presence of a third amplification oligomer does not necessarily imply the presence of both first and second amplification oligomers. For example, it is possible to perform an exponential amplification in the presence only of first and third amplification oligomers. Additionally, a linear amplification can be performed in the presence of a third amplification oligomer without requiring any forward amplification oligomer. In some embodiments, the third amplification oligomer is a promoter primer, such that it may have any of the features of promoter primers discussed above. This note applies mutatis mutandis to other instances where ordinal numerals are used, e.g., the presence of a second capture oligomer does not necessarily imply the presence of a first capture oligomer.

In some embodiments, an initial amplification oligomer is provided. The initial amplification oligomer can be different from the first, second, and third amplification oligomers to the extent that they are present or used. In some embodiments, the initial amplification oligomer has a longer target-hybridizing region than at least one other amplification oligomer, such as the third amplification oligomer, or than the first, second, and third AOs. As described in the examples, it was found that using an initial amplification oligomer comprising a long target-hybridizing region can improve subsequent amplification and quantification of certain HCV genotypes and thereby improve overall detection and quantification performance.

In some embodiments, the target sequence of the initial amplification oligomer comprises position 99 of an HCV genomic nucleic acid such as SEQ ID NO: 75, e.g., positions 98-100, 97-101, 96-102, 95-103, 94-104, 93-105, 92-106, 91-107, 90-108, 89-109, 88-110, 87-111, 86-112, 85-113, 84-114, 83-115, 82-116, 81-117, 80-118, or 80-119. In some embodiments, the initial amplification oligomer comprises a sequence having up to 1 or 2 mismatches relative to SEQ ID NO: 6. In some embodiments, the initial amplification oligomer comprises a sequence of SEQ ID NO: 218 or 219, or a sequence having up to 1 or 2 mismatches relative thereto. In some embodiments, the initial amplification oligomer comprises a target-hybridizing sequence comprising the complement of positions N-119 of SEQ ID NO: 75, where N is 79, 80, 81, 82, 83, 84, 85, 86, 87, 88, 89, 90, 91, 92, 93, 94, or 95, or a sequence having up to 1 or 2 mismatches relative thereto. Various embodiments of the initial amplification oligomer, including with respect to its sequence, are disclosed in the summary above, any of which can be combined to the extent feasible with the features discussed above in this section.

In some embodiments, at least one probe oligomer is provided. Some embodiments of detection probes that hybridize to complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified HCV sequences may be unlabeled and detected indirectly (e.g., by binding of another binding partner to a moiety on the probe) or may be labeled with a variety of detectable labels. A detection probe oligomer may contain a 2'-methoxy backbone at one or more linkages in the nucleic acid backbone.

In some embodiments, a detection probe oligomer in accordance with the present disclosure further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see. e.g., U.S. Pat. Nos. 6,180,340 and 6,350,579, each incorporated by reference herein). Labels may be attached to a probe by various means including covalent linkages, chelation, and ionic interactions, but in some embodiments the label is covalently attached. For example, in some embodiments, a detection probe has an attached chemiluminescent label such as, e.g., an acridinium ester (AE) compound (see. e.g., U.S. Pat. Nos. 5,185,439; 5,639,604; 5,585,481; and 5,656,744; each incorporated by reference herein), which in typical variations is attached to the probe by a non-nucleotide linker (see. e.g., U.S. Pat. Nos. 5,585,481; 5,656,744; and 5,639,604, each incorporated by reference herein).

A detection probe oligomer in accordance with the present disclosure may further include a non-target-hybridizing sequence. In some applications, probes exhibiting at least some degree of self-complementarity are desirable to facilitate detection of probe:target duplexes in a test sample without first requiring the removal of unhybridized probe prior to detection. Specific embodiments of such detection probes include, for example, probes that form conformations held by intramolecular hybridization, such as conformations generally referred to as hairpins. Particularly suitable hairpin probes include a "molecular torch" (see. e.g., U.S. Pat. Nos. 6,849,412; 6,835,542; 6,534,274; and 6,361,945, each incorporated by reference herein) and a "molecular beacon" (see. e.g., Tyagi et al., supra; U.S. Pat. Nos. 5,118,801 and 5,312,728, supra). In yet other embodiments, a detection probe is a linear oligomers that does not substantially form conformations held by intramolecular bonds.

By way of example, structures referred to as "molecular beacons" comprise nucleic acid molecules having a target complementary sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are fully described in U.S. Pat. No. 5,925,517, the disclosure of which is hereby incorporated by reference. Molecular beacons useful for detecting HCV specific nucleic acid sequences may be created by appending to either end of one of the probe (e.g., target-hybridizing) sequences disclosed herein, a first nucleic acid arm comprising a fluorophore and a second nucleic acid arm comprising a quencher moiety. In this configuration, the HCV specific probe sequence disclosed herein serves as the target-complementary "loop" portion of the resulting molecular beacon, while the self-complementary "arms" of the probe represent the "stem" portion of the probe.

Another example of a self-complementary hybridization assay probe that may be used in conjunction with the disclosure is a structure commonly referred to as a "molecular torch" (sometimes referred to simply as a torch). These self-reporting probes are designed to include distinct regions of self-complementarity (coined "the target binding domain" and "the target closing domain") which are connected by a joining region (e.g., a —(CH$_2$)$_9$— linker) and which hybridize to one another under predetermined hybridization assay conditions. When exposed to an appropriate target or denaturing conditions, the two complementary regions (which may be fully or partially complementary) of the molecular torch melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., fluorescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith. Molecular torches are fully described in U.S. Pat. No. 6,361,945, the disclosure of which is hereby incorporated by reference.

Molecular torches and molecular beacons in some embodiments are labeled with an interactive pair of detectable labels. Examples of detectable labels that are members of an interactive pair of labels include those that interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other. This is the case, for example, when a molecular beacon is maintained in the closed state by formation of a stem duplex, and fluorescent emission from a fluorophore attached to one arm of the probe is quenched by a quencher moiety on the opposite arm.

Exemplary label moieties for the disclosed molecular torches and molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are In some embodiments due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same probe is in the open state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used in connection with the disclosure, making no attempt to distinguish FRET from non-FRET pairs, include fluorescein/tetramethylrhodamine, IAEDANS/fluororescein, EDANS/DABCYL, coumarin/DABCYL, fluorescein/fluorescein, Invitrogen™ BODIPY™ FL/BODIPY™ FL, fluorescein/DABCYL, lucifer yellow/DABCYL, BODIPY™/DABCYL, eosine/DABCYL, erythrosine/DABCYL, tetramethylrhodamine/DABCYL, Invitrogen™ Texas Red™/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY7 dyes advantageously eliminate the potential problem of background fluorescence resulting from direct (i.e., non-sensitized) acceptor excitation. Exemplary fluorophore moieties that can be used as one member of a donor-acceptor pair include fluorescein, ROX, and the CY dyes (such as CY5). Exemplary quencher moieties that can be used as another member of a donor-acceptor pair include DABCYL and the BLACK HOLE QUENCHER moieties which are available from Biosearch Technologies, Inc., (Novato, Calif.).

Oligomers that are not intended to be extended by a nucleic acid polymerase, e.g., probe oligomers and capture oligomers, can include a blocker group that replaces the 3' OH to prevent enzyme-mediated extension of the oligomer in an amplification reaction. For example, blocked amplification oligomers and/or detection probes present during amplification in some embodiments do not have a functional 3' OH and instead include one or more blocking groups located at or near the 3' end. A blocking group near the 3' end is in some embodiments within five residues of the 3' end and is sufficiently large to limit binding of a polymerase to the oligomer, and other embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin.

While oligonucleotide probes of different lengths and base composition may be used for detecting HCV nucleic acids, some embodiments of probes in this disclosure are from 10 to 60 bases in length, or between 14 and 50 bases in length, or between 15 and 30 bases in length.

In some embodiments, the target sequence of the probe oligomer comprises position 88 or 89 of an HCV genomic nucleic acid such as SEQ ID NO: 75, e.g., positions 88-89, 87-90, 86-91, 85-92, 84-93, 83-94, 82-95, or 81-96. In some embodiments, the probe oligomer comprises a sequence having up to 1 or 2 mismatches relative to SEQ ID NO: 13. In some embodiments, the probe oligomer comprises a sequence of positions 1-19 of SEQ ID NO: 216 or positions 1-19 of SEQ ID NO: 217, or a sequence having up to 1 or 2 mismatches relative thereto. In some embodiments, the probe oligomer comprises a sequence having up to 1 or 2 mismatches relative to SEQ ID NO: 12. In some embodiments, the probe oligomer comprises a sequence of SEQ ID NO: 216 or 217, or a sequence having up to 1 or 2 mismatches relative thereto. Various embodiments of the probe oligomer, including with respect to its sequence, are disclosed in the summary above, any of which can be combined to the extent feasible with the features discussed above in this section.

In some embodiments, at least one capture oligomer is provided. The capture oligomer comprises a target-hybridizing sequence configured to specifically hybridize to HCV nucleic acid, e.g., from 10 to 60 bases in length, or between 14 and 50 bases in length, or between 15 and 30 bases in length. The target-hybridizing sequence is covalently attached to a sequence or moiety that binds to an immobilized probe, e.g., an oligomer attached to a solid substrate, such as a bead.

In more specific embodiments, the capture probe oligomer includes a tail portion (e.g., a 3' tail) that is not complementary to the HCV target sequence but that specifically hybridizes to a sequence of the immobilized binding partner (e.g., immobilized probe), thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and certain embodiments include a substantially homopolymeric tail ("poly-N sequence") of at least about 10 nt, e.g., about 10 to 40 nt (e.g., $A_{10}$ (positions 1-10 of SEQ ID NO: 22) to $A_{40}$ (SEQ ID NO: 268), such as about 14 to 33 nt (e.g., $A_{14}$ (positions 1-14 of SEQ ID NO: 22) to $A_{30}$ (SEQ ID NO: 22) or $T_3A_{14}$ (positions 1-17 of SEQ ID NO: 21) to $T_3A_{30}$ (SEQ ID NO: 21)), that bind to a complementary immobilized sequence (e.g., poly-T) attached to a solid support, e.g., a matrix or particle. For example, in specific embodiments of a capture probe comprising a 3' tail, the capture probe has a sequence selected from SEQ ID NO:16 or 17.

In some embodiments, a first capture oligomer is provided. In some embodiments, the target sequence of the first capture oligomer comprises position 307 of an HCV genomic nucleic acid such as SEQ ID NO: 75, e.g., positions 306-308, 305-309, 304-310, 303-311, 302-312, 301-313, 300-314, 299-315, or 298-316. In some embodiments, the first capture oligomer comprises a sequence having up to 1 or 2 mismatches relative to SEQ ID NO: 54. In some embodiments, the first capture oligomer comprises a sequence having up to 1 or 2 mismatches relative to SEQ ID NO: 16. In some embodiments, the first capture oligomer comprises a sequence having up to 1 or 2 mismatches relative to positions 1-19 of one of SEQ ID NOS: 161-165. Various embodiments of the first capture oligomer, including with respect to its sequence, are disclosed in the summary above, any of which can be combined to the extent feasible with the features discussed above in this section.

In some embodiments, a second capture oligomer different from the first capture oligomer is provided. In some embodiments, the target sequence of the second capture oligomer comprises position 335 or 336 of an HCV genomic nucleic acid such as SEQ ID NO: 75, e.g., positions 335-336, 334-337, 333-338, 332-339, 331-340, 330-341, 329-342, 328-343, or 327-344. In some embodiments, the second capture oligomer comprises a sequence having up to 1 or 2 mismatches relative to SEQ ID NO: 55. In some embodiments, the second capture oligomer comprises a sequence having up to 1 or 2 mismatches relative to SEQ ID NO: 17. In some embodiments, the first capture oligomer comprises a sequence having up to 1 or 2 mismatches relative to positions 1-19 of one of SEQ ID NOS: 161-165. Various embodiments of the second capture oligomer, including with respect to its sequence, are disclosed in the summary above, any of which can be combined to the extent feasible with the features discussed above in this section.

Various embodiments of the second capture oligomer, including with respect to its sequence, are disclosed in the summary above, any of which can be combined to the extent feasible with the features discussed above in this section.

Internal control oligomers can be provided, e.g., for confirming that a negative result is valid by establishing that conditions were suitable for amplification. An exemplary control target capture oligomer is SEQ ID NO: 15. Exemplary control amplification oligomers are SEQ ID NOS: 18 and 19. An exemplary control probe oligomer is SEQ ID NO:20. A control template that can be amplified by the control amplification oligomers can also be provided. Control templates may be prepared according to known protocols. See, e.g., U.S. Pat. No. 7,785,844, which is incorporated herein by reference, and which describes an internal control consisting of an in vitro synthesized transcript containing a portion of HIV-1 sequence and a unique sequence targeted by the internal control probe.

In certain aspects of the disclosure, a combination of at least two oligomers is provided for determining the presence or absence of HCV or quantifying HCV in a sample. In some embodiments, the oligomer combination includes at least two amplification oligomers suitable for amplifying a target region of an HCV target nucleic acid, e.g., having the sequence of SEQ ID NO: 1, 75, an HCV strain referred to in Table 5, the HCV-derived sequence of any of SEQ ID NO: 63-74, or an HCV construct described in Example 10. In such embodiments, at least one amplification oligomer comprises a target-hybridizing sequence in the sense orientation ("sense THS") and at least one amplification oligomer comprises a target-hybridizing sequence in the antisense orientation ("antisense THS"), where the sense THS and antisense THS are each configured to specifically hybridize to a target sequence within an HCV sequence. It is understood that the target-hybridizing sequences are selected such that the HCV sequence targeted by antisense THS is situated downstream of the HCV sequence targeted by the sense THS (i.e., the at least two amplification oligomers are situated such that they flank the target region to be amplified).

The oligomers can be provided in various combinations (e.g., kits or compositions), e.g., comprising 2, 3, 4, 5, 6, or 7 of a first amplification oligomer, second amplification oligomer, third amplification oligomer, initial amplification oligomer, probe oligomer, first capture oligomer, and second capture oligomer, such as an initial amplification oligomer and at least one capture oligomer; a first capture oligomer and second capture oligomer, optionally further comprising an initial amplification oligomer; a first amplification oligomer and a third amplification oligomer, optionally further comprising a probe oligomer; a first, second, and third amplification oligomer, optionally further comprising a probe oligomer; an initial amplification oligomer, at least one capture oligomer, a first amplification oligomer, and a third amplification oligomer, optionally further comprising a probe oligomer; an initial amplification oligomer, a first capture oligomer, a second capture oligomer, a first amplification oligomer, and a third amplification oligomer, optionally further comprising a probe oligomer; an initial amplification oligomer, at least one capture oligomer, a first amplification oligomer, a second amplification oligomer, and a third amplification oligomer, optionally further comprising a probe oligomer; or an initial amplification oligomer, a first capture oligomer, a second capture oligomer, a first amplification oligomer, a second amplification oligomer, and a third amplification oligomer, optionally further comprising a probe oligomer. Combinations can further comprise a control oligomer or combination thereof, e.g., two control AOs, a control target capture oligomer, and/or a control probe oligomer. In some embodiments, both first and second AOs are present. In some embodiments, both initial and third AOs are present. In some embodiments, both an initial amplification oligomer and a probe oligomer are present, wherein the initial amplification oligomer and probe oligomer anneal to at least one common position, such as at least 5, 10, or 15 common positions, in an HCV nucleic acid.

In some embodiments, a combination does not comprise more than 8, 7, 6, or 5 distinct oligomers, not including control oligomers. In such embodiments, variants present in trace amounts (e.g., about 15 mol % or less or about 10 mol % or less relative to a major species of oligomer, such as the oligomer with the most similar sequence to the variant), such as may result from misincorporation, double incorporation, omission, or other errors during oligomer synthesis, are not considered a distinct oligomer.

In some embodiments, a combination of oligomers is provided as described below in any of the examples or individual reactions described in the examples.

In some embodiments, a combination of oligomers, e.g., in a kit or composition, is configured to specifically hybridize to nucleic acid of at least three, four, five, or six HCV genotypes (e.g., types 1a, 1b, 2b, 3a, 3b, 4h, 5a, 6a), optionally with minimal cross-reactivity to other, non-HCV nucleic acids suspected of being in a sample (e.g., other bloodborne pathogens). In certain variations, compositions of the disclosure further allow detection of HCV sequences that vary from the 5' UTR of the foregoing types, e.g., at least 1, 2, 3, 4, 5, 10, 15, 20, 25, 30, 35, 40, 45, or all HCV strains comprising a sequence of SEQ ID NO: 166-213 or 214 (e.g., strains listed in Table 5). In some embodiments, a combination of oligomers can be used to quantify such strains within 1 log of HCV 1a. In some embodiments, a combination of oligomers can be used to quantify such strains within 0.5 log of HCV 1a. In some aspects, the compositions of the instant disclosure are configured to specifically hybridize to HCV nucleic acid with minimal cross-reactivity to one or more, or all, of Hepatitis A, Hepatitis B, Herpes simplex 1, Herpes simplex 2, HIV, Parvovirus, Rubella, Dengue 2, Dengue 3, Dengue 4, Epstein-Barr, and West Nile viruses. In some embodiments, the compositions of the instant disclosure are configured to specifically hybridize to HCV nucleic acid with minimal cross-reactivity to one or more, or all, of *C. albicans, C. diphtheriae, P. acnes, S. aureus, S. epidermis, S. pneumoniae*. In one aspect, the compositions of the instant disclosure are part of a multiplex system that further includes components and methods for detecting one of more of these organisms.

Also provided by the disclosure is a reaction mixture for determining the presence or absence of an HCV target nucleic acid or quantifying the amount thereof in a sample. A reaction mixture in accordance with the present disclosure at least comprises one or more of the following: an oligomer combination as described herein for amplification of an HCV target nucleic acid; a capture probe oligomer as described herein for purifying the HCV target nucleic acid; a detection probe oligomer as described herein for determining the presence or absence of an HCV amplification product; and a probe protection oligomer as described herein for detuning sensitivity of an assay for detecting the HCV target nucleic acid. In some embodiments, any oligomer combination described above is present in the reaction mixture. The reaction mixture may further include a number of optional components such as, for example, arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which an HCV target nucleic acid may or may not be present. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject disclosure are kits for practicing the methods as described herein. A kit in accordance with the present disclosure at least comprises one or more of the following: an amplification oligomer combination as described herein for amplification of an HCV target nucleic acid; a capture probe oligomer as described herein for purifying the HCV target nucleic acid; a detection probe oligomer as described herein for determining the presence or absence of an HCV amplification product; and a probe protection oligomer as described herein for detuning sensitivity of an assay for detecting the HCV target nucleic acid. In some embodiments, any oligomer combination described above is present in the kit. The kits may further include a number of optional components such as, for example, arrays of capture probe nucleic acids. Other reagents that may be present in the kits include reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). Oligomers as described herein may be packaged in a variety of different embodiments, and those skilled in the art will appreciate that the disclosure embraces many different kit configurations. For example, a kit may include amplification oligomers for only one target region of an HCV genome, or it may include amplification oligomers for multiple HCV target regions. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present disclosure, where the instructions may be associated with a package insert and/or the packaging of the kit or the components thereof.

C. Methods and Uses

Any method disclosed herein is also to be understood as a disclosure of corresponding uses of materials involved in the method directed to the purpose of the method. Any of the oligomers comprising HCV sequence and any combinations (e.g., kits and compositions) comprising such an oligomer are to be understood as also disclosed for use in detecting or quantifying HCV, and for use in the preparation of a composition for detecting or quantifying HCV.

Broadly speaking, methods can comprise one or more of the following components: target capture, in which HCV nucleic acid is annealed to a capture oligomer and optionally to an initial amplification oligomer; isolation, e.g., washing, to remove material not associated with a capture oligomer; linear amplification; exponential amplification; and amplicon detection, e.g., amplicon quantification, which may be performed in real time with exponential amplification. Certain embodiments involve each of the foregoing steps. Certain embodiments involve exponential amplification without linear amplification. Certain embodiments involve washing, isolation, and linear amplification. Certain embodiments involve exponential amplification and amplicon detection. Certain embodiments involve any two of the components listed above. Certain embodiments involve any two components listed adjacently above, e.g., washing and linear amplification, or linear amplification and exponential amplification.

In some embodiments, amplification comprises contacting the sample with at least two oligomers for amplifying an HCV nucleic acid target region corresponding to an HCV target nucleic acid, where the oligomers include at least two amplification oligomers as described above (e.g., one or more oriented in the sense direction and one or more oriented in the antisense direction for exponential amplification); (2) performing an in vitro nucleic acid amplification reaction, where any HCV target nucleic acid present in the sample is used as a template for generating an amplification product; and (3) detecting the presence or absence of the amplification product, thereby determining the presence or absence of HCV in the sample, or quantifying the amount of HCV nucleic acid in the sample.

A detection method in accordance with the present disclosure can further include the step of obtaining the sample to be subjected to subsequent steps of the method. In certain embodiments, "obtaining" a sample to be used includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying the HCV target nucleic acid from other components in the sample, e.g., before an amplification, such as before a capture step. Such purification may include methods of separating and/or concentrating organisms contained in a sample from other sample components, or removing or degrading non-nucleic acid sample components, e.g., protein, carbohydrate, salt, lipid, etc. In some embodiments, DNA in the sample is degraded, e.g., with DNase, and optionally removing or inactivating the DNase or removing degraded DNA.

In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains HCV nucleic acid and other sample components.

Target capture typically occurs in a solution phase mixture that contains one or more capture probe oligomers that hybridize specifically to the HCV target sequence under hybridizing conditions, usually at a temperature higher than the $T_m$ of the tail-sequence:immobilized-probe-sequence duplex. For embodiments comprising a capture probe tail, the HCV-target:capture-probe complex is captured by adjusting the hybridization conditions so that the capture probe tail hybridizes to the immobilized probe. Certain embodiments use a particulate solid support, such as paramagnetic beads.

Isolation can follow capture, wherein the complex on the solid support is separated from other sample components. Isolation can be accomplished by any appropriate technique, e.g., washing a support associated with the HCV-target-sequence one or more times (e.g., 2 or 3 times) to remove other sample components and/or unbound oligomer. In embodiments using a particulate solid support, such as paramagnetic beads, particles associated with the HCV-target may be suspended in a washing solution and retrieved from the washing solution, In some embodiments by using magnetic attraction. To limit the number of handling steps, the HCV target nucleic acid may be amplified by simply mixing the HCV target sequence in the complex on the support with amplification oligomers and proceeding with amplification steps.

Linear amplification can be performed, e.g., by contacting the target nucleic acid sequence with a first phase amplification reaction mixture that supports linear amplification of the target nucleic acid sequence and lacks at least one component that is required for its exponential amplification. In some embodiments, the first phase amplification reaction mixture includes an amplification enzyme selected from a reverse transcriptase, a polymerase, and a combination thereof. The polymerase is typically selected from an RNA-dependent DNA polymerase, a DNA-dependent DNA polymerase, a DNA-dependent RNA polymerase, and a combination thereof. In some embodiments, the first phase amplification reaction mixture further includes a ribonuclease (RNase), such as an RNase H or a reverse transcriptase with an RNase H activity. In some embodiments, the first phase amplification mixture includes a reverse transcriptase with an RNase H activity and an RNA polymerase.

In some embodiments, the first phase amplification mixture may also include an amplification oligonucleotide. The amplification oligonucleotide can include a 5' promoter sequence for an RNA polymerase, such as T7 RNA polymerase, and/or a blocked 3' terminus that prevents its enzymatic extension. In addition, the first phase amplification mixture may sometimes include a blocker oligonucleotide to prevent enzymatic extension of the target nucleic sequence beyond a desired end-point.

As noted above, the key feature of the first phase amplification reaction is its inability to support an exponential amplification reaction because one or more components required for exponential amplification are lacking, and/or an agent is present which inhibits exponential amplification, and/or the temperature of the reaction mixture is not conducive to exponential amplification, etc. Without limitation, the lacking component required for exponential amplification and/or inhibitor and/or reaction condition may be selected from the following group: an amplification oligonucleotide (e.g., an amplification oligonucleotide comprising a 5' promoter sequence for an RNA polymerase, a non-promoter amplification oligonucleotide, or a combination thereof), an enzyme (e.g., a polymerase, such as an RNA polymerase), a nuclease (e.g., an exonuclease, an endonuclease, a cleavase, an RNase, a phosphorylase, a glycosylase, etc), an enzyme co-factor, a chelator (e.g., EDTA or EGTA), ribonucleotide triphosphates (rNTPs), deoxyribonucleotide triphosphates (dNTPs), $Mg^{2+}$, a salt, a buffer, an enzyme inhibitor, a blocking oligonucleotide, pH, temperature, salt concentration and a combination thereof. In some cases, the lacking component may be involved indirectly, such as an agent that reverses the effects of an inhibitor of exponential amplification which is present in the first phase reaction.

Exponentially amplifying an HCV target sequence utilizes an in vitro amplification reaction using at least two amplification oligomers that flank a target region to be amplified. In some embodiments, first and second amplification oligomers as described above are provided in the forward orientation and a third amplification oligomer is provided in the reverse orientation. In particular embodiments, the target region to be amplified substantially corresponds to a region of SEQ ID NO:75 including nucleotide position 79, e.g., about positions 74-84, 69-89, 64-94, 59-99, 59-109, or 52-119 (including oligomer sequences incorporated into the amplification product). Particularly suitable amplification oligomer combinations for amplification of these target regions are described above. Suitable amplification methods include, for example, replicase-mediated amplification, polymerase chain reaction (PCR), ligase chain reaction (LCR), strand-displacement amplification (SDA), and transcription-mediated or transcription-associated amplification (TMA).

For example, some amplification methods that use TMA amplification include the following steps. Briefly, the target nucleic acid that contains the sequence to be amplified is provided as single-stranded nucleic acid (e.g., ssRNA such as HCV RNA). Those skilled in the art will appreciate that, alternatively, DNA can be used in TMA; conventional melting of double stranded nucleic acid (e.g., dsDNA) may be used to provide single-stranded target nucleic acids. A promoter primer (e.g., a third amplification oligomer comprising a promoter as described above) binds specifically to the target nucleic acid at its target sequence and a reverse transcriptase (RT) extends the 3' end of the promoter primer using the target strand as a template to create a cDNA extension product, resulting in an RNA:DNA duplex if ssRNA was the original template. An RNase digests the RNA strand of the RNA:DNA duplex and a second primer binds specifically to its target sequence, which is located on the cDNA strand downstream from the promoter primer end. RT synthesizes a new DNA strand by extending the 3' end of the other primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the other primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The other or "reverse" amplification oligomer is a promoter primer or promoter provider having a target-hybridizing sequence configured to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above in the preceding paragraph for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

The detection step may be performed using any of a variety of known techniques to detect a signal specifically associated with the amplified target sequence, such as, e.g., by hybridizing the amplification product with a labeled detection probe and detecting a signal resulting from the labeled probe. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see. e.g., U.S. Pat. Nos. 5,639,604 and 5,283,174, each incorporated by reference herein). In some embodiments, the nucleic acids are associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. In particular, the amplified product will contain a target sequence in or complementary to a sequence in the HCV genomic RNA, and a probe will bind directly or indirectly to a sequence contained in the amplified product to indicate the presence of HCV nucleic acid in the tested sample.

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476, incorporated by reference herein). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1; each incorporated by reference herein).

In some embodiments, a molecular torch (sometimes referred to simply as a torch) is used for detection. In some embodiments, the torch is a probe oligomer as disclosed above.

In general, the disclosed methods can involve the step of consulting a standard curve that relates pre-amplification amounts of analyte polynucleotide and post-amplification amounts of analyte amplicon.

Since real-time amplification reactions advantageously feature quantitative relationships between the number of analyte polynucleotides input into the reaction and the number of analyte amplicons synthesized as a function of time, the number of analyte polynucleotides present in a test sample can be determined using a standard curve. For example, a plurality of amplification reactions containing known amounts of a polynucleotide standard can be run in parallel with an amplification reaction prepared using a test sample containing an unknown number of analyte polynucleotides. Alternatively, a standard curve can be prepared in advance so that it is unnecessary to prepare a curve each time an analytical procedure is carried out. Such a curve prepared in advance can even be stored electronically in a memory device of a testing instrument. A standard curve having pre-amplification amounts of the polynucleotide standard on a first axis and some indicia of the time required to effect a certain level of nucleic acid amplification (such as a time-of-emergence above a background signal) on a second axis is then prepared. The post-amplification amount of analyte amplicon measured for the test reaction is then located on the post-amplification axis of the standard curve. The corresponding value on the other axis of the curve represents the pre-amplification amount of analyte polynucleotide that was present in the test reaction. Thus, determining the number of molecules of analyte polynucleotide present in the test sample is accomplished by consulting the standard curve, or more particularly by comparing the quantitative results obtained for the test sample with the standard curve, a procedure that will be familiar to those having an ordinary level of skill in the art.

The procedures described herein can easily be used to quantify analyte polynucleotides (e.g., HCV nucleic acid) present in a test sample. Indeed, if a plurality of standard control amplification reactions are initiated using known numbers of an analyte polynucleotide standard, and if a test reaction that includes an unknown number of analyte polynucleotide molecules is carried out, then it becomes possible after measuring the time required to effect a certain level of amplification in each reaction to determine the number of analyte polynucleotide molecules that must have been present in the test sample. The relationship between the number of analyte polynucleotide molecules input into standard amplification reaction and the time required to effect a certain level of amplification is conveniently established using a graph. Determining the number of analyte polynucleotide molecules present in a test sample is simply a matter of determining from the standard graph the number of analyte polynucleotide molecules that correspond to a measured analyte amplicon signal strength. This illustrates how analyte polynucleotide standards can be used in connection with polynucleotide amplification reactions to quantify pre-amplification amounts of analyte polynucleotide contained in test samples.

In some embodiments, a method or use can provide substantially equivalent quantification (e.g., within 1, 0.5, or 0.25 logs) of at least three, four, five, or six HCV genotypes (e.g., types 1a, 1b, 2b, 3a, 3b, 4h, 5a, 6a), optionally with minimal cross-reactivity to other, non-HCV nucleic acids suspected of being in a sample (e.g., other bloodborne pathogens). In certain variations, methods and uses of the disclosure further allow quantification of HCV sequences that vary from the 5' UTR of the foregoing types, e.g., at least 1, 2, 3, 4, 5, 10, 15, 20, 25, 30, 35, 40, 45, or all HCV strains comprising a sequence of SEQ ID NO: 166-213 or 214 (e.g., strains listed in Table 5), e.g., substantially equivalent quantification (e.g., within 1, 0.5, or 0.25 logs) to HCV genotype 1a (e.g., SEQ ID NO: 75). In some aspects, the methods and uses of the instant disclosure show minimal cross-reactivity to one or more, or all, of Hepatitis A, Hepatitis B, Herpes simplex 1, Herpes simplex 2, HIV, Parvovirus, Rubella, Dengue 2, Dengue 3, Dengue 4, Epstein-Barr, and West Nile viruses. In some embodiments, the the methods and uses of the instant disclosure show minimal cross-reactivity to one or more, or all, of C. albicans, C. diphtheriae, P. acnes, S. aureus, S. epidermis, S. pneumoniae. In one aspect, the methods and uses of the instant disclosure are multiplexed with methods for detecting one of more of the foregoing viruses or microbes. In general, minimal cross-reactivity is understood as showing at least about 95% specificity, e.g., at least about 96%, 97%, 98%, or 99%.

EXAMPLES

The following examples are provided to illustrate certain disclosed embodiments and are not to be construed as limiting the scope of this disclosure in any way.

General Reagents and Methods. Unless otherwise indicated, amplifications were performed isothermally using transcription-mediated amplification with T7 RNA polymerase and reverse transcriptase. Standard transcription mediated amplification (TMA) reactions were carried out essentially as described by Kacian et al., in U.S. Pat. No. 5,399,491, which is incorporated herein by reference. Biphasic TMA was carried out essentially as described in U.S. Pat. No. 9,139,870, which is incorporated herein by reference. In general, the last primer added in the biphasic procedures was the T7 primer, or the shorter T7 primer where a combination of two different T7 primer sequences were used.

Amplification reactions were conducted for various primer combinations using about 5 to 10 pmoles per reaction of T7 primer and nonT7 primer.

Detection used molecular torches as probe oligomers which contained a 5'-fluorophore (e.g., FAM or ROX) and a 3'-quencher (e.g., DABCYL) ("5F3D" for FAM and DABCYL or "5R3D" for ROX and DABCYL). Torches are discussed in detail in U.S. Pat. No. 6,849,412, which is incorporated by reference. Torches generally contained a —(CH$_2$)$_9$— linker near the 3'-end (e.g., between the 5$^{th}$ and 6$^{th}$ or between the 4$^{th}$ and 5$^{th}$ nucleotides from the 3'-end). Target capture was performed essentially as described in U.S. Pat. No. 8,034,554, which is incorporated herein by reference.

Exemplary internal control oligomers and template are discussed in U.S. Pat. No. 7,785,844, which is incorporated herein by reference.

Example 1—HCV In Vitro Transcripts for HCV Genotypes and Exemplary Oligomers The 5' untranslated region (UTR) non-coding region of HCV was chosen as the assay target for detecting HCV across genotypes. It was thought that the conserved nature of this region could allow for a genetic test capable of detecting multiple genotypes of HCV using similar primer and detection probes. The length of the 5'-UTR is 341 bases long with ~90% homology between HCV genotypes. The 5' UTR is required for viral RNA replication but is not essential for translation.

An HCV 1a in vitro transcript (IVT) was produced using a pBluescript II® SK (+) vector with a transcript length of 926 bases, and a sequence insert length of 837 base pairs including the HCV 1a 5'-UTR region. Sequence information for this and subsequent IVTs is shown in the Table of Sequences below.

The HCV 2b IVT was originally placed into the pBluescript SK (+) with a transcript length of 998 bases, and a sequence insert length of ~850 base pairs of the HCV 2b 5'-UTR region.

An aliquot of IVT stock made from a HCV 3a clinical sample was used to reverse-transcribe the IVT into a cDNA clone which was inserted into a pBluescript II® SK (+) vector suitable for IVT manufacture. The plasmid insert was sequenced and compared to sequences from the Los Alamos HCV DB, thereby confirming that the clone was consistent with known HCV 3a genotype sequences. IVT from this new plasmid was generated using the T7 promoter resulting in a 861 base IVT containing a large portion of the 5' UTR region and 5'-coding region of HCV 3a. Following initial experiments suggestive that the 3' region of the IVT was forming an inhibitory structure (not shown), the 3' open reading frame (ORF) region was removed from the HCV 3a IVT so that it more closely matches the HCV 3b IVT.

The new Version 2 IVT (3aV2) of HCV 3a had the end of the 3' IVT removed just past the binding site for target capture oligomer HCV0297(-)dT3dA30 (SEQ ID NO: 16) and near the ORF start point resulting in an approximately 400-base-shorter IVT with a final length of 351 bases. This length and region is more similar to the HCV 3b IVT sequence of 322 bases.

An additional type 3a Version 3 (3aV3) was made that differed slightly from the 3a V2 IVT by removing a high GC rich region just 5' of the 52-78 (+) non-T7 primer. The V2 version showed better amplification and detection performance versus the HCV 3b IVT than the V1 or V3 versions of HCV 3a.

A PCR product of the HCV 3b 5'-UTR was inserted into a TOPO cloning plasmid and transcribed off of a SP6 promoter with a transcript length of 422 bases. Subsequently this insert was transferred to a pBluescript II® SK (+) plasmid with a 325 base pair length. The original insert had a mutation that was introduced by the original RT-PCR primers. This mutation was corrected to match the Los Alamos DB for HCV 3b genotype sequences.

An HCV 4h insert sequence with a length of 422 base pairs was originally placed into a TOPO vector containing an SP6 promoter. To be more consistent with other IVTs, the insert was moved into a pBluescript II® SK (+) plasmid with IVT length of 325 bases using a T7 promoter to generate IVT's.

The original TOPO HCV 4h IVT produced was over-quantitating compared to HCV 1a regardless of mismatches. The optical density (OD), molecular weight, and sequence of the HCV 4h IVT were rechecked and found to be correct. Thus, it was concluded that the over-quantitation relative to HCV 1a is intrinsic to the 4h IVT sequence. The effect is less than 0.15 log difference (not shown).

The HCV 5a sequence was originally placed into the TOPO clone ID 100007 with a length of 435 base pairs and IVT generated off the T7 TOPO promoter. The sequence was moved into the pBluescript II® SK (+) vector so that it will have a similar IVT sequence to HCV 3a, 3b, 4h and 6a. IVT's were again made using pBluescript SK (+) T7 promoter. The resulting IVT length of the pBluescript II® (+) plasmid generates a 325-base IVT with the 5' UTR region of HCV 5a.

The HCV 6a sequence was originally placed into the TOPO clone ID 100008 with a base pair length of 438 base pairs and generated using the T7 promoter. The sequence was moved into the pBluescript II® SK (+) vector using a T7 promoter to generate IVT. The resulting IVT length of the pBluescript II® SK (+) vector generates a 328-base IVT with the 5' UTR region of HCV 6a.

Figure 10:
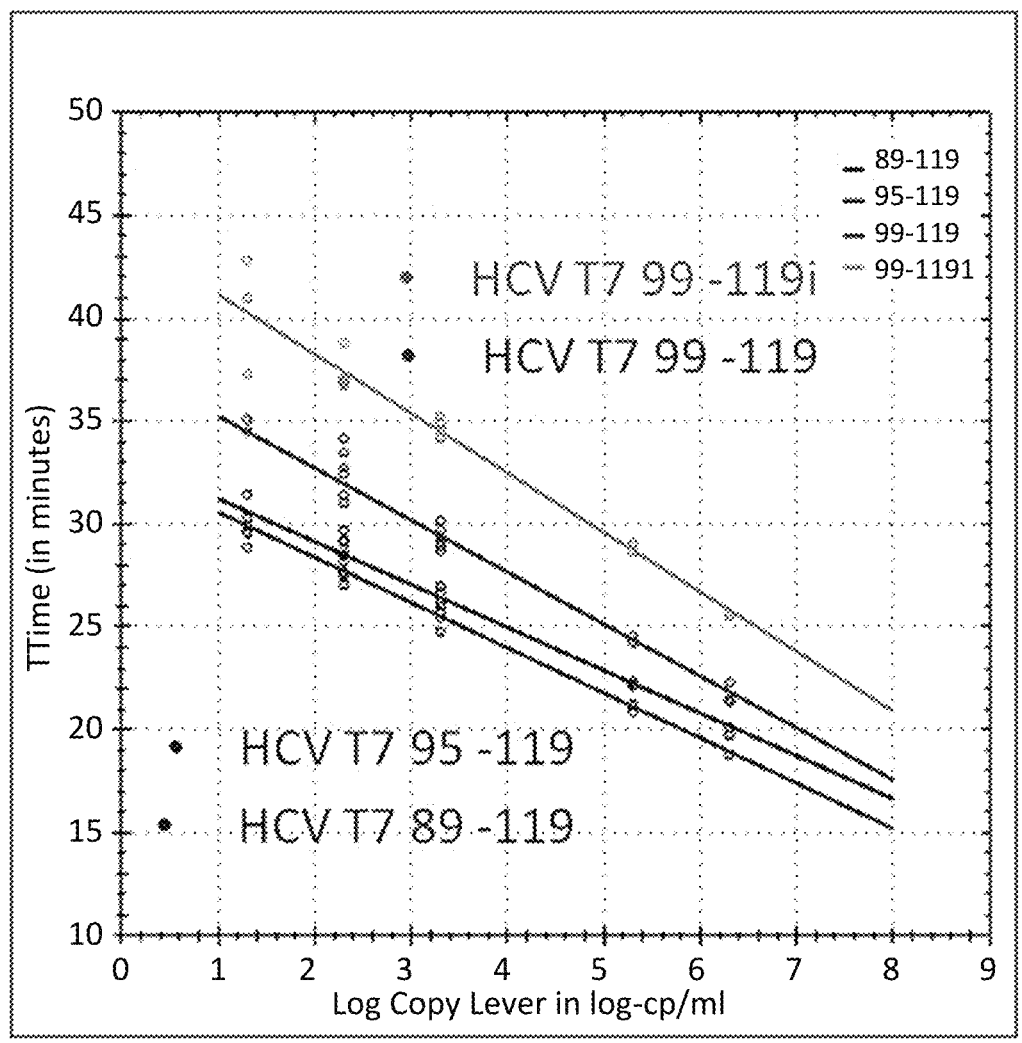
FIG. 10 shows calibration curves with different T7 primers, which are listed in the figure in order from highest to lowest curves.
Figure 12A:
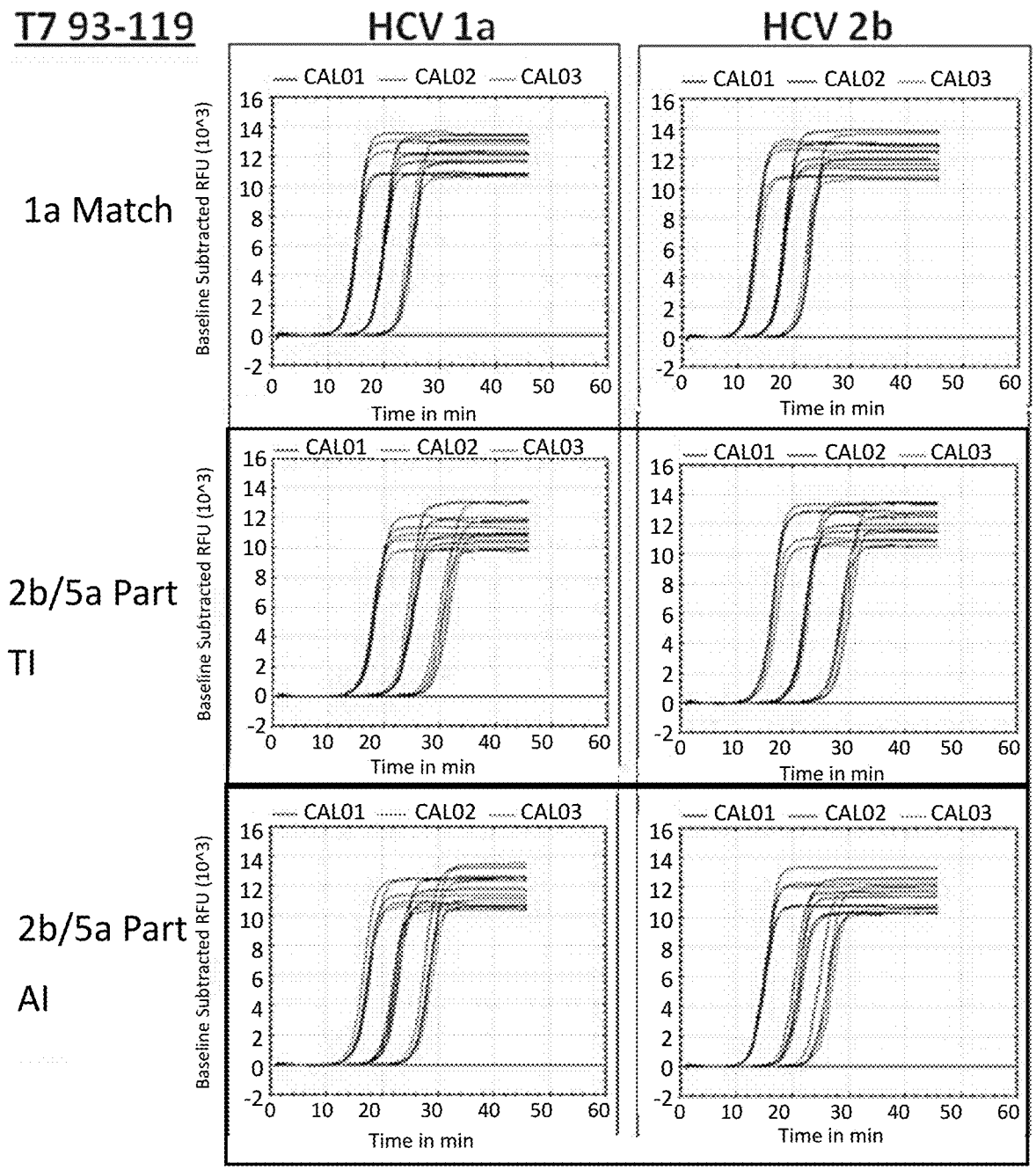
FIGS. 12A, 12B, 12C, and 12D show a series of emergence curves for 3 copy levels with genotypes 1a, 2b, 3a, 3b, 4h, 5a, and 6a for 3 T7 93-119 initial amplification oligomers which either matched genotype 1a sequence (top row in 12A-D) or contained inosines (bottom 2 rows in each of 12A-D). Each plot shows traces for 100, 10000, and 1000000 copies/ml. The arrows (FIGS. 12B-12D) indicate the collapse of the traces when inosine bases were used in the T7 oligomers.
Figure 12B:
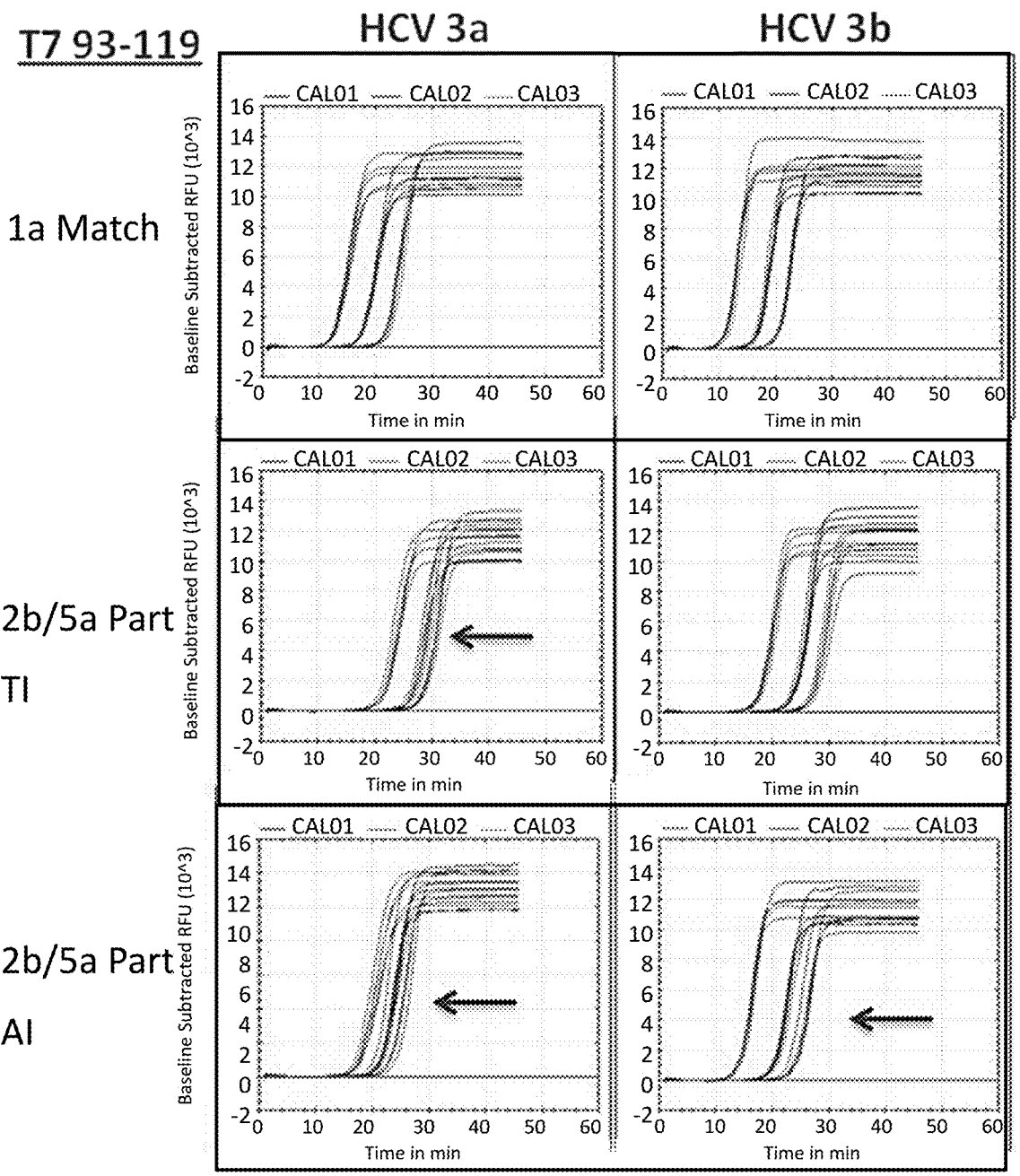
Figure 12C:
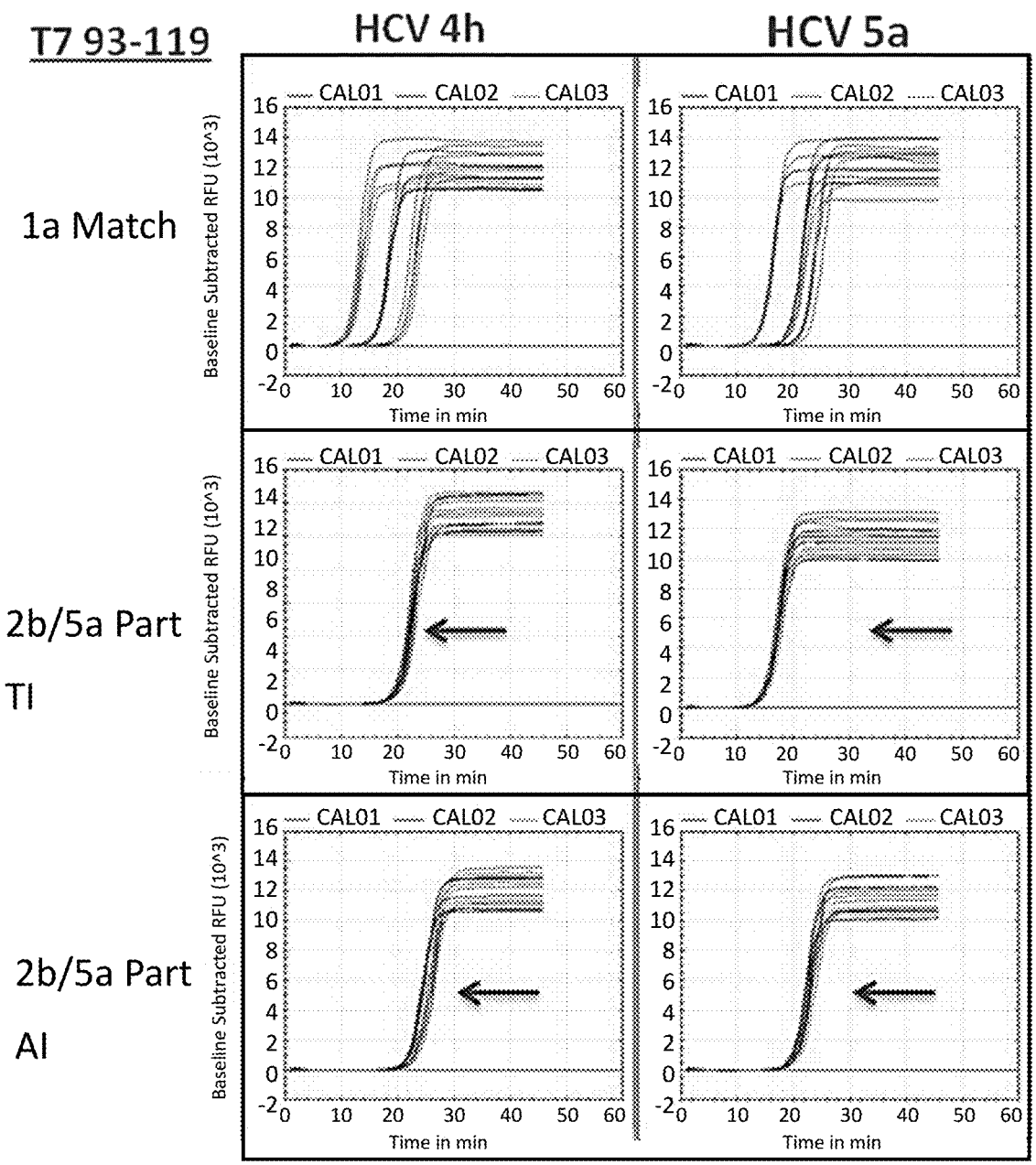
Figure 12D:
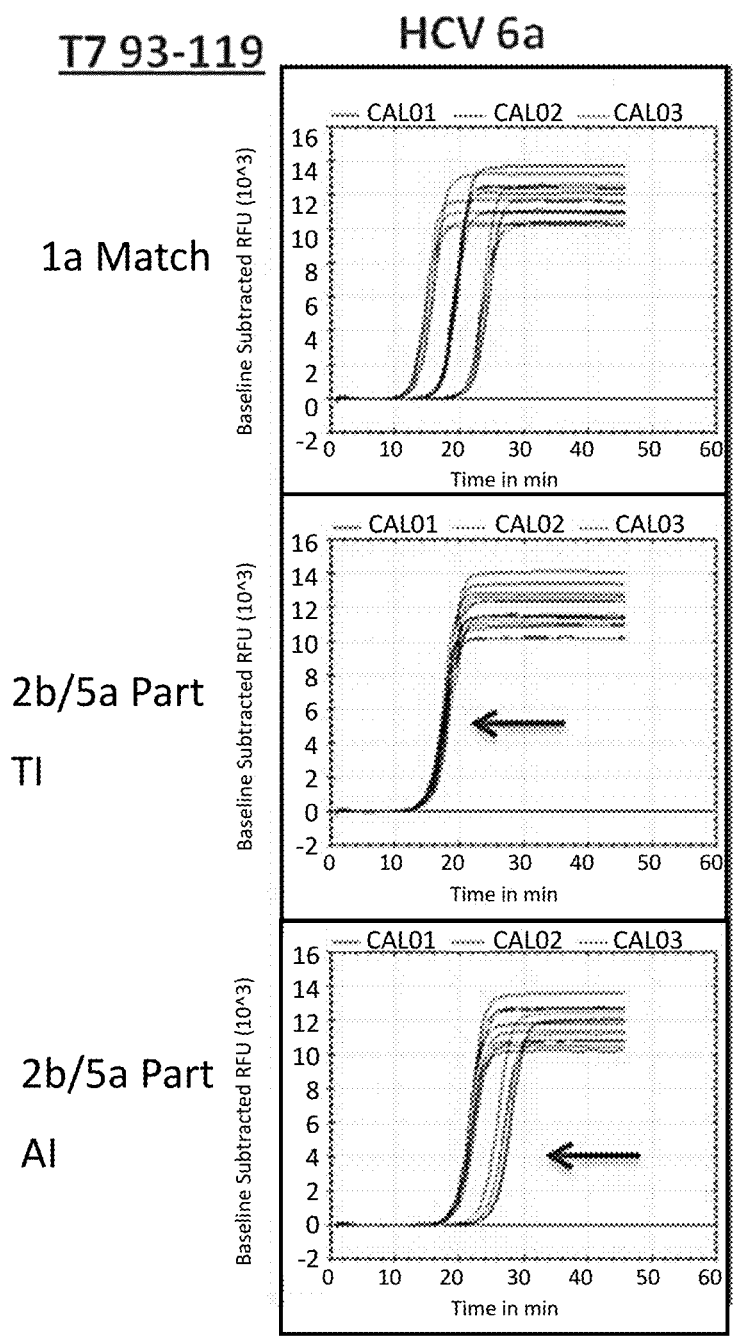

An alignment of selected pBluescript® IVT sequences with exemplary oligomers is shown in FIG. 1.

Example 2—Initial Assay Design

An alignment was created from HCV sequences to identify the sequence differences among various HCV genotypes including sequences from the Los Alamos database (2008) [hcv.lanl.gov]. An initial set of oligomers was designed to target the 5'UTR region of Hepatitis C virus polyprotein precursor (HCV-1), a region that is ~90% homologous among the genotypes, starting at about base 50 from the 5' end. The primer sequences described here align to the HCV-1a mRNA genome sequence (GenBank Accession No. M62321; SEQ ID NO: 75) without mismatches.

This original HCV oligomer set had the following characteristics (circled in FIG. 1). The torch 68-86 oligomer has 2 mismatches for HCV type 3a/b and had poor amplification kinetics, with large differences among the genotypes. The nonT7 50-66 oligomer has 1 mismatch in HCV type 3a and the T7 95-119 has 1 mismatch in each of HCV types 2b, 3a, and 4h. Amplification curves from tests of the original oligomer set are shown in FIGS. 2A-2G, clearly demonstrating differences in quantitation of different HCV genotypes with this oligomer set. For example, under the CAL02 condition ($10^2$ copies/ml), HCV 1a amplified about 5 minutes later than the CAL04 condition ($10^4$ copies/ml); HCV 2b did not meaningfully amplify; and the other tested genotypes showed inconsistent amplification kinetics.

Example 3—HCV nonT7 Primer Selection

New oligomer designs were made. Alternate regions were targeted, including the left boxed region in FIG. 1 for the probe, which matched to all HCV genotypes. NonT7s and T7s were designed around this probe region. A poor region for oligomer design containing a C-rich string is shown in the right-most boxed region in FIG. 1. Oligomers in or amplifying across this region did not amplify or showed very poor amplification.

New sequences for the nonT7 primer were compared with the original sequence. Calibration curves using the original HCV NT7 50-66 oligomers with genotypes 1a and 3a (second highest and highest lines in FIG. 3) compared with HCV NT7 52-78 (green & gold) for HCV 1a and 3a showed that using the NT7 52-78 sequence gave faster emergence time and the genotypes are more similar (lines in the lower group of four in FIG. 3).

Sequence mismatches that affect the nonT7 primer design are mainly in the HCV 3a/3b sequences. In an experiment performed with the HCV 3a IVT, using standard transcription mediated amplification (TMA), new torch and T7 HCV 93-119 (−), a 50:50 mixture of HCV 52-78 NT7 sequences that matched genotypes 1a and 3a showed more equal quantitation than either 52-78 NT7 sequence alone (FIGS. 4A-4C). These oligomers were retested with all genotypes.

All HCV genotypes were tested with different nonT7 primer conditions, including new oligomer HCV nonT7 52-78t (5'-GGAACTTCTGTCTTCACGCAGAAAGCG; SEQ ID NO: 215). The HCV 3a is under quantitated with the HCV nonT7 52-78t (only) (arrow in FIG. 5A) whereas the HCV nonT7 52-78tg (only) shows similarity in quantitation across genotypes (FIG. 5B). HCV 5a is slightly under-quantitated; however, this sequence has two mismatches in the T7 region. These experiments used the TOPO IVT sequences for HCV 4h, 5a and 6a. The HCV NT7 52-78 genotype 3a sequence ("52-78tg", also referred to as 52-78-1; SEQ ID NO: 2) was selected for inclusion in the oligomer set.

Shown in FIG. 6 are confirmatory experimental results for the HCV primer set including the HCV nonT7 52-78 tg (only) in biphasic TMA format (including internal control [IC]). 7 HCV genotypes were tested at 10k copies/ml ("04" items in FIG. 6) and 1M copies/ml ("07" items in FIG. 6) for genotypes 2-6 are shown as log differences relative to target. "CAL" entries in FIG. 6 used genotype 1a; genotypes of other items are indicated by the last two characters, e.g., "2B." IVTs for this experiment were from TOPO plasmids for HCV genotypes 4h, 5a, and 6a; and pBluescript® IVTs for HCV 1a, 2b, 3a (version 1) and 3b.

Example 4—HCV Torch Selection Experiments

With the original oligomer set, the HCV torch 68-86 had two mismatches to the HCV 3a and HCV 3b sequences. Several sequences were tested in the perfect match region (left box in FIG. 1), some with matches to the C's at the edges of the match regions with sequence and without. The original torch HCV 68-86 sequence was compared side-by-side with HCV 80-98 5st a (+) (5'-CUAGCCAUGGCGUUAGUAU-(c9)-gcuag, SEQ ID NO: 216), and the comparison shows that emergence curves are dramatically different for HCV 3a (FIGS. 7A-7D).

The emergence time calibration curves for 3 torches tested with two IVTs, HCV 1a and 3a, are shown in FIG. 8. There is a clear delay of the HCV 3a genotype with the original oligomer set (condition 3; top calibration curve in FIG. 8, indicated with straight arrow). Two HCV torches with the 80-98 target binding region with different stem lengths (torches 80-98_5st (5'-gCUAGCCAUGGCGUUAGUAU-(c9)-cuagc, SEQ ID NO: 217) and 80-98_5sta) move the kinetics closer together for HCV 1a and 3a, relative to the HCV 1a (indicated with curved arrow) and HCV 3a calibration curves for 68-86 (cnd3, control [cnt] set) (FIG. 8).

An exact match to all HCV genotypes with HCV torch 81-96 and 81-97 with pure system (no target capture) shows no difference to HCV torch 80-98 control for HCV 1a (FIG. 9). HCV torch 81-96 was selected for further use and is 3 bases shorter in the target binding region than HCV torch 80-98 5st a.

Example 5—Selection of HCV T7 Primer and Initial Amplification Oligomer

Experiments testing T7 sequences with the original oligomer set, HCV Torch 68-86, and HCV NonT7 50-66 were performed in uniplex HCV amplification using a standard TMA format. The calibration curves for HCV 1a were performed with variations in the T7 sequences, revealing a dependence on the emergence time with the T7 sequence as shown in FIG. 10. The T7 99-119

(5'-AATTTAATACGACTCACTATAGGGAGA
CCTGGAGGCTGCACGACACTC, SEQ ID NO: 218,
target-hybridizing sequence italicized)

has 4 bases removed from the target binding region relative to T7 95-119 resulting in a 5-minute delay in the emergence time at the low end of the assay. T7 99-119I (5'-AATTTAATACGACTCACTATAGGGAGA
CCTGGAGGCTGIACGACACTC, SEQ ID NO: 219,
target-hybridizing sequence italicized)

showed a further delay.

Figure 11:
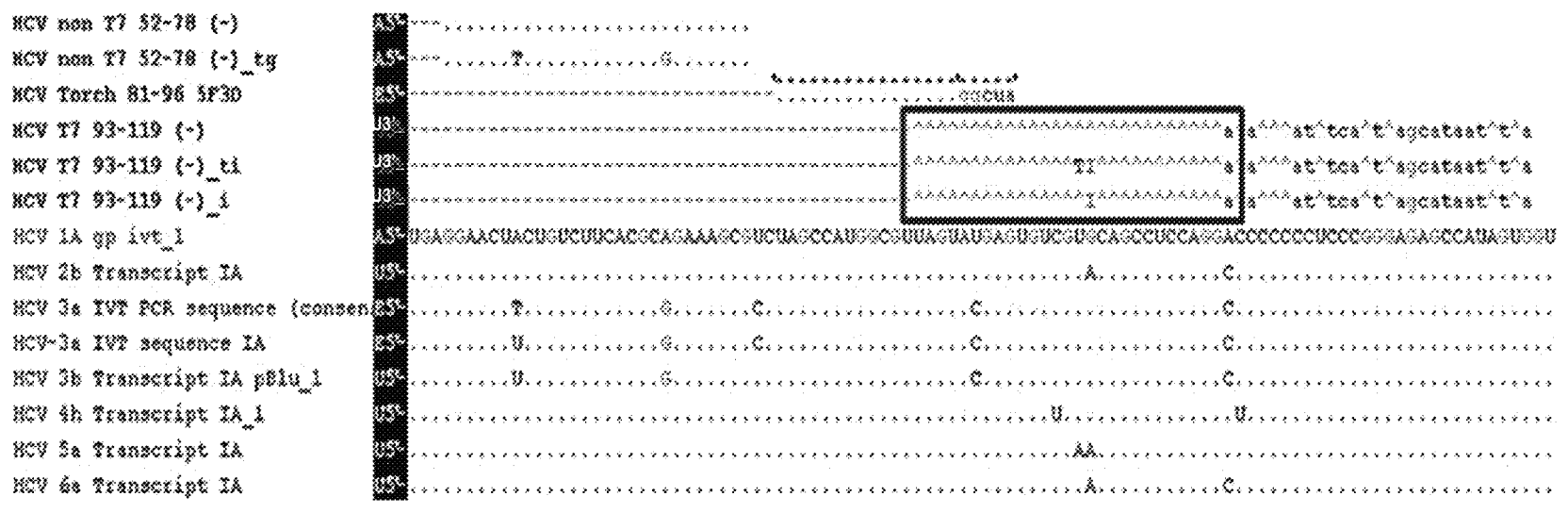

A series of standard T7 primers matching all subtypes, testing singles and mixtures were tested in TCR and AMP2. The HCV 5a genotype was always delayed, unless matched perfectly. However, the primer perfectly matched to 5a delayed HCV 1a, likely due to the AA mismatch in the center of the target binding region of the T7 region (data not shown). Standard T7 primers with inosine bases were also tested attempting to balance amplification among genotype, as indicated by the box in the alignment in FIG. 11. All 7 genotypes were tested in a biphasic TMA format (using TOPO IVTs for HCV 4, 5, and 6 genotypes).

A series of emergence curves for 3 copy levels comparing 3 T7 primers revealed a collapse of the lower concentrations when an inosine base was present as indicated by the arrows in FIGS. 12A-12D. No further studies were performed with inosine bases in primers as no improvements were observed.

T7 primers designed in the C-rich region were also tested in combination with torches and nonT7 primers; however, the level of sensitivity observed did not justify further studies (data not shown).

Figure 13A:
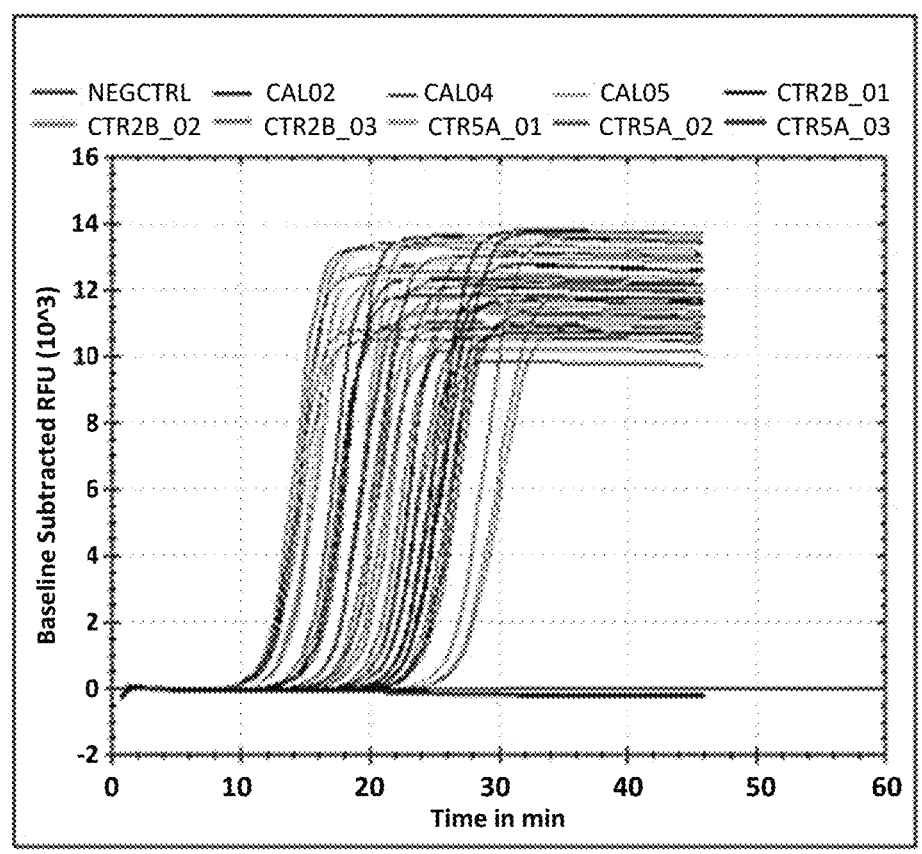
FIGS. 13A, 13B, and 13C show emergence curves using control T7 93-119 (13A), T7 89-119 (13B), and T7 80-119 (13C) primers against genotypes 1a, 2b, and 5a at $10^2$, $10^4$, and $10^6$ copies/ml, showing greater consistency across genotypes and separation of curves for different concentrations for T789-119 and T7 80-119.
Figure 13B:
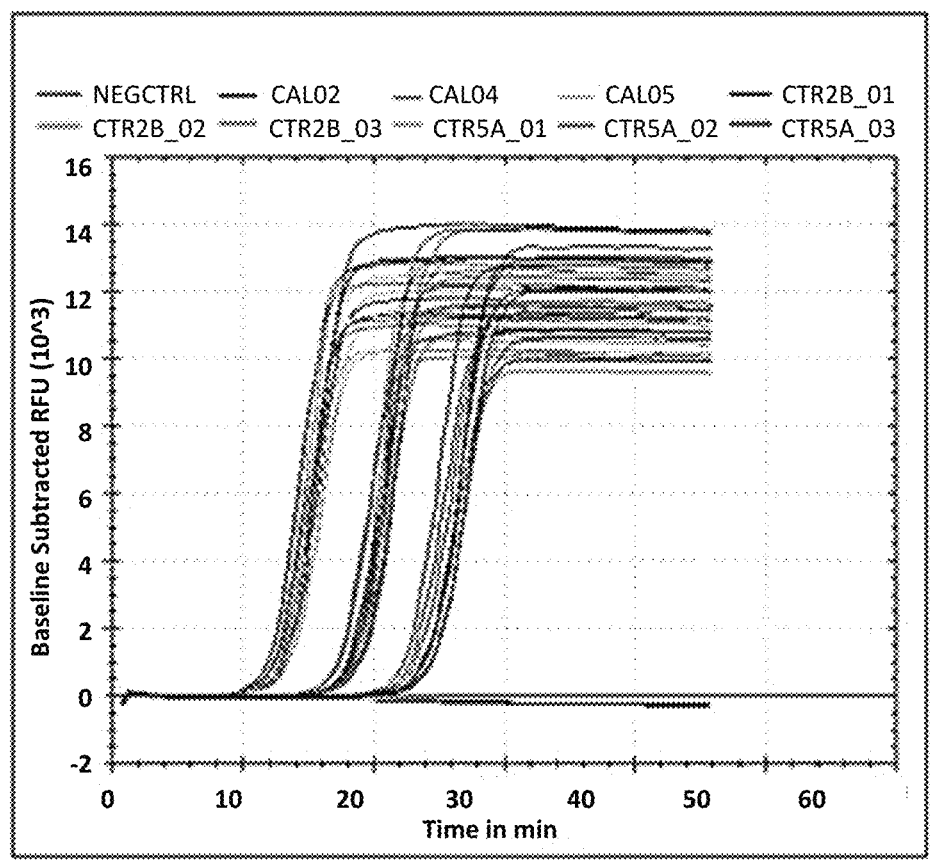
Figure 13C:
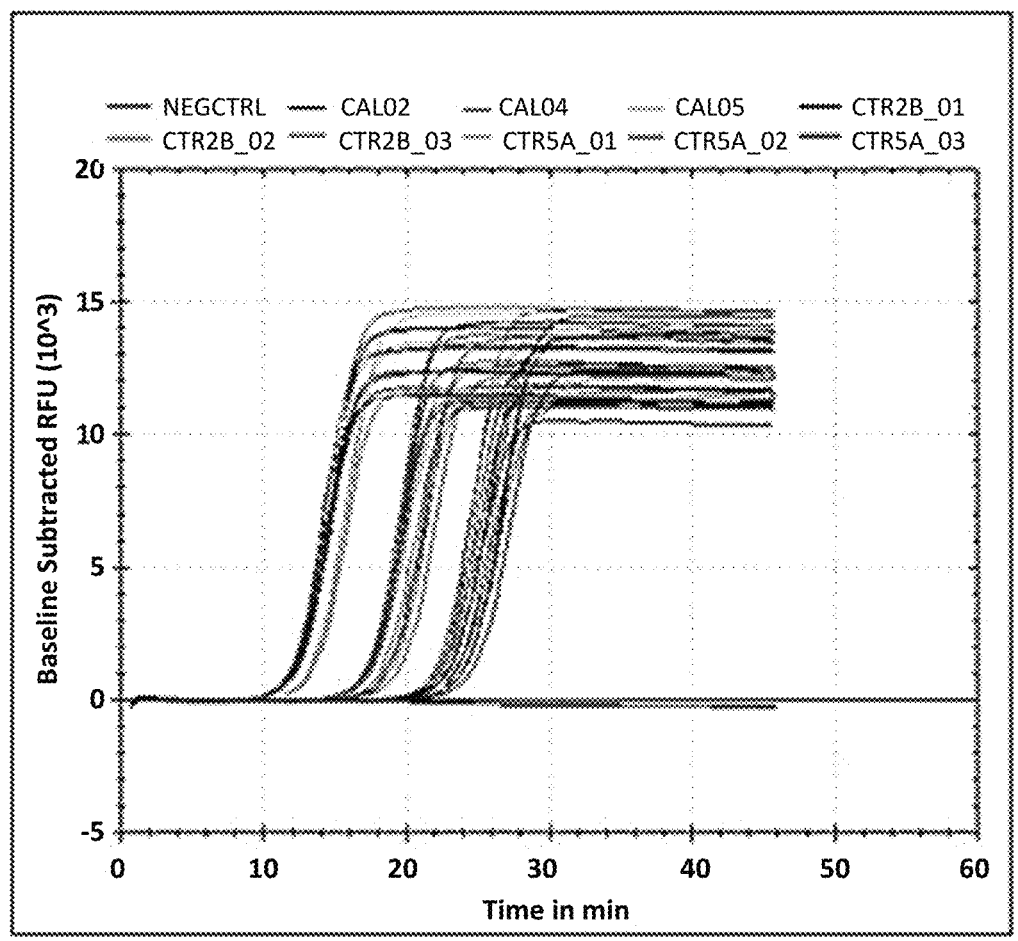

A series of HCV T7 initial amplification oligomers to eliminate mismatches on first round of initiation were tested where the T7 initial amplification oligomer was added to the TCR with all target capture oligomers (TCOs) and the shortest standard T7 HCV 93-119 (match to HCV 1a) was added to the Promoter AMP2 reagent. HCV genotypes 1a, 2b and 5a were initially screened with two candidate initial amplification oligomers T7 89-119 and T7 80-119 versus the control T7 93-119 present in both TCR and AMP2. For the data presented in FIGS. 13A-13C, the calibrators for HCV 1a are Cal02=2.0, Cal04=4.0 and Cal06=6.0 log copies/ml. For the HCV genotypes 2b and 5a, the concentrations are CTR01=2.3, CTR02=4.3 and CTR03=6.3 log copies/ml. The emergence curves show all cals and controls at three levels. The Control Condition (T7 93-119, FIG. 13A) shows the least defined groups of levels among all the genotypes whereas T7 89-119 (FIG. 13B) and T7 80-119 (FIG. 13C) conditions show separated levels (even though T7 89-119 and T7 80-119 have slightly different levels) (FIGS. 13A-13C).

Figure 14:
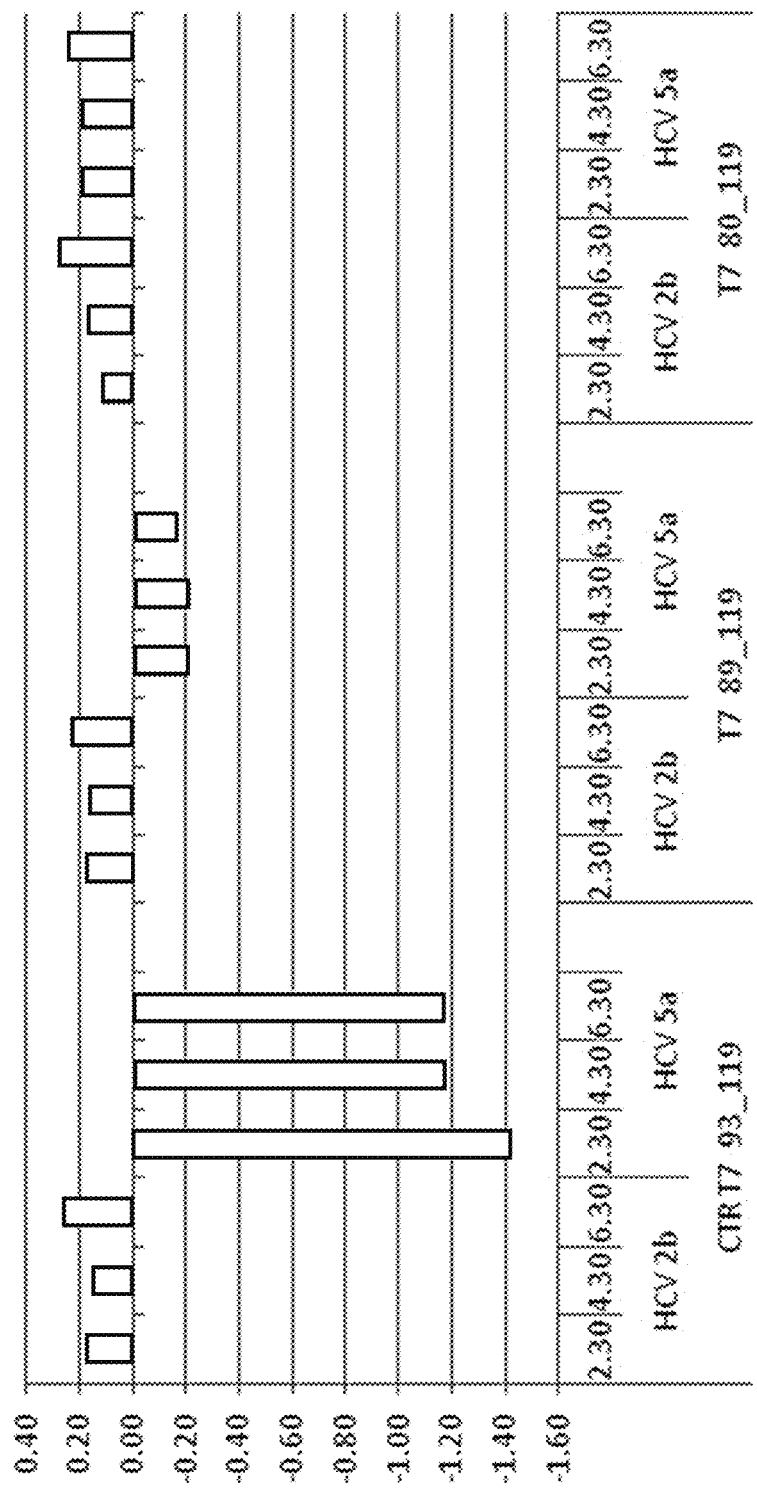
FIG. 14 shows log difference (LogDiff) versus HCV1a for different HCV genotypes at 2.3, 4.3, and 6.3 log copies/ml when T7 93-119, T7 89-119, and T7 80-119 initial amplification oligomers were used.

The HCV 2b and 5a log difference from HCV 1a for each T7 initial amplification oligomer is shown in FIG. 14, with the largest difference for HCV 5a (IVT from TOPO plasmid). There are two AA mismatches in the T7 target binding region of all three primers, but the longer T7 sequences 89-119 and 80-119 overcomes the mismatch for initiation of amplification.

Figure 15A:
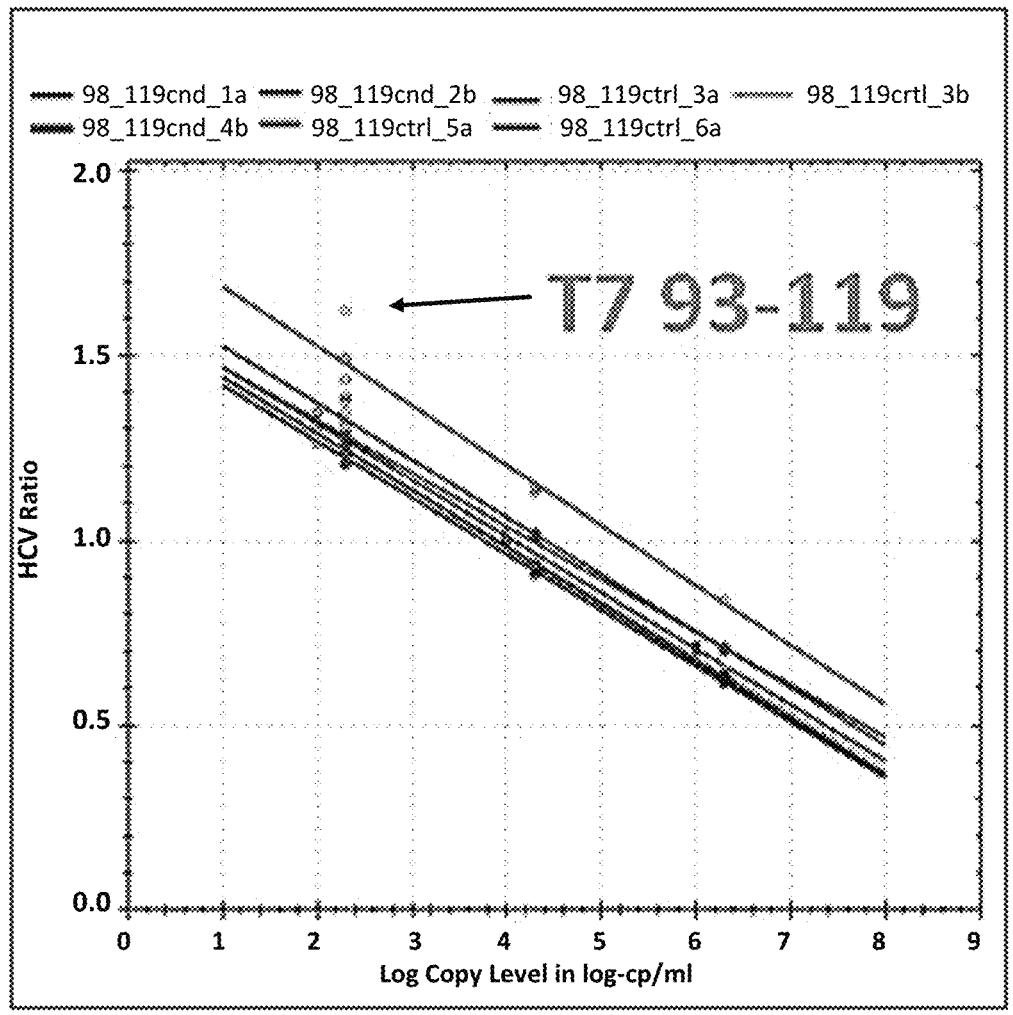
FIGS. 15A, 15B, and 15C show calibration curves for genotypes 1a, 2b, 3a, 3b, 4h, 5a, and 6a when the initial amplification oligomer was T7 93-119 (15A), T7 89-119 (15B), or T7 80-119 (15C). The arrow in FIG. 15A indicates the curve for genotype 5a, which was visibly separated from the curves for other genotypes when T7 93-119 was used but which appeared among the other curves when longer initial amplification oligomers were used.
Figure 15B:
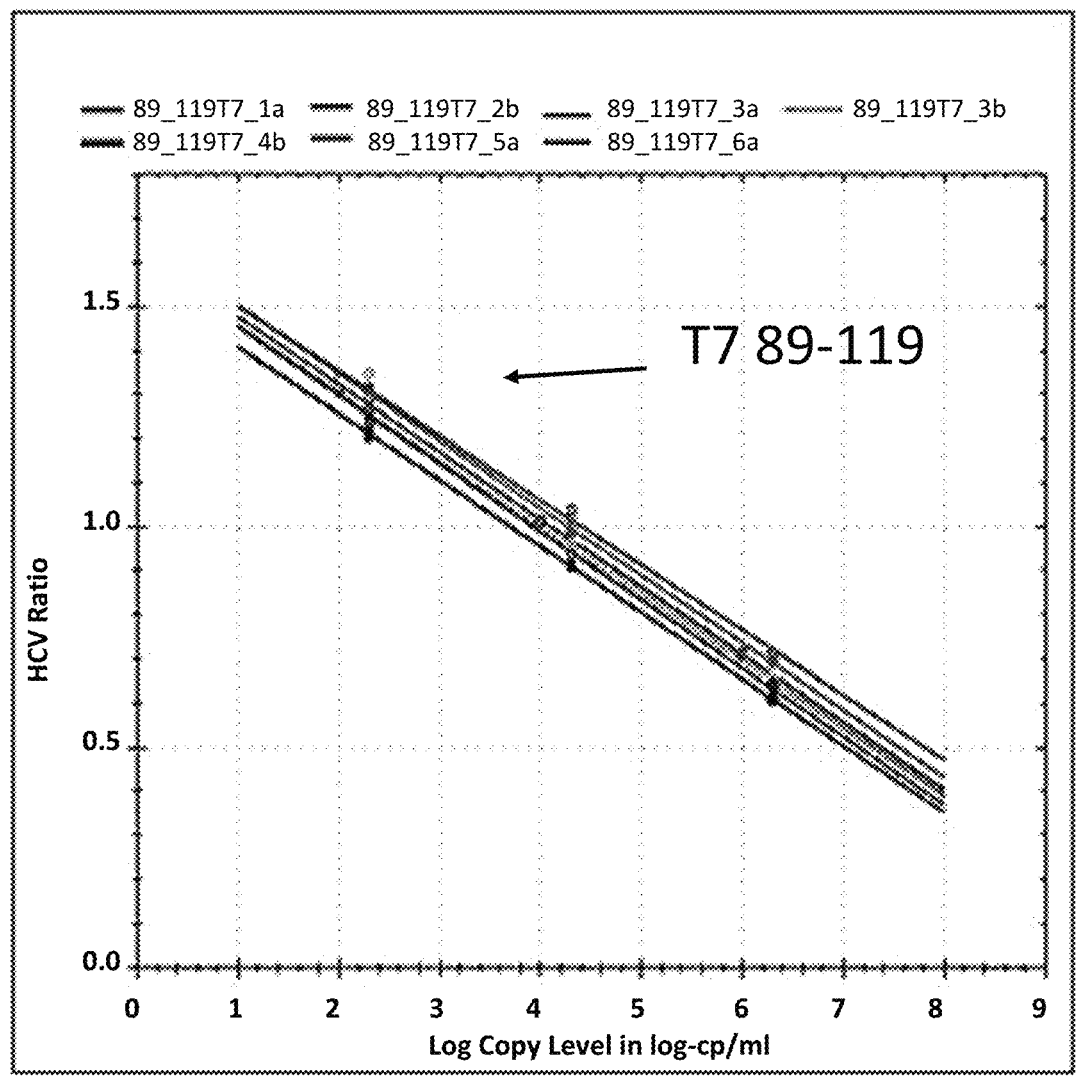
Figure 15C:
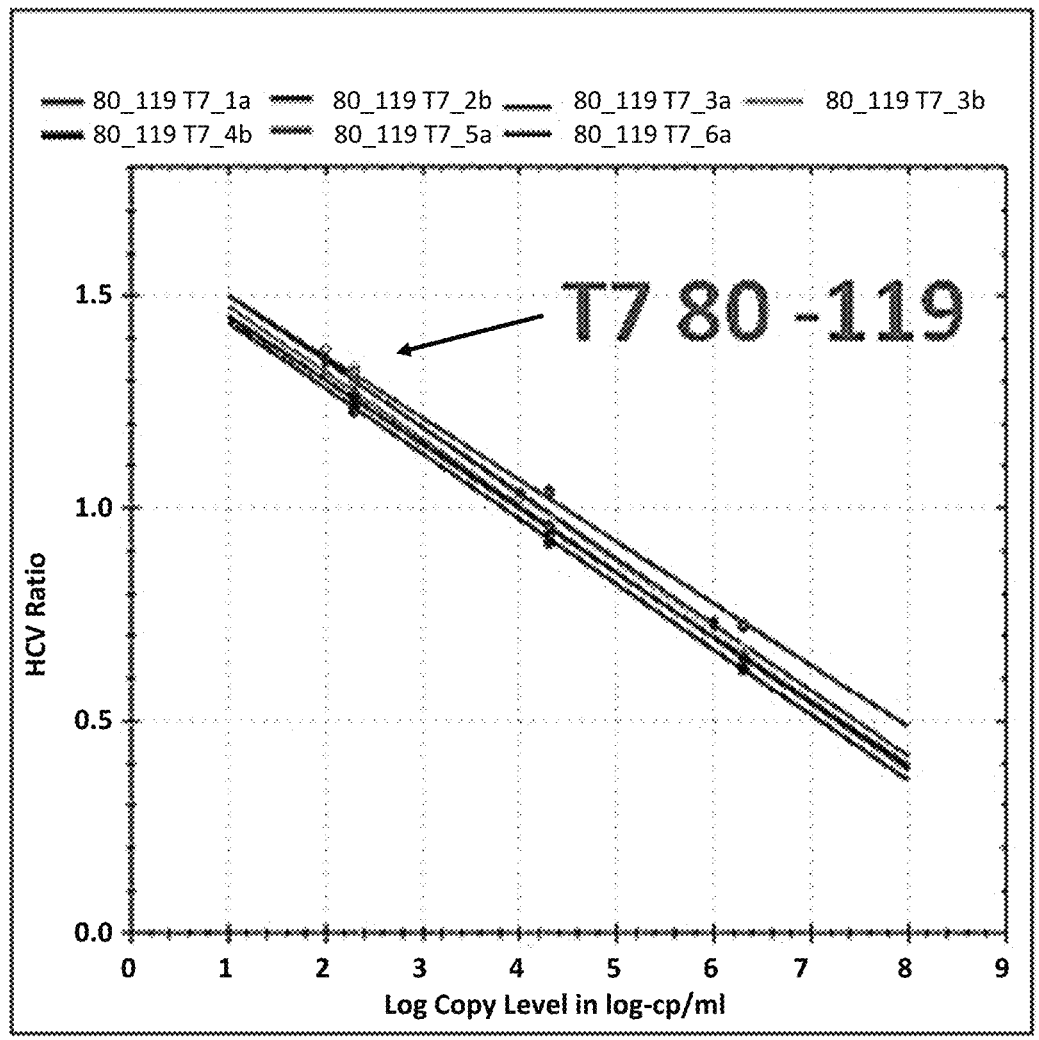

To compare all HCV 6 genotypes to HCV 1a, the same three T7 initial amplification oligomers HCV T7 93-119, T7 89-119, and 80-119 (control and AMP2 for all) were tested with HCV genotypes 1a, 2b, 3a/b, 4h, 5a, and 6a (in TOPO plasmid for HCV genotypes 4-6). The ratio calibration curves for all genotypes plotted as calibrators (same levels as previous experiment) show that the longer initial amplification oligomers (T7 89-119 or 80-119) clearly bring HCV 5a amplification curves more in-line with those of the other genotypes (FIGS. 15A-15C).

Figure 16:
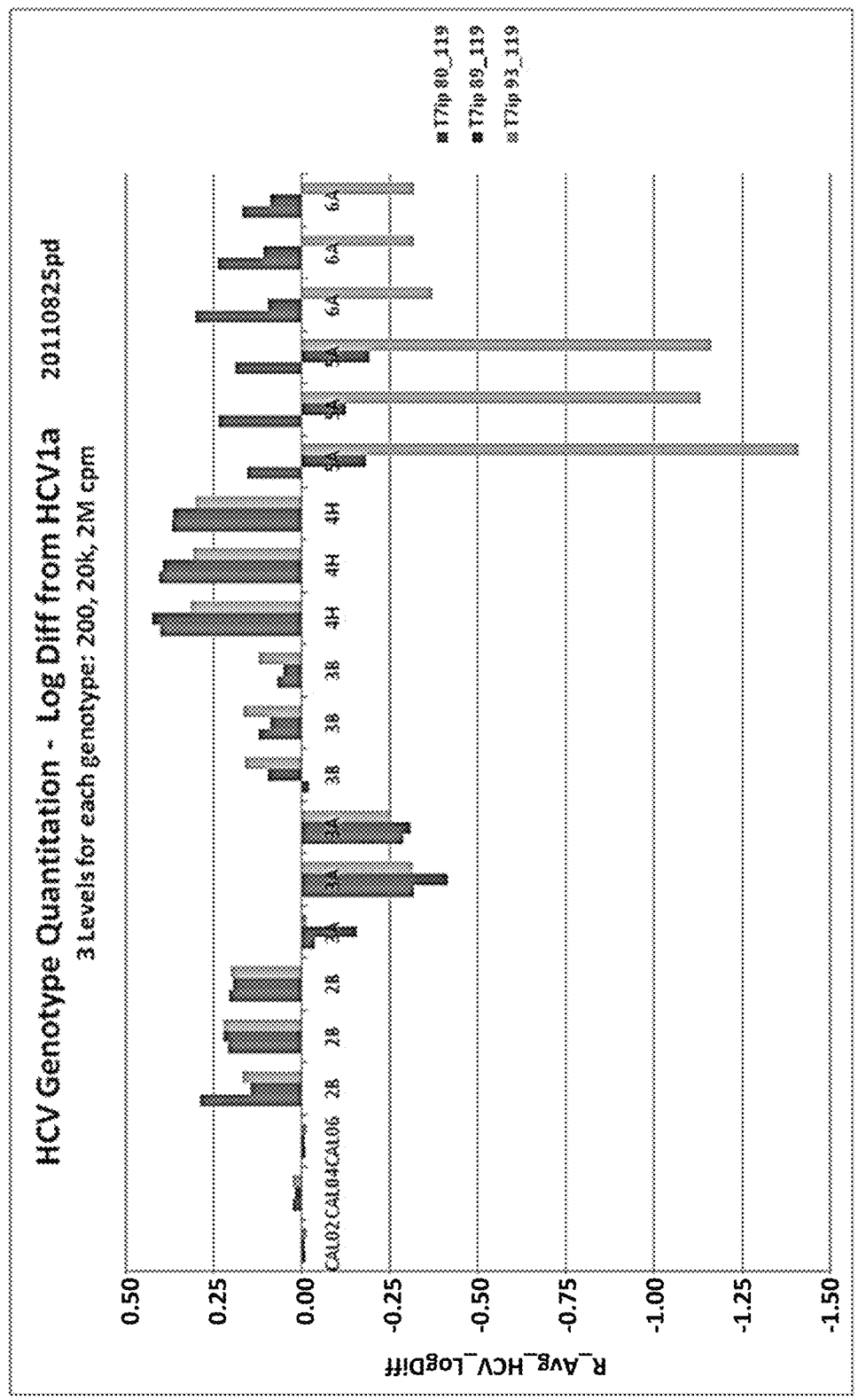
FIG. 16 shows difference in quantitation for various genotypes relative to HCV 1a calibrators when different target concentrations and initial amplification oligomers were used. For each genotype, the 9 bars from left to right are arranged as A1 A2 A3 B1 B2 B3 C1 C2 C3 where A is 200 copies/ml (c/ml), B is 20000 c/ml, C is 2M c/ml, 1 is with the 80-119 T7ip, 2 is with the 89-119 T7ip, and 3 is with the 89-119 T7ip (T7ip=T7 initial amplification oligomer).

This same data set plotted as the difference in quantitation for the genotypes relative to the HCV 1a calibrators is shown in FIG. 16, also illustrating improvement with longer initial amplification oligomers such as the HCV T7 89-119 initial amplification oligomer (center bar in each set of three).

During the original standard TMA screening of HCV T7 primers, HCV T7 89-119 was identified to have a primer interaction with the internal control (IC) primers (not shown). Due to this interaction, its use in standard TMA format was avoided, although HCV T7 89-119 can be used in biphasic TMA format.

Figure 17:
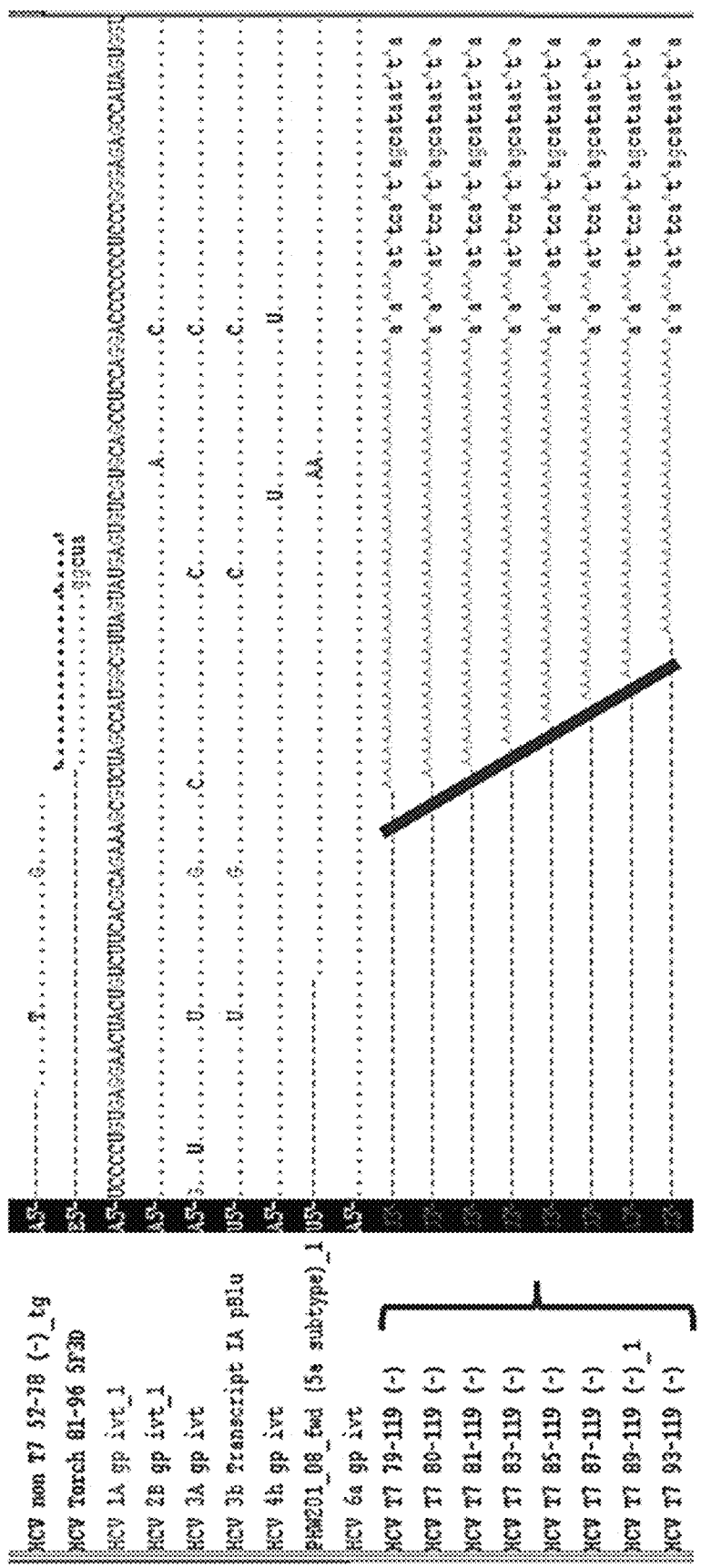
FIG. 17 shows an alignment of T7 initial amplification oligomers with selected HCV genotypes. The aligned sequences in order from top to bottom are SEQ ID NOs: 2, 12, 231, 232, 233, 234, 235, 236, 231, 108, 4, 110, 112, 237, 114, 220, and 5.

To further characterize the log copy difference among the genotypes, a series of T7 initial amplification oligomers was designed and is shown in the alignment next to the diagonal line in FIG. 17.

Figure 18:
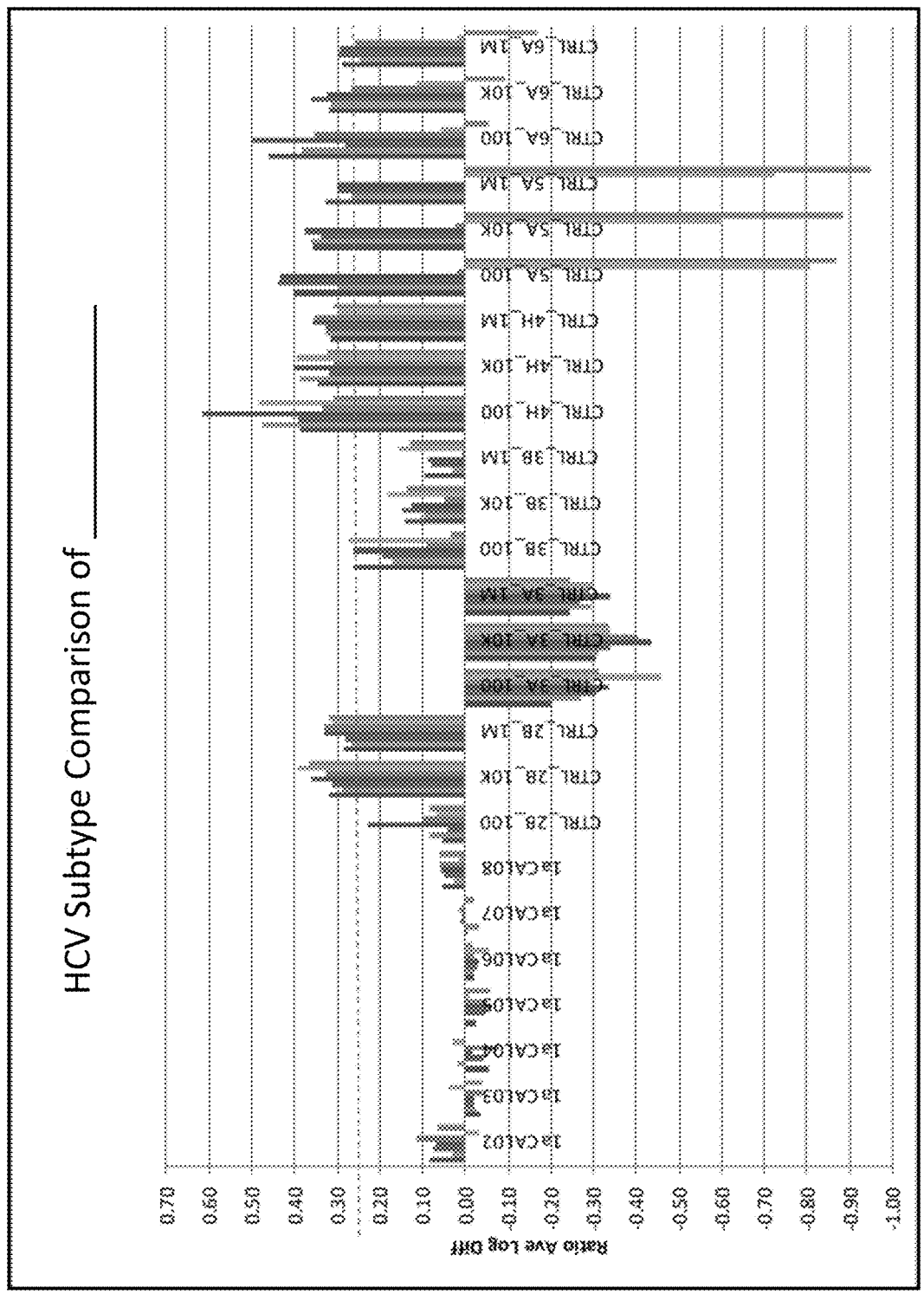
FIG. 18 shows characterization of LogDiff data on HCV genotypes using different T7 initial amplification oligomers. The genotypes and concentrations are as follows from left to right: 1a ($10^2$, $10^3$, $10^4$, $10^5$, $10^6$, $10^7$, $10^8$ c/ml); 2b ($10^2$, $10^4$, $10^6$ c/ml); 3a ($10^2$, $10^4$, $10^6$ c/ml); 3b ($10^2$, $10^4$, $10^6$ c/ml); 4h ($10^2$, $10^4$, $10^6$ c/ml); 5a ($10^2$, $10^4$, $10^6$ c/ml); 6a($10^2$, $10^4$, $10^6$ c/ml). For each genotype and concentration, the seven adjacent bars from left to right represent data with a T7 initial amplification oligomer as follows: 81-119; 83-119; 85-119; 87-119; 89-119; 91-119; 93-119.

A portion of this series of T7 initial amplification oligomers were tested in biphasic format with the A3 amp reagent with HCV 1a calibrator and HCV genotypes 1-6 (using IVTs from TOPO plasmids for genotypes 4-6). All HCV genotypes 2-6 were tested at 3 levels: 100, 10k and 1M copies per ml. Again, T7 89-119 as an initial amplification oligomer performed well, among others. T7 89-119 gave the smallest difference relative to HCV 1a for other HCV genotypes with T7 93-119 present in AMP2 (FIG. 18).

Figure 19:
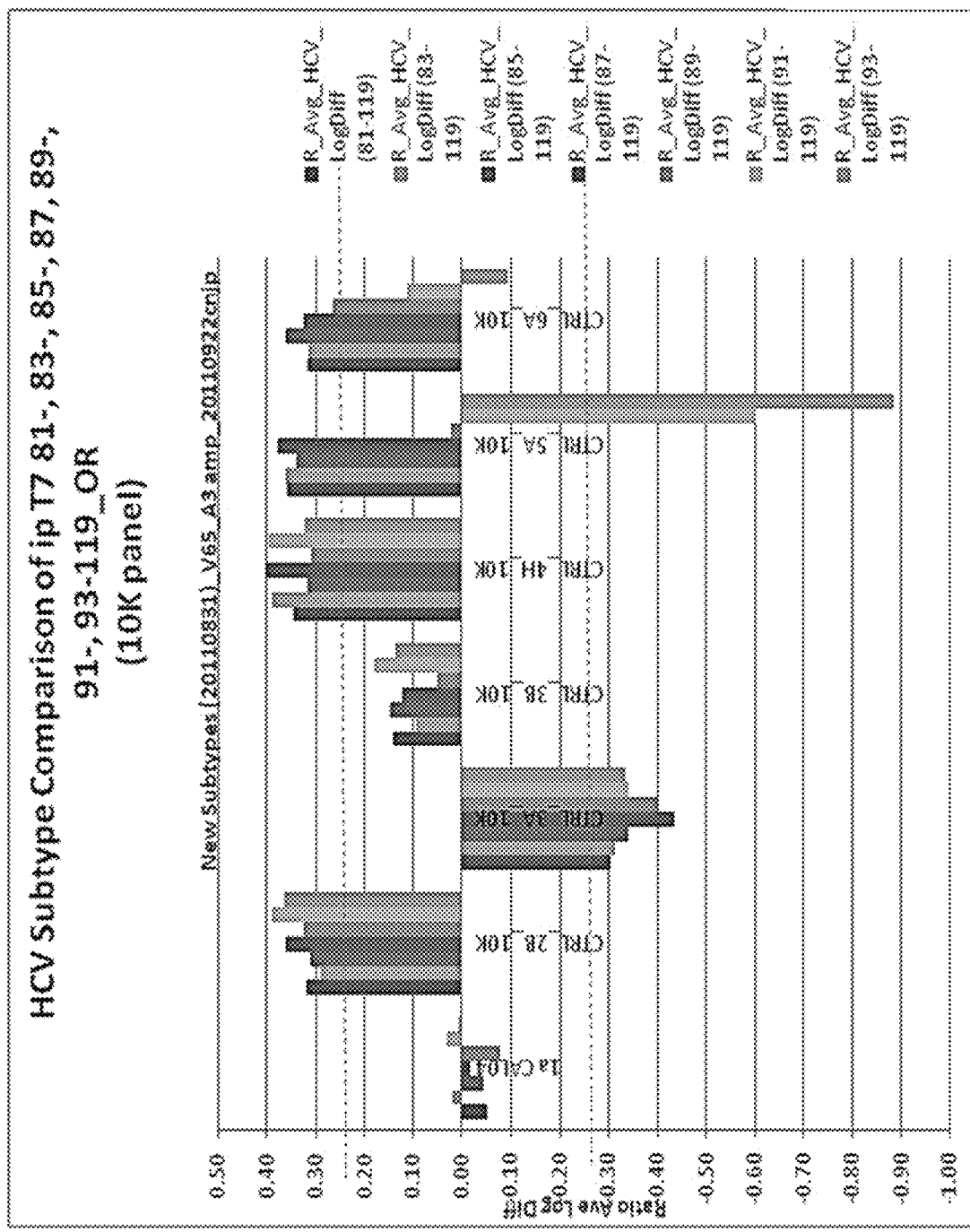
FIG. 19 shows 10K panel results on HCV genotypes for T7 initial amplification oligomers. This is an enlargement of the $10^4$ c/ml data only from FIG. 18 subset of the data, with the genotypes and primers in the same order.

A subset of this data is presented in FIG. 19 for the 10k copies per ml conditions to more clearly show the relative performance of the T7 initial amplification oligomers.

Example 6—Exemplary HCV Oligomer Set

Based in part on the foregoing results, an exemplary HCV oligomer set containing the oligomers listed in Table 1 was designed

TABLE 1

Exemplary HCV biphasic oligomers and IVT sequences

| | |
|---|---|
| Non-T7 Primer:<br>HCV(+)52-78-1 | 5'-GGAACTTCTGTCTTCACGCGGAAAGCG-3'<br>(SEQ ID NO: 2) |
| T7 Primer:<br>HCV(-)93-119 | 3'ATCATACTCACAGCACGTCGGAGGTCCAGAG<br>GGATATCACTCAGCATAATTTAA-5'<br>(SEQ ID NO: 5) |
| T7 initial<br>amplification<br>oligomer:<br>HCV(-)89-119 | 3'CGCAATCATACTCACAGCACGTCGGAGGTCC<br>AGAGGGATATCACTCAGCATAATTTAA-5'<br>(SEQ ID NO: 220) |
| Target Capture<br>Oligomer:<br>HCV0297<br>(-)dT3dA30 | 3'-AAAAAAAAAAAAAAAAAAAAAAAAAAAAAA<br>TTTUCCCACGAACGCUCACGGG-5'<br>(SEQ ID NO: 16) |
| Probe oligomer<br>81-96 5F3D | 5'-uagccauggcguuagu-(c9)-ggcua-3'<br>(SEQ ID NO: 12) |

The oligomer sequences align as follows to the IVT and sequences for different HCV genotypes.

Two mismatched "A" base pairs exist in the non-T7 binding region of the type 1A IVT relative to the (+)52-78 primer. The probe oligomer, initial amplification oligomer, and T7 primers match the rest of the sequence. The type 1a IVT is used as a reference for comparison to the IVTs for the rest of the genotypes;

Two mismatched "A" base pairs exist in the non-T7 binding region for the 52-78 (+) primer and a single "A" mismatch in the T7 binding region. These "A"s are bolded in the entry for the type 2b IVT in the Table of Sequences.

HCV 4h is characterized by two mismatches in the non-T7 52-78 (+) region and a single point U to G mutation in the initiator/T7 region. The torch and target capture oligomers match the HCV 1a genotype sequence.

HCV 5a IVT is characterized by two "A" mismatches in the non-T7 52-78 (+) region and two side by side "AA" mismatches in the middle of the T7 primer.

Initial experiments, without an initiator primer, resulted in poor performance using the HCV 5a genotype. Under-quantitation relative to HCV 1a standard was very apparent due to the double "AA" mismatches in the T7 primer binding region. However, once an initial amplification oligomer was included in the target capture reagent (TCR), the performance of the HCV 5a IVT was comparable to those of other IVT genotypes HCV 6a IVT is characterized by two "A" mismatches in the non-T7 52-78 (+) region and one "A" base mismatch in the middle portion of the T7 binding domain.

Example 7—Internal Control Oligomer Primer Selection

Incorporation of the internal control oligomers was tested with the following set of oligomers: T7 95-119; NT7 52-78; and 80-98-a Torch.

Oligomers according to SEQ ID NO: 15 and 18-20 were evaluated for use as an internal control (a.k.a. general internal control [GIC], IC). The IC oligomers were spiked into the early HCV amp system using standard TMA format on the OEM platform to determine if any primer interactions exist. Spiking one or all of the IC oligomers resulted in some expected slowing based on resource competition (between 1-2 minute difference in emergence time at the low end; data not shown). It was also confirmed that internal control amplification was successful in the presence of the HCV oligomer set (not shown).

Example 8—HCV Genotype Detection with the Biphasic TMA HCV/IC Assay

Figure 20:
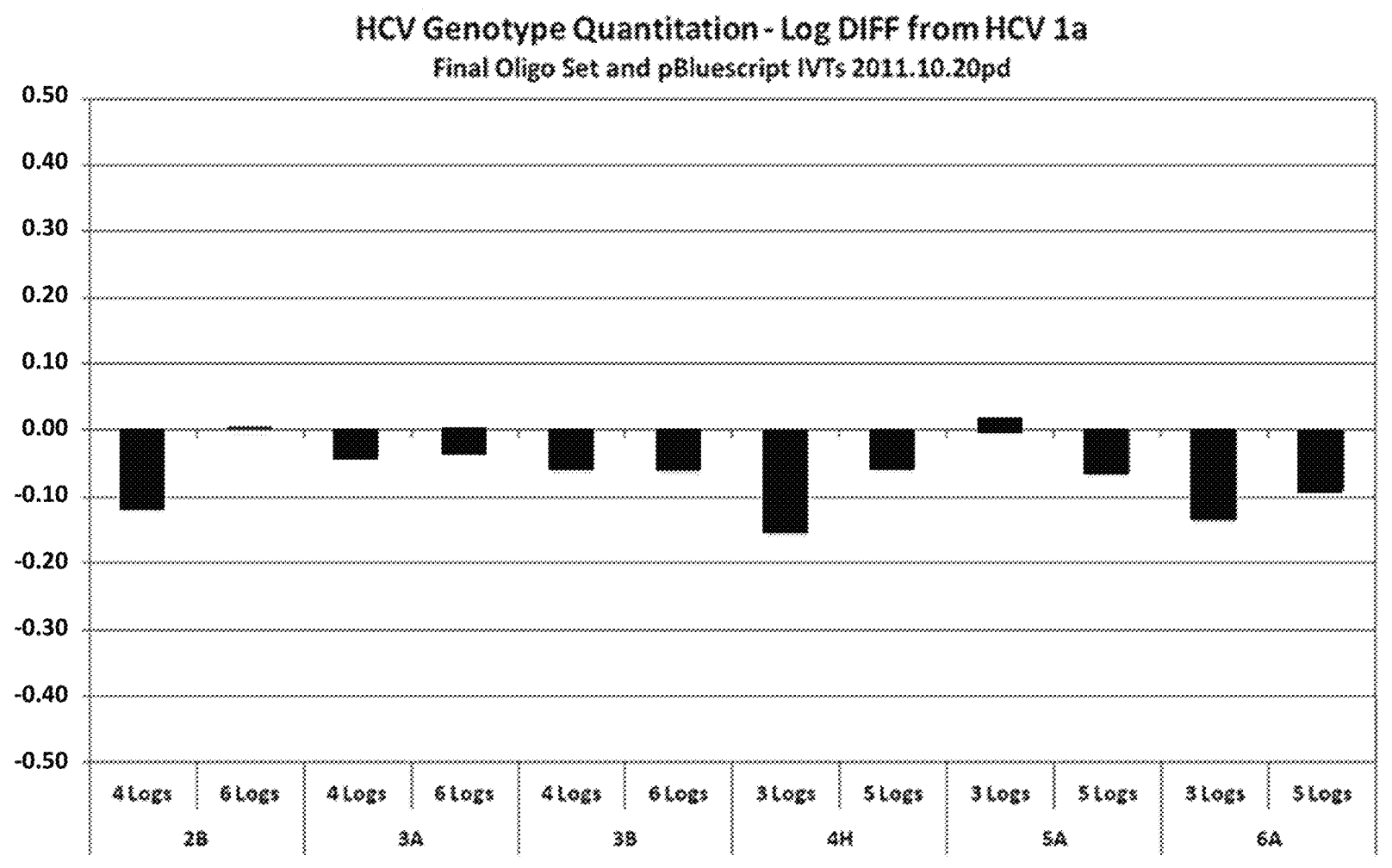

HCV genotype quantitation of the pBluescript® IVTs for HCV genotypes 2b, 3a, 3b, 4h, 5a and 6a with oligomer set of Table 2 were plotted as the difference in quantitation from the HCV 1a calibrators (FIG. 20). HCV genotype quantitation at □0.25 log difference from the HCV 1a calibrators was achieved.

Two T7 amplification oligomers HCV T7 93-119 (SEQ ID NO: 5) and HCV T7 80-119 (SEQ ID NO: 4) in the TCR were tested with negative serum and it was confirmed that the emergence time for internal control amplification was not affected (not shown). The HCV T7 80-119 initial amplification oligomer was also tested to determine if there are false positives in experiments with serum due to T7 carry-over from a TCR that overlaps the torch sequence because of its greater overlap with the HCV torch sequence. One false positive (N=140, specificity=99.3%) occurred at a very low concentration and may be due to operator error during preparation of spiked serum samples; data were excluded due to apparent degradation.

Example 9—Summary and Further Development of HCV Quantification Assay

An HCV quantification assay was designed and performed using biphasic TMA in combination with specific target capture and real time detection. The assay uses the long HCV T7 initial amplification oligomer in the Target capture reagent (TCR) and two HCV NT7 oligomers in the amplification reagent for first round extension and linear amplification. A second HCV T7 in the promoter reagent is used for exponential amplification of the HCV target. An HCV probe in the promoter reagent, labeled with FAM and quenched with Dabcyl is used for real time fluorescent detection.

General internal control (GIC) oligomers were as described in the Sequence Table below (SEQ ID NOs: 15 and 18-20).

Following development of the biphasic format of the assay to detect and equally quantitate the six HCV genotypes, further development of the oligomer set addressed specific HCV sequence mutations, and addition of a second HCV TCO (0327b, SEQ ID NO: 17) addressed target capture from the sample. The Los Alamos HCV sequence database, which provides annotated HCV sequences, was used as an analysis tool.

Oligomers used in the HCV quantification are presented in Table 2.

The amplification primers are targeted to the 5'UTR region of Hepatitis C virus polyprotein precursor (HCV-1), a region with ~90% homology among the genotypes.

HCV primers from the endpoint Procleix® Ultrio® Assay were also tested in the real-time TMA format. None performed well enough to proceed with further.

As discussed above, the earlier HCV oligomer set had mismatches against HCV genotypes (shown in ovals in FIG. 1). The torch 68-86 has 2 mismatches for HCV 3a/b and had poor amplification kinetics, with large differences among the genotypes. The nonT7 50-66 has 1 mismatch in HCV 3a and the T7 95-119 has 1 mismatch in each of HCV 2b, 3a, and 4h. The original set of oligomers did not equally quantitate all genotypes.

Figure 21:
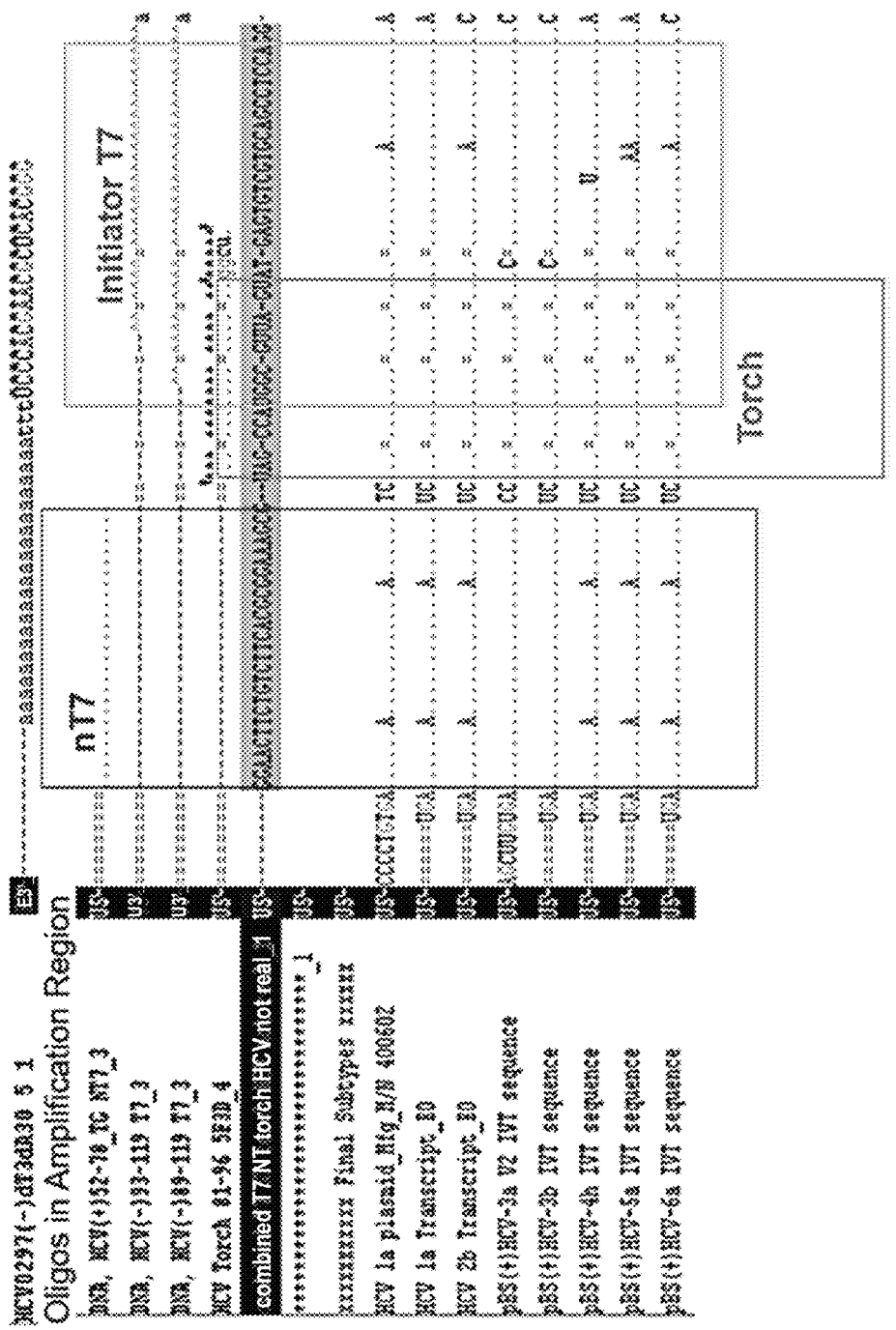
FIG. 21 shows an alignment of oligomers with HCV genotype sequences HCV 1 through HCV 6. The aligned sequences in order from top to bottom are SEQ ID NOs: 238, 2, 5, 220, 12, 239, 240, 241, 242, 243, 244, 245, 246, and 242.

New oligomers were designed in alternate regions and in the Torch boxed region shown in FIG. 21 for the torch sequence with a complete match to all HCV genotypes. NonT7s (NT7) and T7s were designed around this torch region.

Preliminary oligomers chosen for the HCV-Quant Assay are listed in Table 2 with alignment data in FIG. 21.

TABLE 2

Oligomers used in an exemplary HCV Quantification Assay (lower case = 2'-methoxy RNA, uppercase = DNA, underlined = T7 promoter

| Target and Class | Description | bases | MW (g/mol) | Sequence |
|---|---|---|---|---|
| HCV NT7 | DNA, HCV(+) 52-78-1, NT7 | 27 | 8300 | 5' GGAACTTCTGTCTTCACGCGGAAAGCG 3' (SEQ ID NO: 2) |

TABLE 2-continued

Oligomers used in an exemplary HCV Quantification Assay (lower case = 2'-methoxy RNA, uppercase = DNA, underlined = T7 promoter

| Target and Class | Description | bases | MW (g/mol) | Sequence |
|---|---|---|---|---|
| HCV NT7 | DNA, HCV(+) 52-78-2, NT7 | 27 | 8347 | 5' GGAATTACTGTTTTAACGCAGAAAGCG 3' (SEQ ID NO: 3) |
| HCV T7 initial amplification oligomers | DNA, HCV(-) 80-119 T7 | 67 | 20628 | 5' AATTTAATACGACTCACTATAGGGAGACCTGGAGGC TGCACGACACTCATACTAACGCCATGGCTAG 3' (SEQ ID NO: 4) |
| HCV T7 | DNA, HCV(-) 93-119 T7 | 54 | 16607 | 5' AATTTAATACGACTCACTATAGGGAGACCTGGAGGC TGCACGACACTCATACTA 3' (SEQ ID NO: 5) |
| HCV Torch | RNA, HCV(-) 81-96 C9(16,17) 5F3D Torch | 21 | 8238 | 5'-FAM uagccauggcguuagu(c9)ggcua 3'-DABCYL (SEQ ID NO: 12) |
| HCV TCO | RNA/DNA, HCV(-)0297 dT3dA30 TCO | 52 | 16610 | 5' gggcacucgcaagcacccuTTTAAAAAAAAAA AAAAAAAAAAAAAAAAAAAA 3' (SEQ ID NO: 16) |
| HCV TCO | RNA/DNA, HCV0327b (-) dT3dA30 TCO | 51 | 16309 | 5' cauggugcacggucuacgTTTAAAAAAAAAA AAAAAAAAAAAAAAAAAAA 3' (SEQ ID NO: 17) |
| GIC NT7 | DNA, GIC(+) 4102 NT7 | 19 | 5885 | 5' GATTATATAGGACGACAAG 3' (SEQ ID NO: 18) |
| GIC T7 | DNA, GIC(-) 4203, T7 | 49 | 15134 | 5' AATTTAATACGACTCACTATAGGGAGAGATGA TTGACTTGTGATTCCGC 3' (SEQ ID NO: 19) |
| GIC Torch | RNA, GIC(+) 4180-4197 C9(5-6) 5A3R Torch | 23 | 9532 | 5'-ACRIDINE gcaug(c9)gugcgaauugggacaugc 3'-ROX (SEQ ID NO: 20) |
| GIC TCO | DNA, IC CAP (-) 4277 dT3A30 TCO | 57 | 18150 | 5' cguucacuauuggucucugcauucTTTAAAA AAAAAAAAAAAAAAAAAAAAAAAAAA 3' (SEQ ID NO: 15) |

(5F3D: 5'-FAM, 3'- DABCYL. 5A3R: 5'-acridine, 3'-ROX.)

The oligomers in Table 2 were found to perform well with multiple HCV subtypes. However, several were found to have mismatches within the oligomer binding region to certain HCV sequences, which could result in poor quantitation. The sequences were gathered from database sources including HCVdB.org, Genbank, and Los Alamos. Genotype prevalence in these databases is reported below in Table 3, and is similar to US prevalence.

TABLE 3

Genotype prevalence in HCV database sequences

| genotype | n | Prevalence in Database |
|---|---|---|
| 1 | 422 | 49.4% |
| 2 | 63 | 7.4% |
| 3 | 120 | 14.0% |
| 4 | 50 | 5.8% |
| 5 | 10 | 1.2% |
| 6 | 70 | 8.2% |
| 7 | 1 | 0.1% |
| unknown | 119 | 13.9% |
| total | 855 | |

The goal was to provide quantification within +/−0.5 log c/ml of expected concentration regardless of genotype. Out of 855 sequences found from the source databases, there were 81 unique sequences (including perfect matches) in the relevant region for the oligomer set in Table 2. The frequency of mismatches was highest in the T7 and torch sequences as shown in Table 4 below, under effective mismatches. The TCO also had a high prevalence of mismatches (over 5%) but were mostly single-base mismatches, which are not believed to have more than minimal impact on performance.

TABLE 4

Summary of mismatch frequency between preliminary oligomer set and HCV mutant sequences

| # of mismatches | NT7 | T7 (corrected for built-in mismatches) | Torch | torch (no overlap w/T7) | TCO |
|---|---|---|---|---|---|
| total mismatches | 84.1% | 15.0% | 4.3% | 0.9% | 5.6% |
| 1 mismatch | 0.7% | 6.6% | 3.1% | 0.5% | 5.4% |
| 2 mismatch | 81.3% | 7.4% | 0.7% | 0.2% | 0.1% |
| 3 mismatch | 1.7% | 0.5% | 0.3% | 0.1% | 0.1% |
| >=4 mismatch | 0.3% | 0.5% | 0.0% | 0.0% | 0.0% |
| perfect matches | 15.9% | 69.3% | 95.7% | 99.1% | 94.4% |
| N | 860 | 748 | 860 | 860 | 728 |
| Effective Mismatches | 2.8% (note 2) | 15.0% (note 1) | 4.3% | 0.9% | 5.6% |

Note 1:
T7 primer has inherent single base mismatch (G-A) that is common to the HCV-1a, -2b, -5a and -6a used to design the assay (FIG. 21), and is also prevalent in sequences from the databases (see T7 primer box in the far right of FIG. 23). The oligomer set is designed around this specific mismatch, and therefore it was not counted in the table.

Note 2:
NT7 has a (T-A and G-A) mismatch common to the HCV-1a, -2b, -4h, -5a and -6a used to design the assay (FIG. 21), and is also prevalent in 81% of the sequences from the databases. This oligomer set is designed around this specific mismatch and therefore it was not included in the 'Effective Mismatches'.

Fifty of the 81 unique mutant sequences were chosen for synthesis based on the following criteria:

1. >2 mismatches within a given primer or the oligomer sequence

2. All mutant sequences occurring more than once in databases were built and tested.

3. Common mutations. If for example, a "g" was commonly seen instead of a "t" at position "x", then a subset of these types of mutation were made. As this type of single base mutation was very common, only a subset was made.

4. Select deletions and insertions were made and tested.

The identified mutations were incorporated into parental HCV clones by site directed mutagenesis (PCR of the plasmid using primers which contain the base changes). The in vitro transcripts were then made off of these new mutant clones. Table 5 lists the mutants that were synthesized and tested. In Table 5, the "subtype" column indicates the subtype in which the mutation was initially identified, and the clone name includes a designation of the subtype of the parental clone from which the construct for testing was derived.

TABLE 5

In vitro transcript mutants

| SEQ ID NO | Clone name | Sub type | Mutation location | Partial sequence including mutation(s) (underlined) | frequency* | # of mutations | Accession ref (GenBank) |
|---|---|---|---|---|---|---|---|
| 166 | HCV-1a NT7 A Clone | 6m | NT7 | GGAACTAATGT CTTCACGCAGA AAGCG | 7 | 3 | DQ835766 |
| 167 | HCV-1a T7 C-T-A-A Clone | 6q | T7 | GCGTTAGTATG AGCGTTGTACA ACCTCCAGG | 1 | 4 | EF424625 |
| 168 | HCV-1a T7 T-A | 4 | T7 | GCGTTAGTATG AGTGTTGTACA GCCTCCAGG | 35 | 2 | EF392175 |
| 169 | HCV-1a T7 A-A | 7a | T7 | ACGTTAGTATG AGTGTCGTACA GCCTCCAGG | 1 | 2 | EF108306 |
| 170 | HCV-1a NT7 T-T-A | 1b | NT7 | GGAATTACTGT TTTAACGCAGA AAGCG | 1 | 5 | AF165050 |
| 171 | HCV-5a NT7 T | 5 | NT7 | GGAACTACTTT CTTCACGCAGA AAGCG | 1 | 3 | AM502711 |
| 172 | HCV-5a NT7 C-C | 7a | NT7 | GGAACCACTGT CCTCACGCAGA AAGCG | 1 | 4 | EF108306 |
| 173 | HCV-1a NT7 T | 1b | NT7 | GGAACTACTGT CTTCACGCAGA AAGTG | 1 | 3 | X65924 |
| 174 | HCV-1a T7 T-C | 2a | T7 | GCGTTAGTATG AGTGTTGCACA GCCTCCAGG | 1 | 3 | D31604 |

TABLE 5-continued

In vitro transcript mutants

| SEQ ID NO | Clone name | Sub type | Mutation location | Partial sequence including mutation(s) (underlined) | frequency* | # of mutations | Accession ref (GenBank) |
|---|---|---|---|---|---|---|---|
| 175 | HCV-1a T7 A-C-G | 3a | T7 | GCGTTAATACG AGTGTCGTGCA GCCTCCAGG | 1 | 2 | AJ621226 |
| 176 | HCV-1a T7 C-C-C-G | 3a | T7 | GCGTTACCACG AGTGTCGTGCA GCCTCCAGG | 1 | 3 | AJ621237 |
| 177 | HCV-1a Tch A-C | 3 | Torch | TAACCCTGGCG TTAGT | contrived | 2 | AJ621232 ** |
| 178 | HCV-1a Tch C | 3 | Torch | TAGCCCTGGCG TTAGT | 1 | 1 | AJ621232 |
| 179 | HCV-1a NT EF424625 | 6q | NT | GGAACTATTGT CTTCACGCAGA AAGCG | 3 | 3 | EF424625 |
| 180 | HCV-1a NT DQ295833 | 4a | NT | GGTACTACTGT CTTCACGCAGA AAGCG | 1 | 3 | DQ295833 |
| 181 | HCV-1a T7 DQ295833 | 4a | T7 | GCAGTTAGTAT AGAGTGTCGTA CAGCCTCCAGG | 1 | 3 | DQ295833 |
| 182 | HCV-1a TCO DQ295833 | 4a | TCO | AAGGTGCTTGC GAGTCGCC | 1 | 3 | DQ295833 |
| 183 | HCV-1a Tch AJ621232 | 3a | torch | TAGCCCCTGGC GTTAGT | 1 | 2 | AJ621232 |
| 184 | HCV-1a NT EU360317 | 1a | NT | GGAACTGCTGT CTTCCCGCAGA AAGCG | 1 | 3 | EU360317 |
| 185 | HCV-3a NT AJ621233 | 3a | NT | GAACTTTTGTT TTCACGGAAAA GCG | 2 | 4 | AJ621233 |
| 186 | HCV-1a T7 FJ696476 | 1 | T7/torch | GCGTCTGTATG AGTTTCGGGCA GCCTCCAGG | 1 | 4 | FJ696476 |
| 187 | HCV-1a Tch FJ696480 | 1 | torch/T7 | TAGCCATGGCG CTAGT | 13 | 1 | FJ696480 |
| 188 | HCV-1a Tch FJ696498 | 1 | torch/T7 | TAGCCATGGCG CTTGT | 2 | 2 | FJ696498 |
| 189 | HCV-1a T7 FJ696503 | 1 | T7/torch | GCGCTTTTATG AGCGTCGTGCA GCCTCCAGG | 1 | 4 | FJ696503 |
| 190 | HCV-1a Tch EU360323 | 1b | torch | TAGCCATGGCG TCAGT | 3 | 1 | EU360323 |
| 191 | HCV-3a Tch FJ696423 | 3 | torch | TAGCTATGGC- GTTAGT | 1 | 1 | FJ696423 |
| 192 | HCV-1a T7 AJ621237 | 3a | T7 | GCGTTATCCAC GAGTGTCGTGC AGCCTCCAGG | 1 | 4 | AJ621237 |

TABLE 5-continued

In vitro transcript mutants

| SEQ ID NO | Clone name | Sub type | Mutation location | Partial sequence including mutation(s) (underlined) | frequency* | # of mutations | Accession ref (GenBank) |
|---|---|---|---|---|---|---|---|
| 193 | HCV-1a TCO DQ071885 | 1b | TCO | AGGGTGCGTGC AAGTGCCC | 1 | 2 | DQ071885 |
| 194 | HCV-1a T7 FJ696420 | 3 | T7 | GC-GTTAGTAC-GAGTGTCGTGC ACCCTCTAGG | 1 | 3 | FJ696420 |
| 195 | HCV-1a Tch GU451220 | 1b | torch | TAGTGCTGGCG TTAGT | 1 | 3 | GU451220 |
| 196 | HCV-1a TCO EU360321 | 1b | TCO | AGGTTGCTTGC GAGTGCCC | 2 | 1 | EU360321 |
| 197 | HCV-3a TCO HM043011 | 3 | TCO | AGGGCGCTTGC GAGTGCCC | 32 | 1 | HM043011 |
| 198 | HCV-1a T7-NT DQ295833 | 4a | NT & T7 mutated | (NT mutant region) GGTACTACTGT CTTCACGCAGA AAGCG | 1 | 6 | DQ295833 |
| 221 | | | | (T7 mutant region) GCAGTTAGTAT AGAGTGTCGTA CAGCCTCCAGG | | | |
| 199 | HCV-1a T7 FJ696429 E(12) | 1 | T7 | GCGTTAGTATG AGTGTCGTGCA GCCTCCAAG | 12 | 1 | FJ696429 |
| 200 | HCV-1a T7 FJ696458 G(10) | 1 | T7 | GCGCTAGTATG AGTGTCGTGCA GCCTCCAGG | 10 | 1 | FJ696458 |
| 201 | HCV-1a T7 FJ696439 I(4) | 1 | T7 | GCGTTAGTATG AATGTCGTGCA GCCTCCAGG | 4 | 1 | FJ696439 |
| 202 | HCV-1a T7 FJ696473 J(3) | 1 | T7 | GCGTCAGTATG AGTGTCGTGCA GCCTCCAGG | 3 | 1 | FJ696473 |
| 203 | HCV-1a T7 AJ621233 K(2) | 3a | T7 | GCGTTAGACGA GTGTCGTGCAG CCTCCAGG | 2 | 1 | AJ621233 |
| 204 | HCV-1a T7 DQ071885 L(2) | 1b | T7 | GCGTTAGTATG AGTGTCGTGCA GCCTCCATG | 2 | 1 | DQ071885 |
| 205 | HCV-1a T7 AJ621234 M(2) | 3a | T7 | GCGTTAGTACG AGTGTCGTGCA GCATCCAGG | 2 | 2 | AJ621234 |
| 206 | HCV-1a T7 FJ696431 N(2) | 1 | T7 | GCGTTAGTATG AGAGTCGTGCA GCCTCCAGG | 2 | 1 | FJ696431 |
| 207 | HCV-1a T7 EU360320 O(2) | 1b | T7 | GCGTTAGTATG AGTGACGTGCA GCCTCCAGG | 2 | 1 | EU360320 |
| 208 | HCV-1a T7 FJ696486 | 1 | T7 | GCGCTAGTATG AGCGTCGTGCA GCCTCCAGG | 1 | 1 | FJ696486 |

TABLE 5-continued

In vitro transcript mutants

| SEQ ID NO | Clone name | Sub type | Mutation location | Partial sequence including mutation(s) (underlined) | frequency* | # of mutations | Accession ref (GenBank) |
|---|---|---|---|---|---|---|---|
| 209 | HCV-1a T7 FJ696498 | 1 | T7 | GCGCTTGTATG AGTGTCGTGCA GCCTCCAGG | 1 | 2 | FJ696498 |
| 210 | HCV-1a T7 FJ696503 mod | 1 | T7 | GCGTTTTTATG AGCGTCGTGCA GCCTCCAGG | contrived | 3 | FJ696503 |
| 211 | HCV-1a T7 AJ621237 mod | 3a | T7 | GCGTTATCCAT GAGTGTCGTGC AGCCTCCAGG | contrived | 3 | AJ621237 |
| 212 | HCV-1a T7 FJ696428 | 1 | T7 | GCGTTAGTATG AGAGTCGTGCA GCCCCCAGG | 1 | 2 | FJ696428 |
| 213 | HCV-3a NT FJ790793 F(2) | 3a | NT | GGAATTTCTGT CTTCACGCGGA AAGCG | 2 | 1 | FJ790793 |
| 214 | HCV-1a TCO EU360322 H(2) | 1 | TCO | AGGGTGCTTGC GAATGCCC | 2 | 1 | EU360322 |

Figure 22A:
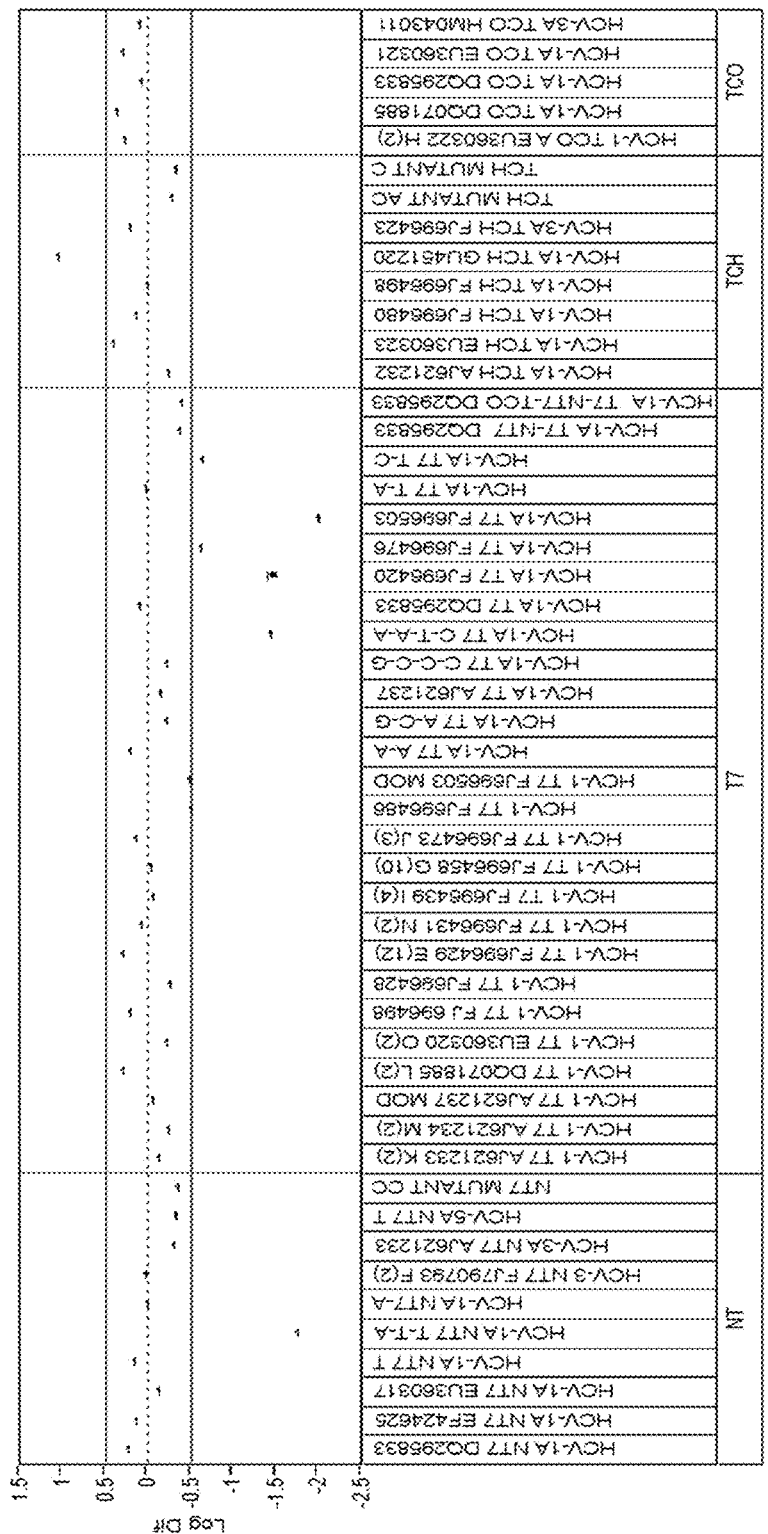

The 50 in vitro transcript mutants were tested with the initial assay feasibility oligomer system (Table 2) and 8 mutants recovered outside 0.5 log c/ml from expected results (FIGS. 22A and 22B) which represent ~1% of the population (8/850). 13 mutants under quantified by >0.4 log c/mL.

Six of the 8 mutants with a log difference of >0.5 logs were located in the T7 and torch region, 1 in the NT7 region, and a single mutant had mutations in T7, NT7 and TCO region (Table 6).

TABLE 6

| Mismatches to oligomer set in selected mutants | |
|---|---|
| Mutation location | # |
| T7 | 3 |
| T7/torch | 2 |

TABLE 6-continued

| Mismatches to oligomer set in selected mutants | |
|---|---|
| Mutation location | # |
| torch | 1 |
| NT | 1 |
| multiple area | 1 |

Figure 23:
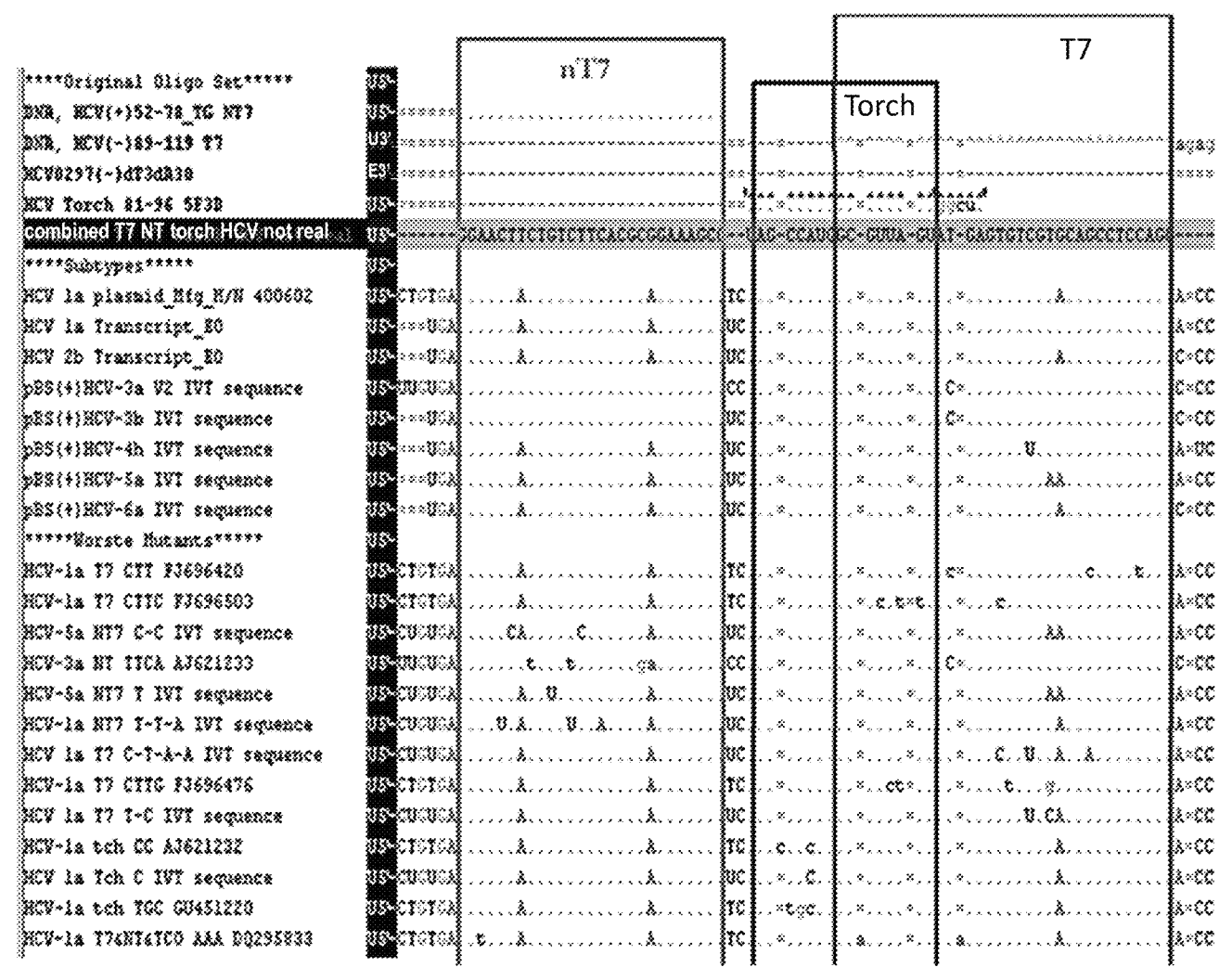

FIG. 23 shows a sequence alignment including the 13 mutants that under quantified by >0.4 log c/mL.

To improve quantitation of mutant HCV, changes were made to the initial oligomer set. The chosen modifications to the initial oligomer set were (1) lengthening the T7 initial amplification oligomer to address the T7 and torch mismatches and (2) adding a second, different NT7 oligomer. The oligomers screened are listed in Table 7.

TABLE 7

Oligomers screened to improve mutant quantitation

| name | type | sequence 5'-3' | SEQ ID NO |
|---|---|---|---|
| DNA, HCV(+)245-266 NT7_1a mtc | NT7 | ATT TGG GCG TGC CCC CGC AAG A | 76 |
| DNA, HCV(+)245-266 NT7_3a mtc | NT7 | ATT TGG GCG TGC CCC CGC GAG A | 77 |
| DNA, HCV(+)270-289 NT7 2 mism | NT7 | CTA GCC GAG TAG TGT TGG GT | 78 |
| DNA, HCV(+)278-304 NT7 3 mism | NT7 | AGT AGT GTT GGG TCG CGA AAG CCT TG | 79 |
| DNA, HCV(+)50-69_TG NT7_64A | NT7 | GAGGAACTACTGTCTTCACG | 80 |

TABLE 7-continued

Oligomers screened to improve mutant quantitation

| name | type | sequence 5'-3' | SEQ ID NO |
|---|---|---|---|
| DNA, HCV(+)52-78_TG NT7_64A | NT7 | GGAACTACTGTCTTCACGCGGAAAGCG | 81 |
| DNA, HCV(+)50-78_TG NT7_64 A | NT7 | GAGGAACTACTGTCTTCACGCGGAAAGCG | 82 |
| DNA, HCV(+)292-318 NT7 | NT7 | GCGAAAGGCCTTGTGGTACTGCCTGAT | 83 |
| DNA, HCV(+)298-324 NT7 | NT7 | GGCCTTGTGGTACTGCCTGATAGGGTG | 84 |
| DNA, HCV(+)66-78_TG NT7 shrt | NT7 | TGTCTTCACGCGGAAAGCG | 85 |
| DNA, HCV(+)245-266 NT7_1a mtch | NT7 | ATTTGGGCGTGCCCCCGCAAGA | 86 |
| DNA, HCV(+)245-266 NT7_3a mtch | NT7 | ATTTGGGCGTGCCCCCGCGAGA | 87 |
| DNA, HCV(+)270-289 NT7 2 mismatches | NT7 | CTAGCCGAGTAGTGTTGGGT | 88 |
| DNA, HCV(+)271-295 NT7 3 mismatches | NT7 | TAGCCGAGTAGTGTTGGGTCGCGAA | 89 |
| DNA, HCV(+)278-304 NT7 3 mismatches | NT7 | AGTAGTGTTGGGTCGCGAAAGGCCTTG | 90 |
| DNA, HCV(+)284-311 NT7 2 mismatches | NT7 | GTTGGGTCGCGAAAGGCCTTGTGGTACT | 91 |
| DNA, HCV(+)292-318 NT7 | NT7 | GCGAAAGGCCTTGTGGTACTGCCTGAT | 92 |
| DNA, HCV(+)298-324 NT7 | NT7 | GGCCTTGTGGTACTGCCTGATAGGGTG | 93 |
| DNA, HCV(+)50-78_TG NT7 | NT7 | GAGGAACTTCTGTCTTCACGCGGAAAGCG | 94 |
| DNA, HCV(+)66-78_TG NT7 shrt | NT7 | TGTCTTCACGCGGAAAGCG | 95 |
| DNA, HCV(+)52-78_TG NT7_71A | NT7 | GGAACTTCTGTCTTCACGCAGAAAGCG | 96 |
| DNA, HCV(+)52-78_TG NT7_71Ino | NT7 | GGAACTTCTGTCTTCACGCIGAAAGCG | 97 |
| DNA, HCV(+)66-78_TG NT7_71A | NT7 | TGTCTTCACGCAGAAAGCG | 98 |
| DNA, HCV(+)50-69_TG NT7 | NT7 | GAGGAACTTCTGTCTTCACG | 99 |
| DNA, HCV(+)52-78_NT7_A64,71 | NT7 | GGAACTACTGTCTTCACGCAGAAAGCG | 100 |
| DNA, HCV(+)52-78_NT7_mut TTA_1 | NT7 | GGAATTACTGTTTTAACGCAGAAAGCG | 3 |
| DNA, HCV(+)271-295 NT7 mtch 2a | NT7 | TAGCCTAGTAGCGTTGGGTTGCGAA | 101 |
| DNA, HCV(+)271-296 mtch 2a | NT7 | TAGCCTAGTAGCGTTGGGTTGCGAAC | 102 |
| DNA, HCV(+)271-295 NT7 mtch 291T | NT7 | TAGCCGAGTAGTGTTGGGTTGCGAA | 103 |
| DNA, HCV(+)271-295 NT7 mtch 2a 271T | NT7 | TAGCCTAGTAGTGTTGGGTCGCGAA | 104 |

TABLE 7-continued

Oligomers screened to improve mutant quantitation

| name | type | sequence 5'-3' | SEQ ID NO |
|---|---|---|---|
| DNA, HCV(+)271-295 NT7 mtch 2a 283C | NT7 | TAGCCGAGTAGCGTTGGGTCGCGAA | 105 |
| DNA, HCV(+)271-295 NT7 mtch 2a, 283, 291 | NT7 | TAGCCGAGTAGCGTTGGGTTGCGAA | 106 |
| DNA, HCV(+)271-295 NT7 mtch 3a | NT7 | TAGCCGAGTAGTGCTGTGTCGCGAA | 107 |
| HCV T7 79-119 (-) | T7 | AAT TTA ATA CGA CTC ACT ATA GGG AGA CCT GGA GGC TGC ACG ACA CTC ATA CTA ACG CCA TGG CTA GA | 108 |
| HCV T7 80-119 (-) | T7 | AAT TTA ATA CGA CTC ACT ATA GGG AGA CCT GGA GGC TGC ACG ACA CTC ATA CTA ACG CCA TGG CTA G | 109 |
| HCV T7 81-119 (-) | T7 | AAT TTA ATA CGA CTC ACT ATA GGG AGA CCT GGA GGC TGC ACG ACA CTC ATA CTA ACG CCA TGG CTA | 110 |
| HCV T7 82-119 (-) | T7 | AAT TTA ATA CGA CTC ACT ATA GGG AGA CCT GGA GGC TGC ACG ACA CTC ATA CTA ACG CCA TGG CT | 111 |
| HCV T7 83-119 (-) | T7 | AAT TTA ATA CGA CTC ACT ATA GGG AGA CCT GGA GGC TGC ACG ACA CTC ATA CTA ACG CCA TGG C | 112 |
| HCV T7 84-119 (-) | T7 | AAT TTA ATA CGA CTC ACT ATA GGG AGA CCT GGA GGC TGC ACG ACA CTC ATA CTA ACG CCA TGG | 113 |
| DNA, HCV(-)87-119 T7 | T7 | AAT TTA ATA CGA CTC ACT ATA GGG AGA CCT GGA GGC TGC ACG ACA CTC ATA CTA ACG CCA | 114 |
| DNA, HCV(-)88-119 T7 | T7 | AAT TTA ATA CGA CTC ACT ATA GGG AGA CCT GGA GGC TGC ACG ACA CTC ATA CTA ACG CC | 115 |
| DNA, HCV(-)89-119 T7_3_ino | T7 | AAT TTA ATA CGA CTC ACT ATA GGG AGA CCT GGA GGC TGI ACI ACA CTC ATA CTA ICG C | 116 |
| DNA, HCV(-)89-119 T7_A105 | T7 | AAT TTA ATA CGA CTC ACT ATA GGG AGA CCT GGA GGC TGC ACA ACA CTC ATA CTA ACG C | 117 |
| DNA, HCV(-)89-119 T7_G92 | T7 | AAT TTA ATA CGA CTC ACT ATA GGG AGA CCT GGA GGC TGC ACG ACA CTC ATA CTA GCG C | 118 |
| DNA, HCV(-)89-119 T7_I105 | T7 | AAT TTA ATA CGA CTC ACT ATA GGG AGA CCT GGA GGC TGC ACI ACA CTC ATA CTA ACG C | 119 |
| DNA, HCV(-)89-119 T7_I92 | T7 | AAT TTA ATA CGA CTC ACT ATA GGG AGA CCT GGA GGC TGC ACG ACA CTC ATA CTA ICG C | 120 |
| DNA, HCV(-)89-119 T7_Ino108 | T7 | AAT TTA ATA CGA CTC ACT ATA GGG AGA CCT GGA GGC TGI ACG ACA CTC ATA CTA ACG C | 121 |
| DNA, HCV(-)89-119 T7_mut CTAA | T7 | AAT TTA ATA CGA CTC ACT ATA GGG AGA CCT GGA GGT TGT ACA ACG CTC ATA CTA ACG C | 122 |
| DNA, HCV(-)89-119 T7_T108 | T7 | AAT TTA ATA CGA CTC ACT ATA GGG AGA CCT GGA GGC TGT ACG ACA CTC ATA CTA ACG C | 123 |

TABLE 7-continued

Oligomers screened to improve mutant quantitation

| name | type | sequence 5'-3' | SEQ ID NO |
|---|---|---|---|
| DNA, HCV(-)89-119 T7_T108_A105 | T7 | AAT TTA ATA CGA CTC ACT ATA GGG AGA CCT GGA GGC TGT ACA ACA CTC ATA CTA ACG C | 124 |
| DNA, HCV(-)90-119 T7 | T7 | AAT TTA ATA CGA CTC ACT ATA GGG AGA CCT GGA GGC TGC ACG ACA CTC ATA CTA ACG | 125 |
| DNA, HCV(-)93-119 T7_A105 | T7 | AAT TTA ATA CGA CTC ACT ATA GGG AGA CCT GGA GGC TGC ACA ACA CTC ATA CTA | 126 |
| DNA, HCV(-)93-119 T7_mut CTAA_ | T7 | AAT TTA ATA CGA CTC ACT ATA GGG AGA CCT GGA GGT TGT ACA ACG CTC ATA CTA | 127 |
| DNA, HCV(-)93-119 T7_T108 | T7 | AAT TTA ATA CGA CTC ACT ATA GGG AGA CCT GGA GGC TGT ACG ACA CTC ATA CTA | 128 |
| DNA, HCV(-)109-119 T7 | T7 | AAT TTA ATA CGA CTC ACT ATA GGG AGA CCT GGA GGC TGC ACG ACA CTC | 129 |
| DNA, HCV(-)109-119 T7_T108_A10 | T7 | AAT TTA ATA CGA CTC ACT ATA GGG AGA CCT GGA GGC TGT ACA ACA CTC | 130 |
| DNA, HCV(-)127-157 T7 | T7 | AAT TTA ATA CGA CTC ACT ATA GGG AGA GTT CCG CAG ACC ACT ATG GCT CTC CCG GGA G | 131 |
| DNA, HCV(-)133-163 T7 | T7 | AAT TTA ATA CGA CTC ACT ATA GGG AGA TCA CCG GTT CCG CAG ACC ACT ATG GCT CTC C | 132 |
| T7 HCV1a 134-158(-) | T7 | AAT TTA ATA CGA CTC ACT ATA GGG AGA GGT TCC GCA GAC CAC TAT GGC TCT C | 133 |
| T7 HCV1a 136-157(-) | T7 | AAT TTA ATA CGA CTC ACT ATA GGG AGA GTT CCG CAG ACC ACT ATG GCT C | 134 |
| 17 HCV1a 139-162 (-) | T7 | AAT TTA ATA CGA CTC ACT ATA GGG AGA CAC CGG TTC CGC AGA CCA CTA TGG | 135 |
| T7 HCV1a 143-166 (-) | T7 | AAT TTA ATA CGA CTC ACT ATA GGG AGA TAC TCA CCG GTT CCG CAG ACC ACT | 136 |
| T7 HCV1a 144-167 (-) | T7 | AAT TTA ATA CGA CTC ACT ATA GGG AGA GTA CTC ACC GGT TCC GCA GAC CAC | 137 |
| T7 HCV1a 146-175 (-) | T7 | AAT TTA ATA CGA CTC ACT ATA GGG AGA ATT CCG GTG TAC TCA CCG GTT CCG CAG ACC | 138 |
| T7 HCV1a 149-172 (-) | T7 | AAT TTA ATA CGA CTC ACT ATA GGG AGA CCG GTG TAC TCA CCG GTT CCG CAG | 139 |
| DNA, HCV(-)303-333 T7 | T7 | AAT TTA ATA CGA CTC ACT ATA GGG AGA ACT CGC AAG CAC CCT ATC AGG CAG TAC CAC A | 140 |
| DNA, HCV(-)308-333 T7 | T7 | AAT TTA ATA CGA CTC ACT ATA GGG AGA ACT CGC AAG CAC CCT ATC AGG CAG TA | 141 |
| DNA, HCV(-)316-345 T7 | T7 | AAT TTA ATA CGA CTC ACT ATA GGG AGA ACC TCC CGG GGC ACT CGC AAG CAC CCT ATC | 142 |
| DNA, HCV(-)327-354 T7 | T7 | AAT TTA ATA CGA CTC ACT ATA GGG AGA GTC TAC GAG ACC TCC CGG GGC ACT CGC A | 143 |
| DNA, HCV(-)329-355 T7 | T7 | AAT TTA ATA CGA CTC ACT ATA GGG AGA GGT CTA CGA GAC CTC CCG GGG CAC TCG | 144 |
| DNA, HCV(-)333-360 T7 | T7 | AAT TTA ATA CGA CTC ACT ATA GGG AGA CAC GGT CTA CGA GAC CTC CGG GGG CA | 145 |

TABLE 7-continued

Oligomers screened to improve mutant quantitation

| name | type | sequence 5'-3' | SEQ ID NO |
|---|---|---|---|
| DNA, T7AHCV0263(-) | T7 | AATTTAATACGACTCACTATAGGGAGAAGTACCAC AAGGCCTTTCGCIACCCAAC | 146 |
| DNA, HCV(-)89-108 T7 | T7 | AATTTAATACGACTCACTATAGGGAGAGACACTCA TACTAACGC | 147 |
| HCV Torch 80-96 5F3D | Tch | CUAGCCAUGGCGUUAGUGCUAG | 148 |
| HCV Torch 81-96 5F3D_93C | Tch | UAGCCCUGGCGUUAGUGGCUA | 149 |
| HCV Torch 81-94 5F3D | Tch | UAGCCAUGGCGUUAGGCUA | 150 |
| HCV Torch 80-94 5F3D | Tch | CUAGCCAUGGCGUUAGCUAG | 151 |
| HCV Torch 292-309 5F3D | Tch | GCGAAAGGCCUUGUGGUAUUCGC | 152 |
| HCV Torch 325-340 5F3D | Tch | CUUGCGAGUGCCCCGGGCAAG | 153 |
| HCV Torch 321-336 5F3D | Tch | GGUGCUUGCGAGUGCCGCACC | 154 |
| HCV Torch 316-331 5F3D | Tch | GAUAGGGUGCUUGCGACUAUC | 155 |
| HCV Torch 314-329 5F3D | Tch | CUGAUAGGGUGCUUGCAUCAG | 156 |
| HCV Torch 310-325 5F3D | Tch | CUGCCUGAUAGGGUGCGGCAG | 157 |
| HCV Torch 307-322 5F3D | Tch | GUACUGCCUGAUAGGGAGUAC | 158 |
| HCV Torch 306-321 5F3D | Tch | GGUACUGCCUGAUAGGGUACC | 159 |
| HCV Torch 300-314 5F3D | Tch | CCUUGUGGUACUGCCCAAGG | 160 |
| HCV0168-186(-)dT3dA30 | TCO | AUUCCGGUGUACUCACCGGUUUAAAAAAAAAAAAA AAAAAAAAA | 161 |
| HCV0157-174(-)dT3dA30 | TCO | UCACCGGUUCCGCAGACCUUUAAAAAAAAAAAAAA AAAAAAAA | 162 |
| HCV0154-173(-)dT3dA30 | TCO | CACCGGUUCCGCAGACCACUUUAAAAAAAAAAAA AAAAAAAAAA | 163 |
| HCV0143-161(-)dT3dA30 | TCO | AGACCACUAUGGCUCUCCCUUUAAAAAAAAAAAAA AAAAAAAA | 164 |
| HCV0141-159(-)dT3dA30 | TCO | ACCACUAUGGCUCUCCCGGUUUAAAAAAAAAAAAA AAAAAAAA | 165 |

NT7 oligomer HCV (+)52-78_NT7_mut TTA_1, also referred to as 52-78-2 (SEQ ID NO: 3), was found to improve quantification in the presence of certain mutations. With the addition of this oligomer to address mutations, there were 2 NT7 primers (HCV (+) 52-78-1, SEQ ID NO: 2; and HCV (+) 52-78-2, SEQ ID NO: 3) in the oligomer set.

Detection results for genotypes including subtype 3a, subtype 3b, and the subtype 1a NT7 TTAA mutant at varying proportions of the two NT7 primers are in Table 8 (given as log difference from target; bold italics indicate more than 0.5 log difference for the NT7 T-T-A mutant or greater than 0.25 log difference for the 3a and 3b genotypes). Using 75% or 50% of the 52-78-2 NT7 oligomer resulted in quantification of all tested sequences within 0.5 logs of target. Using 25% of the 52-78-2 NT7 oligomer resulted in quantification of all tested sequences except the T-T-A mutant within 0.5 logs of target. It was also concluded that a manufacturing tolerance around primer concentrations of approximately +/−10% was acceptable. At 50% 52-78-2, subtype 3a and 3b were quantified within +/−0.25 log difference of target, and the 1a NT7 TTA mutant was quantified within +/−0.5 log c/ml.

TABLE 8

Effect of NT7 oligomer concentrations

| | % HCV (+) 52-78-2/total NT7 primer concentration | | | | | |
|---|---|---|---|---|---|---|
| | 100% | 75% | 50% | 25% | 11% | 0% |
| CAL02 | 0.13 | 0.05 | 0.15 | 0.13 | 0.15 | 0.11 |
| CAL03 | −0.05 | 0.02 | −0.02 | −0.01 | −0.06 | 0.06 |
| CAL04 | −0.14 | −0.11 | −0.18 | −0.17 | −0.17 | −0.30 |
| CAL06 | 0.01 | 0.01 | −0.05 | −0.03 | 0.04 | 0.10 |
| CAL08 | 0.05 | 0.03 | 0.10 | 0.08 | 0.04 | 0.02 |
| CTRL30-1A | 0.01 | 0.15 | 0.09 | 0.07 | 0.26 | 0.30 |
| SEQ ID 170 at 1e4 c/ml | 0.12 | 0.44 | −0.37 | *−1.18* | *−1.50* | *−1.35* |
| SEQ ID 172 at 1e4 c/ml | −0.07 | −0.08 | −0.28 | −0.23 | −0.29 | −0.20 |
| SEQ ID 173 at 1e4 c/ml | −0.24 | −0.23 | −0.34 | −0.27 | −0.33 | −0.26 |
| HCV GENOTYPE 2B | −0.19 | −0.10 | −0.12 | −0.24 | −0.17 | −0.09 |
| HCV GENOTYPE 3A | *−0.70* | *−0.33* | −0.21 | −0.15 | *−0.28* | −0.21 |
| HCV GENOTYPE 3B | *−0.58* | −0.18 | 0.03 | 0.05 | 0.02 | 0.06 |
| HCV GENOTYPE 4H | −0.08 | −0.02 | −0.03 | 0.03 | 0.02 | 0.06 |
| HCV GENOTYPE 5A | −0.03 | 0.04 | 0.05 | 0.02 | 0.01 | 0.14 |
| HCV GENOTYPE 6A | −0.12 | −0.01 | −0.09 | −0.05 | −0.15 | 0.05 |

A longer T7 initial amplification oligomer (HCV (−) 80-119 T7) was designed to address the T7 and torch mutants. By increasing the length of the T7 sequence, oligomer binding overcame isolated mismatches in the T7 region. As a result, the new T7 initial amplification oligomer completely overlaps the torch.

The T7 initial amplification oligomer is located in the target capture reagent. The T7 initial amplification oligomer design overlaps the torch region. Accordingly, to minimize the risk of false positives, free T7 initial amplification oligomer should be removed during the wash step. Spiking T7 initial amplification oligomer directly into the amplification reaction resulted in false positives (data not shown).

Figure 24:
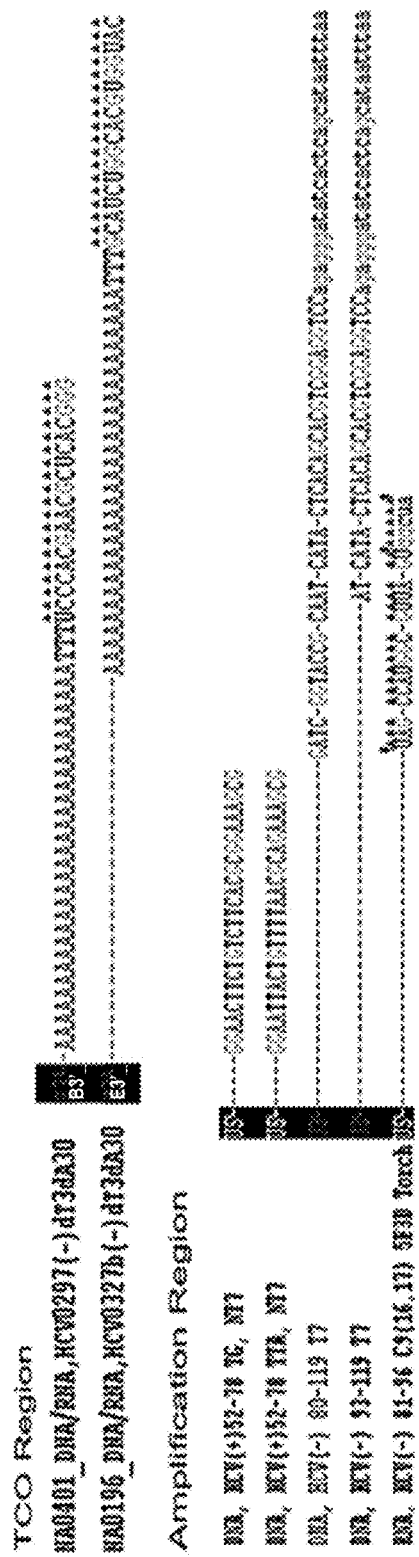
FIG. 24 shows a sequence alignment of an exemplary oligomer set. The aligned sequences in order from top to bottom are SEQ ID NOs: 16, 17, 2, 3, 4, 5, and 12.
Figure 25A:
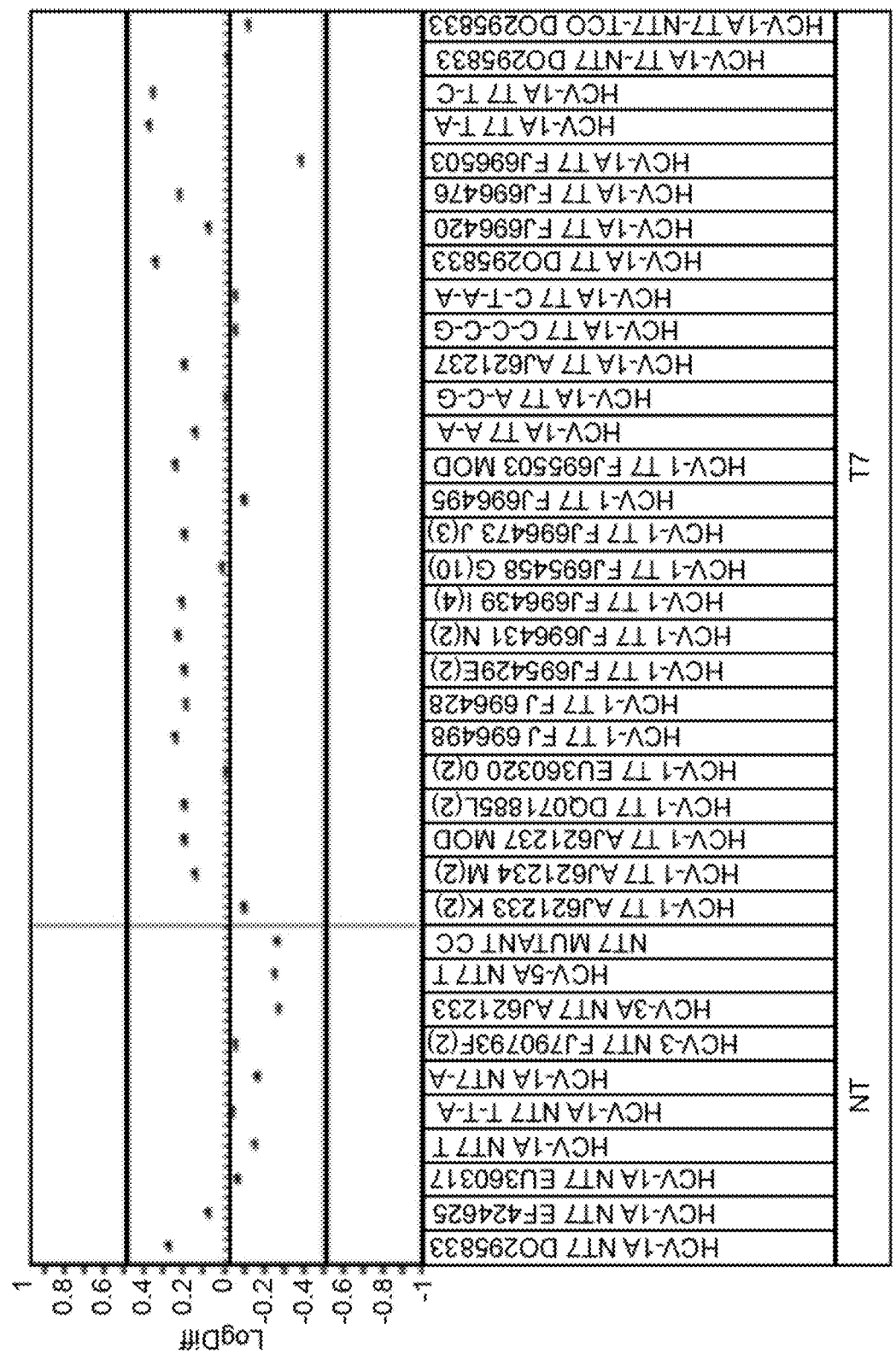
FIGS. 25A-25C show IVT mutant detection across HCV mutants (target concentration: $10^4$c/ml) (FIG. 25A-B) and subtype detection (FIG. 25C) for an exemplary oligomer set.
Figure 25B:
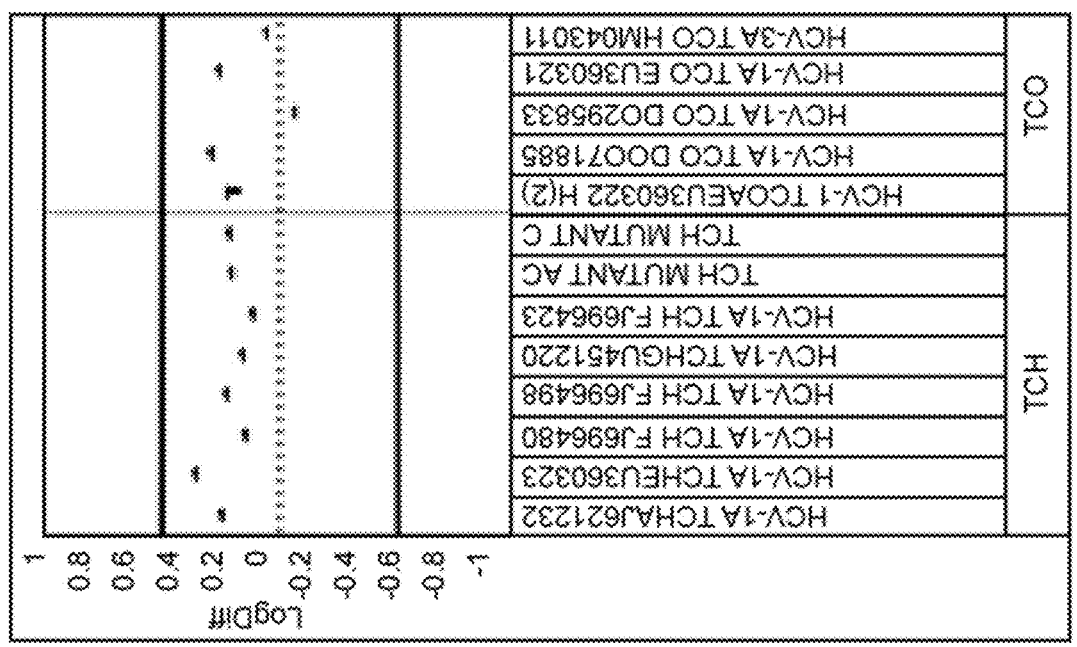
Figure 25C:
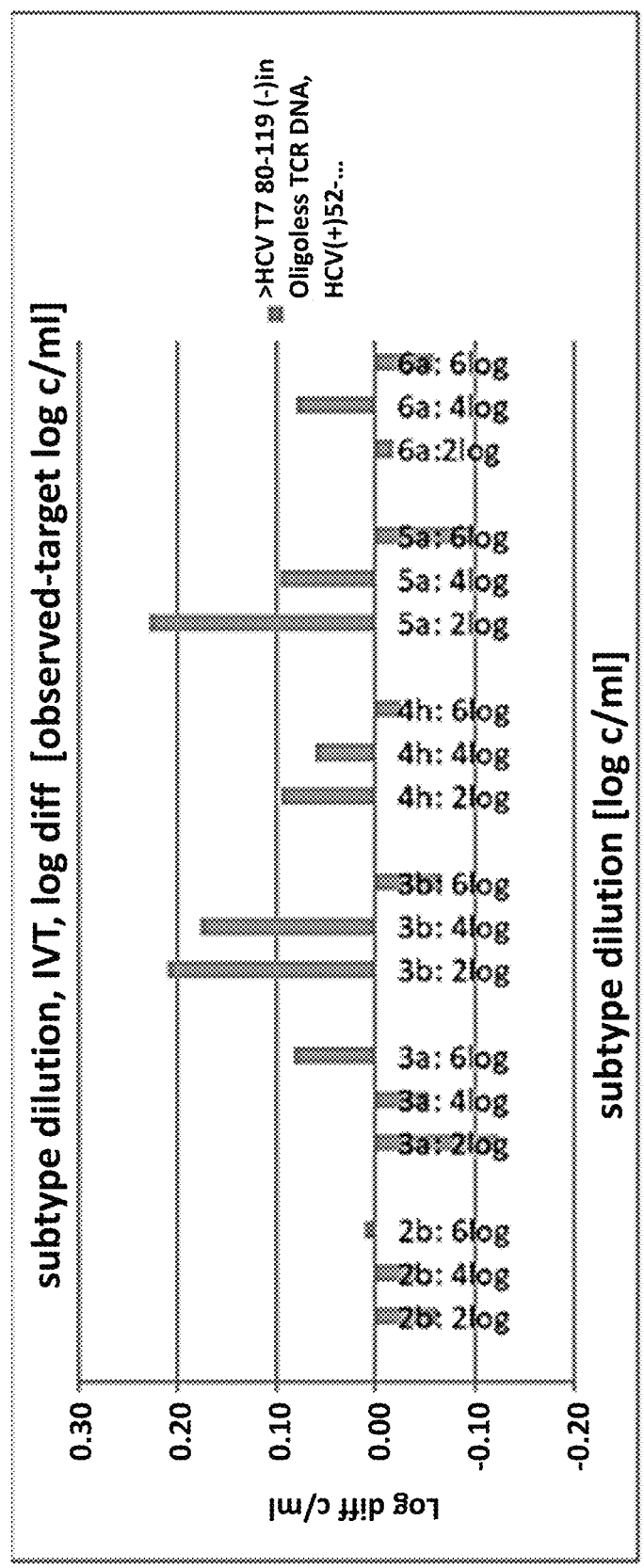

FIG. 24 is a sequence alignment of the oligonucleotides in the HCV oligomer set. With these changes, all IVT mutants recovered within +/−0.5 log c/ml of targeted concentration (FIGS. 25A & 25B) and subtype detection was within +/−0.25 log c/ml of expected value (FIG. 25C). The sequence for the second HCV TCO (0327), which was added during reagent formulation is also shown in FIG. 24.

Example 10—Analytical Specificity Studies

These data were generated using the set of oligomers as presented in Table 2 except that the HCV 0327b(−) capture oligomer was not used.

Several specificity studies were conducted on a series of different instruments using HCV-negative serum prepared in-house, internal amplification control (IAC) buffer, and clinical negative samples, including more viscous clinical samples. No false positives (FP) were seen in 1468 negatives tested resulting in a specificity of 100% (95% CI: 99.7 to 100%) (Table 9).

TABLE 9

Analytical specificity studies

| Instrument# | # of Neg | #FP* | Description |
|---|---|---|---|
| 1 | 45 | 0 | negative serum |
| 1 | 105 | 0 | IAC buffer |
| 1 | 105 | 0 | negative serum |
| 2 | 85 | 0 | IAC buffer |
| 3 | 200 | 0 | Clinical negative plasma |
| 4 | 92 | 0 | auto-immune clinical negatives |
| 3 | 104 | 0 | negative serum |
| 5 | 105 | 0 | negative serum |
| 4 | 102 | 0 | negative serum |
| 1 | 105 | 0 | negative serum |
| 6 | 105 | 0 | negative serum |
| 7 | 105 | 0 | negative serum |
| 8 | 105 | 0 | negative serum |
| 2 | 105 | 0 | negative serum |
| total | 1468 | 0 | |

*RFU range threshold: 1000

Example 11—Analytical Sensitivity and Analysis of Clinical Samples

The data in this example were generated using the set of oligomers in Table 2 except that the HCV0327b(−) capture oligomer was not used.

The studies presented below were performed with virus in plasma, IVT in IAC buffer, and also an artificial AcroMetrix® HCV-S virus panel similar to armored RNA. The AcroMetrix® HCV-S panel is a synthetic sequence of HCV 1b, embedded in a recombinant BVDV (bovine viral diarrhea virus) protein using the SynTura Technology by AcromMetrix, calibrated in IU/mL (Applied Biosystems cat #950350).

Based on preliminary experiments, using the WHO HCV $2^{nd}$ Standard, the HCV assay has a 5 copy/IU conversion factor. Preliminary sensitivity studies were performed with in vitro transcripts indicated in Table 10 in IAC. The positivity rate at 60c/ml was 100%. Using PROBIT analysis, the limit of detection at 95% probability, was 19.58 c/ml or 3.91 U/ml. Probit analysis was performed using R statistical computing software, using a generalized linear model with binomial error distribution, along with the Probit function for response variable. See Tables 10 and 11.

TABLE 10

Analytical sensitivity of in vitro transcript, Sample data

| IVT | copies/ml | N | Negatives | Positives | % Positive |
|---|---|---|---|---|---|
| HCV 1A | 100 | 35 | 0 | 35 | 100% |
| HCV 1A | 60 | 35 | 0 | 35 | 100% |
| HCV 1A | 37 | 35 | 1 | 34 | 97% |
| HCV 1A | 10 | 35 | 4 | 31 | 89% |
| HCV 1A | 5 | 35 | 14 | 21 | 60% |
| Neg. Control | 0 | 4 | 4 | 0 | 0% |

TABLE 11

Analytical sensitivity for IVT - Limit of detection using PROBIT analysis

| Probability | Conc (Copy/mL) | LowerLimit-95% (Copy/mL) | UpperLimit-95% (Copy/mL) | R-squared |
|---|---|---|---|---|
| 50% | 3.54 | 1.49 | 5.20 | 0.997 |
| 95% | 19.58 | 13.22 | 48.22 | 0.997 |

A study was also performed with the Acrometrix® panel in serum. The positivity rate at 12 IU/ml was 100%. Using PROBIT analysis, the limit of detection at 95% probability was 3.13 IU/ml. See Tables 12 and 13.

TABLE 12

Analytical Sensitivity of Acrometrix panel, Sample data

| IU/ml of Acrometrix panel | Reps | # Neg | # Pos | % positive | R_Avg_HCV LogCopy c/ml |
|---|---|---|---|---|---|
| 12 IU/mL | 30 | 0 | 30 | 100% | 1.96 |
| 8 IU_mL | 30 | 0 | 30 | 100% | 1.42 |
| 6 IU_mL | 30 | 0 | 30 | 100% | 1.45 |
| 4 IU_mL | 30 | 1 | 29 | 97% | 1.14 |
| 2 IU_mL | 30 | 5 | 25 | 83% | 1.14 |
| 1 IU_mL | 30 | 10 | 20 | 67% | 0.80 |

TABLE 13

Analytical Sensitivity of Acrometrix panel, Limit of detection using PROBIT analysis

| Probability | Conc (IU/mL) | LowerLimit-95% (IU/mL) | UpperLimit-95% (IU/mL) | R-squared |
|---|---|---|---|---|
| 50% | 0.74 | 0.34 | 1.05 | 0.997 |
| 95% | 3.13 | 2.30 | 5.74 | 0.997 |

Precision was assessed with various low copy-level panels over 3 instruments and 3 days for a total of 60 replicates. The total error was less than 1 log c/ml at 121 U/ml or 1.78 log c/ml. See Table 14.

TABLE 14

Assay precision ≤100 c/ml

| type | n | target log c/ml | target IU/ml | % positive | Observed average LogCopy | log difference | total sd (log c/ml) | total error* |
|---|---|---|---|---|---|---|---|---|
| HCV 1a IVT/IAC | 60 | 1.48 | | 100% | 1.65 | 0.27 | 0.27 | 0.76 |
| HCV 1a virus/serum | 60 | 1.21 | | 98% | 1.48 | 0.30 | 0.33 | 0.92 |
| artificial HCV 1b virus/serum | 60 | | 12 | 100% | 2.04 | 0.16 | 0.16 | 0.45 |
| artificial HCV 1b virus/serum | 60 | | 2 | 93% | 1.21 | 0.50 | 0.49 | 1.39 |

*total error = sqrt(2) × 2 × standard deviation

The precision of the QC calibrators were also assessed at 5 different concentrations in this study. Total error was below 1 log c/ml and sdlog c/ml was <0.20 from 2 log c/ml (~20 IU/ml) to 9 log c/ml (~2e8 IU/ml). See Table 15.

TABLE 15

Precision from 100 c/ml to 1e9 c/ml

| type | n | target log c/ml | Observed average Log Copy | total sdlog c/ml | total error* |
|---|---|---|---|---|---|
| HCV 1a transcript/IAC | 12 | 1.96 | 2.04 | 0.12 | 0.34 |
| HCV 1a transcript/IAC | 12 | 4.18 | 4.02 | 0.10 | 0.28 |
| HCV 1a transcript/IAC | 12 | 5.89 | 5.95 | 0.08 | 0.23 |
| HCV 1a transcript/IAC | 12 | 8.3 | 8.32 | 0.09 | 0.25 |
| HCV 1a transcript/IAC | 12 | 9.1 | 9.05 | 0.06 | 0.17 |

*total error = sqrt(2) × 2 × standard deviation

Figure 26:
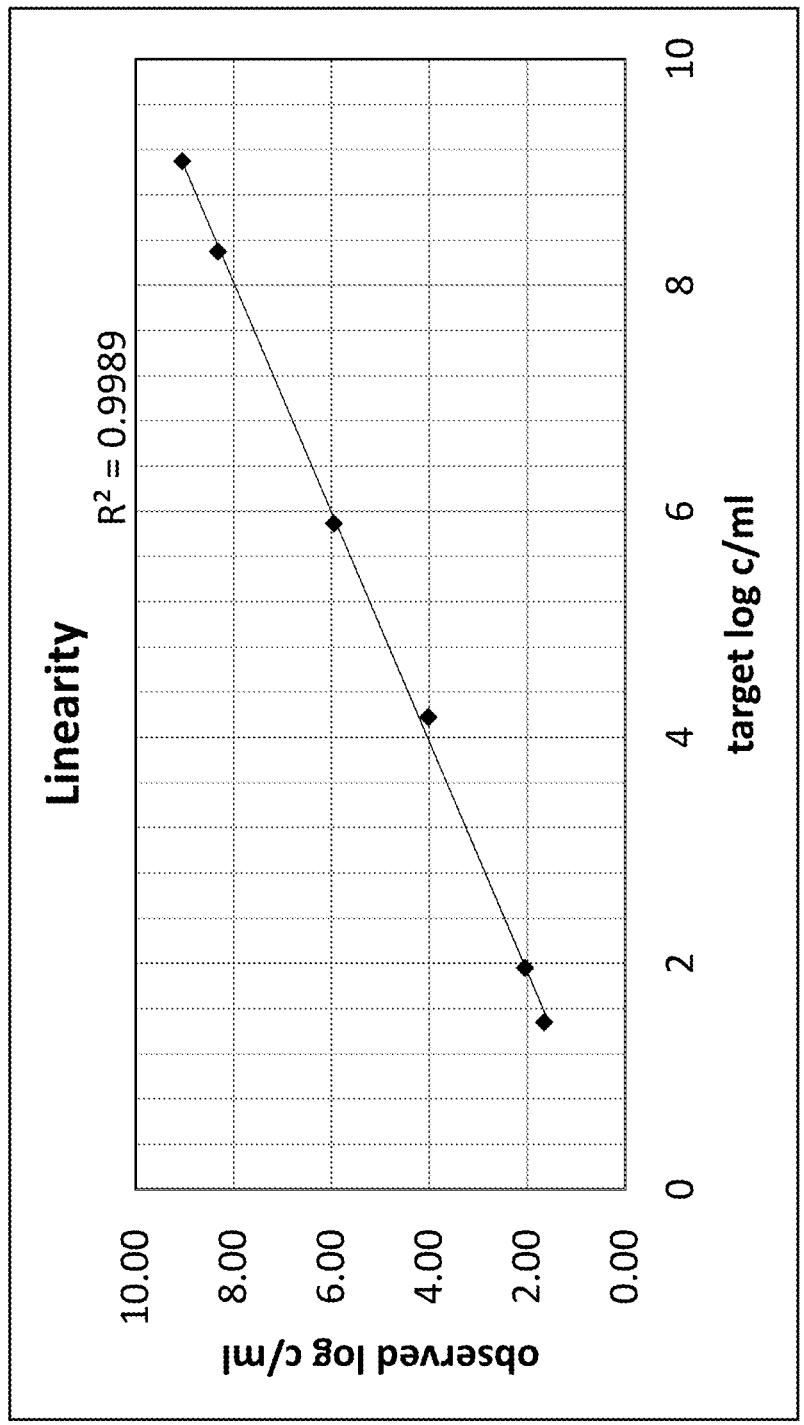
FIG. 26 shows linearity of assay 30-1e9 c/ml (30c/mL n=60, 1e2-1e9c/mL n=12).

FIG. 26 demonstrates that the assay was linear from 1.47 log c/ml (~6IU/ml) to 9 log c/ml (~2e8 IU/ml).

HCV viral load for 91 clinical samples were determined using the assay as described in Example 11 and compared to results from commercial HCV assays from Abbott Molecular Inc. and Roche Molecular Systems Inc. A 5 copy/IU conversion was determined as discussed above. The results of the instant assay were all within one log c/ml of the Abbott results (not shown). When compared to the Roche assay, 2 HCV subtype 4 samples gave more than 1 log over-quantification. The Roche assay is known to under-quantitate HCV subtype 4. See Chevaliez et al., *Journal of Hepatology* Volume 44, Supplement 2, April 2006, Pages S195-S196.

Example 12—Addition of Second Target Capture Oligomer

A second TCO, HCV 0327b(−)dT3dA30 (SEQ ID NO: 17), was evaluated as to whether it impacts performance with respect to target capture. All experiments below were tested with HCV 0327b(−) dT3dA30 (SEQ ID NO: 17) at 6 pmol/reaction unless otherwise stated.

The following conditions were tested to evaluate the impact of the addition of the second TCO and determine the optimal concentration of the second TCO. Six mutant transcripts that have mutations in the TCO (0297) region and genotype transcript panels were tested at 1e4 copies/ml (n=5). The addition of the second TCO (0327b) at 6 and 12 pmol/reaction had similar log copy and precision. All positive panels were 100% positive and within +/−0.5 logs of target log copy. The control (single TCO system, 0297 only) had slightly higher log copy values in the initial run; however, results from the same condition repeated on a different day had results that aligned with the rest of the conditions (not shown), indicating slight day-to-day variability. The second TCO (0327b) alone had delayed emergence times for HCV and GIC by approximately 3 minutes for both (data not shown). The additional second TCO (0327b) at 6 pmol/reaction is thus an acceptable concentration.

The WHO HCV panel was tested with the addition of the second TCO. The study was completed on multiple instruments with total replicates ranging from 15-45 per panel (3 runs). The previous limit of detection (LoD) (95% positive) was determined to be 3.76 IU/mL (3 instruments, n=30-90 per panel or 6 runs). The LoD slightly increased to 5.06 IU/mL which may be variability between experiments, as the previous value of 3.76 IU/ml is within the 95% confidence interval (Table 16).

TABLE 16

Limit of Detection (95% positivitiy) of HCV WHO 2$^{nd}$ Standard

| Condition | Concentration (IU/mL) | Lower Limit 95% | Upper Limit 95% |
|---|---|---|---|
| WHO in plasma (with 2$^{nd}$ TCO) | 5.06 | 3.46 | 10.56 |

The calculated LoQ (limit of quantification, i.e., concentration where the total error equals 1) was 9.748 IU/ml, similar when the single TCO was used (single TCO TE=9.02 IU/mL), demonstrating equivalent precision near the LoD of the assay (Table 17).

TABLE 17

LoQ or Total Error (TE) determination of WHO with addition of second TCO

| Sample | Target IU/mL | TE (log IU/mL) |
|---|---|---|
| WHO0 | 0 | — |
| WHO1 | 1 | 0.792 |
| WHO2 | 2 | 1.358 |
| WHO3 | 3 | 1.358 |
| WHO6 | 6 | 1.273 |
| WHO12 | 12 | 0.764 |

TABLE 17-continued

LoQ or Total Error (TE) determination of WHO with addition of second TCO

| Sample | Target IU/mL | TE (log IU/mL) |
|---|---|---|
| WHO20 | 20 | 0.537 |
| Interpolated based on linear regression line (1 IU/mL excluded) | 9.748 IU/ml | 1 |

The LoD for the same clinical specimens of six HCV genotypes previously tested with only the 0297 TCO were re-tested near the LoD (12 IU/ml) with the second TCO, 0327b (NB3+TCO). The clinical specimens were serially diluted in appropriate plasma or serum diluents beyond the 5 IU/ml from initial testing. For all tested genotypes with the exception of HCV genotype 4, the percent positive results and average log copy at the lowest target concentration were greater with the addition of the second TCO (Table 18). That is, at 1 IU/ml, each of 1b, 2a, 3a, 5a, and 6c showed improved % positives (gains of 13, 20, 26, 13, and 13 percentage points). Specimens of HCV genotype 4 had similar results with addition of the second TCO compared to the single TCO system. All percent positive results were ≥95% at 12IU/mL and ≤0.25 SD log copy at 100 IU/ml.

TABLE 18

Log Copy Results for Clinical Genotype Specimens +/− second TCO (0327b)

| Genotype/sample | Target (IU/mL) | Reps | 0297 TCO only | | | 0297 + 0327b TCOs | | |
|---|---|---|---|---|---|---|---|---|
| | | | % Positive | SD IU/mL | Observed LogIU | % Positive | SD IU/mL | Observed LogIU |
| 1b | 1E+03 | 5 | 100% | 0.01 | 3.03 | 100% | 0.02 | 3.08 |
| Plasma | 1E+02 | 5 | 100% | 0.08 | 2.14 | 100% | 0.05 | 2.15 |
| | 2E+01 | 20 | 100% | 0.30 | 1.18 | 100% | 0.17 | 1.41 |
| | 12 | 30 | 100% | 0.32 | 0.93 | 100% | 0.28 | 1.24 |
| | 5 | 20 | 100% | 0.39 | 0.41 | 100% | 0.40 | 0.68 |
| | 3 | 20 | 85% | 0.48 | 0.36 | 100% | 0.52 | 0.18 |
| | 1 | 15 | 47% | 0.61 | 0.02 | 60% | 0.49 | 0.18 |
| 2a | 1E+03 | 5 | 100% | 0.06 | 2.91 | 100% | 0.10 | 3.03 |
| Serum | 1E+02 | 5 | 100% | 0.14 | 2.11 | 100% | 0.09 | 2.17 |
| | 2E+01 | 20 | 100% | 0.17 | 1.35 | 100% | 0.17 | 1.52 |
| | 12 | 30 | 100% | 0.23 | 0.99 | 100% | 0.23 | 1.29 |
| | 5 | 20 | 100% | 0.38 | 0.50 | 100% | 0.22 | 0.81 |
| | 3 | 20 | 90% | 0.54 | 0.21 | 100% | 0.52 | 0.47 |
| | 1 | 15 | 53% | 0.49 | 0.01 | 73% | 0.49 | −0.06 |
| 3a | 1E+03 | 5 | 100% | 0.07 | 3.10 | 100% | 0.05 | 3.22 |
| Plasma | 1E+02 | 5 | 100% | 0.12 | 2.13 | 100% | 0.08 | 2.27 |
| | 2E+01 | 20 | 100% | 0.19 | 1.31 | 100% | 0.12 | 1.65 |
| | 12 | 30 | 100% | 0.25 | 0.97 | 100% | 0.15 | 1.40 |
| | 5 | 20 | 95% | 0.24 | 0.48 | 100% | 0.24 | 0.96 |
| | 3 | 20 | 100% | 0.30 | 0.46 | 95% | 0.37 | 0.54 |
| | 1 | 15 | 67% | 0.30 | −0.42 | 93% | 0.49 | 0.30 |
| 4 | 1E+03 | 5 | 100% | 0.03 | 2.59 | 100% | 0.04 | 2.72 |
| Plasma | 1E+02 | 5 | 100% | 0.17 | 1.62 | 100% | 0.10 | 1.80 |
| | 2E+01 | 20 | 95% | 0.32 | 0.84 | 100% | 0.42 | 0.96 |
| | 12 | 30 | 100% | 0.38 | 0.43 | 100% | 0.50 | 0.40 |
| | 5 | 19 | 89% | 0.48 | 0.22 | 85% | 0.48 | 0.01 |
| | 3 | 20 | 65% | 0.41 | −0.04 | 65% | 0.42 | −0.01 |
| | 1 | 15 | 27% | 0.40 | −0.22 | 20% | 0.66 | −0.01 |
| 5a | 1E+03 | 5 | 100% | 0.05 | 3.03 | 100% | 0.05 | 3.07 |
| Plasma | 1E+02 | 5 | 100% | 0.17 | 1.96 | 100% | 0.06 | 2.08 |
| | 2E+01 | 20 | 100% | 0.27 | 1.30 | 100% | 0.18 | 1.40 |
| | 12 | 30 | 100% | 0.24 | 1.13 | 100% | 0.16 | 1.12 |
| | 5 | 20 | 100% | 0.42 | 0.59 | 100% | 0.44 | 0.60 |
| | 3 | 20 | 100% | 0.52 | 0.32 | 100% | 0.43 | 0.41 |
| | 1 | 15 | 67% | 0.51 | −0.05 | 80% | 0.42 | 0.08 |
| 6c | 1E+03 | 5 | 100% | 0.06 | 3.10 | 100% | 0.08 | 3.43 |
| Serum | 1E+02 | 5 | 100% | 0.13 | 2.19 | 100% | 0.11 | 2.48 |
| | 2E+01 | 20 | 100% | 0.19 | 1.37 | 100% | 0.21 | 1.80 |
| | 12 | 30 | 100% | 0.22 | 1.12 | 100% | 0.19 | 1.58 |

TABLE 18-continued

Log Copy Results for Clinical Genotype Specimens +/− second TCO (0327b)

| | | | 0297 TCO only | | | 0297 + 0327b TCOs | | |
|---|---|---|---|---|---|---|---|---|
| Genotype/sample | Target (IU/mL) | Reps | % Positive | SD IU/mL | Observed LogIU | % Positive | SD IU/mL | Observed LogIU |
| | 5 | 20 | 100% | 0.36 | 0.63 | 100% | 0.31 | 1.05 |
| | 3 | 20 | 95% | 0.48 | 0.51 | 100% | 0.29 | 0.72 |
| | 1 | 15 | 60% | 0.43 | −0.24 | 73% | 0.52 | 0.22 |

Figure 27A:
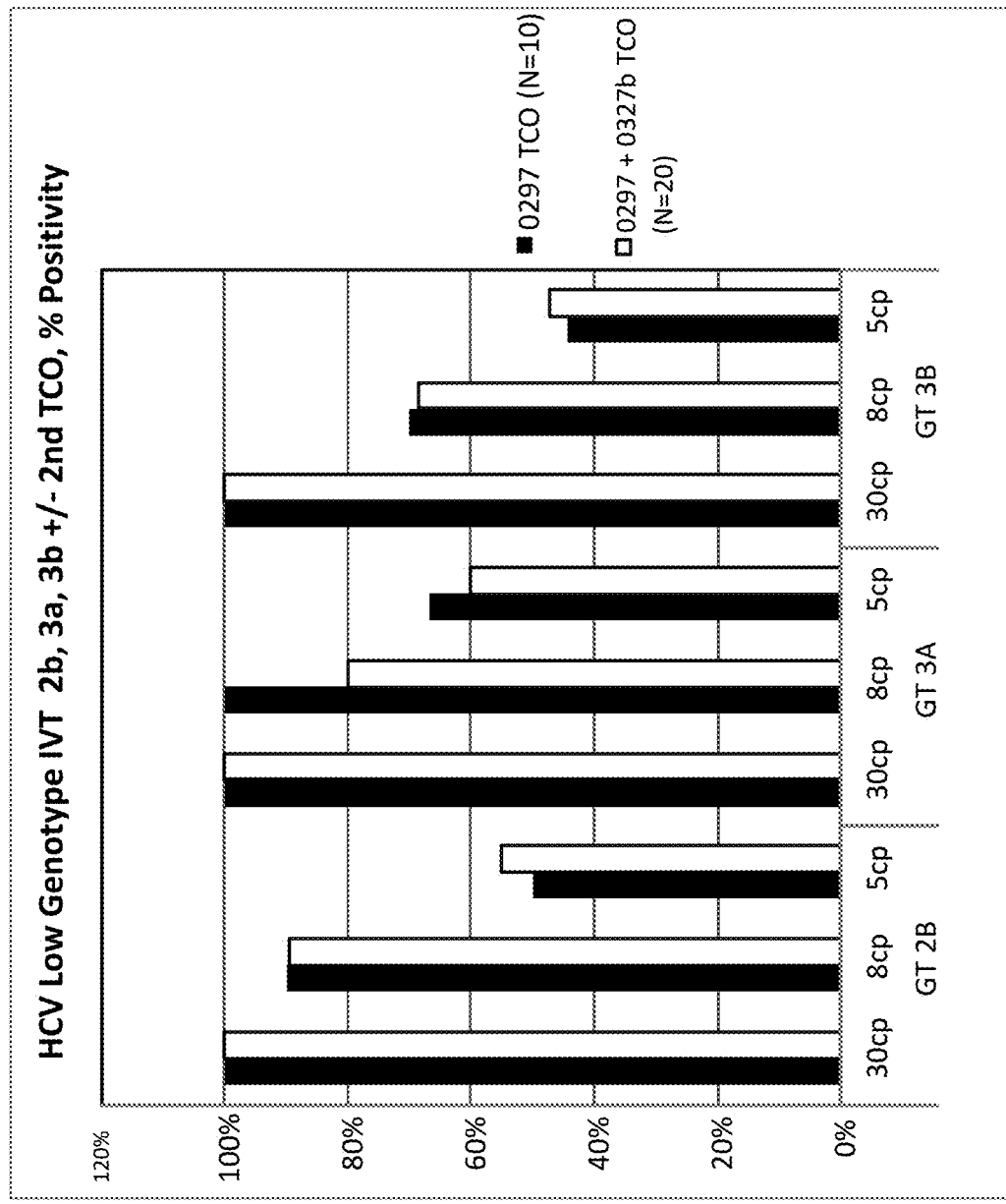
FIGS. 27A and 27B show HCV genotype IVT percent positive results for one target capture oligomer (TCO) (0297; dark bars) and two TCO (0297+0327b; light bars) conditions.
Figure 27B:
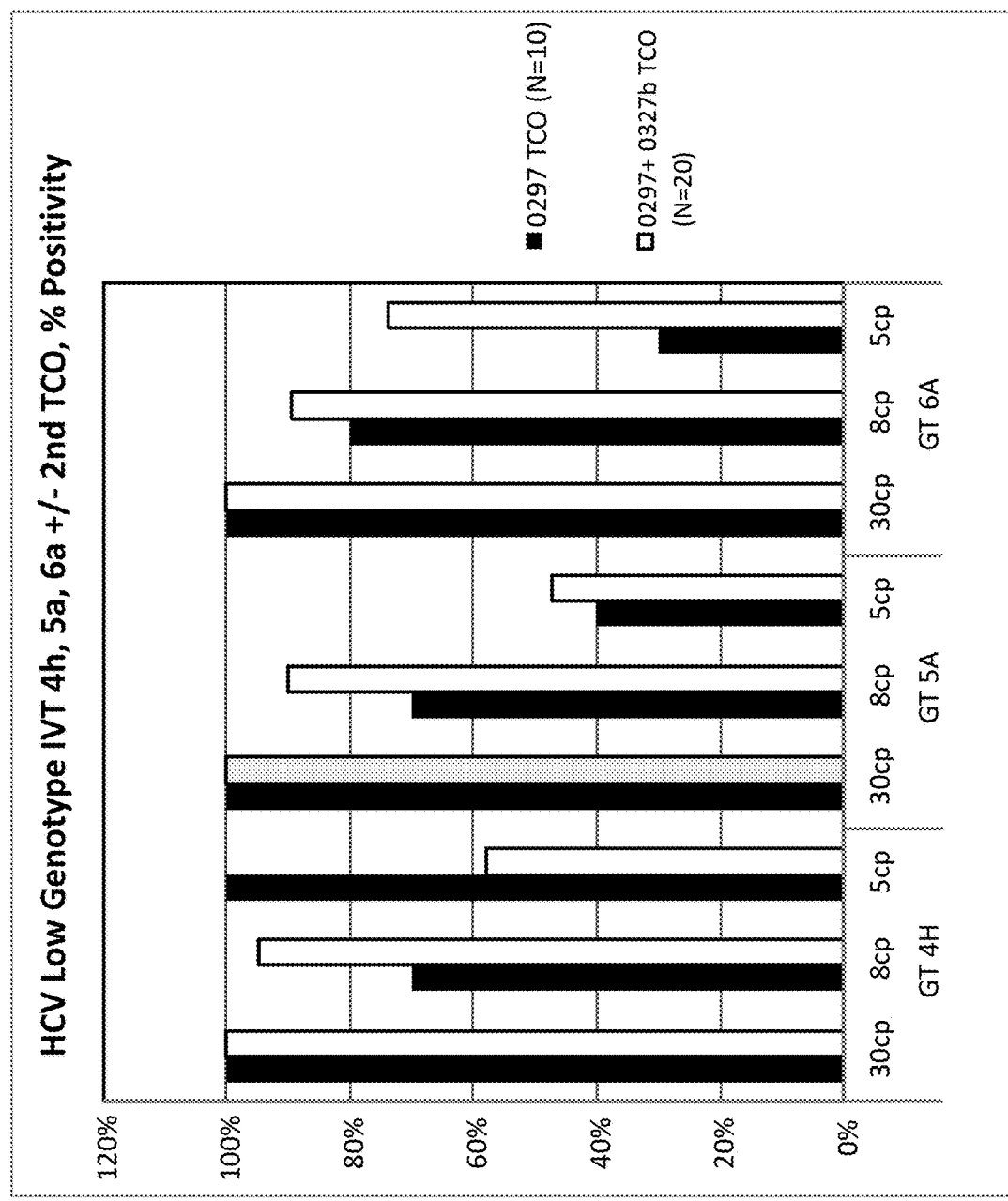

To further confirm performance at low concentration with and without the second TCO, the genotype IVTs were tested with panels at 30, 8 and 5 copies/ml. Each panel was tested using 0297 TCO only (n=10) or 0297 and 0327b TCOs (n=20). The percent positive results were comparable for HCV genotypes 2b, 3a, 3b and 4h, and results were improved with 0297 and 0327b TCOs for genotypes 5a and 6a (FIGS. 27A-B). All conditions produced 100% positive results at 30 copies/mL. The average log copy results were comparable between the conditions for genotypes 2b, 3a and 3b and slightly higher for genotypes 4h, 5a and 6a (not shown). The increase trend in percent positivity with the second TCO at low concentrations for genotypes such as 5a and 6a was confirmed with another 30 replicates of the 8 and 5 copies/ml panel and a separate lot of 0297 TCO (not shown). Data are summarized in Table 19.

TABLE 19

HCV genotype IVT percent positive, average log copy, and standard deviation log copy results with 0297 +/− 0327b TCO

| | | Percent Positive | | Average Observed Log Copy | | Standard Deviation of Observed Log Copy | |
|---|---|---|---|---|---|---|---|
| HCV Genotype | Copies/ml | 0297 TCO (N = 10) | 0297 + 0327b TCO (N = 20) | 0297 TCO (N = 10) | 0297 + 0327b TCO (N = 20) | 0297 TCO (N = 10) | 0297 + 0327b TCO (N = 20) |
| 2B | 30C | 100% | 100% | 1.50 | 1.62 | 0.22 | 0.27 |
| | 8C | 90% | 89% | 0.78 | 0.79 | 0.53 | 0.57 |
| | 5C | 50% | 55% | 0.68 | 0.72 | 0.43 | 0.58 |
| 3A | 30C | 100% | 100% | 1.46 | 1.41 | 0.20 | 0.21 |
| | 8C | 100% | 80% | 1.04 | 0.73 | 0.34 | 0.44 |
| | 5C | 67% | 60% | 0.81 | 0.67 | 0.45 | 0.49 |
| 3B | 30C | 100% | 100% | 1.31 | 1.58 | 0.66 | 0.22 |
| | 8C | 70% | 68% | 0.83 | 0.83 | 0.56 | 0.47 |
| | 5C | 44% | 47% | 1.19 | 0.69 | 0.18 | 0.51 |
| 4H | 30C | 100% | 100% | 1.71 | 1.48 | 0.31 | 0.47 |
| | 8C | 70% | 95% | 1.01 | 0.88 | 0.49 | 0.53 |
| | 5C | 100% | 58% | 0.45 | 0.82 | 0.53 | 0.44 |
| 5A | 30C | 100% | 100% | 1.37 | 1.56 | 0.55 | 0.23 |
| | 8C | 70% | 90% | 0.43 | 0.92 | 0.50 | 0.60 |
| | 5C | 40% | 47% | 1.22 | 1.07 | 0.27 | 0.39 |
| 6A | 30C | 100% | 100% | 1.66 | 1.37 | 0.28 | 0.32 |
| | 8C | 80% | 89% | 0.83 | 1.00 | 0.60 | 0.56 |
| | 5C | 30% | 74% | 0.57 | 0.57 | 0.56 | 0.47 |

Example 13—Cross-Reactivity, Analytical Specificity, and Clinical Specificity

Testing was done with the 0327b TCO included for microorganism cross-reactivity to a panel of viruses (Hepatitis A, Hepatits B, Herpes simplex 1, Herpes simplex 2, HIV, Parvovirus, Rubella, Dengue 2, Dengue 3, Dengue 4, Epstein-Barr, and West Nile) and microbes (C. albicans, C. diphtheriae, P. acnes, S. aureus, S. epidermis, S. pneumoniae) spiked into IAC (internal control buffer) at $10^5$ particle-forming units (PFU)/mL or 50% tissue culture infective dose (TCID50) for viruses and $10^6$ colony-forming units (CFU)/mL for microbes. No positive results were obtained in the absence of HCV nucleic acid. In the presence of HCV (2.3 log copies/ml), there was no significant interference from any virus or microbe in the panel (i.e., quantification was within 0.25 log of control for all spiked samples).

Clinical specificity was repeated using the oligomer set including the 0297 and 0327b TCOs with 961 frozen uninfected specimens (420 individual human serum and 541 individual human plasma). Eight positives occurred during testing, giving a specificity of 99% and a lower bound (95% CI) of 98.4%. Analytical specificity was repeated for informational purposes with a small number of IAC and negative serum samples at n=150 total. No positives occurred for the IAC and negative serum samples (specificity was 100%; lower bound (95% CI) was 98.4%).

No positives had occurred in earlier testing with 1 TCO using the same samples. Testing was repeated with 1 TCO and with 2 TCOs in parallel to determine whether the increase of positives was attributable to addition of the second TCO or an extraneous source such as environmental contamination at the time of testing. Of 410 clinical negative specimens tested in each condition, 2 positives occurred with 2 TCOs and no positives occurred in the control 1 TCO condition. Of 408 IAC negative samples, 2 positives occurred in the control 1 TCO condition and none for 2 TCOs. Thus, both the 1 TCO and 2 TCOs conditions had similar results, and these data confirmed that the addition of the second TCO did not contribute to a higher rate of false positives.

TABLE OF SEQUENCES

| SEQ ID NO | Description | Sequence |
|---|---|---|
| 1 | Representative HCV 1b sequence, GenBank Acc. No. AB016785 | gccagcccctgatgggggcgacactccaccatagatcactccctgtga ggaactactgtcttcacgcagaaagcgtctagccatggcgttagtatgag tgtcgtgcagcctccaggcccccccctcccgggagagccatagtggtctg cggaaccggtgagtacaccggaattgccaggacgacgggtcctttcttg gatcaatcccgctcaatgcctggagatttgggcgtgccccgcgagactg ctagccgagtagtgttgggtcgcgaaaggccttgtggtactgcctgatag ggtgcttgcgagtgccccgggaggtctcgtagaccgtgcaccatgagcac aaatcctaaacctcaaagaaaaaccaaacgtaacaccaaccgccgcccac aggacgtcaagttcccgggcggtggtcagatcgttggtggagtttacctg ttgccgcgcaggggcccccaggttgggtgtgcgcgcgactaggaagacttc cgagcggtcacaacctcgtggaaggcgacaacctatccccaaggctcgcc ggcccgagggcaggacctgggctcagcccgggtacccttggcccctctac ggcaatgagggcctgggtgggcagaatggctcctgtcacccgtggctc tcggcccagttggggcccacggaccccggcgtaggtcgcgtaatttgg gtaaggtcatcgataccctcacatgcgcgcttcgcccgacctcatgggtac attccgctcgtcggcgcccctgggggcgctgccagggccctggcgca tggcgtccgggttctggaggacggcgtgaactacgcaacagggaatctcc ccggttgctctttctctatcttcctcctggctttgctgtcctgtttgacc atcccagcttccgcttatgaagtgcgcaacgtgtccggggtgtaccatgt cacgaacgactgctccaactcaagtattgtgtatggggcggcggacatga tcatgcacaccccgggtgcgtgccctgcgtccgggagaacaattcctct cgttgctgggtagcgcttaccccacgctcgcggccaggaacaggagcat ccccactacgacaatacgacgccatgtcgatttgctcgttggggcggctg cttctgctccgccatgtacgtgggggatctctgcggatctgtcttcctc gtctcccagctgttcactttctcacctcgccggtatgagacagtacaaga ctgcaattgctcgctctatcccggccacgtatcaggtcatcgcatggctt gggatatgatgatgaactggtcacctacagcagccttggtggtatcgcag ctactccggatcccacaagccgtcgtggacatggtgacggggggcccactg gggagtcctggcgggccttgcctactattccatggtggggaactgggcta aggtcttgattgtgatgctactctttgccggcgttgacgggagaaccacc catgtaacgggggggcaaacaggccggaccaccctgggcattacggccat gtttgcgtttggcccgcatcaaaagctccaactcattaacaccaatggca gctggcacatcaacaggaccgccctgaactgcaatgactctctcaacact gggttcctagctgcgctgttttacgcacgcaagttcaactcgtctggatg cccagagcgcatggccagctgccgcccccattgacaagtttgttcagggat ggggtcccatcactcatgctgtgcctgacaacttggaccagaggccttac tgctggcactacgcgccccaaccgtgcggtatcatacccgcgtcacaggt gtgtggtccagtgtattgtttcaccccaagcccgttgtggtggggacga ccgaccgtttcggcgcccctacttacacctgggggggagaatgagacggac gtgctgctccttaacaacacgcggccgccgcaaggcaactggttcggctg tacatggatgaatggcaccgggttcgccaagacgtgcggaggcccccat gtaacatcggggggtcggcaacaacaccttgacctgccctacggattgc ttccgcaagcaccccgaggcacttacaccaaatgcggctcggggccctg gttgacgcctaggtgcatggttgactacccatacagactttggcactacc cctgcactgtcaacttcaccatcttaaagttaggatgtatgtgggggt gtggagcacaggctcaccgccgcgtgcaattggactcgaggagagcgttg tgacttggaggacagggacagatcagaacttagcccgctgctactgtcca cgacagagtggcaggtgctgccctgctccttcaccaccctaccggcttg tccaccggtctgatccacctccatcagaacatcgtggacgtgcaatacct gtatggcgtgggtcagcggtcgtctccattgtcatcaagtgggagtata tcctgctgctcttccttctcctcgcggacgcacgcgtctgcgcctgctta tggatgatgctgctgatagcccaggctgaggccgctttggaaaacctggt ggtcctcaatgcggcgtccgtggccggagcgcatggcactctctccttcc ttgtgttcttctgtgctgcctggtacatcaagggtaggctggtccctggg gcggcatatgcttttacggcgtatgccgctgctcctgctcctgctggc gttaccaccacgagcatacgccatggaccgggagatggctgcatcgtcgg ggggcgcggttttcataggtctagtactcttgacctttgtcgccacactac aaaccatttctcgccaggctcatatggtggttacaatactttatcaccag ggccgaggcgctagtacaggtgtggatcccccctcaacgttcgggggg gccgcgatgccatcatcctcctcacgtgcgcggtccatccgggggctgatt tttgaagtcaccaaaatcttgctcgccatacttggtccgctcacgatact ccaggctggcctaaccagagtgccgtacttcgtgcgcgctcaagggctca ttcgtgcgtgcatgttggtgcggaaagtcgctgggggccactatgttcaa atggctttcatgaagctggccgcactgacgggcacgtacgtttacaacca tcttactccgctgcaggactgggcccacgcgggcctacgagaccttgcgg tggcagttgagcccgtcgtcttctctgacatggagaccaagatcatcacc tgggggcagacaccgcggcgtgtggggacatcatctcaggtctaccgt ctccgcccgaaggggagggagatacttctgggaccggccgacagttttg aggggcgggggtggcgactccttgcccctatcacggcctactcccaacag acgcggggccttcttggcagtatcatcaccagcctcacaggtcgggataa gaaccgggtcgagggggaggttcaagtggtctccaccgcaacgcaatctt |

-continued

TABLE OF SEQUENCES

| SEQ ID NO | Description | Sequence |
|---|---|---|
| | | tcctggcgacctgtatcaacggcgtgtgctggactgtctaccatggtgcc ggctcaaagaccctagccgggccaaagggtccaattacccaaatgtacac caatgtagaccaggacctcgtcggctggccggcgccctcggggcgcgtt ccctgacatcatgcacctgcggcagttcggacctttacttggtcacgaga catgctgacgtcattccggtgcgccggcggggcgacagcagggggagcct actttcccccaggcctgtctcctacttgaagggctcctcgggtggtccgc tgctctgcccctcagggcatactgtgggcatcttccgggctgctgtgtgc acccgggggttgcgaaggcggtggactttatacccgtagagtctatgga aaccactatgcggtctccggtcttcacggacaactcatctccccggccg taccgcagacattccaagtggcccatctacacgcccccaccggcagcggt aagagcactaaagtgccggctgcatatgcagcccaagggtataaggtact cgtcctgaacccgtccgttgccgccaccctaggttttggggcgtatatgt ctaaggcacatggtattgaccctaacattagaactgggg taaggaccatc accacgggcgcccccatcacgtattccacctatggcaagttccttgccga cggtggttgttctgggggcgcctatgacatcataatatgtgatgagtgcc actcaactgactcgacttccatcttgggcattggcacagtcctggaccaa gcggagacggctggagcgcggctcgtcgtgctcgccaccgctacgcctcc gggatcggtcaccgtgccacacccaacatcgaggaggtggccttgtcca atactggagagatcccttctatggcaaagccatccccatcgagaccatc aagggggggaaggcatctcatcttctgtcactccaagaagaaatgtgatga gctcgccgcaaagctgtcggcccttggaatcaatgctgtagcgtactacc ggggcctggatgtgtccgtcataccgacaagcggagacgccgttgtcgtg gcaacagacgctctcatgacgggctataccggcgactttgactcggtgac cgactgcaacacgtgtgtcacccagacagtcgacttcagcttggaccctta ccttcaccatcgaaacgacaaccgtgcctcaagactcggtgtcgcgctcg cagcggcgaggcaggactggtaggggcagaggggg catatacaggtttgt gattccaggggagcggccctcaggcatgttcgattcttcggtcctgtgtg agtgttatgacgcgggctgcgcttggtatgagctcacgcccgccgagacc acggtcaggttgcgggcttacctgaatacaccagggg ttgcccgtctgcca ggaccacctggagttctgggagggcgtcttcacaggcctcacccacatag atgcccacttcttgtcccagactaaacaggcaggagacaacttcccctac ctggtagcataccaggctacagtgtgcgccagggcccaggctccacctcc atcgtgggatcaaatgtggaagtgtctcatacggctaaagccgacgctac acgggccaacacccctgttgtataggctagggg ccgttcaaaacgaggtc accctcacacaccccataaccaaatacatcatgacatgcatgtcggctga cctagaggtcgtcactagcacttgggtgctggtgggcggggtcctcgcag ccctggccgcgtactgcctaacaacgggcagcgtggtcattgtgggcagg atcattttgtctgggaggccggctatcatccccgacagggaagttctcta ccgggagttcgatgaaatggaagagtgcgcctcacacctcccttacatcg aacagggaatacagctcgccgagcaattcaagcagaaggcgctcgggttg ctgcaaacggccaccaagcaagcggaggctgccgccccgtggtggagtc caagtggcgtaccctagaggccttctgggcgaagcacatgtggaatttca tcagcgggatacagtacctagcaggcttgtccactctgcctgggaatccc gcgatagcatcattgatggcattcacagcctctatcaccagcccgctcac catccaacatacccctcctgtttaacatcttggggggtgggtggccgccc aacccgccccccccagcgctgcttcagctttcgtaggcgctggcattgcc ggcgcggctgttggtagcataggtgttgggaaggtgcttgtggacgtttt ggcgggttatggagcaggggtggcaggcggctctcgtggccttt aaggtca tgagcggtgaagtgccctccactgaggacctggtcaacttactccttgcc atcctctctcctggtgccctggtcgtcggagttgtgtgcgcggcaatact gcgtcggcatgtgggcccaggggaggggg ctgtgcagtgggtgaaccggt tgatagcgttcgcttcgcggggtaaccatgttt ccccacgcactatgtg cccgagagcgacgctgcagcgcgtgtcacccagattctctccagccttac catcactcagctgttgaagaggctccaccagtggattaatgaggactgct ccacaccatgctccggctcgtggctcagggatgttt gggactggatatgc acgtgttgaccgacttcaagacctggctccagtccaagctcctgccgcg gttgccaggagttcctttcctttcatgccaacgtgggtacaggggagtct ggcgagggggatggcatcatgcacaccacctgcccatgtggagcacaaatc actggacatgtcaagaacggctccatgaggattgttgggccaaaaacctg tagcaacacgtggcatggaacattcccatcaacacataccaccacggggcc cctgcacaccctcccagcgccaaactattccaaggcgttgtggcgggtg gctgctgaggagtacgtggaggtcacgcgggtgggggatttccattacgt gacgggcatgaccactgacaacgtaaaatgcccatgccaggttccggccc ccgaattctttacagaactggacggggtgcggctacacaggtacgctccg gcgtgcaaacctctcctacgggatgaggtcacactccaggtcgggctcaa ccaataccggtcggtcacagctcccatgtgagcccgaaccggatgtaa cagtgctcacctccatgctcaccgacccctcccacatcacagcagagacg gctaagcgtaggctggctaggggg tctggggtctcccttccttggccag ctcttcggctagccagttgtctgcgccttccttgaaggcgacatgcacta cccatcatgactcccagatgctgacctcattgaggccaacctcctgtgg cggcaggagatgggcgggaacatcacccgcgtggagtcagagaataggg t agtaattctagactcttttgacccgcttcgagcggaagaggatgagaggg aaatatccgttgcggcggatatcttgcggaaaaccaagaaatttccctca gcgatgcccatatgggcacgcccggactacaacccaccactgctggagtc |

| TABLE OF SEQUENCES | | |
|---|---|---|
| SEQ ID NO | Description | Sequence |
| | | ttggaagaacccggactacgtccctccggtggtacacgggtgcccattgt cacctaccagggcccctccaataccgcctccacggaggaagaggacagtt gtcttgacagaatccgccgtgtcttctgccttggcggagcttgctacaaa gaccttcggcagctccgaatcgtcggccgtcgacagcggcacagcgaccg ccccccccggccagtcctctgatgacggtggtacgggatccgacgttgag tcgtactcctccatgccccccttgaggggagccgggggaccccgatct cagcgacgggtcttggtctactgtaagcgaggaggctagcgaggacgtcg tctgctgctcaatgtcctacacgtggacgggtgccctgatcacgccatgc gccgcggaggagagcaagctgcccatcaatgcgctgagcaactctttgct gcgtcaccacaacatggtctatgccacaacatcccgcagcgcaagccagc ggcagaagaaggtcacctttgacagactgcaagtcctggacgaccactac cgggacgtgctcaaggagatgaaggcgaaggcgtccacagttaaggctaa gcttctatccgtagaagaagcctgcaagctgacgccccacattcggcca gatccaagtttggctatggggcaaaggacgtccggaacctgtccagcaag gccgttaaccacatccactccgtgtggaaggacttgctggaagacgatga aacaccaatcaataccaccatcatggcaaaaaatgaggtcttctgtgttc aaccagaaaaaggaggccgcaagccagctcgccttatcgtattcccagat ttaggggtccgcgtgtgcgagaaaatggccctctacgacgtggtctccac tcttcctcaggccgtgatgggctcctcatacgggtttcagtactctcctg gacagcgggtcgagttcttggtgaatgcctggaaatcaaagaagaacccc atgggcttcgcatatgacgcccgctgttttgactcaacggtcaccgagaa tgatatccgtgttgaggagtcaatttaccaatgttgtgacttagccccccg aggccagacaggccataaggtcgctcacagagcggctttacatcgggggc cccctgactaactcaaaaggcagaactgcggttatcgccggtgccgcgc cagcggcgtgctgacgaccaggtgcggtaatacccttacatgtcacttga aggcctctgcagcctgtcgagctgcaaagctccaggattgcacgatgctc gtgtgcggagatgacttgtcgttatctgtgaaagcgcgggaacccagga ggatgcggcgagcctacgagtcttcacggaggctatgactaggtattccg ccccccccggggacccgccccaaccggagtacgacttggagctaataaca tcatgctcctccaacgtgtcggtcgcgcacgatgcatctggcaaacgggt atactacctcacccgcgaccccaccaccccccttgcgcgggctgcgtggg agacagctaggcacactccagtcaactcctggctaggcaacattatcatg tatgcgcccaccttatgggcaagaatgattctgatgactcacttcttctc catccttctagctcaggagcaacttgaaaaagccctagattgtcagatct acggggccacttactccattgaaccacttgacctacctcagatcattcag cgactccatggtcttagcgcattttcactccatagttactctccaggtga gatcaatagggtggcttcatgcctcaggaaacttggggtaccgcccttgc gagtctggagacatcgggccagaagtgtccgcgctaagctactgtcccaa ggggggagggccgccacttgtggcaaatacctcttcaattgggcagtaag gaccaagctcaaactcactccaattccggctgcgtcccagttggacttgt ccggctggttcgttgctggttacagcgggggagacatatatcacagcctg tctcgtgcccgaccccgctggttcatgtggtgcctactcctactctctgt aggggtaggcatctacttgctccccaaccggtgaacggggagctaaacac tccaggccaataggccgtcctgttttttttttttttttggtggctcca tcttagccctagtcacggctagctgtgaaaggtccgtgagccgcatgact gcagagagtgctgatactggcctctctgcagatcatgt |
| 2 | amplification oligomer 52-78-1 | GGAACTTCTGTCTTCACGCGGAAAGCG |
| 3 | amplification oligomer 52-78-2 | GGAATTACTGTTTTAACGCAGAAAGCG |
| 4 | T7 amplification oligomer 80-119 | AATTTAATACGACTCACTATAGGGAGACCTGGAGGCTGCACGACACTCAT ACTAACGCCATGGCTAG |
| 5 | T7 amplification oligomer 93-119 | AATTTAATACGACTCACTATAGGGAGACCTGGAGGCTGCACGACACTCAT ACTA |
| 6 | amplification oligomer 80-119 | CCTGGAGGCTGCACGACACTCATACTAACGCCATGGCTAG |
| 7 | amplification oligomer 93-119 | CCTGGAGGCTGCACGACACTCATACTA |
| 8 | Exemplary T7 promoter | TAATACGACTCACTATAG |
| 9 | Sequence comprising T7 promoter | TAATACGACTCACTATAGGGAGA |

-continued

| TABLE OF SEQUENCES | | |
|---|---|---|
| SEQ ID NO | Description | Sequence |
| 10 | Sequence comprising T7 promoter | AATTTAATACGACTCACTATAG |
| 11 | Sequence comprising T7 promoter | AATTTAATACGACTCACTATAGGGAGA |
| 12 | Probe oligomer 81-96 | uagccauggcguuagu(c9)ggcua |
| 13 | Probe oligomer 81-96 target hybridizing sequence | uagccauggcguuagu |
| 14 | HCV 1b subsequence, positions 86-95 | uggcguuagu |
| 15 | Control capture oligomer | cguucacuauuggucucugcauucTTTAAAAAAAAAAAAAAAAAAAAAAAAAAAA |
| 16 | Capture oligomer 0297 | gggcacucgcaagcacccuTTTAAAAAAAAAAAAAAAAAAAAAAAAAAAA |
| 17 | Capture oligomer 0327b | cauggugcacggucuacgTTTAAAAAAAAAAAAAAAAAAAAAAAAAAAAA |
| 18 | Control NT7 amplification oligomer | GATTATATAGGACGACAAG |
| 19 | Control T7 amplification oligomer | AATTTAATACGACTCACTATAGGGAGAGATGATTGACTTGTGATTCCGC |
| 20 | Control probe oligomer 4180-4197 | gcaug(c9)gugcgaauugggacaugc |
| 21 | T3A30 | TTTAAAAAAAAAAAAAAAAAAAAAAAAAAAAAA |
| 22 | A30 | AAAAAAAAAAAAAAAAAAAAAAAAAAAAAA |
| 23 | amplification oligomer 52-78-1 subsequence | GCGGAAAGCG |
| 24 | amplification oligomer 52-78-1 subsequence | TTCACGCGGA |
| 25 | amplification oligomer 52-78-1 subsequence | CTGTCTTCAC |
| 26 | amplification oligomer 52-78-1 subsequence | AACTTCTGTC |
| 27 | amplification oligomer 52-78-1 subsequence | GGAACTTCTG |
| 28 | amplification oligomer 52-78-2 subsequence | GCAGAAAGCG |
| 29 | amplification oligomer 52-78-2 subsequence | TTAACGCAGA |

-continued

TABLE OF SEQUENCES

| SEQ ID NO | Description | Sequence |
|---|---|---|
| 30 | amplification oligomer 52-78-2 subsequence | CTGTTTTAAC |
| 31 | amplification oligomer 52-78-2 subsequence | AATTACTGTT |
| 32 | amplification oligomer 52-78-2 subsequence | GGAATTACTG |
| 33 | amplification oligomer 93-119 subsequence | ACTCATACTA |
| 34 | amplification oligomer 93-119 subsequence | ACGACACTCA |
| 35 | amplification oligomer 93-119 subsequence | GCTGCACGAC |
| 36 | amplification oligomer 93-119 subsequence | TGGAGGCTGC |
| 37 | amplification oligomer 93-119 subsequence | CCTGGAGGCT |
| 38 | amplification oligomer 80-119 subsequence | ACGCCATGGCTAG |
| 39 | amplification oligomer 80-119 subsequence | CCATGGCTAG |
| 40 | amplification oligomer 80-119 subsequence | TAACGCCATG |
| 41 | amplification oligomer 80-119 subsequence | TACTAACGCC |
| 42 | T7 amplification oligomer 93-119 subsequence | GGAGACCTGG |
| 43 | T7 amplification oligomer 93-119 subsequence | TAGGGAGACCTGG |
| 44 | T7 amplification oligomer 93-119 subsequence | TAATACGACTCACTATAGGGAGACCTGG |
| 45 | T7 amplification oligomer 93-119 subsequence | GGAGACCTGGAGGCT |
| 46 | T7 amplification oligomer 93-119 subsequence | AGGGAGACCTGGAGGCT |
| 47 | T7 amplification oligomer 93-119 subsequence | TAATACGACTCACTATAGGGAGACCTGGAGGCT |

-continued

| SEQ ID NO | Description | Sequence |
|---|---|---|
| 48 | Probe oligomer 81-96 subsequence | uuaguggcua |
| 49 | Probe oligomer 81-96 subsequence | uuagu(c9)ggcua |
| 50 | Probe oligomer 81-96 subsequence | uggcguuagu |
| 51 | Probe oligomer 81-96 subsequence | agccauggcg |
| 52 | Probe oligomer 81-96 subsequence | uagccauggc |
| 53 | Control capture oligomer target hybridizing sequence | cguucacuauuggucucugcauuc |
| 54 | Capture oligomer 0297 target hybridizing sequence | gggcacucgcaagcacccu |
| 55 | Capture oligomer 0327b target hybridizing sequence | cauggugcacggucuacg |
| 56 | Control amplification oligomer target hybridizing sequence | GATGATTGACTTGTGATTCCGC |
| 57 | Capture oligomer 0297 subsequence | caagcacccu |
| 58 | Capture oligomer 0297 subsequence | acucgcaagc |
| 59 | Capture oligomer 0297 subsequence | gggcacucgc |
| 60 | Capture oligomer 0327b subsequence | acggucuacg |
| 61 | Capture oligomer 0327b subsequence | uggugcacgg |
| 62 | Capture oligomer 0327b subsequence | cauggugcac |
| 63 | HCV 1a Transcript MW = 298,334 g/mol, 926 b | GGGCGAAUUGGAGCUCCACCGCGGUGGCGGCCGCUCUAGAACUAGUGGAU CCCCCGGGCUGCAGGAAUUCGCCCUUUCACUCCCCUGUGAGGAACUACUG UCUUCACGCAGAAAGCGUCUAGCCAUGGCGUUAGUAUGAGUGUCGUGCAG CCUCCAGGACCCCCCUCCCGGGAGAGCCAUAGUGGUCUGCGGAACCGGU GAGUACACCGGAAUUGCCAGGACGACCGGGUCCUUUCUUGGAUCAACCCG CUCAAUGCCUGGAGAUUUGGGCGUGCCCCCGCAAGACUGCUAGCCGAGUA GUGUUGGGUCGCGAAAGGCCUUGUGGUACUGCCUGAUAGGGUGCUUGCGA |

TABLE OF SEQUENCES

| SEQ ID NO | Description | Sequence |
|---|---|---|
| | | GUGCCCCGGGAGGUCUCGUAGACCGUGCACCAUGAGCACGAAUCCUAAAC CUCAAAAAAAAAACAAACGUAACACCAACCGUCGCCCACAGGACGUCAAG UUCCCGGGUGGCGGUCAGAUCGUUGGUGGAGUUUACUUGUUGCCGCGCAG GGGCCCUAGAUUGGGUGUGCGCGCGACGAGAAAGACUUCCGAGCGGUCGC AACCUCGAGGUAGACGUCAGCCUAUCCCCAAGGCUCGUCGGCCCGAGGGC AGGACCUGGGCUCAGCCCGGGUACCCUUGGCCCCUCUAUGGCAAUGAGGG CUGCGGGUGGCGGGAUGGCUCCUGUCUCCCCGUGGCUCUCGGCCUAGCU GGGGCCCCACAGACCCCCGGCGUAGGUCGCGCAAUUUGGGUAAGGUCAUC GAUACCCUUACGUGCGGCUUCGCCGACCUCAUGGGGUACAUACCGCUCGU CGGCGCCCCUCUUGGAGGCGCUGCCAGGGCCCUGGCGCAUGGCGUCCGGG UUCUGGAAGACGGCGUGAACUAUGCAACAGGGAACCUUCCUGGUUGCUCU UUCUCUAUCUUCCGAAUUCGAUAUCA |
| 64 | HCV 2b Transcript MW = 321,358 g/mol, 998 b | GGGCGAAUUGGGUACCGGGCCCCCCCUCGAGGUCGACGGUAUCGAUAAGC UUGAUAUCGAAUUCCUGCAGCCCGGGGGAUCCACUAGUAACGGCCGCCAG UGUGCUGGAAUUCGCCCUUUCACUCCCCUGUGAGGAACUACUGUCUUCAC GCAGAAAGCGUCUAGCCAUGGCGUUAGUAUGAGUGUCGUACAGCCUCCAG GCCCCCCCCUCCCGGGAGAGCCAUAGUGGUCUGCGGAACCGGUGAGUACA CCGGAAUUGCCGAAAGACUGGGUCCUUUCUUGGABAAACCCACUCUAUG UCCGGUCAUUUGGGCGUGCCCCCGCAAGACUGCUAGCCUAGUAGCGUUGG GUUGCGAACGGCCUUGUGGGUACUGCCUGAUAGGGUGCUUGCGAGUGCCC GGGAGGUCUCGUAGACCGUGCAUCAUGAGCACAAAUUCUAAACCUCAAAG AAAAACCAAAAGAAACACAAACCGCCGCCCACAGGACGUCAAGUUCCCGG GUGGCGGCCAGAUCGUUGGCGGAGUUUACUUGCUGCCGCGCAGGGGCCCC AGGUUGGUGUGCGCGCGACAAGGAAGACUUCUGAGCGAUCCCAGCCGCG UGGGAGACGCCAGCCCAUCCCGAAAGAUCGGCGCUCCACCGGCAAGUCCU GGGGAAAGCCAGGAUAUCCUUGGCCUCUGUAUGGAAACGAGGGCUGUGGC UGGGCAGGUUGGCUCCUGUCCCCCGCGGGUCUCGUCCUACUUGGGGCCC CACUGACCCCCGGCAUAGAUCACGCAAUCUGGGCAGAGUCAUCGAUACCA UUACGUGUGGUUUUGCCGACCUCAUGGGGUACAUCCCUGUCGUUGGCGCC CCAGUCGAGGCGUCGCCAGAGCUUUGGCACACGGUGUUAGGGUCCUGGA AGACGGGAUAAAUUAUGCAACAGGGAACCUACCUGGUUGCUCUUUUUCUA UCUUUUUGCUUGCUAAGGGCGAAUUCUGCAGAUAUCCAUCACACUGGC |
| 65 | pBluescript II SK (+) HCV 3a V1 MW = 277,725 g/mol, 861 b | GGGCGAAUUGGGUACCGGGCCCCCCCUCGAGGUCGACGGUAUCGAUAAGC UUGUGAGGAACUUCUGUCUUCACGCGGAAAGCGCCUAGCCAUGGCGUUAG UACGAGUGUCGUGCAGCCUCCAGGCCCCCCCUCCCGGGAGAGCCAUAGU GGUCUGCGGAACCGGUGAGUACACCGGAAUCGCUGGGGUGACCGGGUCCU UCUUGGAGCAACCCGCUCAAUACCCAGAAAUUUGGGCGUGCCCCGCGA GAUCACUAGCCGAGUAGUGCUGUGUCGCGAAAGGCCUUGUGGUACUGCCU GAUAGGGUGCUUGCGAGUGCCCCGGAGGUCUCGUAGACCAUGCAACAUG AGCACACUUCCUAAACCUCAAAGAAAAACCAAAAGAAACACCAUCCGUCG CCCACAGGACGUUAAGUUCCGGGCGGCGGACAGAUCGUUGGUGGAGUAU ACGUGUUGCCGCGCAGGGGCCCACGAUUGGAUGUGCGCGACGCGUAAA ACUUCUGAACGGUCGCAGCCUCGCGGACGACGACAGCCUAUCCCCAAGGC ACGUCGGAGUGAAGGCCGGUCCUGGGCUCAGCCCGGGUACCCUUGGCCCU UCUAUGGUAACGAGGGCUGCGGGUGGGCAGGAUGGCUCCUGUCCCCACGU GGCUCCCGUCCAUCUUGGGGCCCAAACGACCCCGGCGACGGUCCCACAA CUUGGGUAAAGUCAUCGAUACCCUUACGUACGGAUUCGCCGACCUCAUGG GGUACAUCCCGCUCGUCGGCGCUCUCCGUAGGAGGCGUCGCAAGAGCCUC GCACAUGGCGUGAGGGCCCUUGAGGACGGGAUAAAUUUCGCAACAGGGAA CUUGCGGAAUU |
| 66 | pBluescript II SK (+) HCV 3a V2: MW = 113,268 g/mol; 351 b | AUUGGGUACCGGGCCCCCCCUCGAGGUCGACGGUAUCGAUAAGCUUGUGA GGAACUUCUGUCUUCACGCGGAAAGCGCCUAGCCAUGGCGUUAGUACGAG UGUCGUGCAGCCUCCAGGCCCCCCCUCCCGGGAGAGCCAUAGUGGUCUG CGGAACCGGUGAGUACACCGGAAUCGCUGGGGUGACCGGGUCCUUUCUUG GAGCAACCCGCUCAAUACCCAGAAAUUUGGGCGUGCCCCCGCGAGAUCAC UAGCCGAGUAGUGCUGUGUCGCGAAAGGCCUUGUGGUACUGCCUGAUAGG GUGCUUGCGAGUGCCCCGGAGGUCUCGUAGACCAUGCAGGAAUU |
| 67 | pBluescript II SK (+) HCV 3a V3: MW = 104,770 g/mol; 325 b | GGGCGAAUUGGGUACCUCACUCCCCUGUGAGGAACUUCUGUCUUCACGCG GAAAGCGCCUAGCCAUGGCGUUAGUACGAGUGUCGUGCAGCCUCCAGGCC CCCCCUCCCGGGAGAGCCAUAGUGGUCUGCGGAACCGGUGAGUACACCG GAAUCGCUGGGGUGACCGGGUCCUUUCUUGGAGCAACCCGCUCAAUACCC AGAAAUUUGGGCGUGCCCCCGCGAGAUCACUAGCCGAGUAGUGCUGUGUC GCGAAAGGCCUUGUGGUACUGCCUGAUAGGGUGCUUGCGAGUGCCCCGGG AGGUCUCGUAGACCGUGCAGGAAUU |
| 68 | TOPO HCV 3b: MW = 135,874 g/mol, 422 b | GAAUACUCAAGCUAUGCAUCAAGCUUGGUACCGAGCUCGGAUCCACUAGU AACGGCCGCCAGUGUGCUGGAAUUCGCCCUUUCACUCCCCUGUGAGGAAC UACUGUCUUCACGCGGAAAGCGUCUAGCCAUGGCGUUAGUACGAGUGUCG UGCAGCCUCCAGGCCCCCCCUCCCGGGAGAGCCAUAGUGGUCUGCGGAA CCGGUGAGUACACCGGAAUCGCCGGGAUGACCGGGUCCUUUCUUGGAACA |

TABLE OF SEQUENCES

| SEQ ID NO | Description | Sequence |
|---|---|---|
| | | ACCCGCUCAAUGCCUGGAAAUUUGGGCGUGCCCCCGCGAGAUCACUAGCC GAGUAGUGUUGGGUCGCGAAAGGCCUUGUGGUACUGCCUGAUAGGGUGCU UGCGAGUGCCCCGGGAGGUCUCGUAGACCGUGCAAAGGGCGAAUUCUGCA GAUAUCCAUCACACUGGCGGCC |
| 69 | pBluescript II SK (+) HCV 3b:<br>MW = 104,810 g/mol, 325 b | GGGCGAAUUGGGUACCUCACUCCCCUGUGAGGAACUUCUGUCUUCACGCG GAAAGCGUCUAGCCAUGGCGUUAGUACGAGUGUCGUGCAGCCUCCAGGCC CCCCCUCCCGGGAGAGCCAUAGUGGUCUGCGGAACCGGUGAGUACACCG GAAUCGCCGGGAUGACCGGGUCCUUUCUUGGAACAACCCGCUCAAUGCCU GGAAAUUUGGGCGUGCCCCCGCGAGAUCACUAGCCGAGUAGUGUUGGGUC GCGAAAGGCCUUGUGGUACUGCCUGAUAGGGUGCUUGCGAGUGCCCCGGG AGGUCUCGUAGACCGUGCAGGAAUU |
| 70 | TOPO HCV 4h:<br>MW = 135,878 g/mol, 422 b | GAAUACUCAAGCUAUGCAUCAAGCUUGGUACCGAGCUCGGAUCCACUAGU AACGGCCGCCAGUGUGCUGGAAUUCGCCCUUUCACUCCCCUGUGAGGAAC UACUGUCUUCACGCAGAAAGCGUCUAGCCAUGGCGUUAGUAUGAGUGUUG UGCAGCCUCCAGGAUCCCCCCUCCCGGGAGAGCCAUAGUGGUCUGCGGAA CCGGUGAGUACACCGGAAUCGCCGGGAUGACCGGGUCCUUUCUUGGAUUA ACCCGCUCAAUGCCCGGAAAUUUGGGCGUGCCCCCGCGAGACUGCUAGCC GAGUAGUGUUGGGUCGCGAAAGGCCUUGUGGUACUGCCUGAUAGGGUGCU UGCGAGUGCCCCGGGAGGUCUCGUAGACCGUGCAAAGGGCGAAUUCUGCA GAUAUCCAUCACACUGGCGGCC |
| 71 | pBluescript II SK (+) HCV 4h:<br>MW = 104,811 g/mol, 325 b | GGGCGAAUUGGGUACCUCACUCCCCUGUGAGGAACUACUGUCUUCACGCA GAAAGCGUCUAGCCAUGGCGUUAGUAUGAGUGUUGUGCAGCCUCCAGGAU CCCCCCUCCCGGGAGAGCCAUAGUGGUCUGCGGAACCGGUGAGUACACCG GAAUCGCCGGGAUGACCGGGUCCUUUCUUGGAUUAACCCGCUCAAUGCCC GGAAAUUUGGGCGUGCCCCCGCGAGACUGCUAGCCGAGUAGUGUUGGGUC GCGAAAGGCCUUGUGGUACUGCCUGAUAGGGUGCUUGCGAGUGCCCCGGG AGGUCUCGUAGACCGUGCAGGAAUU |
| 72 | TOPO HCV 5a:<br>MW = 140,284 g/mol, 435 b | GGGCGAAUUGGGCCCUCUAGAUGCAUGCUCGAGCGGCCGCCAGUGUGAUG GAUAUCUGCAGAAUUCGCCCUUUCACUCCCCUGUGAGGAACUACUGUCUU CACGCAGAAAGCGUCUAGCCAUGGCGUUAGUAUGAGUGUCGAACAGCCUC CAGGACCCCCCUCCCGGGAGAGCCAUAGUGGUCUGCGAACCGGUGAGU ACACCGGAAUUGCCGGGACGACCGGGUCCUUUCUUGGAUAAACCCGCUCA AUGCCCGGAGAUUUGGGCGUGCCCCCGCGAGACUGCUAGCCGAGUAGUGU UGGGUCGCGAAAGGCCUUGUGGUACUGCCUGAUAGGGUGCUUGCGAGUGC CCCGGGAGGUCUCGUAGACCGUGCAAAGGGCGAAUUCAGCACACUGGCG GCCGUUACUAGUGGAUCCGAGCUCGGUACCAAGCU |
| 73 | pBluescript II SK (+) HCV-6a:<br>MW = 105,744 g/mol, 328 b | GGGCGAAUUGGGUACCUCACUCCCCUGUGAGGAACUACUGUCUUCACGCA GAAAGCGUCUAGCCAUGGCGUUAGUAUGAGUGUCGUACAGCCUCCAGGCC CCCCCUCCCGGGAGAGCCAUAGUGGUCUGCGGAACCGGUGAGUACACCG GAAUUGCCAGGAUGACCGGGUCCUUUCCAUUGGAUCAAACCCGCUCAAUG CCUGGAGAUUUGGGCGUGCCCCCGCAAGACUGCUAGCCGAGUAGCGUUGG GUUGCGAAAGGCCUUGUGGUACUGCCUGAUAGGGUGCUUGCGAGUGCCCC GGGAGGUCUCGUAGACCGUGCAGGAAUU |
| 74 | pBluescript II SK (+) HCV-5a:<br>MW = 104,881 g/mol, 325 b | GGGCGAAUUGGGUACCUCACUCCCCUGUGAGGAACUACUGUCUUCACGCA GAAAGCGUCUAGCCAUGGCGUUAGUAUGAGUGUCGAACAGCCUCCAGGAC CCCCCUCCCGGGAGAGCCAUAGUGGUCUGCGAACCGGUGAGUACACCG GAAUUGCCGGGACGACCGGGUCCUUUCUUGGAUAAACCCGCUCAAUGCCC GGAGAUUUGGGCGUGCCCCCGCGAGACUGCUAGCCGAGUAGUGUUGGGUC GCGAAAGGCCUUGUGGUACUGCCUGAUAGGGUGCUUGCGAGUGCCCCGGG AGGUCUCGUAGACCGUGCAGGAAUU |
| 75 | HCV-1a mRNA genome sequence (GenBank Accession No. M62321) | gccagccccc tgatggggc gacactccac catgaatcac tccctgtga ggaactactg tcttcacgca gaaagcgtct agccatggcg ttagtatgag tgtcgtgcag cctccaggac ccccctccc gggagagcca tagtggtctg cggaaccggt gagtacaccg gaattgccag gacgaccggg tccttttctt gatcaacccg ctcaatgcct ggagatttgg gcgtgccccc gcaagactgc tagccgagta gtgttgggtc gcgaaaggcc ttgtggtact gcctgatagg gtgcttgcga gtgccccggg aggtctcgta gaccgtgcac catgagcacg aatcctaaac ctcaaaaaaa aacaaacgt aacaccaacc gtcgcccaca ggacgtcaag ttcccgggtg |

Note:
additional sequences numbered higher than SEQ ID NO: 75 appear above, in the specification.

In the following table, lower case letters indicate RNA (for HCV sequences) or 2'-O-methyl RNA (for oligomer sequences and subsequences) and upper case letters indicate DNA. "(c9)" indicates a —(CH$_2$)$_9$— linker. Underlining indicates heterologous fusion sequence, e.g., a promoter or subsequence thereof (underlining not shown for T$_3$A$_{30}$ sequences).

What is claimed is:

1. A composition or kit comprising:

at least first and second amplification oligomers, wherein: the first amplification oligomer comprises a target-hybridizing sequence comprising at least 10 contiguous nucleotides of SEQ ID NO: 2, including at least a portion of the nucleotide sequence containing positions 5, 7, 12, and 15 of SEQ ID NO: 2; and the second amplification oligomer comprises a target-hybridizing sequence comprising at least 10 contiguous nucleotides of SEQ ID NO: 3 including at least a portion of the nucleotide sequence containing positions 5, 7, 12, and 15 of SEQ ID NO: 3;

the target-hybridizing sequences of the first and second amplification oligomers each comprise at least about 14 contiguous nucleotides of Hepatitis C virus sequence; and the kit or composition comprises at least one of: (i) an amplification oligomer that is a promoter-primer; or (ii) a probe oligomer, wherein the probe oligomer comprises a non-nucleotide detectable label and/or wherein at least about half of the sugar moieties in the probe oligomer are 2'-O-methyl-ribose.

2. The composition or kit of claim 1, wherein the first amplification oligomer comprises a target-hybridizing sequence comprising at least one, two, three, or four of SEQ ID NOs: 23-27; or wherein the first amplification oligomer comprises at least 11, 12, 13, 14, 15, 16, 17, 18, 19, 20, 21, 22, 23, 24, 25, or 26 contiguous nucleotides of SEQ ID NO: 2; or wherein the first amplification oligomer comprises the sequence of SEQ ID NO: 2.

3. The composition or kit of claim 1, wherein the second amplification oligomer comprises a target-hybridizing sequence comprising at least one, two, three, or four of SEQ ID NOs: 28-32; or wherein the second amplification oligomer comprises at least 11, 12, 13, 14, 15, 16, 17, 18, 19, 20, 21, 22, 23, 24, 25, or 26 contiguous nucleotides of SEQ ID NO: 3; or wherein the second amplification oligomer comprises the sequence of SEQ ID NO: 3.

4. The composition or kit of claim 1, further comprising a third amplification oligomer, wherein the third amplification oligomer comprises at least about 14 contiguous nucleotides of antisense Hepatitis C virus sequence and is configured to specifically hybridize downstream of position 78 of SEQ ID NO: 75, and the third amplification oligomer does not anneal downstream of an HCV genomic position selected from a position in at least one HCV type that corresponds to position 120, 125, 130, 135, 140, 145, or 150 of SEQ ID NO: 75.

5. The composition or kit of claim 4, wherein the at least one HCV type includes one or more of HCV types 1a, 1b, 2b, 3b, 4b, 5a, and 6a.

6. The composition or kit of claim 1, further comprising a third amplification oligomer, wherein the third amplification oligomer comprises at least about 14 contiguous nucleotides of antisense Hepatitis C virus sequence and is configured to specifically hybridize downstream of position 78 of SEQ ID NO: 75, and: wherein the third amplification oligomer is configured to specifically hybridize to a site comprising at least a portion of the nucleotide sequence containing positions 80-119 of SEQ ID NO: 75; or wherein the third amplification oligomer comprises a target-hybridizing sequence comprising at least 10 contiguous nucleotides of SEQ ID NO: 6 or 7; or wherein the third amplification oligomer comprises a target-hybridizing sequence comprising at least one, two, three, or four of SEQ ID NOs: 33-37; or wherein the third amplification oligomer comprises 11, 12, 13, 14, 15, 16, 17, 18, 19, 20, 21, 22, 23, 24, 25, or 26 contiguous nucleotides of SEQ ID NO: 7; or wherein the third amplification oligomer comprises the sequence of SEQ ID NO: 7; or wherein the third amplification oligomer comprises the sequence of at least one, two, three, four, or five of SEQ ID NOs: 42-47; or wherein the third amplification oligomer comprises the sequence of SEQ ID NO: 5.

7. The composition or kit of claim 1, wherein the first and second amplification oligomers are present in relative molar amounts (first:second) ranging from about 8.5:1.5 to about 1.5:8.5, about 7.5:2.5 to about 2.5:7.5, about 8:2 to about 7:3, about 7:3 to about 6:4, about 6:4 to about 5:5, about 5:5 to about 4:6, about 4:6 to about 3:7, or about 3:7 to about 2:8; or wherein the first and second amplification oligomers are present in relative molar amounts (first:second) ranging from about 6:4 to about 1.5:8.5, about 4:6 to about 6:4, or about 4.5:5.5 to about 5.5:4.5.

8. The composition or kit of claim 1, wherein the composition or kit further comprises an initial amplification oligomer, and the initial amplification oligomer comprises a target-hybridizing sequence comprising at least one, two, three, four, five, six, or seven of SEQ ID NOs: 33-41; or wherein the initial amplification oligomer comprises 11, 12, 13, 14, 15, 16, 17, 18, 19, 20, 21, 22, 23, 24, 25, 26, 27, 28, 29, 30, 31, 32, 33, 34, 35, 36, 37, 38, or 39 contiguous nucleotides of SEQ ID NO: 6; or wherein the initial amplification oligomer comprises the sequence of SEQ ID NO: 6; or wherein the initial amplification oligomer comprises the sequence of at least one, two, three, four, or five of SEQ ID NOs: 42-47; or wherein the initial amplification oligomer comprises the sequence of SEQ ID NO: 4.

9. The composition or kit of claim 1, wherein the probe oligomer comprises a target-hybridizing sequence comprising at least one or two of SEQ ID NOs: 50-52; or wherein the probe oligomer comprises the sequence of SEQ ID NO: 48 or 49; or wherein the probe oligomer comprises at least 11, 12, 13, 14, or 15 contiguous nucleotides of SEQ ID NO: 12; or wherein the probe oligomer comprises a target-hybridizing sequence comprising at least 11, 12, 13, 14, or 15 contiguous nucleotides of SEQ ID NO: 13; or wherein the probe oligomer comprises a first self-complementary region at its 5' end and a second self-complementary region at its 3' end; or wherein the probe oligomer comprises a first self-complementary region at its 5' end and a second self-complementary region at its 3' end and wherein the self-complementary regions can hybridize to form about 4 to 7 Watson-Crick or wobble base pairs; or wherein the probe oligomer comprises a first self-complementary region at its 5' end and a second self-complementary region at its 3' end and wherein the self-complementary regions can hybridize to form about 5 Watson-Crick or wobble base pairs; or wherein the probe oligomer comprises the sequence of SEQ ID NO: 12; or wherein the probe oligomer comprises a target-hybridizing sequence comprising the sequence of SEQ ID NO: 13.

10. The composition or kit of claim 9, wherein the probe oligomer comprises a non-nucleotide detectable label.

11. The composition or kit of claim 10, wherein the non-nucleotide detectable label is a fluorescent label.

12. The composition or kit of claim 10, wherein the probe oligomer comprises a quencher.

13. The composition or kit of claim 12, wherein the non-nucleotide detectable label is a fluorescent label and the quencher absorbs fluorescence to a greater extent when the probe is free than when the probe is annealed to a target nucleic acid.

14. The composition or kit of claim 11, wherein the fluorescent label is fluorescein, hexachlorofluorescein, carboxyrhodamine, or acridine.

15. The composition or kit of claim 12, wherein the quencher is DABCYL.

16. The composition or kit of claim 13, wherein the fluorescent label is attached to the 5'-terminus of the probe oligomer and the quencher is attached to the 3'-terminus of the probe oligomer, or the fluorescent label is attached to the 3'-terminus of the probe oligomer and the quencher is attached to the 5'-terminus of the probe oligomer.

17. The composition or kit of claim 9, wherein at least about half, at least about 90%, or all of the sugar moieties in the probe oligomer are 2'-O-methyl-ribose.

18. The composition or kit of claim 1, wherein the kit or composition comprises at least one amplification oligomer that is a promoter-primer; or wherein the composition or kit comprises one or more promoter-primers comprising the sequence of SEQ ID NO: 8, 9, 10, or 11.

19. The composition or kit of claim 18, wherein the composition or kit comprises a third amplification oligomer that comprises at least about 14 contiguous nucleotides of antisense Hepatitis C virus sequence, is configured to specifically hybridize downstream of position 78 of SEQ ID NO: 75, and is a promoter-primer.

20. The composition or kit of claim 18, wherein one or more of the promoter-primers comprises a T7 promoter located 5' of the target-hybridizing sequence.

21. A method of:
detecting Hepatitis C virus nucleic acid in a sample, comprising:
providing a composition according to claim 1 that further comprises the sample and a third amplification oligomer,
performing a nucleic acid amplification reaction in the composition which produces one or more amplicons in the presence of a Hepatitis C virus nucleic acid,
and detecting the amplicon, wherein:
the third amplification oligomer comprises at least about 14 contiguous nucleotides of antisense Hepatitis C virus sequence and is configured to specifically hybridize to downstream of position 78 of SEQ ID NO: 75; and
the one or more amplicons are produced through extension of the first and third amplification oligomers or second and third amplification oligomers in the presence of the Hepatitis C virus nucleic acid.

* * * * *

UNITED STATES PATENT AND TRADEMARK OFFICE
CERTIFICATE OF CORRECTION

| | |
|---|---|
| PATENT NO. | : 11,447,835 B2 |
| APPLICATION NO. | : 15/787344 |
| DATED | : September 20, 2022 |
| INVENTOR(S) | : Miick et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 548 days.

Signed and Sealed this
First Day of October, 2024

Katherine Kelly Vidal
*Director of the United States Patent and Trademark Office*